(12) United States Patent
Planken et al.

(10) Patent No.: US 7,919,488 B2
(45) Date of Patent: Apr. 5, 2011

(54) THERAPEUTIC COMPOUNDS

(75) Inventors: Simon Paul Planken, San Diego, CA (US); Scott Channing Sutton, San Diego, CA (US); Rongliang Chen, San Diego, CA (US)

(73) Assignee: Pfizer Inc., New York, NY (US)

( * ) Notice: Subject to any disclaimer, the term of this patent is extended or adjusted under 35 U.S.C. 154(b) by 400 days.

(21) Appl. No.: 11/770,698

(22) Filed: Jun. 28, 2007

(65) Prior Publication Data

US 2008/0021011 A1    Jan. 24, 2008

Related U.S. Application Data

(60) Provisional application No. 60/941,808, filed on Jun. 4, 2007, provisional application No. 60/910,988, filed on Apr. 10, 2007, provisional application No. 60/806,596, filed on Jul. 5, 2006.

(51) Int. Cl.
| | |
|---|---|
| A61K 31/397 | (2006.01) |
| A61K 31/415 | (2006.01) |
| A61K 31/454 | (2006.01) |
| A61K 31/496 | (2006.01) |
| C07D 211/80 | (2006.01) |
| C07D 401/14 | (2006.01) |
| C07D 403/02 | (2006.01) |
| C07D 405/06 | (2006.01) |
| C07D 413/14 | (2006.01) |

(52) U.S. Cl. ........... 514/210.2; 514/254.05; 514/318; 514/341; 514/397; 514/406; 544/371; 546/193; 546/269.1; 546/275.4; 548/255; 548/312.4

(58) Field of Classification Search ................ None
See application file for complete search history.

(56) References Cited

U.S. PATENT DOCUMENTS
| | | | |
|---|---|---|---|
| 7,008,953 B2 * | 3/2006 | Kephart et al. | 514/339 |
| 2003/0018197 A1 | 1/2003 | Dymock et al. | 546/514 |
| 2006/0009645 A1 | 1/2006 | Smith et al. | 548/265.8 |
| 2007/0167497 A1 | 7/2007 | Nambu et al. | 514/352 |

FOREIGN PATENT DOCUMENTS
| | | |
|---|---|---|
| RU | 2270832 | 10/2001 |
| WO | 02085897 | 10/2002 |

* cited by examiner

*Primary Examiner* — Kamal A Saeed
(74) *Attorney, Agent, or Firm* — Jennifer A. Kispert; J. Michael Dixon

(57) ABSTRACT

The present invention provides compounds of formula (I),

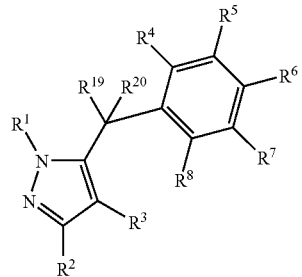

or pharmaceutically acceptable salts or solvates thereof, methods for their preparation, methods for their use, and pharmaceutical formulations comprising them.

14 Claims, 5 Drawing Sheets

THERAPEUTIC COMPOUNDS

This application claims the benefit of U.S. Application No. 60/806,596, filed Jul. 5, 2006, U.S. Application No. 60/910,988, filed Apr. 10, 2007, and U.S. Application No. 60/941,808, filed Jun. 4, 2007, all of which are herein incorporated by reference in their entirety.

BACKGROUND

The cytochrome P450 (CYP450) enzyme system is responsible for the biotransformation of drugs from active to inactive metabolites that are readily excreted by the body. Furthermore, the rapid metabolism of certain drugs by the CYP450 enzyme system can markedly alter their pharmacokinetic (PK) profile and can result in sub-therapeutic plasma levels of those drugs over time. In the area of anti-infective therapy, such as treating viral infections such as human immunodeficiency virus (HIV) infections, such sub-therapeutic drug plasma levels can lead to an increase in resistance of the virus.

Ritonavir (RTV) is a marketed HIV protease inhibitor (PI) that, due to its ability to inhibit the cytochrome P450 3A4 enzyme, is also used to "boost" the pharmacokinetic exposure of many co-administered anti-retrovirals. However, RTV is associated with clinically significant gastrointestinal and metabolic side effects including nausea, emesis, diarrhea, and dyslipidemia. Administering low doses of a compound with potent antiviral activity may also contribute to the selection of drug-resistant strains of HIV. A novel CYP3A4 inhibitor capable of boosting antivirals as effectively as RTV but devoid of antiviral activity and significant side-effects would offer significant advantages and therapeutic value in the treatment of those suffering from infection with the HIV virus. The present invention discloses compounds that are useful in the inhibition of the CYP450 enzyme system and may be used to boost the pharmacokinetic exposure of co-administered drugs, including anti-retrovirals. It also discloses pharmaceutical formulations comprising such compounds, methods of making them, and methods of using them.

SUMMARY

In one embodiment, the present invention provides compounds of formula (I),

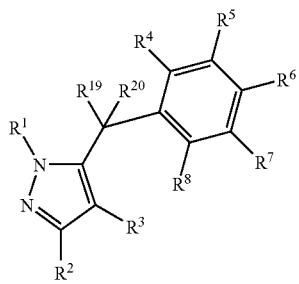

(I)

wherein:

$R^1$ is $C_1$-$C_8$ alkyl, —$(CR^9R^{10})_tR^{11}$, —$(CR^9R^{10})_tC(O)R^{11}$, —$(CR^9R^{10})_tC(O)N(R^{13}R^{14})$, —$(CR^9R^{10})_t$-(3-10 membered heterocyclyl)-$R^{11}$, or —$(CR^9R^{10})_t$-(5-9 membered heteroaryl)-$R^{11}$;

$R^2$ is 5-9 membered heteroaryl, optionally substituted with one or more $R^{11}$ groups;

$R^3$, $R^4$, $R^5$, $R^6$, $R^7$, and $R^8$ are each independently selected from hydrogen, halo, $C_1$-$C_8$ alkyl, $C_2$-$C_8$ alkenyl, $C_2$-$C_8$ alkynyl, —$(CR^9R^{10})_t(C_3$-$C_8$ cycloalkyl), —$(CR^9R^{10})_tOR^{11}$, —$(CR^9R^{10})_tN(R^{11}R^{12})$, —CN, —$NO_2$, —$CF_3$, —$C(O)R^9$, and —$C(O)_2R^9$;

each $R^9$ and $R^{10}$ is independently selected from hydrogen, $C_1$-$C_8$ alkyl, $C_3$-$C_8$ cycloalkyl, $C_6$-$C_{10}$ aryl, 3-10 membered heterocyclyl, and 5-9 membered heteroaryl;

each $R^{11}$ and $R^{12}$ is independently selected from hydrogen, $C_1$-$C_8$ alkyl, $C_3$-$C_8$ cycloalkyl, $C_6$-$C_{10}$ aryl, 3-10 membered heterocyclyl, 5-9 membered heteroaryl, —CN, halo, —$(CR^{16}R^{17})_tOR^{18}$, and —$(CR^{16}R^{17})_tC(O)R^{18}$, wherein each of said $C_1$-$C_8$ alkyl, $C_3$-$C_8$ cycloalkyl, $C_6$-$C_{10}$ aryl, 3-10 membered heterocyclyl, and 5-9 membered heteroaryl groups is optionally substituted with one more $R^{15}$ groups;

$R^{13}$ and $R^{14}$ are independently selected from hydrogen, $C_1$-$C_8$ alkyl and $C_3$-$C_8$ cycloalkyl, wherein said $C_1$-$C_8$ alkyl and $C_3$-$C_8$ cycloalkyl groups are optionally substituted with one or more $R^{15}$ groups; or $R^{13}$ and $R^{14}$, together with the nitrogen atom to which they are attached, form a 3-10 membered heterocyclyl group, optionally substituted with one or more $R^{15}$ groups;

each $R^{15}$ is independently selected from —$(CR^9R^{10})_tR^{16}$, —$(CR^9R^{10})_t$(3-10 membered heterocyclyl), —$(CR^9R^{10})_t(C_3$-$C_8$ cycloalkyl), —$(CR^9R^{10})_t$(5-9 membered heteroaryl), —$(CR^9R^{10})_t(C_6$-$C_{10}$ aryl), —$(CR^9R^{11})_tN(R^{16}R^{17})$, —$(CR^9R^{10})_tNR^{16}C(O)R^{17}$, —$(CR^9R^{10})_tOR^{16}$, —$(CR^9R^{10})_tC(O)R^{16}$, —$(CR^9R^{10})_tC(O)_2R^{16}$, —$(CR^9R^{10})_tC(O)N(R^{16}R^{17})$, —$(CR^9R^{10})_tNR^{16}C(O)OR^{17}$ —$(CR^9R^{10})_tNR^{16}S(O)N(R^{17}R^{18})$, —$(CR^9R^{10})_tNR^{16}S(O)_2N(R^{17}R^{18})$, —$(CR^9R^{10})_tNR^{16}S(O)R^{17}$, —$(CR^9R^{10})_tNR^{16}S(O)_2R^{17}$, —$(CR^9R^{10})_tNR^{16}C(O)N(R^{17}R^{18})$, —$(CR^9R^{10})_t$(halo), —$(CR^9R^{10})_t$—$OR^{16}$, and —$(CR^9R^{10})_tS(O)_2R^{16}$, wherein each said 3-10 membered heterocyclyl, $C_3$-$C_8$ cycloalkyl, 5-9 membered heteroaryl, and $C_6$-$C_{10}$ aryl is optionally substituted with one or more $R^{16}$ groups;

each $R^{16}$, $R^{17}$, and $R^{18}$ is independently selected from hydrogen, $C_1$-$C_8$ alkyl, —$(CH_2)_t(C_3$-$C_8$ cycloalkyl), —$(CH_2)_t(C_6$-$C_{10}$ aryl), —$(CH_2)_t$(5-9 membered heteroaryl), —$(CH_2)_t$(3-10 membered heterocyclyl), halo, —$OCH_3$, and —OH;

$R^{19}$ and $R^{20}$ are independently selected from hydrogen and $C_1$-$C_8$ alkyl; and each t is independently selected from 0, 1, 2, 3, and 4; or a pharmaceutically acceptable salt or solvate thereof.

In another embodiment are provided compounds of formula (I), wherein $R^{13}$ and $R^{14}$ are independently selected from hydrogen, $C_1$-$C_8$ alkyl and $C_3$-$C_8$ cycloalkyl, wherein said $C_1$-$C_8$ alkyl and $C_3$-$C_8$ cycloalkyl groups are optionally substituted with one or more $R^{15}$ groups.

In still another embodiment are provided compounds of formula (I), wherein $R^{13}$ and $R^{14}$, together with the nitrogen atom to which they are attached, form a 3-10 membered heterocyclyl group, optionally substituted with one or more $R^{15}$ groups.

A further embodiment provides compounds of formula (IIa),

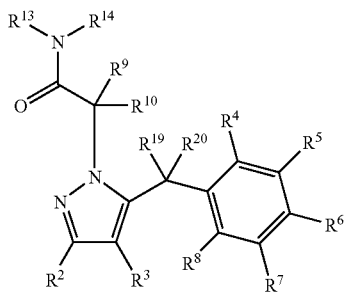

(IIa)

wherein:
R$^2$ is 5-9 membered heteroaryl, optionally substituted with one or more R$^{11}$ group;

R$^3$, R$^4$, R$^5$, R$^6$, R$^7$, and R$^8$ are each independently selected from hydrogen, halo, C$_1$-C$_8$ alkyl, C$_2$-C$_8$ alkenyl, C$_2$-C$_8$ alkynyl, —(CR$^9$R$^{10}$)$_t$(C$_3$-C$_8$ cycloalkyl), —(CR$^9$R$^{10}$)$_t$OR$^{11}$, —(CR$^9$R$^{10}$)$_t$N(R$^{11}$R$^{12}$), —CN, —NO$_2$, —CF$_3$, —C(O)R$^9$, and —C(O)$_2$R$^9$;

each R$^9$ and R$^{10}$ is independently selected from hydrogen, C$_1$-C$_8$ alkyl, C$_3$-C$_8$ cycloalkyl, C$_6$-C$_{10}$ aryl, 3-10 membered heterocyclyl, and 5-9 membered heteroaryl;

each R$^{11}$ and R$^{12}$ is independently selected from hydrogen, C$_1$-C$_8$ alkyl, C$_3$-C$_8$ cycloalkyl, C$_6$-C$_{10}$ aryl, 3-10 membered heterocyclyl, 5-9 membered heteroaryl, —CN, halo, —(CR$^{16}$R$^{17}$)$_t$OR$^{18}$, and —(CR$^{16}$R$^{17}$)$_t$C(O)R$^{18}$, wherein each of said C$_1$-C$_8$ alkyl, C$_3$-C$_8$ cycloalkyl, C$_6$-C$_{10}$ aryl, 3-10 membered heterocyclyl, and 5-9 membered heteroaryl groups is optionally substituted with one more R$^{15}$ groups;

R$^{13}$ and R$^{14}$ are independently selected from hydrogen, C$_1$-C$_8$ alkyl and C$_3$-C$_8$ cycloalkyl, wherein said C$_1$-C$_8$ alkyl and C$_3$-C$_8$ cycloalkyl groups are optionally substituted with one or more R$^{15}$ groups; or R$^{13}$ and R$^{14}$, together with the nitrogen atom to which they are attached, form a 3-10 membered heterocyclyl group, optionally substituted with one or more R$^{15}$ groups;

each R$^{15}$ is independently selected from —(CR$^9$R$^{10}$)$_t$R$^{16}$, —(CR$^9$R$^{10}$)$_t$(3-10 membered heterocyclyl), —(CR$^9$R$^{10}$)$_t$(C$_3$-C$_8$ cycloalkyl), —(CR$^9$R$^{10}$)$_t$(5-9 membered heteroaryl), —(CR$^9$R$^{10}$)$_t$(C$_6$-C$_{10}$ aryl), —(CR$^9$R$^{10}$)$_t$N(R$^{16}$R$^{17}$), —(CR$^9$R$^{10}$)$_t$NR$^{16}$C(O)R$^{17}$, —(CR$^9$R$^{10}$)$_t$OR$^{16}$, —(CR$^9$R$^{10}$)$_t$C(O)R$^{16}$, —(CR$^9$R$^{10}$)$_t$C(O)$_2$R$^{16}$, —(CR$^9$R$^{10}$)$_t$C(O)N(R$^{16}$R$^{17}$), —(CR$^9$R$^{10}$)$_t$NR$^{16}$C(O)OR$^{17}$, —(CR$^9$R$^{10}$)$_t$NR$^{16}$S(O)N(R$^{17}$R$^{18}$), —(CR$^9$R$^{10}$)$_t$NR$^{16}$S(O)$_2$N(R$^{17}$R$^{18}$), —(CR$^9$R$^{10}$)$_t$NR$^{16}$S(O)R$^{17}$, —(CR$^9$R$^{10}$)$_t$NR$^{16}$S(O)$_2$R$^{17}$, —(CR$^9$R$^{10}$)$_t$NR$^{16}$C(O)N(R$^{17}$R$^{18}$), —(CR$^9$R$^{10}$)$_t$(halo), —(CR$^9$R$^{10}$)$_t$—OR$^{16}$, and —(CR$^9$R$^{10}$)$_t$S(O)$_2$R$^{16}$, wherein each said 3-10 membered heterocyclyl, C$_3$-C$_8$ cycloalkyl, 5-9 membered heteroaryl, and C$_6$-C$_{10}$ aryl is optionally substituted with one or more R$^{16}$ group;

each R$^{16}$, R$^{17}$, and R$^{18}$ is independently selected from hydrogen, C$_1$-C$_8$ alkyl, —(CH$_2$)$_t$(C$_3$-C$_8$ cycloalkyl), —(CH$_2$)$_t$(C$_6$-C$_{10}$ aryl), —(CH$_2$)$_t$(5-9 membered heteroaryl), —(CH$_2$)$_t$(3-10 membered heterocyclyl), halo, —OCH$_3$, and —OH;

R$^{19}$ and R$^{20}$ are independently selected from hydrogen and C$_1$-C$_8$ alkyl; and each t is independently selected from 0, 1, 2, 3, and 4; or a pharmaceutically acceptable salt or solvate thereof.

Further provided are compounds of formula (IIa), wherein R$^{13}$ and R$^{14}$ are independently selected from hydrogen, C$_1$-C$_8$ alkyl and C$_3$-C$_8$ cycloalkyl, wherein said C$_1$-C$_8$ alkyl and C$_3$-C$_8$ cycloalkyl groups are optionally substituted with one or more R$^{15}$ groups.

Another embodiment provides compounds of formula (IIa), wherein R$^{13}$ and R$^{14}$, together with the nitrogen atom to which they are attached, form a 3-10 membered heterocyclyl group, optionally substituted with one or more R$^{15}$ groups.

Further provided herein are compounds of formula (IIb),

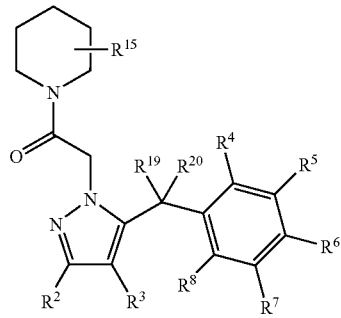

(IIb)

wherein:
R$^2$ is 5-9 membered heteroaryl, optionally substituted with one or more R$^{11}$ groups;

R$^3$, R$^4$, R$^5$, R$^6$, R$^7$, and R$^8$ are each independently selected from hydrogen, halo, C$_1$-C$_8$ alkyl, C$_2$-C$_8$ alkenyl, C$_2$-C$_8$ alkynyl, —(CR$^9$R$^{10}$)$_t$(C$_3$-C$_8$ cycloalkyl), —(CR$^9$R$^{10}$)$_t$OR$^{11}$, —(CR$^9$R$^{10}$)$_t$N(R$^{11}$R$^{12}$), —CN, —NO$_2$, —CF$_3$, —C(O)R$^9$, and —C(O)$_2$R$^9$;

each R$^9$ and R$^{10}$ is independently selected from hydrogen, C$_1$-C$_8$ alkyl, C$_3$-C$_8$ cycloalkyl, C$_6$-C$_{10}$ aryl, 3-10 membered heterocyclyl, and 5-9 membered heteroaryl;

each R$^{11}$ and R$^{12}$ is independently selected from hydrogen, C$_1$-C$_8$ alkyl, C$_3$-C$_8$ cycloalkyl, C$_6$-C$_{10}$ aryl, 3-10 membered heterocyclyl, 5-9 membered heteroaryl, —CN, halo, —(CR$^{16}$R$^{17}$)$_t$OR$^{18}$, and —(CR$^{16}$R$^{17}$)$_t$C(O)R$^{18}$, wherein each of said C$_1$-C$_8$ alkyl, C$_3$-C$_8$ cycloalkyl, C$_6$-C$_{10}$ aryl, 3-10 membered heterocyclyl, and 5-9 membered heteroaryl groups is optionally substituted with one more R$^{15}$ groups;

each R$^{15}$ is independently selected from —(CR$^9$R$^{10}$)$_t$R$^{16}$, —(CR$^9$R$^{10}$)$_t$(3-10 membered heterocyclyl), —(CR$^9$R$^{10}$)$_t$(C$_3$-C$_8$ cycloalkyl), —(CR$^9$R$^{10}$)$_t$(5-9 membered heteroaryl), —(CR$^9$R$^{10}$)$_t$(C$_6$-C$_{10}$ aryl), —(CR$^9$R$^{11}$)$_t$N(R$^{16}$R$^{17}$), —(CR$^9$R$^{10}$)$_t$NR$^{16}$C(O)R$^{17}$, —(CR$^9$R$^{10}$)$_t$OR$^{16}$, —(CR$^9$R$^{10}$)$_t$C(O)R$^{16}$, —(CR$^9$R$^{10}$)$_t$C(O)$_2$R$^{16}$, —(CR$^9$R$^{10}$)$_t$C(O)N(R$^{16}$R$^{17}$), —(CR$^9$R$^{10}$)$_t$NR$^{16}$C(O)OR$^{17}$, —(CR$^9$R$^{10}$)$_t$NR$^{16}$S(O)N(R$^{17}$R$^{18}$), —(CR$^9$R$^{10}$)$_t$NR$^{16}$S(O)$_2$N(R$^{17}$R$^{18}$), —(CR$^9$R$^{10}$)$_t$NR$^{16}$S(O)R$^{17}$, —(CR$^9$R$^{10}$)$_t$NR$^{16}$S(O)$_2$R$^{17}$, —(CR$^9$R$^{10}$)$_t$NR$^{16}$C(O)N(R$^{17}$R$^{18}$), —(CR$^9$R$^{10}$)$_t$(halo), —(CR$^9$R$^{10}$)$_t$—OR$^{16}$, and —(CR$^9$R$^{10}$)$_t$S(O)$_2$R$^{16}$, wherein each said 3-10 membered heterocyclyl, C$_3$-C$_8$ cycloalkyl, 5-9 membered heteroaryl, and C$_6$-C$_{10}$ aryl is optionally substituted with one or more R$^{16}$ groups;

each R$^{16}$, R$^{17}$, and R$^{18}$ is independently selected from hydrogen, C$_1$-C$_8$ alkyl, —(CH$_2$)$_t$(C$_3$-C$_8$ cycloalkyl), —(CH$_2$)$_t$(C$_6$-C$_{10}$ aryl), —(CH$_2$)$_t$(5-9 membered heteroaryl), —(CH$_2$)$_t$(3-10 membered heterocyclyl), halo, —OCH$_3$, and —OH;

R$^{19}$ and R$^{20}$ are independently selected from hydrogen and C$_1$-C$_8$ alkyl; and each t is independently selected from 0, 1, 2, 3, and 4; or a pharmaceutically acceptable salt or solvate thereof.

Also provided herein are compounds of formula (IIb), wherein:

$R^2$ is 5-9 membered heteroaryl, optionally substituted with one or more $R^{11}$ groups;

$R^3$ is hydrogen;

$R^4$, $R^5$, $R^6$, $R^7$, and $R^8$ are each independently selected from hydrogen, halo, $C_1$-$C_8$ alkyl, $C_2$-$C_8$ alkenyl, $C_2$-$C_8$ alkynyl, —$(CR^9R^{10})_t(C_3$-$C_8$ cycloalkyl), —$(CR^9R^{10})_tOR^{11}$, —$(CR^9R^{10})_tN(R^{11}R^{12})$, —CN, —$NO_2$, —$CF_3$, —$C(O)R^9$, and —$C(O)_2R^9$;

each $R^9$ and $R^{10}$ is independently selected from hydrogen, $C_1$-$C_8$ alkyl, $C_3$-$C_8$ cycloalkyl, $C_6$-$C_{10}$ aryl, 3-10 membered heterocyclyl, and 5-9 membered heteroaryl;

each $R^{11}$ and $R^{12}$ is independently selected from hydrogen, $C_1$-$C_8$ alkyl, $C_3$-$C_8$ cycloalkyl, $C_6$-$C_{10}$ aryl, 3-10 membered heterocyclyl, 5-9 membered heteroaryl, —CN, halo, —$(CR^{16}R^{17})_tOR^{18}$, and —$(CR^{16}R^{17})_tC(O)R^{18}$, wherein each of said $C_1$-$C_8$ alkyl, $C_3$-$C_8$ cycloalkyl, $C_6$-$C_{10}$ aryl, 3-10 membered heterocyclyl, and 5-9 membered heteroaryl groups is optionally substituted with one more $R^{15}$ groups;

each $R^{15}$ is independently selected from —$(CR^9R^{10})_tR^{16}$, —$(CR^9R^{10})_t$(3-10 membered heterocyclyl), —$(CR^9R^{10})_t$($C_3$-$C_8$ cycloalkyl), —$(CR^9R^{10})_t$(5-9 membered heteroaryl), —$(CR^9R^{10})_t(C_6$-$C_{10}$ aryl), —$(CR^9R^{11})_tN(R^{16}R^{17})$, —$(CR^9R^{10})_tNR^{16}C(O)R^{17}$, —$(CR^9R^{10})_tOR^{16}$, —$(CR^9R^{10})_tC(O)R^{16}$, —$(CR^9R^{10})_tC(O)_2R^{16}$, —$(CR^9R^{10})_tC(O)N(R^{16}R^{17})$, —$(CR^9R^{10})_tNR^{16}C(O)OR^{17}$ —$(CR^9R^{10})_tNR^{16}S(O)N(R^{17}R^{18})$, —$(CR^9R^{10})_tNR^{16}S(O)_2N(R^{17}R^{18})$, —$(CR^9R^{10})_tNR^{16}S(O)R^{17}$, —$(CR^9R^{10})_tNR^{16}S(O)_2R^{17}$, —$(CR^9R^{10})_tNR^{16}C(O)N(R^{17}R^{18})$, —$(CR^9R^{10})_t$(halo), —$(CR^9R^{10})_t$—$OR^{16}$, and —$(CR^9R^{10})_tS(O)_2R^{16}$, wherein each said 3-10 membered heterocyclyl, $C_3$-$C_8$ cycloalkyl, 5-9 membered heteroaryl, and $C_6$-$C_{10}$ aryl is optionally substituted with one or more $R^{16}$ groups;

each $R^{16}$, $R^{17}$, and $R^{18}$ is independently selected from hydrogen, $C_1$-$C_8$ alkyl, —$(CH_2)_t(C_3$-$C_8$ cycloalkyl), —$(CH_2)_t(C_6$-$C_{10}$ aryl), —$(CH_2)_t$(5-9 membered heteroaryl), —$(CH_2)_t$(3-10 membered heterocyclyl), halo, —$OCH_3$, and —OH;

$R^{19}$ and $R^{20}$ are hydrogen; and each t is independently selected from 0, 1, 2, 3, and 4; or a pharmaceutically acceptable salt or solvate thereof.

Further provided are compounds of formula (IIb), wherein:

$R^2$ is pyridyl, pyrazolyl, pyrimidinyl, and imidazolyl, optionally substituted with one or more $R^{11}$ group;

$R^3$ is hydrogen;

$R^4$, $R^5$, $R^7$, and $R^8$ are hydrogen;

$R^6$ is halo;

each $R^9$ and $R^{10}$ is independently selected from hydrogen, $C_1$-$C_8$ alkyl, $C_3$-$C_8$ cycloalkyl, $C_6$-$C_{10}$ aryl, 3-10 membered heterocyclyl, and 5-9 membered heteroaryl;

$R^{11}$ is selected from hydrogen, $C_1$-$C_8$ alkyl, $C_3$-$C_8$ cycloalkyl, $C_6$-$C_{10}$ aryl, 3-10 membered heterocyclyl, 5-9 membered heteroaryl, —CN, halo, —$(CR^{16}R^{17})_tOR^{18}$, and —$(CR^{16}R^{17})_tC(O)R^{19}$, wherein each of said $C_1$-$C_9$ alkyl, $C_3$-$C_8$ cycloalkyl, $C_6$-$C_{10}$ aryl, 3-10 membered heterocyclyl, and 5-9 membered heteroaryl groups is optionally substituted with one more $R^{15}$ groups;

each $R^{15}$ is independently selected from —$(CR^9R^{10})_tR^{16}$, —$(CR^9R^{10})_t$(3-10 membered heterocyclyl), —$(CR^9R^{10})_t$($C_3$-$C_8$ cycloalkyl), —$(CR^9R^{10})_t$(5-9 membered heteroaryl), —$(CR^9R^{10})_t(C_6$-$C_{10}$ aryl), —$(CR^9R^{10})_tN(R^{16}R^{17})$, —$(CR^9R^{10})_tNR^{16}C(O)R^{17}$, —$(CR^9R^{10})_tOR^{16}$, —$(CR^9R^{10})_tC(O)R^{16}$, —$(CR^9R^{10})_tC(O)_2R^{16}$, —$(CR^9R^{10})_tC(O)N(R^{16}R^{17})$, —$(CR^9R^{10})_tNR^{16}C(O)OR^{17}$ —$(CR^9R^{10})_tNR^{16}S(O)N(R^{17}R^{18})$, —$(CR^9R^{10})NR^{16}S(O)_2N(R^{17}R^{17})$, —$(CR^9R^{10})_tNR^{16}S(O)R^{17}$, —$(CR^9R^{10})_tNR^{16}S(O)_2R^{17}$, —$(CR^9R^{10})_tNR^{16}C(O)N(R^{17}R^{18})$, —$(CR^9R^{10})_t$(halo), —$(CR^9R^{10})_t$—$OR^{16}$, and —$(CR^9R^{10})_tS(O)_2R^{16}$, wherein each said 3-10 membered heterocyclyl, $C_3$-$C_8$ cycloalkyl, 5-9 membered heteroaryl, and $C_6$-$C_{10}$ aryl is optionally substituted with one or more $R^{16}$ groups;

each $R^{16}$, $R^{17}$, and $R^{18}$ is independently selected from hydrogen, $C_1$-$C_8$ alkyl, —$(CH_2)_t(C_3$-$C_8$ cycloalkyl), —$(CH_2)_t(C_6$-$C_{10}$ aryl), —$(CH_2)_t$(5-9 membered heteroaryl), —$(CH_2)_t$(3-10 membered heterocyclyl), halo, —$OCH_3$, and —OH;

$R^{19}$ and $R^{20}$ are hydrogen; and each t is independently selected from 0, 1, 2, 3, and 4; or a pharmaceutically acceptable salt or solvate thereof.

In another embodiment are provided compounds of formula (IIb), wherein:

$R^2$ is pyridyl;

$R^3$ is hydrogen;

$R^4$, $R^5$, $R^7$, and $R^8$ are hydrogen;

$R^6$ is halo;

each $R^9$ and $R^{10}$ is independently selected from hydrogen, $C_1$-$C_8$ alkyl, $C_3$-$C_8$ cycloalkyl, $C_6$-$C_{10}$ aryl, 3-10 membered heterocyclyl, and 5-9 membered heteroaryl;

$R^{15}$ is independently selected from —$(CR^9R^{10})_tR^{16}$, —$(CR^9R^{10})_t$(3-10 membered heterocyclyl), —$(CR^9R^{10})_t$($C_3$-Cl cycloalkyl), —$(CR^9R^{10})_t$(5-9 membered heteroaryl), —$(CR^9R^{10})_t(C_6$-$C_{10}$ aryl), —$(CR^9R^{10})_tN(R^{16}R^{17})$, —$(CR^9R^{10})_tNR^{16}C(O)R^{17}$, —$(CR^9R^{10})_tOR^{16}$, —$(CR^9R^{10})_tC(O)R^{16}$, —$(CR^9R^{10})_tC(O)_2R^{16}$, —$(CR^9R^{10})_tC(O)N(R^{16}R^{17})$, —$(CR^9R^{10})_tNR^{16}C(O)OR^{17}$ —$(CR^9R^{10})_tNR^{16}S(O)N(R^{17}R^{18})$, —$(CR^9R^{10})_tNR^{16}S(O)_2N(R^{17}R^{18})$, —$(CR^9R^{10})_tNR^{16}S(O)R^{17}$, —$(CR^9R^{10})_tNR^{16}S(O)_2R^{17}$, —$(CR^9R^{10})_tNR^{16}C(O)N(R^{17}R^{18})$, —$(CR^9R^{10})_t$(halo), —$(CR^9R^{10})_t$—$OR^{16}$, and —$(CR^9R^{10})_tS(O)_2R^{16}$ wherein each said 3-10 membered heterocyclyl, $C_3$-$C_8$ cycloalkyl, 5-9 membered heteroaryl, and $C_6$-$C_{10}$ aryl is optionally substituted with one or more $R^{16}$ groups;

each $R^{16}$, $R^{17}$, and $R^{18}$ is independently selected from hydrogen, $C_1$-$C_8$ alkyl, —$(CH_2)_t(C_3$-$C_8$ cycloalkyl), —$(CH_2)_t(C_6$-$C_{10}$ aryl), —$(CH_2)_t$(5-9 membered heteroaryl), —$(CH_2)_t$(3-10 membered heterocyclyl), halo, —$OCH_3$, and —OH;

$R^{19}$ and $R^{20}$ are hydrogen; and each t is independently selected from 0, 1, 2, 3, and 4; or a pharmaceutically acceptable salt or solvate thereof.

In another embodiment are provided compounds of formula (IIc),

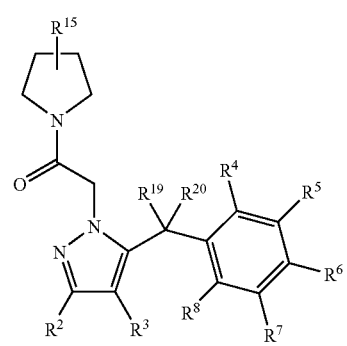

(IIc)

wherein:

$R^2$ is 5-9 membered heteroaryl, optionally substituted with one or more $R^{11}$ groups;

$R^3$, $R^4$, $R^5$, $R^6$, $R^7$, and $R^8$ are each independently selected from hydrogen, halo, $C_1$-$C_8$ alkyl, $C_2$-$C_8$ alkenyl, $C_2$-$C_8$ alkynyl, —$(CR^9R^{10})_t(C_3$-$C_8$ cycloalkyl), —$(CR^9R^{10})_tOR^{11}$, —$(CR^9R^{10})_tN(R^{11}R^{12})$, —CN, —$NO_2$, —$CF_3$, —$C(O)R^9$, and —$C(O)_2R^9$;

each $R^9$ and $R^{10}$ is independently selected from hydrogen, $C_1$-$C_8$ alkyl, $C_3$-$C_8$ cycloalkyl, $C_6$-$C_{10}$ aryl, 3-10 membered heterocyclyl, and 5-9 membered heteroaryl;

each $R^{11}$ and $R^{12}$ is independently selected from hydrogen, $C_1$-$C_8$ alkyl, $C_3$-$C_8$ cycloalkyl, $C_6$-$C_{10}$ aryl, 3-10 membered heterocyclyl, 5-9 membered heteroaryl, —CN, halo, —$(CR^{16}R^{17})_tOR^{18}$, and —$(CR^{16}R^{17})_tC(O)R^{18}$, wherein each of said $C_1$-$C_8$ alkyl, $C_3$-$C_8$ cycloalkyl, $C_6$-$C_{10}$ aryl, 3-10 membered heterocyclyl, and 5-9 membered heteroaryl groups is optionally substituted with one more $R^{15}$ groups;

each $R^{15}$ is independently selected from —$(CR^9R^{10})_tR^{16}$, —$(CR^9R^{10})_t$(3-10 membered heterocyclyl), —$(CR^9R^{10})_t$($C_3$-$C_8$ cycloalkyl), —$(CR^9R^{10})_t$(5-9 membered heteroaryl), —$(CR^9R^{10})_t(C_6$-$C_{10}$ aryl), —$(CR^9R^{11})_tN(R^{16}R^{17})$, —$(CR^9R^{10})_tNR^{16}C(O)R^{17}$, —$(CR^9R^{10})_tOR^{16}$, —$(CR^9R^{10})_tC(O)R^{16}$, —$(CR^9R^{10})_tC(O)_2R^{16}$, —$(CR^9R^{10})_tC(O)N(R^{16}R^{17})$, —$(CR^9R^{10})_tNR^{16}C(O)OR^{17}$ —$(CR^9R^{10})_tNR^{16}S(O)N(R^{17}R^{18})$, —$(CR^9R^{10})_tNR^{16}S(O)_2N(R^{17}R^{18})$, —$(CR^9R^{10})_tNR^{16}S(O)R^{17}$, —$(CR^9R^{10})_tNR^{16}S(O)_2R^{17}$, —$(CR^9R^{10})_tNR^{16}C(O)N(R^{17}R^{18})$, —$(CR^9R^{10})_t$(halo), —$(CR^9R^{10})_t$—$OR^{16}$, and —$(CR^9R^{10})_tS(O)_2R^{16}$, wherein each said 3-10 membered heterocyclyl, $C_3$-$C_8$ cycloalkyl, 5-9 membered heteroaryl, and $C_6$-$C_{10}$ aryl is optionally substituted with one or more $R^{16}$ groups;

each $R^{16}$, $R^{17}$, and $R^{18}$ is independently selected from hydrogen, $C_1$-$C_8$ alkyl, —$(CH_2)_t(C_3$-$C_8$ cycloalkyl), —$(CH_2)_t(C_6$-$C_{10}$ aryl), —$(CH_2)_t$(5-9 membered heteroaryl), —$(CH_2)_t$(3-10 membered heterocyclyl), halo, —$OCH_3$, and —OH;

$R^{19}$ and $R^{20}$ are independently selected from hydrogen and $C_1$-$C_8$ alkyl; and each t is independently selected from 0, 1, 2, 3, and 4; or a pharmaceutically acceptable salt or solvate thereof.

In another embodiment are provided compounds of formula (IId),

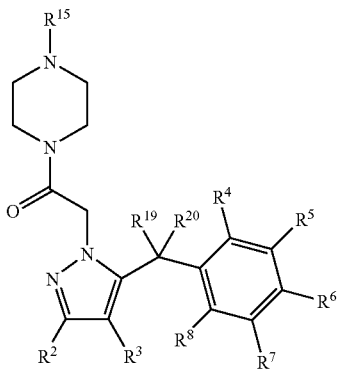

(IId)

wherein:

$R^2$ is 5-9 membered heteroaryl, optionally substituted with one or more $R^{11}$ groups;

$R^3$, $R^4$, $R^5$, $R^6$, $R^7$, and $R^8$ are each independently selected from hydrogen, halo, $C_1$-$C_8$ alkyl, $C_2$-$C_8$ alkenyl, $C_2$-$C_8$ alkynyl, —$(CR^9R^{10})_t(C_3$-$C_8$ cycloalkyl), —$(CR^9R^{10})_tOR^{11}$, —$(CR^9R^{10})_tN(R^{11}R^{12})$, —CN, —$NO_2$, —$CF_3$, —$C(O)R^9$, and —$C(O)_2R^9$;

each $R^9$ and $R^{10}$ is independently selected from hydrogen, $C_1$-$C_8$ alkyl, $C_3$-$C_8$ cycloalkyl, $C_6$-$C_{10}$ aryl, 3-10 membered heterocyclyl, and 5-9 membered heteroaryl;

each $R^{11}$ and $R^{12}$ is independently selected from hydrogen, $C_1$-$C_8$ alkyl, $C_3$-$C_8$ cycloalkyl, $C_6$-$C_{10}$ aryl, 3-10 membered heterocyclyl, 5-9 membered heteroaryl, —CN, halo, —$(CR^{16}R^{17})_tOR^{18}$, and —$(CR^{16}R^{17})_tC(O)R^{18}$, wherein each of said $C_1$-$C_8$ alkyl, $C_3$-$C_8$ cycloalkyl, $C_6$-$C_{10}$ aryl, 3-10 membered heterocyclyl, and 5-9 membered heteroaryl groups is optionally substituted with one more $R^{15}$ groups;

each $R^{15}$ is independently selected from —$(CR^9R^{10})_tR^{16}$, —$(CR^9R^{10})_t$(3-10 membered heterocyclyl), —$(CR^9R^{10})_t$($C_3$-$C_8$ cycloalkyl), —$(CR^9R^{10})_t$(5-9 membered heteroaryl), —$(CR^9R^{10})_t(C_6$-$C_{10}$ aryl), —$(CR^9R^{11})_tN(R^{16}R^{17})$, —$(CR^9R^{10})_tNR^{16}C(O)R^{17}$, —$(CR^9R^{10})_tOR^{16}$, —$(CR^9R^{10})_tC(O)R^{16}$, —$(CR^9R^{10})_tC(O)_2R^{16}$, —$(CR^9R^{10})_tC(O)N(R^{16}R^{17})$, —$(CR^9R^{10})_tNR^{16}C(O)OR^{17}$ —$(CR^9R^{10})_tNR^{16}S(O)N(R^{17}R^{18})$, —$(CR^9R^{10})_tNR^{16}S(O)_2N(R^{17}R^{18})$, —$(CR^9R^{10})_tNR^{16}S(O)R^{17}$, —$(CR^9R^{10})_tNR^{16}S(O)_2R^{17}$, —$(CR^9R^{10})_tNR^{16}C(O)N(R^{17}R^{18})$, —$(CR^9R^{10})_t$(halo), —$(CR^9R^{10})_t$—$OR^{16}$, and —$(CR^9R^{10})_tS(O)_2R^{16}$, wherein each said 3-10 membered heterocyclyl, $C_3$-$C_8$ cycloalkyl, 5-9 membered heteroaryl, and $C_6$-$C_{10}$ aryl is optionally substituted with one or more $R^{16}$ groups;

each $R^{16}$, $R^{17}$, and $R^{18}$ is independently selected from hydrogen, $C_1$-$C_8$ alkyl, —$(CH_2)_t(C_3$-$C_8$ cycloalkyl), —$(CH_2)_t(C_6$-$C_{10}$ aryl), —$(CH_2)_t$(5-9 membered heteroaryl), —$(CH_2)_t$(3-10 membered heterocyclyl), halo, —$OCH_3$, and —OH;

$R^{19}$ and $R^{20}$ are independently selected from hydrogen and $C_1$-$C_8$ alkyl; and each t is independently selected from 0, 1, 2, 3, and 4; or a pharmaceutically acceptable salt or solvate thereof.

A further embodiment provides compounds of formula (IIe),

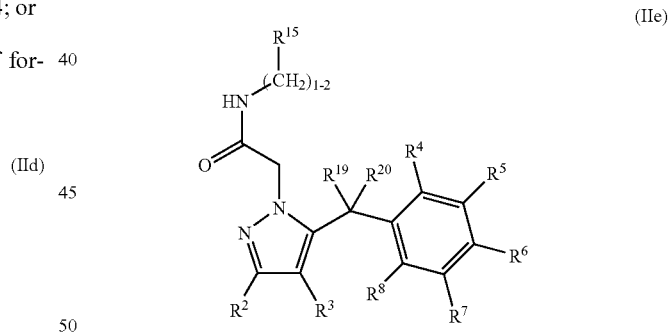

(IIe)

wherein:

$R^2$ is 5-9 membered heteroaryl, optionally substituted with one or more $R^{11}$ groups;

$R^3$, $R^4$, $R^5$, $R^6$, $R^7$, and $R^8$ are each independently selected from hydrogen, halo, $C_1$-$C_8$ alkyl, $C_2$-$C_8$ alkenyl, $C_2$-$C_8$ alkynyl, —$(CR^9R^{10})_t(C_3$-$C_8$ cycloalkyl), —$(CR^9R^{10})_tOR^{11}$, —$(CR^9R^{10})_tN(R^{11}R^{12})$, —CN, —$NO_2$, —$CF_3$, —$C(O)R^9$, and —$C(O)_2R^9$;

each $R^9$ and $R^{10}$ is independently selected from hydrogen, $C_1$-$C_8$ alkyl, $C_3$-$C_8$ cycloalkyl, $C_6$-$C_{10}$ aryl, 3-10 membered heterocyclyl, and 5-9 membered heteroaryl;

each $R^{11}$ and $R^{12}$ is independently selected from hydrogen, $C_1$-$C_8$ alkyl, $C_3$-$C_8$ cycloalkyl, $C_6$-$C_{10}$ aryl, 3-10 membered heterocyclyl, 5-9 membered heteroaryl, —CN, halo, —$(CR^{16}R^{17})_tOR^{18}$, and —$(CR^{16}R^{17})_tC(O)R^{18}$, wherein each of said $C_1$-$C_8$ alkyl, $C_3$-$C_8$ cycloalkyl, $C_6$-$C_{10}$ aryl, 3-10 membered heterocyclyl, and 5-9 membered heteroaryl groups is optionally substituted with one more $R^{15}$ groups;

each $R^{15}$ is independently selected from —$(CR^9R^{10})_tR^{16}$, —$(CR^9R^{10})_t$(3-10 membered heterocyclyl), —$(CR^9R^{10})_t$(C$_3$-C$_8$ cycloalkyl), —$(CR^9R^{10})_t$(5-9 membered heteroaryl), —$(CR^9R^{10})_t$(C$_6$-C$_{10}$ aryl), —$(CR^9R^{11})_tN(R^{16}R^{17})$, —$(CR^9R^{10})_tNR^{16}C(O)R^{17}$, —$(CR^9R^{10})_tOR^{16}$, —$(CR^9R^{10})_tC(O)R^{16}$, —$(CR^9R^{10})_tC(O)_2R^{16}$, —$(CR^9R^{10})_tC(O)N(R^{16}R^{17})$, —$(CR^9R^{10})_tNR^{16}C(O)OR^{17}$ —$(CR^9R^{10})_tNR^{16}S(O)N(R^{17}R^{18})$, —$(CR^9R^{10})_tNR^{16}S(O)_2N(R^{17}R^{18})$, —$(CR^9R^{10})_tNR^{16}S(O)R^{17}$, —$(CR^9R^{10})_tNR^{16}S(O)_2R^{17}$, —$(CR^9R^{10})_tNR^{16}C(O)N(R^{17}R^{18})$, —$(CR^9R^{10})_t$(halo), —$(CR^9R^{10})_t$—$OR^{16}$, and —$(CR^9R^{10})_tS(O)_2R^{16}$, wherein each said 3-10 membered heterocyclyl, C$_3$-C$_8$ cycloalkyl, 5-9 membered heteroaryl, and C$_6$-C$_{10}$ aryl is optionally substituted with one or more $R^{16}$ groups;

each $R^{16}$, $R^{17}$, and $R^{18}$ is independently selected from hydrogen, C$_1$-C$_8$ alkyl, —$(CH_2)_t$(C$_3$-C$_8$ cycloalkyl), —$(CH_2)_t$(C$_6$-C$_{10}$ aryl), —$(CH_2)_t$(5-9 membered heteroaryl), —$(CH_2)_t$(3-10 membered heterocyclyl), halo, —$OCH_3$, and —OH;

$R^{19}$ and $R^{20}$ are independently selected from hydrogen and C$_1$-C$_8$ alkyl; and each t is independently selected from 0, 1, 2, 3, and 4; or a pharmaceutically acceptable salt or solvate thereof.

Further provided herein are compounds of formula (IIf),

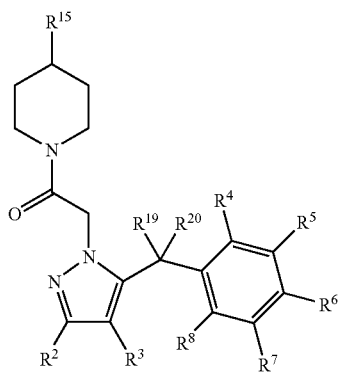

(IIf)

wherein:

$R^2$ is 5-9 membered heteroaryl, optionally substituted with one or more $R^{11}$ groups;

$R^3$, $R^4$, $R^5$, $R^6$, $R^7$, and $R^8$ are each independently selected from hydrogen, halo, C$_1$-C$_8$ alkyl, C$_2$-C$_8$ alkenyl, C$_2$-C$_8$ alkynyl, —$(CR^9R^{10})_t$(C$_3$-C$_8$ cycloalkyl), —$(CR^9R^{10})_tOR^{11}$, —$(CR^9R^{10})_tN(R^{11}R^{12})$, —CN, —NO$_2$, —CF$_3$, —C(O)R$^9$, and —C(O)$_2$R$^9$;

each $R^9$ and $R^{10}$ is independently selected from hydrogen, C$_1$-C$_8$ alkyl, C$_3$-C$_8$ cycloalkyl, C$_6$-C$_{10}$ aryl, 3-10 membered heterocyclyl, and 5-9 membered heteroaryl;

each $R^{11}$ and $R^{12}$ is independently selected from hydrogen, C$_1$-C$_8$ alkyl, C$_3$-C$_8$ cycloalkyl, C$_6$-C$_{10}$ aryl, 3-10 membered heterocyclyl, 5-9 membered heteroaryl, —CN, halo, —$(CR^{16}R^{17})_tOR^{18}$, and —$(CR^{16}R^{17})_tC(O)R^{18}$, wherein each of said C$_1$-C$_8$ alkyl, C$_3$-C$_8$ cycloalkyl, C$_6$-C$_{10}$ aryl, 3-10 membered heterocyclyl, and 5-9 membered heteroaryl groups is optionally substituted with one more $R^{15}$ groups;

each $R^{15}$ is independently selected from —$(CR^9R^{10})_tR^{16}$, —$(CR^9R^{10})_t$(3-10 membered heterocyclyl), —$(CR^9R^{10})_t$(C$_3$-C$_8$ cycloalkyl), —$(CR^9R^{10})_t$(5-9 membered heteroaryl), —$(CR^9R^{10})_t$(C$_6$-C$_{10}$ aryl), —$(CR^9R^{11})_tN(R^{16}R^{17})$, —$(CR^9R^{10})_tNR^{16}C(O)R^{17}$, —$(CR^9R^{10})_tOR^{16}$, —$(CR^9R^{10})_tC(O)R^{16}$, —$(CR^9R^{10})_tC(O)_2R^{16}$, —$(CR^9R^{10})_tC(O)N(R^{16}R^{17})$, —$(CR^9R^{10})_tNR^{16}C(O)OR^{17}$ —$(CR^9R^{10})_tNR^{16}S(O)N(R^{17}R^{18})$, —$(CR^9R^{10})_tNR^{16}S(O)_2N(R^{17}R^{18})$, —$(CR^9R^{10})_tNR^{16}S(O)R^{17}$, —$(CR^9R^{10})_tNR^{16}S(O)_2R^{17}$, —$(CR^9R^{10})_tNR^{16}C(O)N(R^{17}R^{18})$, —$(CR^9R^{10})_t$(halo), —$(CR^9R^{10})_t$—$OR^{16}$, and —$(CR^9R^{10})_tS(O)_2R^{16}$, wherein each said 3-10 membered heterocyclyl, C$_3$-C$_8$ cycloalkyl, 5-9 membered heteroaryl, and C$_6$-C$_{10}$ aryl is optionally substituted with one or more $R^{16}$ groups;

each $R^{16}$, $R^{17}$, and $R^{18}$ is independently selected from hydrogen, C$_1$-C$_8$ alkyl, —$(CH_2)_t$(C$_3$-C$_8$ cycloalkyl), —$(CH_2)_t$(C$_6$-C$_{10}$ aryl), —$(CH_2)_t$(5-9 membered heteroaryl), —$(CH_2)_t$(3-10 membered heterocyclyl), halo, —$OCH_3$, and —OH;

$R^{19}$ and $R^{20}$ are hydrogen; and each t is independently selected from 0, 1, 2, 3, and 4; or a pharmaceutically acceptable salt or solvate thereof.

Further provided are compounds of formula (IIf), wherein:

$R^2$ is pyridyl, pyrazolyl, pyrimidinyl, and imidazolyl, optionally substituted with one or more $R^{11}$ group;

$R^3$ is hydrogen;
$R^4$, $R^5$, $R^7$, and $R^8$ are hydrogen;
$R^6$ is halo;
each $R^9$ and $R^{10}$ is independently selected from hydrogen, $C_1$-$C_8$ alkyl, $C_3$-$C_8$ cycloalkyl, $C_6$-$C_{10}$ aryl, 3-10 membered heterocyclyl, and 5-9 membered heteroaryl;
$R^{11}$ is selected from hydrogen, $C_1$-$C_8$ alkyl, $C_3$-$C_8$ cycloalkyl, $C_6$-$C_{10}$ aryl, 3-10 membered heterocyclyl, 5-9 membered heteroaryl, —CN, halo, —$(CR^{16}R^{17})_tOR^{18}$, and —$(CR^{16}R^{17})_tC(O)R^{18}$, wherein each of said $C_1$-$C_8$ alkyl, $C_3$-$C_8$ cycloalkyl, $C_6$-$C_{10}$ aryl, 3-10 membered heterocyclyl, and 5-9 membered heteroaryl groups is optionally substituted with one more $R^{15}$ groups;
each $R^{15}$ is independently selected from —$(CR^9R^{10})_tR^{16}$, —$(CR^9R^{10})_t$(3-10 membered heterocyclyl), —$(CR^9R^{10})_t$($C_3$-$C_8$ cycloalkyl), —$(CR^9R^{10})_t$(5-9 membered heteroaryl), —$(CR^9R^{10})_t$($C_6$-$C_{10}$ aryl), —$(CR^9R^{11})_tN(R^{16}R^{17})$, —$(CR^9R^{10})_tNR^{16}C(O)R^{17}$, —$(CR^9R^{10})_tOR^{16}$, —$(CR^9R^{10})_tC(O)R^{16}$, —$(CR^9R^{10})_tC(O)_2R^{16}$, —$(CR^9R^{10})_tC(O)N(R^{16}R^{17})$, —$(CR^9R^{10})_tNR^{16}C(O)OR^{17}$ —$(CR^9R^{10})_tNR^{16}S(O)N(R^{17}R^{18})$, —$(CR^9R^{10})_tNR^{16}S(O)_2N(R^{17}R^{18})$, —$(CR^9R^{10})_tNR^{16}S(O)R^{17}$, —$(CR^9R^{10})_tNR^{16}S(O)_2R^{17}$, —$(CR^9R^{10})_tNR^{16}C(O)N(R^{17}R^{18})$, —$(CR^9R^{10})_t$(halo), —$(CR^9R^{10})_t$—$OR^{16}$, and —$(CR^9R^{10})_tS(O)_2R^{16}$, wherein each said 3-10 membered heterocyclyl, $C_3$-$C_8$ cycloalkyl, 5-9 membered heteroaryl, and $C_6$-$C_{10}$ aryl is optionally substituted with one or more $R^{16}$ groups;
each $R^{16}$, $R^{17}$, and $R^{18}$ is independently selected from hydrogen, $C_1$-$C_8$ alkyl, —$(CH_2)_t$($C_3$-$C_8$ cycloalkyl), —$(CH_2)_t$($C_6$-$C_{10}$ aryl), —$(CH_2)_t$(5-9 membered heteroaryl), —$(CH_2)_t$(3-10 membered heterocyclyl), halo, —$OCH_3$, and —OH;
$R^{19}$ and $R^{20}$ are hydrogen; and
each t is independently selected from 0, 1, 2, 3, and 4; or
a pharmaceutically acceptable salt or solvate thereof.

In another embodiment are provided compounds of formula (IIf), wherein:
$R^2$ is pyridyl;
$R^3$ is hydrogen;
$R^4$, $R^5$, $R^7$, and $R^8$ are hydrogen;
$R^6$ is halo;
each $R^9$ and $R^{10}$ is independently selected from hydrogen, $C_1$-$C_8$ alkyl, $C_3$-$C_8$ cycloalkyl, $C_6$-$C_{10}$ aryl, 3-10 membered heterocyclyl, and 5-9 membered heteroaryl;
each $R^{15}$ is independently selected from —$(CR^9R^{10})_tR^{16}$, —$(CR^9R^{10})_t$(3-10 membered heterocyclyl), —$(CR^9R^{10})_t$($C_3$-$C_8$ cycloalkyl), —$(CR^9R^{10})_t$(5-9 membered heteroaryl), —$(CR^9R^{10})_t$($C_6$-$C_{10}$ aryl), —$(CR^9R^{11})_tN(R^{16}R^{17})$, —$(CR^9R^{10})_tNR^{16}C(O)R^{17}$, —$(CR^9R^{10})_tOR^{16}$, —$(CR^9R^{10})_tC(O)R^{16}$, —$(CR^9R^{10})_tC(O)_2R^{16}$, —$(CR^9R^{10})_tC(O)N(R^{16}R^{17})$, —$(CR^9R^{10})_tNR^{16}C(O)OR^{17}$ —$(CR^9R^{10})_tNR^{16}S(O)N(R^{17}R^{18})$, —$(CR^9R^{10})_tNR^{16}S(O)_2N(R^{17}R^{18})$, —$(CR^9R^{10})_tNR^{16}S(O)R^{17}$, —$(CR^9R^{10})_tNR^{16}S(O)_2R^{17}$, —$(CR^9R^{10})_tNR^{16}C(O)N(R^{17}R^{18})$, —$(CR^9R^{10})_t$(halo), —$(CR^9R^{10})_t$—$OR^{16}$, and —$(CR^9R^{10})_tS(O)_2R^{16}$, wherein each said 3-10 membered heterocyclyl, $C_3$-$C_8$ cycloalkyl, 5-9 membered heteroaryl, and $C_6$-$C_{10}$ aryl is optionally substituted with one or more $R^{16}$ groups;
each $R^{16}$, $R^{17}$, and $R^{18}$ is independently selected from hydrogen, $C_1$-$C_8$ alkyl, —$(CH_2)_t$($C_3$-$C_8$ cycloalkyl), —$(CH_2)_t$($C_6$-$C_{10}$ aryl), —$(CH_2)_t$(5-9 membered heteroaryl), —$(CH_2)_t$(3-10 membered heterocyclyl), halo, —$OCH_3$, and —OH;
$R^{19}$ and $R^{20}$ are hydrogen; and
each t is independently selected from 0, 1, 2, 3, and 4; or
a pharmaceutically acceptable salt or solvate thereof.

Further provided herein are compounds of formula (IIg), (IIg)

wherein:
$R^2$, $R^3$, $R^4$, $R^5$, $R^6$, $R^7$, $R^8$, $R^{19}$, and $R^{20}$ are as defined for compounds of formula (IIb);
$R^{21}$ is hydrogen or $C_1$-$C_8$ alkyl;
$R^{22}$ is selected from hydrogen, —$C(O)R^{23}$, —$C(O)_2R^{23}$, —$S(O)R^{23}$, —$S(O)_2R^{23}$, —$S(O)N(R^{23}R^{24})$, —$S(O)_2N(R^{23}R^{24})$, and —$C(O)N(R^{23}R^{24})$; and
each $R^{23}$ and $R^{24}$ is independently selected from hydrogen and $C_1$-$C_8$ alkyl; or
a pharmaceutically acceptable salt of solvate thereof.

In still another embodiment is provided compounds of formula (IIg), wherein:
$R^2$ is pyridyl;
$R^3$ is hydrogen;
$R^4$, $R^5$, $R^7$, and $R^8$ are hydrogen;
$R^6$ is halo;
$R^{19}$ and $R^{20}$ are hydrogen;
$R^{21}$ is hydrogen or $C_1$-$C_8$ alkyl;
$R^{22}$ is selected from hydrogen, —$C(O)R^{23}$, —$C(O)_2R^{23}$, —$S(O)R^{23}$, -$S(O)_2R^{23}$, —$S(O)N(R^{23}R^{24})$, —$S(O)_2N(R^{23}R^{24})$, and —$C(O)N(R^{23}R^{24})$; and
each $R^{23}$ and $R^{24}$ is independently selected from hydrogen and $C_1$-$C_8$ alkyl; or
a pharmaceutically acceptable salt of solvate thereof.

A further embodiment provides compounds of formula (IIg), wherein:
$R^2$ is pyridyl;
$R^3$ is hydrogen;
$R^4$, $R^5$, $R^7$, and R8 are hydrogen;
$R^6$ is fluoro;
$R^{19}$ and $R^{20}$ are hydrogen;
$R^{21}$ is hydrogen or $C_1$-$C_8$ alkyl;
$R^{22}$ is selected from hydrogen, —$C(O)R^{23}$, —$C(C)_2R^{23}$, —$S(O)R^{23}$, —$S(O)_2R^{23}$, —$S(O)N(R^{23}R^{24})$, —$S(O)_2N(R^{23}R^{24})$, and —$C(O)N(R^{23}R^{24})$; and
each $R^{23}$ and $R^{24}$ is independently selected from hydrogen and $C_1$-$C_8$ alkyl; or
a pharmaceutically acceptable salt of solvate thereof.

A further embodiment provides compounds of formula (IIg), wherein:
$R^2$, $R^3$, $R^4$, $R^5$, $R^6$, $R^7$, $R^8$, $R^{19}$, and $R^{20}$ are as defined for compounds of formula (IIb); and
$R^{21}$ and $R^{22}$, together with the nitrogen atom to which they are attached, form a 3- to 10-membered heterocyclyl group; or
a pharmaceutically acceptable salt of solvate thereof.

Another embodiment provides compounds of formula (IIg), wherein:
$R^2$ is pyridyl;
$R^3$ is hydrogen;
$R^4$, $R^5$, $R^7$, and $R^8$ are hydrogen;
$R^6$ is halo;
$R^{19}$ and $R^{20}$ are hydrogen; and
$R^{21}$ and $R^{22}$, together with the nitrogen atom to which they are attached, form a 3- to 10-membered heterocyclyl group; or
a pharmaceutically acceptable salt of solvate thereof.

Another embodiment provides compounds of formula (IIg), wherein:
$R^2$ is pyridyl;
$R^3$ is hydrogen;
$R^4$, $R^5$, $R^7$, and $R^8$ are hydrogen;
$R^6$ is fluoro;
$R^{19}$ and $R^{20}$ are hydrogen; and
$R^{21}$ and $R^{22}$, together with the nitrogen atom to which they are attached, form a 3- to 10-membered heterocyclyl group; or
a pharmaceutically acceptable salt of solvate thereof.

In still a further embodiment are provided compounds of formula (IIIa), (IIIa)

$R^2$ is 5-9 membered heteroaryl, optionally substituted with one or more $R^{11}$ groups;
$R^3$, $R^4$, $R^5$, $R^6$, $R^7$, and $R^8$ are each independently selected from hydrogen, halo, $C_1$-$C_8$ alkyl, $C_2$-$C_8$ alkenyl, $C_2$-$C_8$ alkynyl, $-(CR^9R^{10})_t(C_3$-$C_8$ cycloalkyl), $-(CR^9R^{10})_tOR^{11}$, $-(CR^9R^{10})_tN(R^{11}R^{12})$, $-CN$, $-NO_2$, $-CF_3$, $-C(O)R^9$, and $-C(O)_2R^9$;
each $R^9$ and $R^{10}$ is independently selected from hydrogen, $C_1$-$C_8$ alkyl, $C_3$-$C_8$ cycloalkyl, $C_6$-$C_{10}$ aryl, 3-10 membered heterocyclyl, and 5-9 membered heteroaryl;
each $R^{11}$ and $R^{12}$ is independently selected from hydrogen, $C_1$-$C_8$ alkyl, $C_3$-$C_8$ cycloalkyl, $C_6$-$C_{10}$ aryl, 3-10 membered heterocyclyl, 5-9 membered heteroaryl, $-CN$, halo, $-(CR^{16}R^{17})_tOR^{18}$, and $-(CR^{16}R^{17})_tC(O)R^{18}$, wherein each of said $C_1$-$C_8$ alkyl, $C_3$-$C_8$ cycloalkyl, $C_6$-$C_{10}$ aryl, 3-10 membered heterocyclyl, and 5-9 membered heteroaryl groups is optionally substituted with one more $R^{15}$ groups;
each $R^{15}$ is independently selected from $-(CR^9R^{10})_tR^{16}$, $-(CR^9R^{10})_t(3$-10 membered heterocyclyl), $-(CR^9R^{10})_t(C_3$-$C_8$ cycloalkyl), $-(CR^9R^{10})_t(5$-9 membered heteroaryl), $-(CR^9R^{10})_t(C_6$-$C_{10}$ aryl), $-(CR^9R^{11})_tN(R^{16}R^{17})$, $-(CR^9R^{10})_tNR^{16}C(O)R^{17}$, $-(CR^9R^{10})_tOR^{16}$, $-(CR^9R^{10})_tC(O)R^{16}$, $-(CR^9R^{10})_tC(O)_2R^{16}$, $-(CR^9R^{10})_tC(O)N(R^{16}R^{17})$, $-(CR^9R^{10})_tNR^{16}C(O)OR^{17}$ $-(CR^9R^{10})_tNR^{16}S(O)N(R^{17}R^{18})$, $-(CR^9R^{10})_tNR^{16}S(O)_2N(R^{17}R^{18})$, $-(CR^9R^{10})_tNR^{16}S(O)R^{17}$, $-(CR^9R^{10})_tNR^{16}S(O)_2R^{17}$, $-(CR^9R^{10})_tNR^{16}C(O)N(R^{17}R^{18})$, $-(CR^9R^{10})_t(halo)$, $-(CR^9R^{10})_t-OR^{16}$, and $-(CR^9R^{10})_tS(O)_2R^{16}$, wherein each said 3-10 membered heterocyclyl, $C_3$-$C_8$ cycloalkyl, 5-9 membered heteroaryl, and $C_6$-$C_{10}$ aryl is optionally substituted with one or more $R^{16}$ groups;
each $R^{16}$, $R^{17}$, and $R^{18}$ is independently selected from hydrogen, $C_1$-$C_8$ alkyl, $-(CH_2)_t(C_3$-$C_8$ cycloalkyl), $-(CH_2)_t(C_6$-$C_{10}$ aryl), $-(CH_2)_t(5$-9 membered heteroaryl), $-(CH_2)_t(3$-10 membered heterocyclyl), halo, $-OCH_3$, and $-OH$;
$R^{19}$ and $R^{20}$ are independently selected from hydrogen and $C_1$-$C_8$ alkyl; and
each t is independently selected from 0, 1, 2, 3, and 4; or
a pharmaceutically acceptable salt or solvate thereof.

Still another embodiment provides compounds of formula (IIIb), (IIIb)

$R^2$ is 5-9 membered heteroaryl, optionally substituted with one or more $R^{11}$ groups;
$R^3$, $R^4$, $R^5$, $R^6$, $R^7$, and $R^8$ are each independently selected from hydrogen, halo, $C_1$-$C_8$ alkyl, $C_2$-$C_8$ alkenyl, $C_2$-$C_8$ alkynyl, $-(CR^9R^{10})_t(C_3$-$C_8$ cycloalkyl), $-(CR^9R^{10})_tOR^{11}$, $-(CR^9R^{10})_tN(R^{11}R^{12})$, $-CN$, $-NO_2$, $-CF_3$, $-C(O)R^9$, and $-C(O)_2R^9$;
each $R^9$ and $R^{10}$ is independently selected from hydrogen, $C_1$-$C_8$ alkyl, $C_3$-$C_8$ cycloalkyl, $C_6$-$C_{10}$ aryl, 3-10 membered heterocyclyl, and 5-9 membered heteroaryl;
each $R^{11}$ and $R^{12}$ is independently selected from hydrogen, $C_1$-$C_8$ alkyl, $C_3$-$C_8$ cycloalkyl, $C_6$-$C_{10}$ aryl, 3-10 membered heterocyclyl, 5-9 membered heteroaryl, $-CN$, halo, $-(CR^{16}R^{17})_tOR^{18}$, and $-(CR^{16}R^{17})_tC(O)R^{18}$, wherein each of said $C_1$-$C_8$ alkyl, $C_3$-$C_8$ cycloalkyl, $C_6$-$C_{10}$ aryl, 3-10 membered heterocyclyl, and 5-9 membered heteroaryl groups is optionally substituted with one more $R^{15}$ groups;
each $R^{15}$ is independently selected from $-(CR^9R^{10})_tR^{16}$, $-(CR^9R^{10})_t(3$-10 membered heterocyclyl), $-(CR^9R^{10})_t(C_3$-$C_8$ cycloalkyl), $-(CR^9R^{10})_t(5$-9 membered heteroaryl), $-(CR^9R^{10})_t(C_6$-$C_{10}$ aryl), $-(CR^9R^{11})_tN(R^{16}R^{17})$, $-(CR^9R^{10})_tNR^{16}C(O)R^{17}$, $-(CR^9R^{10})_tOR^{16}$, $-(CR^9R^{10})_tC(O)R^{16}$, $-(CR^9R^{10})_tC(O)_2R^{16}$, $-(CR^9R^{10})_tC(O)N(R^{16}R^{17})$, $-(CR^9R^{10})_tNR^{16}C(O)OR^{17}$ $-(CR^9R^{10})_tNR^{16}S(O)N(R^{17}R^{18})$, $-(CR^9R^{10})_tNR^{16}S(O)_2N(R^{17}R^{18})$, $-(CR^9R^{10})_tNR^{16}S(O)R^{17}$, $-(CR^9R^{10})_tNR^{16}S(O)_2R^{17}$, $-(CR^9R^{10})_tNR^{16}C(O)N(R^{17}R^{18})$, $-(CR^9R^{10})_t(halo)$, $-(CR^9R^{10})_t-OR^{16}$, and $-(CR^9R^{10})_tS(O)_2R^{16}$, wherein each said 3-10 membered heterocyclyl, $C_3$-$C_8$ cycloalkyl, 5-9 membered heteroaryl, and $C_6$-$C_{10}$ aryl is optionally substituted with one or more $R^{16}$ groups;
each $R^{16}$, $R^{17}$, and $R^{18}$ is independently selected from hydrogen, $C_1$-$C_8$ alkyl, $-(CH_2)_t(C_3$-$C_8$ cycloalkyl), $-(CH_2)_t(C_6$-$C_{10}$ aryl), $-(CH_2)_t(5$-9 membered heteroaryl), $-(CH_2)_t(3$-10 membered heterocyclyl), halo, $-OCH_3$, and $-OH$;
$R^{19}$ and $R^{20}$ are independently selected from hydrogen and $C_1$-$C_8$ alkyl; and
each t is independently selected from 0, 1, 2, 3, and 4; or
a pharmaceutically acceptable salt or solvate thereof.

Another embodiment provides compounds of formula (IIIb), wherein $R^{11}$ is 5-9 membered heteroaryl, wherein said heteroaryl is optionally substituted with or more $R^{15}$ groups. In one embodiment, in the compounds of formula (IIIb), $R^{11}$ is 5-membered heteroaryl, wherein said heteroaryl is optionally substituted with one or more $R^{15}$ groups.

A further embodiment provides compounds of formula (IIIb), wherein $R^{11}$ is

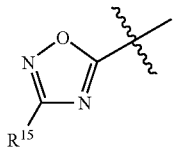

In another embodiment are provided compounds of formula (IVa), (3-10 membered heterocyclyl)-$R^{11}$

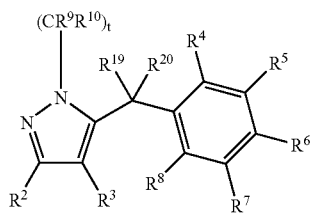

wherein:

$R^2$ is 5-9 membered heteroaryl, optionally substituted with one or more $R^{11}$ groups;

$R^3$, $R^4$, $R^5$, $R^6$, $R^7$, and $R^8$ are each independently selected from hydrogen, halo, $C_1$-$C_8$ alkyl, $C_2$-$C_8$ alkenyl, $C_2$-$C_8$ alkynyl, —$(CR^9R^{10})_t(C_3$-$C_8$ cycloalkyl), —$(CR^9R^{10})_tOR^{11}$, —$(CR^9R^{10})_tN(R^{11}R^{12})$, —CN, —$NO_2$, —$CF_3$, —$C(O)R^9$, and —$C(O)_2R^9$;

each $R^9$ and $R^{10}$ is independently selected from hydrogen, $C_1$-$C_8$ alkyl, $C_3$-$C_8$ cycloalkyl, $C_6$-$C_{10}$ aryl, 3-10 membered heterocyclyl, and 5-9 membered heteroaryl;

each $R^{11}$ and $R^{12}$ is independently selected from hydrogen, $C_1$-$C_8$ alkyl, $C_3$-$C_8$ cycloalkyl, $C_6$-$C_{10}$ aryl, 3-10 membered heterocyclyl, 5-9 membered heteroaryl, —CN, halo, —$(CR^{16}R^{17})_tOR^{18}$, and —$(CR^{16}R^{17})_tC(O)R^{18}$, wherein each of said $C_1$-$C_8$ alkyl, $C_3$-$C_8$ cycloalkyl, $C_6$-$C_{10}$ aryl, 3-10 membered heterocyclyl, and 5-9 membered heteroaryl groups is optionally substituted with one more $R^{15}$ groups;

each $R^{15}$ is independently selected from —$(CR^9R^{10})_tR^{16}$, —$(CR^9R^{10})_t(3$-10 membered heterocyclyl), —$(CR^9R^{10})_t(C_3$-$C_8$ cycloalkyl), —$(CR^9R^{10})_t(5$-9 membered heteroaryl), —$(CR^9R^{10})_t(C_6$-$C_{10}$ aryl), —$(CR^9R^{11})_tN(R^{16}R^{17})$, —$(CR^9R^{10})_tNR^{16}C(O)R^{17}$, —$(CR^9R^{10})_tOR^{16}$, —$(CR^9R^{10})_tC(O)R^{16}$, —$(CR^9R^{10})_tC(O)_2R^{16}$, —$(CR^9R^{10})_tC(O)N(R^{16}R^{17})$, —$(CR^9R^{10})_tNR^{16}C(O)OR^{17}$ —$(CR^9R^{10})_tNR^{16}S(O)N(R^{17}R^{18})$, —$(CR^9R^{10})_tNR^{16}S(O)_2N(R^{17}R^{18})$, —$(CR^9R^{10})_tNR^{16}S(O)R^{17}$, —$(CR^9R^{10})_tNR^{16}S(O)_2R^{17}$, —$(CR^9R^{10})_tNR^{16}C(O)N(R^{17}R^{18})$, —$(CR^9R^{10})_t(halo)$, —$(CR^9R^{10})_t—OR^{16}$, and —$(CR^9R^{10})_tS(O)_2R^{16}$, wherein each said 3-10 membered heterocyclyl, $C_3$-$C_8$ cycloalkyl, 5-9 membered heteroaryl, and $C_6$-$C_{10}$ aryl is optionally substituted with one or more $R^{16}$ groups;

each $R^{16}$, $R^{17}$, and $R^{18}$ is independently selected from hydrogen, $C_1$-$C_8$ alkyl, —$(CH_2)_t(C_3$-$C_8$ cycloalkyl), —$(CH_2)_t(C_6$-$C_{10}$ aryl), —$(CH_2)_t(5$-9 membered heteroaryl), —$(CH_2)_t(3$-10 membered heterocyclyl), halo, —$OCH_3$, and —OH;

$R^{19}$ and $R^{20}$ are independently selected from hydrogen and $C_1$-$C_8$ alkyl; and each t is independently selected from 0, 1, 2, 3, and 4; or a pharmaceutically acceptable salt or solvate thereof.

Yet another embodiment provides compounds of formula (IVb),

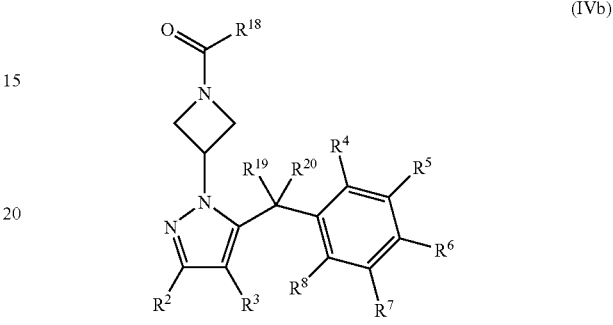

wherein:

$R^2$ is 5-9 membered heteroaryl, optionally substituted with one or more $R^{11}$ groups;

$R^3$, $R^4$, $R^5$, $R^6$, $R^7$, and $R^8$ are each independently selected from hydrogen, halo, $C_1$-$C_8$ alkyl, $C_2$-$C_8$ alkenyl, $C_2$-$C_8$ alkynyl, —$(CR^9R^{10})_t(C_3$-$C_8$ cycloalkyl), —$(CR^9R^{10})_tOR^{11}$, —$(CR^9R^{10})_tN(R^{11}R^{12})$, —CN, —$NO_2$, —$CF_3$, —$C(O)R^9$, and —$C(O)_2R^9$;

each $R^9$ and $R^{10}$ is independently selected from hydrogen, $C_1$-$C_8$ alkyl, $C_3$-$C_8$ cycloalkyl, $C_6$-$C_{10}$ aryl, 3-10 membered heterocyclyl, and 5-9 membered heteroaryl;

each $R^{11}$ and $R^{12}$ is independently selected from hydrogen, $C_1$-$C_8$ alkyl, $C_3$-$C_8$ cycloalkyl, $C_6$-$C_{10}$ aryl, 3-10 membered heterocyclyl, 5-9 membered heteroaryl, —CN, halo, —$(CR^{16}R^{17})_tOR^{18}$, and —$(CR^{16}R^{17})_tC(O)R^{18}$, wherein each of said $C_1$-$C_8$ alkyl, $C_3$-$C_8$ cycloalkyl, $C_6$-$C_{10}$ aryl, 3-10 membered heterocyclyl, and 5-9 membered heteroaryl groups is optionally substituted with one more $R^{15}$ groups;

each $R^{15}$ is independently selected from —$(CR^9R^{10})_tR^{16}$, —$(CR^9R^{10})_t(3$-10 membered heterocyclyl), —$(CR^9R^{10})_t(C_3$-$C_8$ cycloalkyl), —$(CR^9R^{10})_t(5$-9 membered heteroaryl), —$(CR^9R^{10})_t(C_6$-$C_{10}$ aryl), —$(CR^9R^{11})_tN(R^{16}R^{17})$, —$(CR^9R^{10})_tNR^{16}C(O)R^{17}$, —$(CR^9R^{10})_tOR^{16}$, —$(CR^9R^{10})_tC(O)R^{16}$, —$(CR^9R^{10})_tC(O)_2R^{16}$, —$(CR^9R^{10})_tC(O)N(R^{16}R^{17})$, —$(CR^9R^{10})_tNR^{16}C(O)OR^{17}$ —$(CR^9R^{10})_tNR^{16}S(O)N(R^{17}R^{18})$, —$(CR^9R^{10})_tNR^{16}S(O)_2N(R^{17}R^{18})$, —$(CR^9R^{10})_tNR^{16}S(O)R^{17}$, —$(CR^9R^{10})_tNR^{16}S(O)_2R^{17}$, —$(CR^9R^{10})_tNR^{16}C(O)N(R^{17}R^{18})$, —$(CR^9R^{10})_t(halo)$, —$(CR^9R^{10})_t—OR^{16}$, and —$(CR^9R^{10})_tS(O)_2R^{16}$, wherein each said 3-10 membered heterocyclyl, $C_3$-$C_8$ cycloalkyl, 5-9 membered heteroaryl, and $C_6$-$C_{10}$ aryl is optionally substituted with one or more $R^{16}$ groups;

each $R^{16}$, $R^{17}$, and $R^{18}$ is independently selected from hydrogen, $C_1$-$C_8$ alkyl, —$(CH_2)_t(C_3$-$C_8$ cycloalkyl), —$(CH_2)_t(C_6$-$C_{10}$ aryl), —$(CH_2)_t(5$-9 membered heteroaryl), —$(CH_2)_t(3$-10 membered heterocyclyl), halo, —$OCH_3$, and —OH;

$R^{19}$ and $R^{20}$ are independently selected from hydrogen and $C_1$-$C_8$ alkyl; and each t is independently selected from 0, 1, 2, 3, and 4; or a pharmaceutically acceptable salt or solvate thereof.

In another embodiment are provided any compounds of formula (I), (IIa), (IIb), (IIc), (IId), (IIe), (IIf), (IIg), (IIIa), (IIIb), (IVa), or (IVb), wherein $R^2$ is selected from pyridyl, pyrazolyll, pyrimidinyl, and imidazolyl. Further provided are any compounds of (I), (IIa), (IIb), (IIc), (IId), (IIe), (IIf), (IIIa), (IIIb), (IVa), or (IVb), wherein $R^2$ is selected from 2-pyridinyl, 3-pyridinyl, 4-pyridinyl, 4-pyrazolyl, 3-pyrimidinyl, and 4-imidazolyl. In another embodiment are provided any compounds of formula (I), (IIa), (IIb), (IIc), (IId), (IIe), (IIf), (IIg), (IIIa), (IIIb), (IVa), or (IVb), wherein $R^2$ is 4-pyridinyl.

A further embodiment provides any compounds of formula (I), (IIa), (IIb), (IIc), (IId), (IIe), (IIf), (IIg), (IIIa), (IIIb), (IVa), or (IVb), wherein $R^3$ is hydrogen.

In yet another embodiment are provided any compounds of formula (I), (IIa), (IIb), (IIc), (IId), (IIe), (IIf), (IIg), (IIIa), (IIIb), (IVa), or (IVb), wherein $R^{19}$ and $R^{20}$ are hydrogen.

Also provided herein are any compounds of formula (I), (IIa), (IIb), (IIc), (IId), (IIe), (IIf), (IIg), (IIIa), (IIIb), (IVa), or (IVb), wherein $R^4, R^5, R^7$, and $R^8$ are hydrogen and $R^6$ is halo. Also provided are any compounds of formula (I), (IIa), (IIb), (IIc), (IId), (IIe), (IIf), (IIg), (IIIa), (IIIb), (IVa), or (IVb), wherein $R^6$ is chlorine or fluorine. Another embodiment provides any compounds of formula (I), (IIa), (IIb), (IIc), (IId), (IIe), (IIf), (IIg), (IIIa), (IIIb), (IVa), or (IVb), wherein $R^6$ is fluorine.

A further embodiment provides compounds selected from:
4-[5-(4-fluorobenzyl)-1-(2-methoxyethyl)-1H-pyrazol-3-yl]pyridine;
1-[5-(4-fluorobenzyl)-3-pyridin-4-yl-1H-pyrazol-1-yl]propan-2-ol;
N-cyclobutyl-2-[5-(4-fluorobenzyl)-3-pyridin-4-yl-1H-pyrazol-1-yl]acetamide;
N-(1,1-dimethyl-2-morpholin-4-ylethyl)-2-[5-(4-fluorobenzyl)-3-pyridin-4-yl-1H-pyrazol-1-yl]acetamide;
2-[5-(4-fluorobenzyl)-3-pyridin-4-yl-1H-pyrazol-1-yl]-N-(2-morpholin-4-ylethyl)acetamide;
2-(4-{[5-(4-fluorobenzyl)-3-pyridin-4-yl-1H-pyrazol-1-yl]acetyl}piperazin-1-yl)pyrimidine;
N-(2-amino-2-methylpropyl)-2-[5-(4-fluorobenzyl)-3-pyridin-4-yl-1H-pyrazol-1-yl]acetamide;
2-[5-(4-fluorobenzyl)-3-pyridin-4-yl-1H-pyrazol-1-yl]-N-isopropylacetamide;
4-{5-(4-fluorobenzyl)-1-[(3-methyl-1,2,4-oxadiazol-5-yl)methyl]-1H-pyrazol-3-yl}pyridine;
2-[5-(4-fluorobenzyl)-3-pyridin-4-yl-1H-pyrazol-1-yl]-N-(2-hydroxy-2-methylpropyl)acetamide;
1-{[5-(4-fluorobenzyl)-3-pyridin-4-yl-1H-pyrazol-1-yl]acetyl}-4-methylpiperazine;
1-{[5-(4-fluorobenzyl)-3-pyridin-4-yl-1H-pyrazol-1-yl]acetyl}piperazine;
2-[5-(4-fluorobenzyl)-3-pyridin-4-yl-1H-pyrazol-1-yl]-N-[(2R)-2-hydroxypropyl]acetamide;
2-[5-(4-fluorobenzyl)-3-pyridin-4-yl-1H-pyrazol-1-yl]-N-[(2S)-2-hydroxypropyl]acetamide;
(3R)-1-{[5-(4-fluorobenzyl)-3-pyridin-4-yl-1H-pyrazol-1-yl]acetyl}pyrrolidin-3-amine;
4-[5-(4-fluorobenzyl)-1-(1-propionylazetidin-3-yl)-1H-pyrazol-3-yl]pyridine;
4-(3-{3-[5-(4-fluorobenzyl)-3-pyridin-4-yl-1H-pyrazol-1-yl]azetidin-1-yl}-3-oxopropyl)morpholine;
2-({3-[5-(4-fluorobenzyl)-3-pyridin-4-yl-1H-pyrazol-1-yl]azetidin-1-yl}carbonyl)pyrimidine;
5-{[5-(4-fluorobenzyl)-3-pyridin-4-yl-1H-pyrazol-1-yl]methyl}-1,2,4-oxadiazole-3-carboxamide;
4-(5-{[5-(4-fluorobenzyl)-3-pyridin-4-yl-1H-pyrazol-1-yl]methyl}-1,2,4-oxadiazol-3-yl)morpholine;
N-[2-(acetylamino)-2-methylpropyl]-2-[5-(4-fluorobenzyl)-3-pyridin-4-yl-1H-pyrazol-1-yl]acetamide;
(3R)-1-{[5-(4-fluorobenzyl)-3-pyridin-4-yl-1H-pyrazol-1-yl]acetyl}-N,N-dimethylpyrrolidin-3-amine;
(3S)-1-{[5-(4-fluorobenzyl)-3-pyridin-4-yl-1H-pyrazol-1-yl]acetyl}-N,N-dimethylpyrrolidin-3-amine;
1-{[5-(4-fluorobenzyl)-3-pyridin-4-yl-1H-pyrazol-1-yl]acetyl}-N-methylpyrrolidin-3-amine;
[(2R)-1-{[5-(4-fluorobenzyl)-3-pyridin-4-yl-1H-pyrazol-1-yl]acetyl}pyrrolidin-2-yl]methanol;
1-{[5-(4-fluorobenzyl)-3-pyridin-4-yl-1H-pyrazol-1-yl]acetyl}piperidin-3-ol;
[(2S)-1-{[5-(4-fluorobenzyl)-3-pyridin-4-yl-1H-pyrazol-1-yl]acetyl}pyrrolidin-2-yl]methanol;
2-[5-(4-fluorobenzyl)-3-pyridin-4-yl-1H-pyrazol-1-yl]-N-(2-pyrazin-2-ylethyl)acetamide;
N-[(1-ethyl-1H-imidazol-2-yl)methyl]-2-[5-(4-fluorobenzyl)-3-pyridin-4-yl-1H-pyrazol-1-yl]acetamide;
N-[(5-ethyl-1,2,4-oxadiazol-3-yl)methyl]-2-[5-(4-fluorobenzyl)-3-pyridin-4-yl-1H-pyrazol-1-yl]acetamide;
2-[5-(4-fluorobenzyl)-3-pyridin-4-yl-1H-pyrazol-1-yl]-N-[(5-fluoropyrimidin-2-yl)methyl]acetamide;
2-[5-(4-fluorobenzyl)-3-pyridin-4-yl-1H-pyrazol-1-yl]-N-(1-methyl-2-pyrazin-2-ylethyl)acetamide;
2-[5-(4-fluorobenzyl)-3-pyridin-4-yl-1H-pyrazol-1-yl]-N-(trans-4-hydroxycyclohexyl)-N-methylacetamide;
(1R,2S)-2-({[5-(4-fluorobenzyl)-3-pyridin-4-yl-1H-pyrazol-1-yl]acetyl}amino)cyclopentanecarboxamide;
2-[5-(4-fluorobenzyl)-3-pyridin-4-yl-1H-pyrazol-1-yl]-N-[1-(1-methyl-1H-pyrazol-4-yl)ethyl]acetamide;
2-[5-(4-fluorobenzyl)-3-pyridin-4-yl-1H-pyrazol-1-yl]-N-[(3-methylisoxazol-5-yl)methyl]acetamide;
2-[5-(4-fluorobenzyl)-3-pyridin-4-yl-1H-pyrazol-1-yl]-N-[(1-methyl-1H-imidazol-2-yl)methyl]acetamide;
2-[5-(4-fluorobenzyl)-3-pyridin-4-yl-1H-pyrazol-1-yl]-N-[(5-methylisoxazol-3-yl)methyl]acetamide;
N-[(1,5-dimethyl-1H-pyrazol-4-yl)methyl]-2-[5-(4-fluorobenzyl)-3-pyridin-4-yl-1H-pyrazol-1-yl]acetamide;
2-[5-(4-fluorobenzyl)-3-pyridin-4-yl-1H-pyrazol-1-yl]-N-[(3-methyl-1,2,4-oxadiazol-5-yl)methyl]acetamide;
2-[5-(4-fluorobenzyl)-3-pyridin-4-yl-1H-pyrazol-1-yl]-N-[2-(3-methyl-1,2,4-oxadiazol-5-yl)ethyl]acetamide;
1-{[5-(4-fluorobenzyl)-3-pyridin-4-yl-1H-pyrazol-1-yl]acetyl}-4-[methyl(propyl)amino]piperidine-4-carboxamide;
N-(1,1-dioxidotetrahydro-3-thienyl)-2-[5-(4-fluorobenzyl)-3-pyridin-4-yl-1H-pyrazol-1-yl]acetamide;
2-[5-(4-fluorobenzyl)-3-pyridin-4-yl-1H-pyrazol-1-yl]-N-[(1R)-2-hydroxy-1-methylethyl]acetamide;
2-[5-(4-fluorobenzyl)-3-pyridin-4-yl-1H-pyrazol-1-yl]-N-(cis-4-hydroxycyclohexyl)acetamide;
2-[5-(4-fluorobenzyl)-3-pyridin-4-yl-1H-pyrazol-1-yl]-N-(trans-4-hydroxycyclohexyl)acetamide;
4-{5-(4-fluorobenzyl)-1-[2-oxo-2-(4-pyridin-2-ylpiperazin-1-yl)ethyl]-1H-pyrazol-3-yl}pyrimidine;
1-{[5-(4-fluorobenzyl)-3-pyridin-4-yl-1H-pyrazol-1-yl]acetyl}azetidin-3-ol;
N-(1-{[5-(4-fluorobenzyl)-3-pyridin-4-yl-1H-pyrazol-1-yl]acetyl}pyrrolidin-3-yl)-N-methylacetamide;
N-[(3R)-1-{2-[5-(4-fluorobenzyl)-3-pyridin-4-yl-1H-pyrazol-1-yl]acetyl}pyrrolidin-3-yl]acetamide;
N-(1-{2-[5-(4-fluorobenzyl)-3-pyridin-4-yl-1H-pyrazol-1-yl]acetyl}piperidin-4-yl)propanamide;
N-(1-{2-[5-(4-fluorobenzyl)-3-pyridin-4-yl-1H-pyrazol-1-yl]acetyl}piperidin-4-yl)ethanesulfonamide;
4-[(3R)-1-{[5-(4-fluorobenzyl)-3-pyridin-4-yl-1H-pyrazol-1-yl]acetyl}pyrrolidin-3-yl]morpholine;

N-(1-{[5-(4-fluorobenzyl)-3-pyridin-4-yl-1H-pyrazol-1-yl]
acetyl}piperidin-4-yl)-2-methylpropanamide;
methyl(1-{[5-(4-fluorobenzyl)-3-pyridin-4-yl-1H-pyrazol-
1-yl]acetyl}piperidin-4-yl)carbamate;
1-ethyl-3-(1-{[5-(4-fluorobenzyl)-3-pyridin-4-yl-1H-pyra-
zol-1-yl]acetyl}piperidin-4-yl)urea;
1-(1-{[5-(4-fluorobenzyl)-3-pyridin-4-yl-1H-pyrazol-1-yl]
acetyl}piperidin-4-yl)-3-methylurea;
2-(4-{[5-(4-fluorobenzyl)-3-(1H-imidazol-4-yl)-1H-pyra-
zol-1-yl]acetyl}piperazin-1-yl)pyrimidine;
N-(1-{[5-(4-fluorobenzyl)-3-pyridin-4-yl-1H-pyrazol-1-yl]
acetyl}piperidin-4-yl)-N-methylacetamide;
N-(1-{[5-(4-fluorobenzyl)-3-pyridin-4-yl-1H-pyrazol-1-yl]
acetyl}piperidin-4-yl)-N-methylethanesulfonamide;
2-[5-(4-fluorobenzyl)-3-(1H-imidazol-4-yl)-1H-pyrazol-1-
yl]-N-isopropylacetamide;
isopropyl(1-{[5-(4-fluorobenzyl)-3-pyridin-4-yl-1H-pyra-
zol-1-yl]acetyl}piperidin-4-yl)methylcarbamate;
ethyl(1-{[5-(4-fluorobenzyl)-3-pyridin-4-yl-1H-pyrazol-1-
yl]acetyl}piperidin-4-yl)methylcarbamate;
ethyl(1-{[5-(4-fluorobenzyl)-3-pyridin-4-yl-1H-pyrazol-1-
yl]acetyl}piperidin-4-yl)carbamate;
3-ethyl-1-(1-{[5-(4-fluorobenzyl)-3-pyridin-4-yl-1H-pyra-
zol-1-yl]acetyl}piperidin-4-yl)-1-methylurea;
isopropyl(1-{[5-(4-fluorobenzyl)-3-pyridin-4-yl-1H-pyra-
zol-1-yl]acetyl}piperidin-4-yl)carbamate;
1-(1-{[5-(4-fluorobenzyl)-3-pyridin-4-yl-1H-pyrazol-1-yl]
acetyl}piperidin-4-yl)-1,3-dimethylurea;
3-(1-{[5-(4-fluorobenzyl)-3-pyridin-4-yl-1H-pyrazol-1-yl]
acetyl}piperidin-4-yl)-1,3-oxazolidin-2-one;
N-(1-{2-[5-(4-fluorobenzyl)-3-(1H-imidazol-4-yl)-1H-
pyrazol-1-yl]acetyl}piperidin-4-yl)methanesulfonamide;
4-[1-{2-[4-(1,1-dioxidoisothiazolidin-2-yl)piperidin-1-yl]-
2-oxoethyl}-5-(4-fluorobenzyl)-1H-pyrazol-3-yl]pyri-
dine;
4-(1-{[5-(4-fluorobenzyl)-3-pyridin-4-yl-1H-pyrazol-1-yl]
acetyl}azetidin-3-yl)morpholine;
N-(1-{[5-(4-fluorobenzyl)-3-(1H-imidazol-4-yl)-1H-pyra-
zol-1-yl]acetyl}piperidin-4-yl)-N-methylacetamide;
2-[5-(4-fluorobenzyl)-3-(1H-imidazol-4-yl)-1H-pyrazol-1-
yl]-N-(trans-4-hydroxycyclohexyl)-N-methylacetamide;
methyl(1-{[5-(4-fluorobenzyl)-3-pyridin-4-yl-1H-pyrazol-
1-yl]acetyl}azetidin-3-yl)carbamate;
N-(1-{2-[5-(4-fluorobenzyl)-3-pyridin-4-yl-1H-pyrazol-1-
yl]acetyl}azetidin-3-yl)methanesulfonamide;
1-(1-{[5-(4-fluorobenzyl)-3-pyridin-4-yl-1H-pyrazol-1-yl]
acetyl}azetidin-3-yl)-3-methylurea;
N-(1-{2-[5-(4-fluorobenzyl)-3-pyridin-4-yl-1H-pyrazol-1-
yl]acetyl}azetidin-3-yl)acetamide;
methyl(1-{[5-(4-fluorobenzyl)-3-pyridin-4-yl-1H-pyrazol-
1-yl]acetyl}pyrrolidin-3-yl)methylcarbamate;
1-(1-{[5-(4-fluorobenzyl)-3-pyridin-4-yl-1H-pyrazol-1-yl]
acetyl}pyrrolidin-3-yl)-1,3-dimethylurea;
methyl[(3S)-1-{[5-(4-fluorobenzyl)-3-pyridin-4-yl-1H-
pyrazol-1-yl]acetyl}pyrrolidin-3-yl]carbamate;
1-{[5-(4-fluorobenzyl)-3-pyridin-4-yl-1H-pyrazol-1-yl]
acetyl}-4-[2-(methylsulfonyl)ethyl]piperazine;
4-[5-(4-fluorobenzyl)-1-{2-[3-(methylsulfonyl)pyrrolidin-
1-yl]-2-oxoethyl}-1H-pyrazol-3-yl]pyridine; and
N-(1,1-dimethyl-2-morpholin-4-ylethyl)-2-[5-(4-fluoroben-
zyl)-3-pyridazin-4-yl-1H-pyrazol-1-yl]acetamide; or
a pharmaceutically acceptable salt thereof.
In another embodiment provides compounds selected
from:
1-(1-{[5-(4-fluorobenzyl)-3-pyridin-4-yl-1H-pyrazol-1-yl]
acetyl}piperidin-4-yl)pyrrolidin-2-one;
4-(5-(4-fluorobenzyl)-1-{2-[4-(methylsulfonyl)piperidin-1-
yl]-2-oxoethyl}-1H-pyrazol-3-yl)pyridine;
1-{[5-(4-fluorobenzyl)-3-pyridin-4-yl-1H-pyrazol-1-yl]
acetyl}-N-methylpiperidin-4-amine;
1-{[5-(4-fluorobenzyl)-3-pyridin-4-yl-1H-pyrazol-1-yl]
acetyl}piperidin-4-amine;
1-{[5-(4-fluorobenzyl)-3-pyridin-4-yl-1H-pyrazol-1-yl]
acetyl}-N-isopropylpiperidin-4-amine;
N-(1-{[5-(4-fluorobenzyl)-3-pyridin-4-yl-1H-pyrazol-1-yl]
acetyl}piperidin-4-yl)-N-methylpropanamide;
N-(1-{[5-(4-fluorobenzyl)-3-pyridin-4-yl-1H-pyrazol-1-yl]
acetyl}piperidin-4-yl)-N,2-dimethylpropanamide;
N-(1-{[5-(4-fluorobenzyl)-3-pyridin-4-yl-1H-pyrazol-1-yl]
acetyl}piperidin-4-yl)-N-methylcyclobutanecarboxam-
ide;
N-(1-{[5-(4-fluorobenzyl)-3-pyridin-4-yl-1H-pyrazol-1-yl]
acetyl}piperidin-4-yl)-N-methylcyclopropanecarboxam-
ide;
N-(1-{[5-(4-fluorobenzyl)-3-pyridin-4-yl-1H-pyrazol-1-yl]
acetyl}piperidin-4-yl)-N-methylmethanesulfonamide;
methyl(1-{[5-(4-fluorobenzyl)-3-pyridin-4-yl-1H-pyrazol-
1-yl]acetyl}piperidin-4-yl)methylcarbamate;
N-(1-{[5-(4-fluorobenzyl)-3-pyridin-4-yl-1H-pyrazol-1-yl]
acetyl}piperidin-4-yl)-N'-isopropyl-N-methyl urea;
N-(1-{[5-(4-fluorobenzyl)-3-pyridin-4-yl-1H-pyrazol-1-yl]
acetyl}piperidin-4-yl)-N'-isopropylurea;
N-(1-{2-[5-(4-fluorobenzyl)-3-pyridin-4-yl-1H-pyrazol-1-
yl]acetyl}piperidin-4-yl)cyclobutanecarboxamide;
N-(1-{2-[5-(4-fluorobenzyl)-3-pyridin-4-yl-1H-pyrazol-1-
yl]acetyl}piperidin-4-yl)methanesulfonamide;
1-{[5-(4-fluorobenzyl)-3-pyridin-4-yl-1H-pyrazol-1-yl]
acetyl}piperidin-3-ol;
1-{[5-(4-fluorobenzyl)-3-pyridin-4-yl-1H-pyrazol-1-yl]
acetyl}-4-[methyl(propyl)amino]piperidine-4-carboxam-
ide;
N-(1-{2-[5-(4-fluorobenzyl)-3-pyridin-4-yl-1H-pyrazol-1-
yl]acetyl}piperidin-4-yl)propanamide;
N-(1-{2-[5-(4-fluorobenzyl)-3-pyridin-4-yl-1H-pyrazol-1-
yl]acetyl}piperidin-4-yl)ethanesulfonamide;
N-(1-{[5-(4-fluorobenzyl)-3-pyridin-4-yl-1H-pyrazol-1-yl]
acetyl}piperidin-4-yl)-2-methylpropanamide;
methyl(1-{[5-(4-fluorobenzyl)-3-pyridin-4-yl-1H-pyrazol-
1-yl]acetyl}piperidin-4-yl)carbamate;
1-ethyl-3-(1-{[5-(4-fluorobenzyl)-3-pyridin-4-yl-1H-pyra-
zol-1-yl]acetyl}piperidin-4-yl)urea;
1-(1-{[5-(4-fluorobenzyl)-3-pyridin-4-yl-1H-pyrazol-1-yl]
acetyl}piperidin-4-yl)-3-methylurea;
N-(1-{[5-(4-fluorobenzyl)-3-pyridin-4-yl-1H-pyrazol-1-yl]
acetyl}piperidin-4-yl)-N-methylacetamide;
N-(1-{[5-(4-fluorobenzyl)-3-pyridin-4-yl-1H-pyrazol-1-yl]
acetyl}piperidin-4-yl)-N-methylethanesulfonamide;
isopropyl(1-{[5-(4-fluorobenzyl)-3-pyridin-4-yl-1H-pyra-
zol-1-yl]acetyl}piperidin-4-yl)methylcarbamate;
ethyl(1-{[5-(4-fluorobenzyl)-3-pyridin-4-yl-1H-pyrazol-1-
yl]acetyl}piperidin-4-yl)methylcarbamate;
ethyl(1-{[5-(4-fluorobenzyl)-3-pyridin-4-yl-1H-pyrazol-1-
yl]acetyl}piperidin-4-yl)carbamate;
3-ethyl-1-(1-{[5-(4-fluorobenzyl)-3-pyridin-4-yl-1H-pyra-
zol-1-yl]acetyl}piperidin-4-yl)-1-methylurea;
isopropyl(1-{[5-(4-fluorobenzyl)-3-pyridin-4-yl-1H-pyra-
zol-1-yl]acetyl}piperidin-4-yl)carbamate;
1-(1-{[5-(4-fluorobenzyl)-3-pyridin-4-yl-1H-pyrazol-1-yl]
acetyl}piperidin-4-yl)-1,3-dimethylurea;
3-(1-{[5-(4-fluorobenzyl)-3-pyridin-4-yl-1H-pyrazol-1-yl]
acetyl}piperidin-4-yl)-1,3-oxazolidin-2-one;
N-(1-{2-[5-(4-fluorobenzyl)-3-(1H-imidazol-4-yl)-1H-
pyrazol-1-yl]acetyl}piperidin-4-yl)methanesulfonamide;

4-[1-{2-[4-(1,1-dioxidoisothiazolidin-2-yl)piperidin-1-yl]-2-oxoethyl}-5-(4-fluorobenzyl)-1H-pyrazol-3-yl]pyridine; and N-(1-{[5-(4-fluorobenzyl)-3-(1H-imidazol-4-yl)-1H-pyrazol-1-yl]acetyl}piperidin-4-yl)-N-methylacetamide; or a pharmaceutically acceptable salt or solvate thereof.

In another embodiment are provided compounds selected from:

1-acetyl-4-{[5-(4-fluorobenzyl)-3-pyridin-4-yl-1H-pyrazol-1-yl]acetyl}piperazine; 2-[5-(4-fluorobenzyl)-3-pyridin-4-yl-1H-pyrazol-1-yl]-N-(cis-4-hydroxycyclohexyl)-N-methylacetamide; 1'-{[5-(4-fluorobenzyl)-3-pyridin-4-yl-1H-pyrazol-1-yl]acetyl}-1,4'-bipiperidin-2-one; and 4-(1-{[5-(4-fluorobenzyl)-3-pyridin-4-yl-1H-pyrazol-1-yl]acetyl}piperidin-4-yl)morpholine; or a pharmaceutically acceptable salt or solvate thereof.

In yet another embodiment are provided compounds selected from:

N-(1-{[5-(4-fluorobenzyl)-3-pyridin-4-yl-1H-pyrazol-1-yl]acetyl}piperidin-4-yl)-N-methylacetamide; N-(1-{[5-(4-fluorobenzyl)-3-pyridin-4-yl-1H-pyrazol-1-yl]acetyl}piperidin-4-yl)-N-methylpropanamide; N-(1-{[5-(4-fluorobenzyl)-3-pyridin-4-yl-1H-pyrazol-1-yl]acetyl}piperidin-4-yl)-N,2-dimethylpropanamide; 4-[1-{2-[4-(1,1-dioxidoisothiazolidin-2-yl)piperidin-1-yl]-2-oxoethyl}-5-(4-fluorobenzyl)-1H-pyrazol-3-yl]pyridine; and N-(1-{2-[5-(4-fluorobenzyl)-3-pyridin-4-yl-1H-pyrazol-1-yl]acetyl}piperidin-4-yl)methanesulfonamide; or a pharmaceutically acceptable salt or solvate thereof. In still another embodiment is provided the compound N-(1-{2-[5-(4-fluorobenzyl)-3-pyridin-4-yl-1H-pyrazol-1-yl]acetyl}piperidin-4-yl)methanesulfonamide, or a pharmaceutically acceptable salt or solvate thereof.

Further provided are pharmaceutically acceptable salts of the compounds included herein, wherein such salts are selected from mesylate and phosphate, or pharmaceutically acceptable solvates thereof. In another embodiment are provided pharmaceutically acceptable salts of the compounds included herein, wherein such salts are selected from mesylate, or pharmaceutically acceptable solvates thereof. Further provided are pharmaceutically acceptable salts of N-(1-{2-[5-(4-fluorobenzyl)-3-pyridin-4-yl-1H-pyrazol-1-yl]acetyl}piperidin-4-yl)methanesulfonamide, wherein such salts are selected from mesylate and phosphate. In another embodiment is provided a mesylate salt of N-(1-{2-[5-(4-fluorobenzyl)-3-pyridin-4-yl-1H-pyrazol-1-yl]acetyl}piperidin-4-yl)methanesulfonamide. In still another embodiment are provided a hydrate and anhydrous form of the mesylate salt of N-(1-{2-[5-(4-fluorobenzyl)-3-pyridin-4-yl-1H-pyrazol-1-yl]acetyl}piperidin-4-yl)methanesulfonamide. Further included herein is a phosphate salt of N-(1-{2-[5-(4-fluorobenzyl)-3-pyridin-4-yl-1H-pyrazol-1-yl]acetyl}piperidin-4-yl)methanesulfonamide.

Further provided herein are solid forms of any of the compounds included herein, or their pharmaceutically acceptable salts or solvates, including the amorphous forms of such compounds as well as crystalline forms, including all polymorphic forms of such crystalline forms.

In another embodiment is provided a crystalline form of N-(1-{2-[5-(4-fluorobenzyl)-3-pyridin-4-yl-1H-pyrazol-1-yl]acetyl}piperidin-4-yl)methanesulfonamide exhibiting a characteristic peak in the powder x-ray diffraction pattern, expressed in degrees two-theta, of about 20.47. Another embodiment provides a crystalline form of N-(1-{2-[5-(4-fluorobenzyl)-3-pyridin-4-yl-1H-pyrazol-1-yl]acetyl}piperidin-4-yl)methanesulfonamide exhibiting characteristic peaks in the powder x-ray diffraction pattern, expressed in degrees two-theta, of about 20.47 and about 13.80. Further provided is a crystalline form of N-(1-{2-[5-(4-fluorobenzyl)-3-pyridin-4-yl-1H-pyrazol-1-yl]acetyl}piperidin-4-yl)methanesulfonamide exhibiting characteristic peaks in the powder x-ray diffraction pattern, expressed in degrees two-theta, of about 20.47, about 13.80, and about 18.44. Also included herein is a crystalline form of N-(1-{2-[5-(4-fluorobenzyl)-3-pyridin-4-yl-1H-pyrazol-1-yl]acetyl}piperidin-4-yl)methanesulfonamide exhibiting characteristic peaks in the powder x-ray diffraction pattern, expressed in degrees two-theta, of about 20.47, about 13.80, about 18.44, and about 19.32. Further provided is a crystalline form of N-(1-{2-[5-(4-fluorobenzyl)-3-pyridin-4-yl-1H-pyrazol-1-yl]acetyl}piperidin-4-yl)methanesulfonamide exhibiting a characteristic peak in the powder x-ray diffraction pattern, expressed in degrees two-theta, of 20.47±0.05. Another embodiment provides a crystalline form of N-(1-{2-[5-(4-fluorobenzyl)-3-pyridin-4-yl-1H-pyrazol-1-yl]acetyl}piperidin-4-yl)methanesulfonamide exhibiting characteristic peaks in the powder x-ray diffraction pattern, expressed in degrees two-theta, of 20.47±0.05 and 13.80±0.05. Further provided is a crystalline form of N-(1-{2-[5-(4-fluorobenzyl)-3-pyridin-4-yl-1H-pyrazol-1-yl]acetyl}piperidin-4-yl)methanesulfonamide exhibiting characteristic peaks in the powder x-ray diffraction pattern, expressed in degrees two-theta, of 20.47±0.05, 13.80±0.05, and 18.44±0.05. Also included herein is a crystalline form of N-(1-{2-[5-(4-fluorobenzyl)-3-pyridin-4-yl-1H-pyrazol-1-yl]acetyl}piperidin-4-yl)methanesulfonamide exhibiting characteristic peaks in the powder x-ray diffraction pattern, expressed in degrees two-theta, of 20.47±0.05, 13.80±0.05, 18.44±0.05, and 19.32±0.05.

Also provided is provided a crystalline form of N-(1-{2-[5-(4-fluorobenzyl)-3-pyridin-4-yl-1H-pyrazol-1-yl]acetyl}piperidin-4-yl)methanesulfonamide exhibiting a melting temperature of between about 128° C. and about 139° C.

Another embodiment affords a crystalline form of N-(1-{2-[5-(4-fluorobenzyl)-3-pyridin-4-yl-1H-pyrazol-1-yl]acetyl}piperidin-4-yl)methanesulfonamide exhibiting a characteristic peak in the powder x-ray diffraction pattern, expressed in degrees two-theta, of about 17.99. Also provided is a crystalline form of N-(1-{2-[5-(4-fluorobenzyl)-3-pyridin-4-yl-1H-pyrazol-1-yl]acetyl}piperidin-4-yl)methanesulfonamide exhibiting characteristic peaks in the powder x-ray diffraction pattern, expressed in degrees two-theta, of about 17.99 and about 14.36. Further included is a crystalline form of N-(1-{2-[5-(4-fluorobenzyl)-3-pyridin-4-yl-1H-pyrazol-1-yl]acetyl}piperidin-4-yl)methanesulfonamide exhibiting characteristic peaks in the powder x-ray diffraction pattern, expressed in degrees two-theta, of about 17.99, about 14.36, and about 22.27. Another embodiment affords a crystalline form of N-(1-{2-[5-(4-fluorobenzyl)-3-pyridin-4-yl-1H-pyrazol-1-yl]acetyl}piperidin-4-yl)methanesulfonamide exhibiting a characteristic peak in the powder x-ray diffraction pattern, expressed in degrees two-theta, of 17.99±0.05. Also provided is a crystalline form of N-(1-{2-[5-(4-fluorobenzyl)-3-pyridin-4-yl-1H-pyrazol-1-yl]acetyl}piperidin-4-yl)methanesulfonamide exhibiting characteristic peaks in the powder x-ray diffraction pattern, expressed in degrees two-theta, of 17.99±0.05 and 14.36±0.05. Further included is a crystalline form of N-(1-{2-[5-(4-fluorobenzyl)-3-pyridin-4-yl-1H-pyrazol-1-yl]acetyl}piperidin-4-yl)methanesulfonamide exhibiting characteristic peaks in the powder x-ray diffraction pattern, expressed in degrees two-theta, of 17.99±0.05, 14.36±0.05, and 22.27±0.05.

Also provided is provided a crystalline form of N-(1-{2-[5-(4-fluorobenzyl)-3-pyridin-4-yl-1H-pyrazol-1-yl]acetyl}piperidin-4-yl)methanesulfonamide exhibiting a melting temperature of between about 180° C. and about 183° C.

A further embodiment affords a crystalline form of a mesylate salt of N-(1-{2-[5-(4-fluorobenzyl)-3-pyridin-4-yl-1H-pyrazol-1-yl]acetyl}piperidin-4-yl)methanesulfonamide exhibiting a characteristic peak in the powder x-ray diffraction pattern, expressed in degrees two-theta, of about 19.46. Further provided is a crystalline form of a mesylate salt of N-(1-{2-[5-(4-fluorobenzyl)-3-pyridin-4-yl-1H-pyrazol-1-yl]acetyl}piperidin-4-yl)methanesulfonamide exhibiting characteristic peaks in the powder x-ray diffraction pattern, expressed in degrees two-theta, of about 19.46 and about 15.03. Also included is a crystalline form of a mesylate salt of N-(1-{2-[5-(4-fluorobenzyl)-3-pyridin-4-yl-1H-pyrazol-1-yl]acetyl}piperidin-4-yl)methanesulfonamide exhibiting characteristic peaks in the powder x-ray diffraction pattern, expressed in degrees two-theta, of about 19.46, about 15.03, and about 21.70. A further embodiment affords a crystalline form of a mesylate salt of N-(1-{2-[5-(4-fluorobenzyl)-3-pyridin-4-yl-1H-pyrazol-1-yl]acetyl}piperidin-4-yl)methanesulfonamide exhibiting a characteristic peak in the powder x-ray diffraction pattern, expressed in degrees two-theta, of 19.46±0.05. Further provided is a crystalline form of a mesylate salt of N-(1-{2-[5-(4-fluorobenzyl)-3-pyridin-4-yl-1H-pyrazol-1-yl]acetyl}piperidin-4-yl)methanesulfonamide exhibiting characteristic peaks in the powder x-ray diffraction pattern, expressed in degrees two-theta, of 19.46±0.05 and 15.03±0.05. Also included is a crystalline form of a mesylate salt of N-(1-{2-[5-(4-fluorobenzyl)-3-pyridin-4-yl-1H-pyrazol-1-yl]acetyl}piperidin-4-yl)methanesulfonamide exhibiting characteristic peaks in the powder x-ray diffraction pattern, expressed in degrees two-theta, of 19.46±0.05, 15.03±0.05, and 21.70±0.05.

A further embodiment affords a crystalline form of a mesylate salt of N-(1-{2-[5-(4-fluorobenzyl)-3-pyridin-4-yl-1H-pyrazol-1-yl]acetyl}piperidin-4-yl)methanesulfonamide exhibiting a characteristic peak in the powder x-ray diffraction pattern, expressed in degrees two-theta, of about 18.78. Further provided is a crystalline form of a mesylate salt of N-(1-{2-[5-(4-fluorobenzyl)-3-pyridin-4-yl-1H-pyrazol-1-yl]acetyl}piperidin-4-yl)methanesulfonamide exhibiting characteristic peaks in the powder x-ray diffraction pattern, expressed in degrees two-theta, of about 18.78 and about 20.15. Further provided is a crystalline form of a mesylate salt of N-(1-{2-[5-(4-fluorobenzyl)-3-pyridin-4-yl-1H-pyrazol-1-yl]acetyl}piperidin-4-yl)methanesulfonamide exhibiting characteristic peaks in the powder x-ray diffraction pattern, expressed in degrees two-theta, of about 18.78, about 20.15, and about 16.51. A further embodiment affords a crystalline form of a mesylate salt of N-(1-{2-[5-(4-fluorobenzyl)-3-pyridin-4-yl-1H-pyrazol-1-yl]acetyl}piperidin-4-yl)methanesulfonamide exhibiting a characteristic peak in the powder x-ray diffraction pattern, expressed in degrees two-theta, of 18.78±0.05. Further provided is a crystalline form of a mesylate salt of N-(1-{2-[5-(4-fluorobenzyl)-3-pyridin-4-yl-1H-pyrazol-1-yl]acetyl}piperidin-4-yl)methanesulfonamide exhibiting characteristic peaks in the powder x-ray diffraction pattern, expressed in degrees two-theta, of 18.78±0.05 and 20.15±0.05. Further provided is a crystalline form of a mesylate salt of N-(1-{2-[5-(4-fluorobenzyl)-3-pyridin-4-yl-1H-pyrazol-1-yl]acetyl}piperidin-4-yl)methanesulfonamide exhibiting characteristic peaks in the powder x-ray diffraction pattern, expressed in degrees two-theta, of 18.78±0.05, 20.15±0.05, and 16.51±0.05.

Also provided is provided a crystalline form of a mesylate salt of N-(1-{2-[5-(4-fluorobenzyl)-3-pyridin-4-yl-1H-pyrazol-1-yl]acetyl}piperidin-4-yl)methanesulfonamide exhibiting a melting temperature of between about 197° C. and about 201° C.

A further embodiment affords a crystalline form of a phosphate salt of N-(1-{2-[5-(4-fluorobenzyl)-3-pyridin-4-yl-1H-pyrazol-1-yl]acetyl}piperidin-4-yl)methanesulfonamide exhibiting a characteristic peak in the powder x-ray diffraction pattern, expressed in degrees two-theta, of about 20.68. Also included is a crystalline form of a phosphate salt of N-(1-{2-[5-(4-fluorobenzyl)-3-pyridin-4-yl-1H-pyrazol-1-yl]acetyl}piperidin-4-yl)methanesulfonamide exhibiting characteristic peaks in the powder x-ray diffraction pattern, expressed in degrees two-theta, of about 20.68 and about 18.33. Also included is a crystalline form of a phosphate salt of N-(1-{2-[5-(4-fluorobenzyl)-3-pyridin-4-yl-1H-pyrazol-1-yl]acetyl}piperidin-4-yl)methanesulfonamide exhibiting characteristic peaks in the powder x-ray diffraction pattern, expressed in degrees two-theta, of about 20.68, about 18.33, and about 19.43. A further embodiment affords a crystalline form of a phosphate salt of N-(1-{2-[5-(4-fluorobenzyl)-3-pyridin-4-yl-1H-pyrazol-1-yl]acetyl}piperidin-4-yl)methanesulfonamide exhibiting a characteristic peak in the powder x-ray diffraction pattern, expressed in degrees two-theta, of 20.68±0.05. Also included is a crystalline form of a phosphate salt of N-(1-{2-[5-(4-fluorobenzyl)-3-pyridin-4-yl-1H-pyrazol-1-yl]acetyl}piperidin-4-yl)methanesulfonamide exhibiting characteristic peaks in the powder x-ray diffraction pattern, expressed in degrees two-theta, of 20.68 and 18.33±0.05. Also provided is a crystalline form of a phosphate salt of N-(1-{2-[5-(4-fluorobenzyl)-3-pyridin-4-yl-1H-pyrazol-1-yl]acetyl}piperidin-4-yl)methanesulfonamide exhibiting characteristic peaks in the powder x-ray diffraction pattern, expressed in degrees two-theta, of 20.68±0.05, 18.33±0.05, and 19.43±0.05.

Also provided is provided a crystalline form of a phosphate salt of N-(1-{2-[5-(4-fluorobenzyl)-3-pyridin-4-yl-1H-pyrazol-1-yl]acetyl}piperidin-4-yl)methanesulfonamide exhibiting a melting temperature of between about 213° C. and 220° C.

In other embodiments are provided pharmaceutical compositions, comprising an effective amount of at least one of any compound of formula (I), (IIa), (IIb), (IIc), (IId), (IIe), (IIf), (IIg), (IIIa), (IIIIb), (IVa), or (IVb), and a pharmaceutically acceptable carrier.

The present invention also provides pharmaceutical compositions, comprising an effective amount of at least one compound of formula (I), (IIa), (IIb), (IIc), (IId), (IIe), (IIf), (IIg), (IIIa), (IIIIb), (IVa), or (IVb), and a pharmaceutically acceptable carrier. Also provided herein are such pharmaceutical compositions, further comprising an effective amount of at least one additional compound that is metabolized by cytochrome P450. Also provided are such pharmaceutical compositions, wherein said at least one additional compound is 6-cyclopentyl-6-[2-(2,6-diethypyridin-4-yl)ethyl]-3-[(5,7-diemethyl[1,2,4]triazolo[1,5-a]pyrimidin-2-yl)methyl]-4-hydroxy-5,6-dihydro-2H-pyran-2-one, or a pharmaceutically acceptable salt thereof.

Further provided are such pharmaceutical compositions, wherein said at least one additional compound is an anti-HIV compound. Also provided are such pharmaceutical compositions, wherein said at least one additional compound is an HIV protease inhibitor. In yet another embodiment are provided such pharmaceutical compositions, wherein said at least one additional compound is selected from amprenavir, CGP-73547, CGP-61755, DMP-450, nelfinavir, ritonavir, saquinavir, invirase, lopinavir, TMC-126, atazanavir, palinavir, GS-3333, KN I-413, KNI-272, LG-71350, CGP-61755, PD 173606, PD 177298, PD 178390, PD 178392, U-140690, ABT-378, DMP-450, AG-1776, MK-944, VX-478, indinavir, tipranavir, duranavir, DPC-681, DPC-684, (4R)-N-allyl-3-{(2S,3S)-2-hydroxy-3-[(3-hydroxy-2-methylbenzoyl)amino]-4-phenylbutanoyl}-5,5-dimethyl-1,3-thiazolidine-4-carboxamide, and fosamprenavir calcium. Still another embodiment provides such pharmaceutical compositions, wherein said at least one additional compound is selected from amprenavir, nelfinavir, ritonavir, saquinavir, invirase, lopinavir, atazanavir, palinavir, indinavir, tipranavir, duranavir, (4R)-N-allyl-3-{(2S,3S)-2-hydroxy-3-[(3-hydroxy-2-methylbenzoyl)amino]-4-phenylbutanoyl}-5,5-dimethyl-1,3-thiazolidine-4-carboxamide, and fosamprenavir calcium. Another embodiment provides such pharmaceutical compositions, wherein said at least one additional compound is (4R)-N-allyl-3-{(2S,3S)-2-hydroxy-3-[(3-hydroxy-2-methylbenzoyl)amino]-4-phenylbutanoyl}-5,5-dimethyl-1,3-thiazolidine-4-carboxamide.

Yet another embodiment provides such pharmaceutical compositions, comprising at least one compound of formula (I), (IIa), (IIb), (IIc), (IId), (IIe), (IIf), (IIg), (IIIa), (IIIb), (IVa), or (IVb), and an anti-HIV compound as a combined preparation for simultaneous, separate, or sequential administration to an HIV-infected mammal for the treatment of HIV in said mammal.

Still another embodiment affords pharmaceutical compositions, comprising an effective amount of (N-{(1S)-3-[3-isopropyl-5-methyl-4H-1,2,4-triazole-4-yl]-exo-8-azabicyclo[3.2.1]oct-8-yl}-1-phenylpropyl)-4,4-difluorocyclohexanecarboxamide), ethyl 1-endo-{8-[(3S)-3-(acetylamino)-3-(3-fluorophenyl)propyl]-8-azabicyclo[3.2.1]oct-3-yl}-2-methyl-4,5,6,7-tetrahydro-1H-imidazo[4,5-c]pyridine-5-carboxylate, or N-{(1S)-3-[3-endo-(5-Isobutyryl-2-methyl-4,5,6,7-tetrahydro-1H-imidazo[4,5-c]pyridin-1-yl)-8-azabicyclo[3.2.1]oct-8-yl]-1-(3-fluorophenyl)propyl}acetamide), at least one compound of formula (I), (IIa), (IIb), (IIc), (IId), (IIe), (IIf), (IIg), (IIIa), (IIIb), (IVa), or (IVb), and a pharmaceutically acceptable carrier. Still another embodiment provides such pharmaceutical compositions, comprising an effective amount of (N-{(1S)-3-[3-isopropyl-5-methyl-4H-1,2,4-triazole-4-yl]-exo-8-azabicyclo[3.2.1]oct-8-yl}-1-phenylpropyl)-4,4-difluorocyclohexanecarboxamide), at least compound of formula (I), (IIa), (IIb), (IIc), (IId), (IIe), (IIf), (IIg), (IIIa), (IIIb), (IVa), or (IVb), and a pharmaceutically acceptable carrier.

A further embodiment provides methods of inhibiting the metabolism in a mammal of a first compound that is metabolized by cytochrome P450, comprising administering to said mammal said first compound and an effective amount of a second compound, wherein said second compound is selected from those of formula (I), (IIa), (IIb), (IIc), (IId), (IIe), (IIf), (IIg), (IIIa), (IIIb), (IVa), or (IVb). Further provided are such methods, wherein said first compound is an anti-HIV compound. Also provided are such methods, wherein said anti-HIV compound is an HIV protease inhibitor. In yet another embodiment are provided such methods, wherein said HIV protease inhibitor is selected from amprenavir, CGP-73547, CGP-61755, DMP-450, nelfinavir, ritonavir, saquinavir, invirase, lopinavir, TMC-126, atazanavir, palinavir, GS-3333, KN I-413, KNI-272, LG-71350, CGP-61755, PD 173606, PD 177298, PD 178390, PD 178392, U-140690, ABT-378, DMP-450, AG-1776, MK-944, VX-478, indinavir, tipranavir, duranavir, DPC-681, DPC-684, (4R)-N-allyl-3-{(2S,3S)-2-hydroxy-3-[(3-hydroxy-2-methylbenzoyl)amino]-4-phenylbutanoyl}-5,5-dimethyl-1,3-thiazolidine-4-carboxamide, and fosamprenavir calcium. In still a further embodiment are provided such methods, wherein said HIV protease inhibitor is selected from amprenavir, nelfinavir, ritonavir, saquinavir, invirase, lopinavir, atazanavir, palinavir, indinavir, tipranavir, duranavir, (4R)-N-allyl-3-{(2S,3S)-2-hydroxy-3-[(3-hydroxy-2-methylbenzoyl)amino]-4-phenylbutanoyl}-5,5-dimethyl-1,3-thiazolidine-4-carboxamide, and fosamprenavir calcium. Also included are such methods, wherein said HIV protease inhibitor is (4R)-N-allyl-3-{(2S,3S)-2-hydroxy-3-[(3-hydroxy-2-methylbenzoyl)amino]-4-phenylbutanoyl}-5,5-dimethyl-1,3-thiazolidine-4-carboxamide.

Further provided are methods of inhibiting the metabolism in a mammal of a first compound that is metabolized by cytochrome P450, comprising administering to said mammal said first compound and an effective amount of a second compound, wherein said first compound is 6-cyclopentyl-6-[2-(2,6-diethylpyridin-4-yl)ethyl]-3-[(5,7-dimethyl[1,2,4]triazolo[1,5-a]pyrimidin-2-yl)methyl]-4-hydroxy-5,6-dihydro-2H-pyran-2-one, or a pharmaceutically acceptable salt thereof, and the second compound is any one of formula (I), (IIa), (IIb), (IIc), (IId), (IIe), (IIf), (IIg), (IIIa), (IIIb), (IVa), or (IVb).

Further included herein are methods of inhibiting the metabolism in a mammal of a first compound that is metabolized by cytochrome P450, comprising administering to said mammal said first compound and an effective amount of a second compound, wherein said first compound is (N-{(1S)-3-[3-isopropyl-5-methyl-4H-1,2,4-triazole-4-yl]-exo-8-azabicyclo[3.2.1]oct-8-yl}-1-phenylpropyl)-4,4-difluorocyclohexanecarboxamide), ethyl 1-endo-{8-[(3S)-3-(acetylamino)-3-(3-fluoropheny)propyl]-8-azabicyclo[3.2.1]oct-3-yl}-2-methyl-4,5,6,7-tetrahydro-1H-imidazo[4,5-c]pyridine-5-carboxylate, or N-{(1S)-3-[3-endo-(5-Isobutyryl-2-methyl-4,5,6,7-tetrahydro-1H-imidazo[4,5-c]pyridin-1-yl)-8-azabicyclo[3.2.1]oct-8-yl]-1-(3-fluorophenyl)propyl}acetamide), and said second compound is any one of formula (I), (IIa), (IIb), (IIc), (IId), (IIe), (IIf), (IIg), (IIIa), (IIIb), (IVa), or (IVb). Further provided herein are such methods, wherein said first compound is (N-{(1S)-3-[3-isopropyl-5-methyl-4H-1,2,4-triazole-4-yl]-exo-8-azabicyclo[3.2.1]oct-8-yl}-1-phenylpropyl)-4,4-difluorocyclohexanecarboxamide).

In another embodiment are provided methods of improving the pharmacokinetics in a mammal of a first compound, comprising administering to said mammal said first compound and an effective amount of a second compound, wherein said second compound is selected from those of formula (I), (IIa), (IIb), (IIc), (IId), (IIe), (IIf), (IIg), (IIIa), (IIIb), (IVa), or (IVb). Further included herein are such methods, wherein said first compound is 6-cyclopentyl-6-[2-(2,6-diethylpyridin-4-yl)ethyl]-3-[(5,7-dimethyl[1,2,4]triazolo[1,5-a]pyrimidin-2-yl)methyl]-4-hydroxy-5,6-dihydro-2H-pyran-2-one, or a pharmaceutically acceptable salt thereof. A further embodiment provides such methods, wherein said first compound is (N-{(1S)-3-[3-isopropyl-5-methyl-4H-1,2,4-triazole-4-yl]-exo-8-azabicyclo[3.2.1]oct-8-yl}-1-phenylpropyl)-4,4-difluorocyclohexanecarboxamide), ethyl 1-endo-{8-[(3S)-3-(acetylamino)-3-(3-fluorophenyl)propyl]-8-azabicyclo[3.2.1]oct-3-yl}-2-methyl-4,5,6,7-tetrahydro-1H-imidazo[4,5-c]pyridine-5-carboxylate, or N-{(1S)-3-[3-endo-(5-Isobutyryl-2-methyl-4,5,6,7-tetrahydro-1H-imidazo[4,5-c]pyridin-1-yl)-8-azabicyclo[3.2.1]oct-8-yl]-1-(3-fluorophenyl)propyl}acetamide). Also included herein are such methods, wherein said first compound is (N-{(1S)-3-[3-isopropyl-5-methyl-4H-1,2,4-triazole-4-yl]- exo-8-azabicyclo[3.2.1]oct-8-yl}-1-phenylpropyl)-4,4-difluorocyclohexanecarboxamide).

Further included herein are methods of improving the pharmacokinetics in a mammal of a first compound, comprising administering to said mammal said first compound and an effective amount of a second compound, wherein said first compound is an anti-HIV compound and wherein said second compound is selected from those of formula (I), (IIa), (IIb), (IIc), (IId), (IIe), (IIf), (IIg), (IIIa), (IIIb), (IVa), or (IVb). Also included herein are such methods, wherein said anti-HIV compound is an HIV protease inhibitor. In another embodiment are provided such methods, wherein said HIV protease inhibitor is selected from amprenavir, CGP-73547, CGP-61755, DMP-450, nelfinavir, ritonavir, saquinavir, invirase, lopinavir, TMC-126, atazanavir, palinavir, GS-3333, KN I-413, KNI-272, LG-71350, CGP-61755, PD 173606, PD 177298, PD 178390, PD 178392, U-140690, ABT-378, DMP-450, AG-1776, MK-944, VX-478, indinavir, tipranavir, duranavir, DPC-681, DPC-684, (4R)-N-allyl-3-{(2S,3S)-2-hydroxy-3-[(3-hydroxy-2-methylbenzoyl)amino]-4-phenylbutanoyl}-5,5-dimethyl-1,3-thiazolidine-4-carboxamide, and fosamprenavir calcium. Further included are such methods, wherein said HIV protease inhibitor is selected from amprenavir, nelfinavir, ritonavir, saquinavir, invirase, lopinavir, atazanavir, palinavir, indinavir, tipranavir, duranavir, (4R)-N-allyl-3-{(2S,3S)-2-hydroxy-3-[(3-hydroxy-2-methylbenzoyl)amino]-4-phenylbutanoyl}-5,5-dimethyl-1,3-thiazolidine-4-carboxamide, and fosamprenavir calcium. Another embodiment provides such methods, wherein said HIV protease inhibitor is (4R)-N-allyl-3-{(2S,3S)-2-hydroxy-3-[(3-hydroxy-2-methylbenzoyl)amino]-4-phenylbutanoyl}-5,5-dimethyl-1,3-thiazolidine-4-carboxamide. A further embodiment provides any of the above methods, wherein the administration of said first and second compounds occurs sequentially, or wherein the administration of said first and second compounds occurs at the same time.

Another embodiment provides methods of treating HIV in an HIV-infected mammal, comprising administering to said mammal an effective amount of a first compound and an effective amount of a second compound, wherein said first compound is an anti-HIV compound and said second compound is selected from those of formula (I), (IIa), (IIb), (IIc), (IId), (IIe), (IIf), (IIg), (IIIa), (IIIb), (IVa), or (IVb). Another embodiment provides such methods, wherein said first compound is (N-{(1S)-3-[3-isopropyl-5-methyl-4H-1,2,4-triazole-4-yl]-exo-8-azabicyclo[3.2.1]oct-8-yl}-1-phenylpropyl)-4,4-difluorocyclohexanecarboxamide), ethyl 1-endo-{8-[(3S)-3-(acetylamino)-3-(3-fluorophenyl)propyl]-8-azabicyclo[3.2.1]oct-3-yl}-2-methyl-4,5,6,7-tetrahydro-1H-imidazo[4,5-c]pyridine-5-carboxylate, or N-{(1S)-3-[3-endo-(5-Isobutyryl-2-methyl-4,5,6,7-tetrahydro-1H-imidazo[4,5-c]pyridin-1-yl)-8-azabicyclo[3.2.1]oct-8-yl]-1-(3-fluorophenyl)propyl}acetamide). In yet another embodiment are provided such methods, wherein said first compound is (N-{(1S)-3-[3-isopropyl-5-methyl-4H-1,2,4-triazole-4-yl]-exo-8-azabicyclo[3.2.1]oct-8-yl}-1-phenylpropyl)-4,4-difluorocyclohexanecarboxamide). A further embodiment provides such methods, where said first compound is an HIV protease inhibitor. A further embodiment provides such methods, wherein said first compound is selected from amprenavir, CGP-73547, CGP-61755, DMP-450, nelfinavir, ritonavir, saquinavir, invirase, lopinavir, TMC-126, atazanavir, palinavir, GS-3333, KN I-413, KNI-272, LG-71350, CGP-61755, PD 173606, PD 177298, PD 178390, PD 178392, U-140690, ABT-378, DMP-450, AG-1776, MK-944, VX-478, indinavir, tipranavir, duranavir, DPC-681, DPC-684, (4R)-N-allyl-3-{(2S,3S)-2-hydroxy-3-[(3-hydroxy-2-methylbenzoyl)amino]-4-phenylbutanoyl}-5,5-dimethyl-1,3-thiazolidine-4-carboxamide, and fosamprenavir calcium. Yet another embodiment provides such methods, wherein said first compound is selected from amprenavir, nelfinavir, ritonavir, saquinavir, invirase, lopinavir, atazanavir, palinavir, indinavir, tipranavir, duranavir, (4R)-N-allyl-3-{(2S,3S)-2-hydroxy-3-[(3-hydroxy-2-methylbenzoyl)amino]-4-phenylbutanoyl}-5,5-dimethyl-1,3-thiazolidine-4-carboxamide, and fosamprenavir calcium. Additionally provided herein are such methods, wherein said first compound is (4R)-N-allyl-3-{(2S,3S)-2-hydroxy-3-[(3-hydroxy-2-methylbenzoyl)amino]-4-phenylbutanoyl}-5,5-dimethyl-1,3-thiazolidine-4-carboxamide. A further embodiment provides any of the above methods, wherein the administration of said first and second compounds occurs sequentially, or wherein the administration of said first and second compounds occurs at the same time.

Also provided herein are methods of inhibiting HIV replication in an HIV-infected mammal, comprising administering to said mammal an effective amount of a first compound and an effective amount of a second compound, wherein said first compound is an HIV replication-inhibiting compound and said second compound is selected from those of formula (I), (IIa), (IIb), (IIc), (IId), (IIe), (IIf), (IIg), (IIIa), (IIIb), (IVa), or (IVb). Also provided are such methods, wherein said first compound is (N-{(1S)-3-[3-isopropyl-5-methyl-4H-1,2,4-triazole-4-yl]-exo-8-azabicyclo[3.2.1]oct-8-yl}-1-phenylpropyl)-4,4-difluorocyclohexanecarboxamide), ethyl 1-endo-{8-[(3S)-3-(acetylamino)-3-(3-fluorophenyl)propyl]-8-azabicyclo[3.2.1]oct-3-yl}-2-methyl-4,5,6,7-tetrahydro-1H-imidazo[4,5-c]pyridine-5-carboxylate, or N-{(1S)-3-[3-endo-(5-Isobutyryl-2-methyl-4,5,6,7-tetrahydro-1H-imidazo[4,5-c]pyridin-1-yl)-8-azabicyclo[3.2.1]oct-8-yl]-1-(3-fluorophenyl)propyl}acetamide). Further included are such methods wherein said first compound is (N-{(1S)-3-[3-isopropyl-5-methyl-4H-1,2,4-triazole-4-yl]-exo-8-azabicyclo[3.2.1]oct-8-yl}-1-phenylpropyl)-4,4-difluorocyclohexanecarboxamide). In still another embodiment are afforded such methods, where said first compound is an HIV protease inhibitor. Another embodiment affords such methods, wherein said first compound is selected from amprenavir, CGP-73547, CGP-61755, DMP-450, nelfinavir, ritonavir, saquinavir, invirase, lopinavir, TMC-126, atazanavir, palinavir, GS-3333, KN I-413, KNI-272, LG-71350, CGP-61755, PD 173606, PD 177298, PD 178390, PD 178392, U-140690, ABT-378, DMP-450, AG-1776, MK-944, VX-478, indinavir, tipranavir, duranavir, DPC-681, DPC-684, (4R)-N-allyl-3-{(2S,3S)-2-hydroxy-3-[(3-hydroxy-2-methylbenzoyl)amino]-4-phenylbutanoyl}-5,5-dimethyl-1,3-thiazolidine-4-carboxamide, and fosamprenavir calcium. Further included are such methods, wherein said first compound is selected from amprenavir, nelfinavir, ritonavir, saquinavir, invirase, lopinavir, atazanavir, palinavir, indinavir, tipranavir, duranavir, (4R)-N-allyl-3-{(2S,3S)-2-hydroxy-3-[(3-hydroxy-2-methylbenzoyl)amino]-4-phenylbutanoyl}-5,5-dimethyl-1,3-thiazolidine-4-carboxamide, and fosamprenavir calcium. Still another embodiment provides such methods, wherein said first compound is (4R)-N-allyl-3-{(2S,3S)-2-hydroxy-3-[(3-hydroxy-2-methylbenzoyl)amino]-4-phenylbutanoyl}-5,5-dimethyl-1,3-thiazolidine-4-carboxamide. Further included are any such methods, wherein the administration of said first and second compounds occurs sequentially, or wherein the administration of said first and second compounds occurs at the same time.

A further embodiment affords the use of a first compound and a second compound in the preparation of a medicament for the treatment of HIV infection in an HIV-infected mammal, wherein said first compound is selected from those of formula (I), (IIa), (IIb), (IIc), (IId), (IIe), (IIf), (IIg), (IIIa), (IIIb), (IVa), or (IVb), and said second compound is an anti-HIV compound. Another embodiment includes such uses, wherein said second compound is (N-{(1S)-3-[3-isopropyl-5-methyl-4H-1,2,4-triazole-4-yl]-exo-8-azabicyclo[3.2.1]oct-8-yl}-1-phenylpropyl)-4,4-difluorocyclohexanecarboxamide), ethyl 1-endo-{8-[(3S)-3-(acetylamino)-3-(3-fluorophenyl)propyl]-8-azabicyclo[3.2.1]oct-3-yl}-2-methyl-4,5,6,7-tetrahydro-1H-imidazo[4,5-c]pyridine-5-carboxylate, or N-{(1S)-3-[3-endo-(5-Isobutyryl-2-methyl-4,5,6,7-tetrahydro-1H-imidazo[4,5-c]pyridin-1-yl)-8-azabicyclo[3.2.1]oct-8-yl]-1-(3-fluorophenyl)propyl}acetamide). Further included herein are such uses, wherein said second compound is (N-{(1S)-3-[3-isopropyl-5-methyl-4H-1,2,4-triazole-4-yl]-exo-8-azabicyclo[3.2.1]oct-8-yl}-1-phenylpropyl)-4,4-difluorocyclohexanecarboxamide). Additionally included are such uses, wherein said second compound is an HIV protease inhibitor. Also included are such uses, wherein said second compound is selected from amprenavir, CGP-73547, CGP-61755, DMP-450, nelfinavir, ritonavir, saquinavir, invirase, lopinavir, TMC-126, atazanavir, palinavir, GS-3333, KN I-413, KNI-272, LG-71350, CGP-61755, PD 173606, PD 177298, PD 178390, PD 178392, U-140690, ABT-378, DMP-450, AG-1776, MK-944, VX-478, indinavir, tipranavir, duranavir, DPC-681, DPC-684, (4R)-N-allyl-3-{(2S,3S)-2-hydroxy-3-[(3-hydroxy-2-methylbenzoyl)amino]-4-phenylbutanoyl}-5,5-dimethyl-1,3-thiazoldine-4-carboxamide, and fosamprenavir calcium. Further provided herein are such uses, wherein said second compound is selected from amprenavir, nelfinavir, ritonavir, saquinavir, invirase, lopinavir, atazanavir, palinavir, indinavir, tipranavir, duranavir, (4R)-N-allyl-3-{(2S,3S)-2-hydroxy-3-[(3-hydroxy-2-methylbenzoyl)amino]-4-phenylbutanoyl}-5,5-dimethyl-1,3-thiazolidine-4-carboxamide, and fosamprenavir calcium. In yet another embodiment are provided such uses, wherein said second compound is (4R)-N-allyl-3-{(2S,3S)-2-hydroxy-3-[(3-hydroxy-2-methylbenzoyl)amino]-4-phenylbutanoyl}-5,5-dimethyl-1,3-thiazolidine-4-carboxamide.

Another embodiment included herein provides the use of a first compound and a second compound in the preparation of a medicament for improving the pharmacokinetics of said second compound in a mammal, wherein said first compound is selected from those of formula (I), (IIa), (IIb), (IIc), (IId), (IIe), (IIf), (IIg), (IIIa), (IIIb), (IVa), or (IVb), and said second compound is metabolized by cytochrome P450. Further provided herein are such uses, wherein said second compound is (N-{(1S)-3-[3-isopropyl-5-methyl-4H-1,2,4-triazole-4-yl]-exo-8-azabicyclo[3.2.1]oct-8-yl}-1-phenylpropyl)-4,4-difluorocyclohexanecarboxamide), ethyl 1-endo-{8-[(3S)-3-(acetylamino)-3-(3-fluorophenyl)propyl]-8-azabicyclo[3.2.1]oct-3-yl}-2-methyl-4,5,6,7-tetrahydro-1H-imidazo[4,5-c]pyridine-5-carboxylate, or N-{(1S)-3-[3-endo-(5-Isobutyryl-2-methyl-4,5,6,7-tetrahydro-1H-imidazo[4,5-c]pyridin-1-yl)-8-azabicyclo[3.2.1]oct-8-yl]-1-(3-fluorophenyl)propyl}acetamide). A further embodiment provides such uses, wherein said second compound is (N-{(1S)-3-[3-isopropyl-5-methyl-4H-1,2,4-triazole-4-yl]-exo-8-azabicyclo[3.2.1]oct-8-yl}-1-phenylpropyl)-4,4-difluorocyclohexanecarboxamide). Another embodiment affords such uses, wherein said second compound is an anti-HIV compound. Still further are included such uses wherein the second compound is an HIV protease inhibitor. Further provided are such uses, wherein said second compound is selected from amprenavir, CGP-73547, CGP-61755, DMP-450, nelfinavir, ritonavir, saquinavir, invirase, lopinavir, TMC-126, atazanavir, palinavir, GS-3333, KN I-413, KNI-272, LG-71350, CGP-61755, PD 173606, PD 177298, PD 178390, PD 178392, U-140690, ABT-378, DMP-450, AG-1776, MK-944, VX-478, indinavir, tipranavir, duranavir, DPC-681, DPC-684, (4R)-N-allyl-3-{(2S,3S)-2-hydroxy-3-[(3-hydroxy-2-methylbenzoyl)amino]-4-phenylbutanoyl}-5,5-dimethyl-1,3-thiazolidine-4-carboxamide, and fosamprenavir calcium. Still further are provided such uses, wherein said second compound is selected from amprenavir, nelfinavir, ritonavir, saquinavir, invirase, lopinavir, atazanavir, palinavir, indinavir, tipranavir, duranavir, (4R)-N-allyl-3-{(2S,3S)-2-hydroxy-3-[(3-hydroxy-2-methylbenzoyl)amino]-4-phenylbutanoyl}-5,5-dimethyl-1,3-thiazolidine-4-carboxamide, and fosamprenavir calcium. A further embodiment provides such uses, wherein said second compound is (4R)-N-allyl-3-{(2S,3S)-2-hydroxy-3-[(3-hydroxy-2-methylbenzoyl)amino]-4-phenylbutanoyl}-5,5-dimethyl-1,3-thiazolidine-4-carboxamide.

Further provided are any of the medicaments described herein, wherein said medicament is for simultaneous, separate, or sequential administration to an HIV-infected mammal for the treatment of HIV.

In another embodiment are provided any of the above-described methods or uses wherein the cytochrome P450 enzyme is the 3A4 isoform.

As used herein, the terms "comprising" and "including" are used in their open, non-limiting sense.

As used herein, the term "HIV" means Human Immunodeficiency Virus. The term "HIV integrase," as used herein, means the Human Immunodeficiency Virus integrase enzyme.

The term "$C_1$-$C_8$ alkyl," as used herein, means saturated monovalent hydrocarbon radicals having straight or branched moieties and containing from 1 to 8 carbon atoms. Examples of such groups include, but are not limited to, methyl, ethyl, propyl, iso-propyl, n-butyl, iso-butyl, and tert-butyl.

The term "$C_2$-$C_8$ alkenyl", as used herein, unless otherwise indicated, includes alkyl moieties having at least one carbon-carbon double bond wherein alkyl is as defined above and including E and Z isomers of said alkenyl moiety, and having from 2 to 8 carbon atoms.

The term "$C_2$-$C_8$ alkynyl", as used herein, unless otherwise indicated, includes alkyl moieties having at least one carbon-carbon triple bond wherein alkyl is as defined above, and containing from 2-8 carbon atoms.

The term "$C_3$-$C_8$ cycloalkyl" means a saturated, monocyclic, fused, or spiro, polycyclic ring structure having a total of from 3 to 8 carbon ring atoms. Examples of such groups include, but are not limited to, cyclopropyl, cyclobutyl, cyclopentyl, cyclopentenyl, cyclohexyl, cycloheptyl, and adamantyl.

The term "$C_6$-$C_{10}$ aryl", as used herein, means a group derived from an aromatic hydrocarbon containing from 6 to 10 carbon atoms. Examples of such groups include, but are not limited to, phenyl or naphthyl. The terms "Ph" and "phenyl," as used herein, mean a —$C_6H_5$ group. The term "benzyl," as used herein, means a —$CH_2C_6H_5$ group.

The term "3-10 membered heterocyclyl" as used herein, means a non-aromatic, monocyclic, bicyclic, tricyclic, or tetracyclic group having a total of from 3 to 10 atoms in its ring system, and containing from 1 to 9 carbon atoms and from one to four heteroatoms each independently selected from O, S and N, and with the proviso that the ring of said group does not contain two adjacent O atoms or two adjacent S atoms. Furthermore, such 3-10 membered heterocyclyl groups may comprise polycyclic, spiro ring systems. Also, such groups may be optionally benzofused. Additionally, such 3-10 membered heterocyclyl groups may contain an oxo substituent at any available atom that will result in a stable compound. For example, such a group may contain an oxo atom at an available carbon or nitrogen atom. Such a group may contain more than one oxo substituent if chemically feasible. In addition, it is to be understood that when such a $C_2$-$C_{10}$ heterocyclyl group contains a sulfur atom, said sulfur atom may be oxidized with one or two oxygen atoms to afford either a sulfoxide or sulfone. An example of a 4-membered heterocyclic group is azetidinyl (derived from azetidine). An example of a 5-membered heterocyclic group is thiazolyl and an example of a 10 membered heterocyclic group is quinolinyl. Further examples of such $C_2$-$C_{10}$ heterocyclyl groups include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl.

The term "5-9 membered heteroaryl," as used herein, means an aromatic heterocyclic group having a total of from 5 to 9 atoms in its ring, and containing from 1 to 8 carbon atoms and from one to four heteroatoms each independently selected from O, S and N, and with the proviso that the ring of said group does not contain two adjacent O atoms or two adjacent S atoms. The heterocyclic groups include benzo-fused ring systems. Examples of aromatic heterocyclic groups are pyridinyl, imidazolyl, 1,2,4-oxadiazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The heteroaryl groups may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached).

The terms "halogen" and "halo," as used herein, mean fluorine, chlorine, bromine or iodine.

The term "substituted," means that the specified group or moiety bears one or more substituents. The term "unsubstituted," means that the specified group bears no substituents. The term "optionally substituted" means that the specified group is unsubstituted or substituted by one or more substituents. It is to be understood that in the compounds of the present invention when a group is said to be "unsubstituted," or is "substituted" with fewer groups than would fill the valencies of all the atoms in the compound, the remaining valencies on such a group are filled by hydrogen. For example, if a $C_6$ aryl group, also called "phenyl" herein, is substituted with one additional substituent, one of ordinary skill in the art would understand that such a group has 4 open positions left on carbon atoms of the $C_6$ aryl ring (6 initial positions, minus one to which the remainder of the compound of the present invention is bonded, minus an additional substituent, to leave 4). In such cases, the remaining 4 carbon atoms are each bound to one hydrogen atom to fill their valencies. Similarly, if a $C_6$ aryl group in the present compounds is said to be "disubstituted," one of ordinary skill in the art would understand it to mean that the $C_6$ aryl has 3 carbon atoms remaining that are unsubstituted. Those three unsubstituted carbon atoms are each bound to one hydrogen atom to fill their valencies.

The term "solvate," as used herein, means a pharmaceutically acceptable solvate form of a compound of the present invention that retains the biological effectiveness of such compound. Examples of solvates include, but are not limited to, compounds of the invention in combination with water, isopropanol, ethanol, methanol, dimethylsulfoxide (DMSO), ethyl acetate, acetic acid, ethanolamine, or mixtures thereof. It is specifically contemplated that in the present invention one solvent molecule can be associated with one molecule of the compounds of the present invention, such as a hydrate. Furthermore, it is specifically contemplated that in the present invention, more than one solvent molecule may be associated with one molecule of the compounds of the present invention, such as a dihydrate. Additionally, it is specifically contemplated that in the present invention less than one solvent molecule may be associated with one molecule of the compounds of the present invention, such as a hemihydrate. Furthermore, solvates of the present invention are contemplated as solvates of compounds of the present invention that retain the biological effectiveness of the non-hydrate form of the compounds.

The term "pharmaceutically acceptable salt," as used herein, means a salt of a compound of the present invention that retains the biological effectiveness of the free acids and bases of the specified derivative and that is not biologically or otherwise undesirable.

The terms "cytochrome P450-inhibiting amount" and "cytochrome P450 enzyme activity-inhibiting amount," as used herein, refer to an amount of a compound required to decrease the activity of cytochrome P450 enzymes or a particular cytochrome P450 enzyme isoform in the presence of such compound. Whether a particular compound of decreases cytochrome P450 enzyme activity and the amount of such a compound required to do so, can be determined by methods known to those of ordinary skill in the art and the methods described herein.

The terms "inhibiting" or "inhibition," as used herein, refer to decreasing the activity of a cytochrome P450 enzyme or enzymes using an agent that is capable of decreasing such activity either in vitro or in vivo after administration to a mammal, such as a human. Such inhibition may take place by the compound binding directly to the cytochrome P450 enzyme or enzymes. In addition, the activity of such cytochrome P450 enzymes may be decreased in the presence of such a compound when such direct binding between the enzyme and the compound does not take place. Furthermore, such inhibition may be competitive, non-competitive, or uncompetitive, as described in T. F. Woolf, *Handbook of Drug Metabolism*, Marcel Dekker, Inc., New York, 1999. Such inhibition may be determined using in vitro or in vivo systems, or a combination of both, using methods known to those of ordinary skill in the art.

As used herein, the term "bioavailability" refers to the systemic availability of a given amount of a chemical compound administered to a mammal. Bioavailability can be assessed by measuring the area under the curve (AUC) or the maximum serum or plasma concentration ($C_{max}$) of the unchanged form of a compound following administration of the compound to a mammal. AUC is a determination of the Area Under the Curve plotting the serum or plasma concentration of a compound along the ordinate (Y-axis) against time along the abscissa (X-axis). Generally, the AUC for a particular compound can be calculated using methods known to those of ordinary skill in the art and as described in G. S. Banker, *Modern Pharmaceutics, Drugs and the Pharmaceutical Sciences*, v. 72, Marcel Dekker, New York, Inc., 1996. The $C_{max}$ value is defined as the maximum concentration of the compound achieved in the serum or plasma of a mammal following administration of the compound to the mammal. The $C_{max}$ value of a particular compound can be measured using methods known to those of ordinary skill in the art. The phrase "increasing bioavailability," as used herein means that the systemic availability of a first compound, measured as AUC or $C_{max}$, in a mammal is greater when co-administered with a compound of the present invention than when such co-administration does not take place.

The term "improving the pharmacokinetics in a mammal" of a compound, as used herein, means increasing the overall exposure of a mammal to a particular compound. The term "exposure," as used herein, refers to the concentration of a particular compound in the plasma of a mammal as measured over a period of time. An increase of the exposure of a mammal to a particular compound can be measured by first administering the compound to a mammal in an appropriate form and in the absence of the administration of a compound of the invention, including those of formula (I), (IIa), (IIb), (IIc), (IId), (IIe), (IIf), (IIg), (IIIa), (IIIb), (IVa), or (IVb), withdrawing plasma samples at predetermined times, and measuring the amount of the compound in the plasma using an appropriate analytical technique, such as liquid chromatography or liquid chromatography/mass spectroscopy. The same study is then repeated, except that a compound of the present invention, including those of formula (I), (IIa), (IIb), (IIc), (IId), (IIe), (IIf), (IIg), (IIIa), (IIIb), (IVa), or (IVb), is co-administered with the particular compound. The amount of the particular compound present in the plasma at a certain time is determined and the concentration and time data from all the samples are plotted to afford a curve. The area under this curve is calculated and affords the exposure of the mammal to the particular compound. The difference in the areas under the curve in the presence and absence of a compound of the present invention, including those of formula (I), (IIa), (IIb), (IIc), (IId), (IIe), (IIf), (IIg), (IIIa), (IIIb), (IVa), or (IVb), affords a measure of the increase of the exposure to the particular compound in the plasma of the mammal. The terms "exposure," "area under the curve," and "area under the concentration/time curve" are intended to have the same meaning and may be used interchangeably throughout.

The terms "administration", "administering", "dosage," and "dosing," as used herein refer to the delivery of a compound, or a pharmaceutically acceptable salt or solvate thereof, or of a pharmaceutical composition containing the compound, or a pharmaceutically acceptable salt or solvate thereof, to a mammal such that the compound is absorbed into the serum or plasma of the mammal.

The terms "co-administration" or "co-administering," as used herein, refer to the administration of a combination of a first compound and a compound of the present invention, or a pharmaceutically acceptable salt or solvate thereof. Such co-administration can be performed such that the first compound and the compound of the present invention are part of the same composition or part of the same unitary dosage form. Co-administration also includes administering a first compound and a compound of the present invention separately, but as part of the same therapeutic regimen. The two components, if administered separately, need not necessarily be administered at essentially the same time, although they can be if so desired. Thus co-administration includes, for example, administering a first compound and a compound of the present invention as separate dosages or dosage forms, but at the same time. Co-administration also includes separate administration at different times and in any order.

The term "pharmaceutically acceptable formulation," as used herein, means a combination of a compound of the invention, or a pharmaceutically acceptable salt or solvate thereof, and a carrier, diluent, and/or excipients that are compatible with a compound of the present invention, and is not deleterious to the recipient thereof. Pharmaceutical formulations can be prepared by procedures known to those of ordinary skill in the art. For example, the compounds of the present invention can be formulated with common excipients, diluents, or carriers, and formed into tablets, capsules, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as povidone, sodium starch glycolate, sodium carboxymethylcellulose, agar, calcium carbonate, and sodium bicarbonate; agents for retarding dissolution such as paraffin; resorption accelerators such as quaternary ammonium compounds; surfacelactive agents such as cetyl alcohol, glycerol monostearate; adsorptive carriers such as kaolin and bentonite; and lubricants such as talc, calcium and magnesium stearate and solid polyethylene glycols. Final pharmaceutical forms may be pills, tablets, powders, lozenges, saches, cachets, or sterile packaged powders, and the like, depending on the type of excipient used. Additionally, it is specifically contemplated that pharmaceutically acceptable formulations of the present invention can contain more than one active ingredient. For example, such formulations may contain more than one compound according to the present invention. Alternatively, such formulations may contain one or more compounds of the present invention and one or more additional anti-HIV agents.

The term "inhibiting HIV replication" means inhibiting human immunodeficiency virus (HIV) replication in a cell. Such a cell may be present in vitro, or it may be present in vivo, such as in a mammal, such as a human. Such inhibition may be accomplished by administering a compound of the present invention, or a pharmaceutically acceptable salt or solvate thereof, to the cell, such as in a mammal, in an HIV-inhibiting amount. The quantification of inhibition of HIV replication in a cell, such as in a mammal, can be measured using methods known to those of ordinary skill in the art. For example, an amount of a compound of the invention may be administered to a mammal, either alone or as part of a pharmaceutically acceptable formulation. Blood samples may then be withdrawn from the mammal and the amount of HIV virus in the sample may be quantified using methods known to those of ordinary skill in the art. A reduction in the amount of HIV virus in the sample compared to the amount found in the blood before administration of a compound of the invention would represent inhibition of the replication of HIV virus in the mammal. The administration of a compound of the invention to the cell, such as in a mammal, may be in the form of single dose or a series of doses. In the case of more than one dose, the doses may be administered in one day or they may be administered over more than one day.

The terms "anti-HIV compound" and "HIV-inhibiting agent," as used herein, mean a compound or combination of compounds capable of inhibiting the replication of HIV in a cell, such as a cell in a mammal. Such compounds may inhibit the replication of HIV through any mechanism known to those of ordinary skill in the art.

The terms "human immunodeficiency virus-inhibiting amount," "HIV-inhibiting amount," and "HIV replication-inhibiting amount" as used herein, refer to the amount of an anti-HIV compound, or a pharmaceutically acceptable salt of solvate thereof, required to inhibit replication of the human immunodeficiency virus (HIV) in vivo, such as in a mammal, or in vitro. The amount of such compounds required to cause such inhibition can be determined without undue experimentation using methods described herein and those known to those of ordinary skill in the art.

The terms "therapeutically effective amount" or "effective amount," as used herein, means an amount of a compound of the present invention, or a pharmaceutically acceptable salt or solvate thereof, that, when administered to a mammal in need of such treatment, is sufficient to effect treatment, as defined herein. Thus, a therapeutically effective amount or effective amount of a compound of the present invention, or a pharmaceutically acceptable salt or solvate thereof, is a quantity sufficient to modulate or inhibit the activity of a particular enzyme target or biological process. In particular, the compounds of the present invention, including those of formula (I), (IIa), (IIb), (IIc), (IId), (IIe), (IIf), (IIg), (IIIa), (IIIb), (IVa), or (IVb), are intended to modulate or inhibit the activity of a cytochrome P450 enzyme or enzyme, or a particular P450 enzyme isoform, such as the 3A4 isoform, such that the metabolism of an additional compound by such cytochrome P450 enzyme or enzymes is reduced. When the compounds of the present invention, including those of formula (I), (IIa), (IIb), (IIc), (IId), (IIe), (IIf), (IIg), (IIIa), (IIIb), (IVa), or (IVb), are administered to a mammal in addition to a second compound that is useful for the treatment of a particular disease, it is contemplated that the compounds of the present invention will reduce the metabolism of the second compound such that the exposure of the mammal to the second compound is increased. Increasing the exposure of the mammal to such second compound results in improved treatment of a particular disease or condition that the second compound is intended to treat.

The terms "treat", "treating", and "treatment" refer to any treatment of any disease or condition in a mammal, particularly a human, and include: (i) preventing the disease or condition from occurring in a subject which may be predisposed to the condition, such that the treatment constitutes prophylactic treatment for the pathologic condition; (ii) modulating or inhibiting the disease or condition, i.e., arresting its development; (iii) relieving the disease or condition, i.e., causing regression of the disease or condition; or (iv) relieving and/or alleviating the disease or condition or the symptoms resulting from the disease or condition, e.g., relieving an inflammatory response without addressing the underlying disease or condition.

The terms "resistant," "resistance," and "resistant HIV," as used herein, refer to HIV virus demonstrating a reduction in sensitivity to a particular drug. A mammal infected with HIV that is resistant to a particular anti-HIV agent or combination of agents usually manifests an increase in HIV viral load despite continued administration of the agent or agents. Resistance may be either genotypic, meaning that a mutation in the HIV genetic make-up has occurred, or phenotypic, meaning that resistance is discovered by successfully growing laboratory cultures of HIV virus in the presence of an anti-HIV agent or a combination of such agents.

The terms "protease inhibitor" and "HIV protease inhibitor," as used herein, refer to compounds or combinations of compounds that interfere with the proper functioning of the HIV protease enzyme that is responsible for cleaving long strands of viral protein into the separate proteins making up the viral core.

The terms "viral load" and "HIV viral load," as used herein, mean the amount of HIV in the circulating blood of a mammal, such as a human. The amount of HIV virus in the blood of mammal can be determined by measuring the quantity of HIV RNA in the blood using methods known to those of ordinary skill in the art.

The term, "compound of the present invention" refers to any of the above-mentioned compounds, as well as those in the Examples that follow, and include those generically described or those described as species. The term also refers to pharmaceutically acceptable salts or solvates of these compounds.

The term "crystalline," as used herein, means a particular solid form of a compound of the invention that exhibits long-range order in three dimensions. Material that is crystalline may be characterized by techniques known in the art such as powder x-ray diffraction (PXRD) crystallography, solid state NMR, or thermal techniques such as differential scanning calorimetry (DSC).

The term "amorphous," as used herein, means a particular solid form of a compound of the invention that has essentially no order in three dimensions. The term "amorphous" is intended to include not only material which has essentially no order, but also material which may have some small degree of order, but the order is in less than three dimensions and/or is only over short distances. Amorphous material may be characterized by techniques known in the art such as powder x-ray diffraction (PXRD) crystallography, solid state NMR, or thermal techniques such as differential scanning calorimetry (DSC).

DETAILED DESCRIPTION

Figure 1:
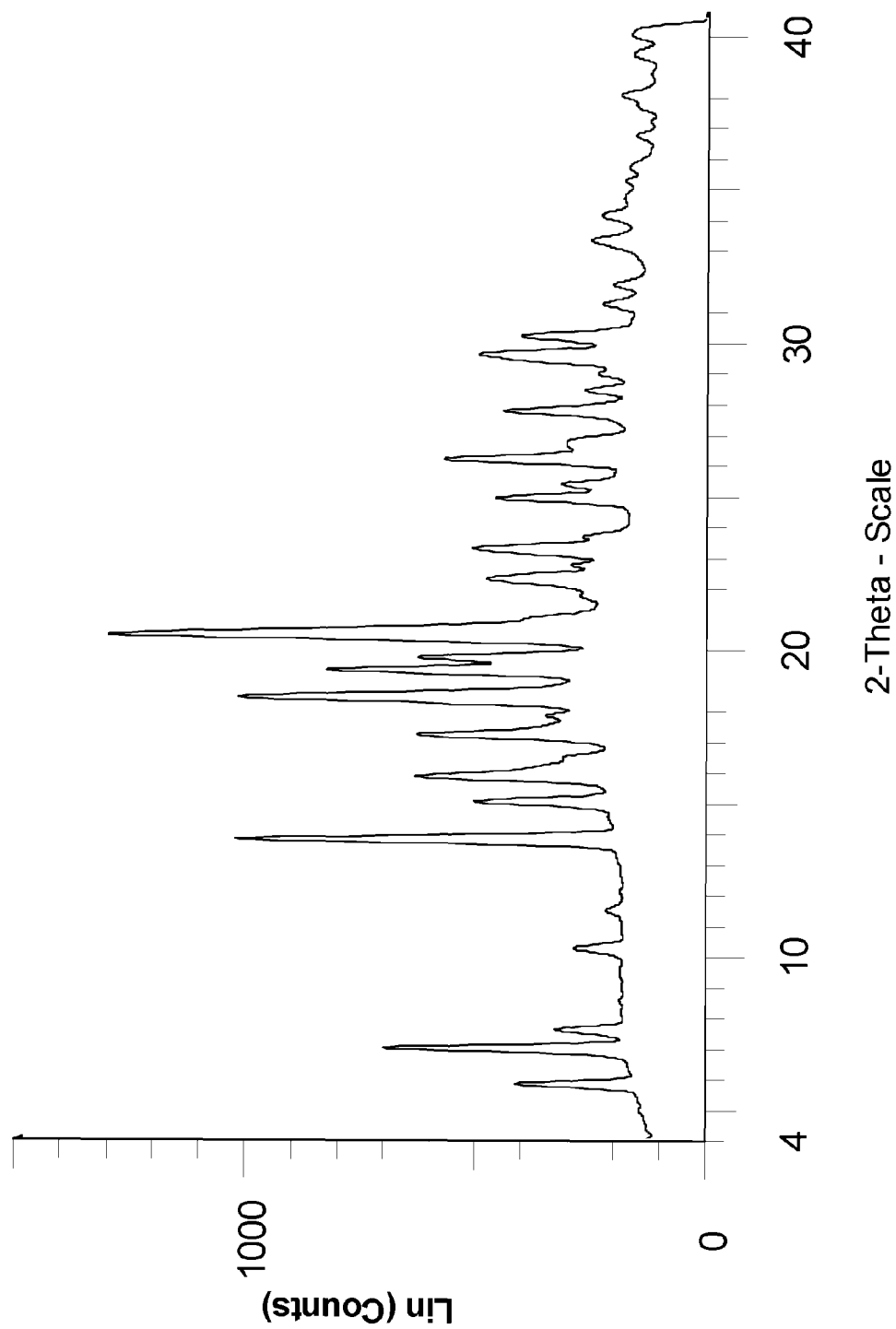
FIG. 1 is an X-ray diffraction pattern of a crystalline form of N-(1-{2-[5-(4-fluorobenzyl)-3-pyridin-4-yl-1H-pyrazol-1-yl]acetyl}piperidin-4-yl)methanesulfonamide from Example 19.
Figure 2:
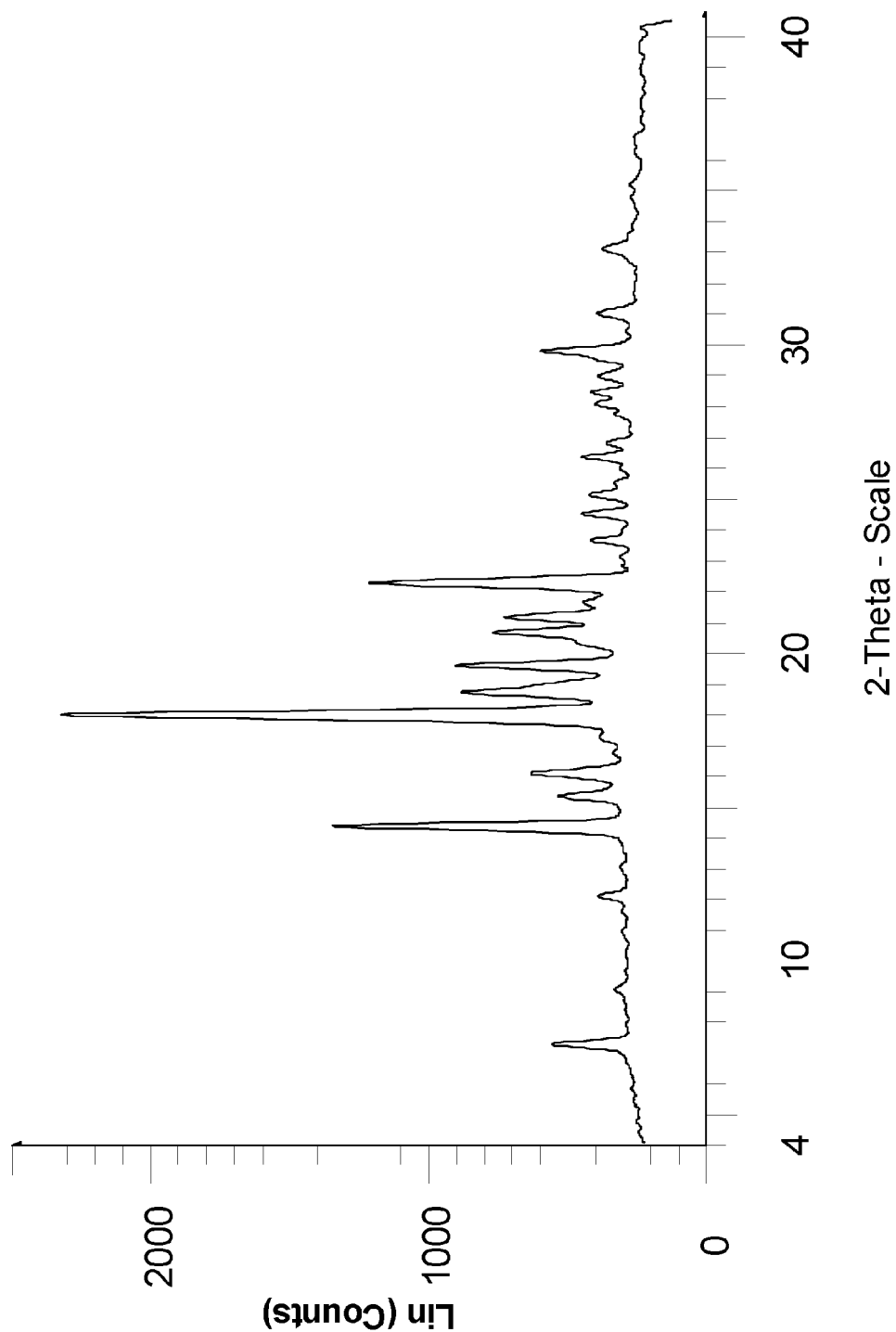
FIG. 2 is an X-ray diffraction pattern of a crystalline form of N-(1-{2-[5-(4-fluorobenzyl)-3-pyridin-4-yl-1H-pyrazol-1-yl]acetyl}piperidin-4-yl)methanesulfonamide from Example 141.
Figure 3:
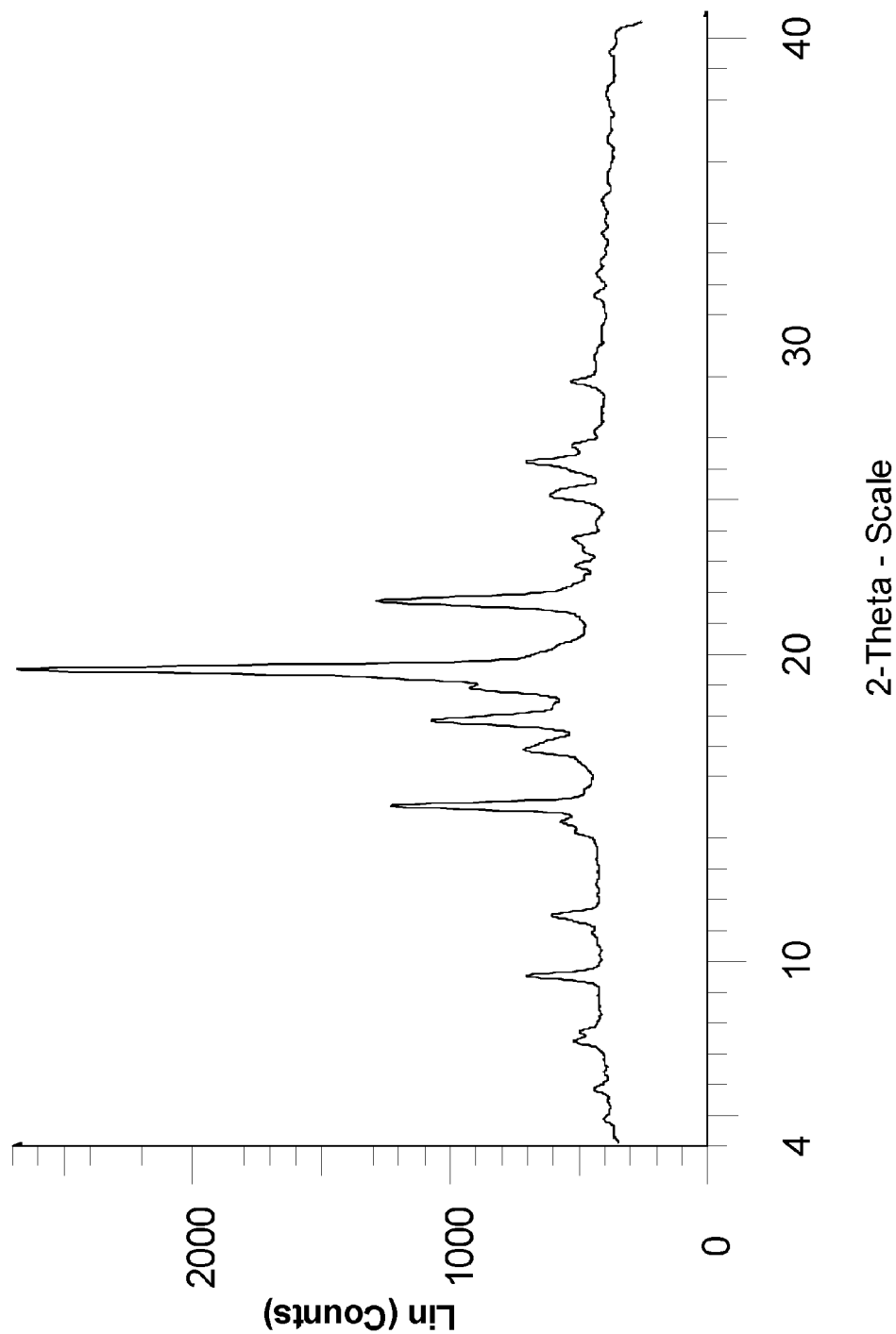
FIG. 3 is an X-ray diffraction pattern of a crystalline form of a hydrate of a mesylate salt of N-(1-{2-[5-(4-fluorobenzyl)-3-pyridin-4-yl-1H-pyrazol-1-yl]acetyl}piperidin-4-yl)methanesulfonamide from Example 142.
Figure 4:
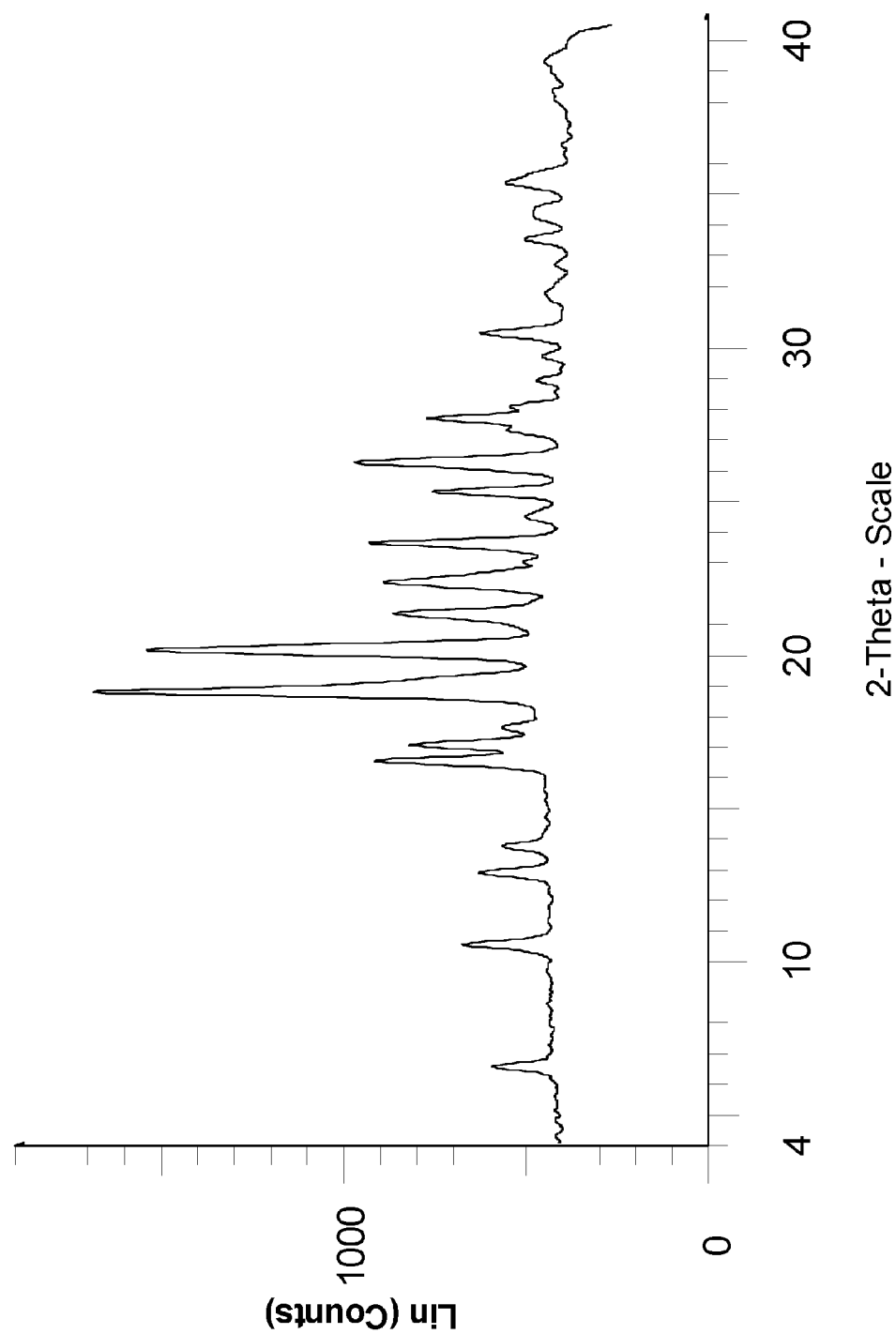
FIG. 4 is an X-ray diffraction pattern of a crystalline form of an anhydrous form of a mesylate salt of N-(1-{2-[5-(4-fluorobenzyl)-3-pyridin-4-yl-1H-pyrazol-1-yl]acetyl}piperidin-4-yl)methanesulfonamide from Example 143.
Figure 5:
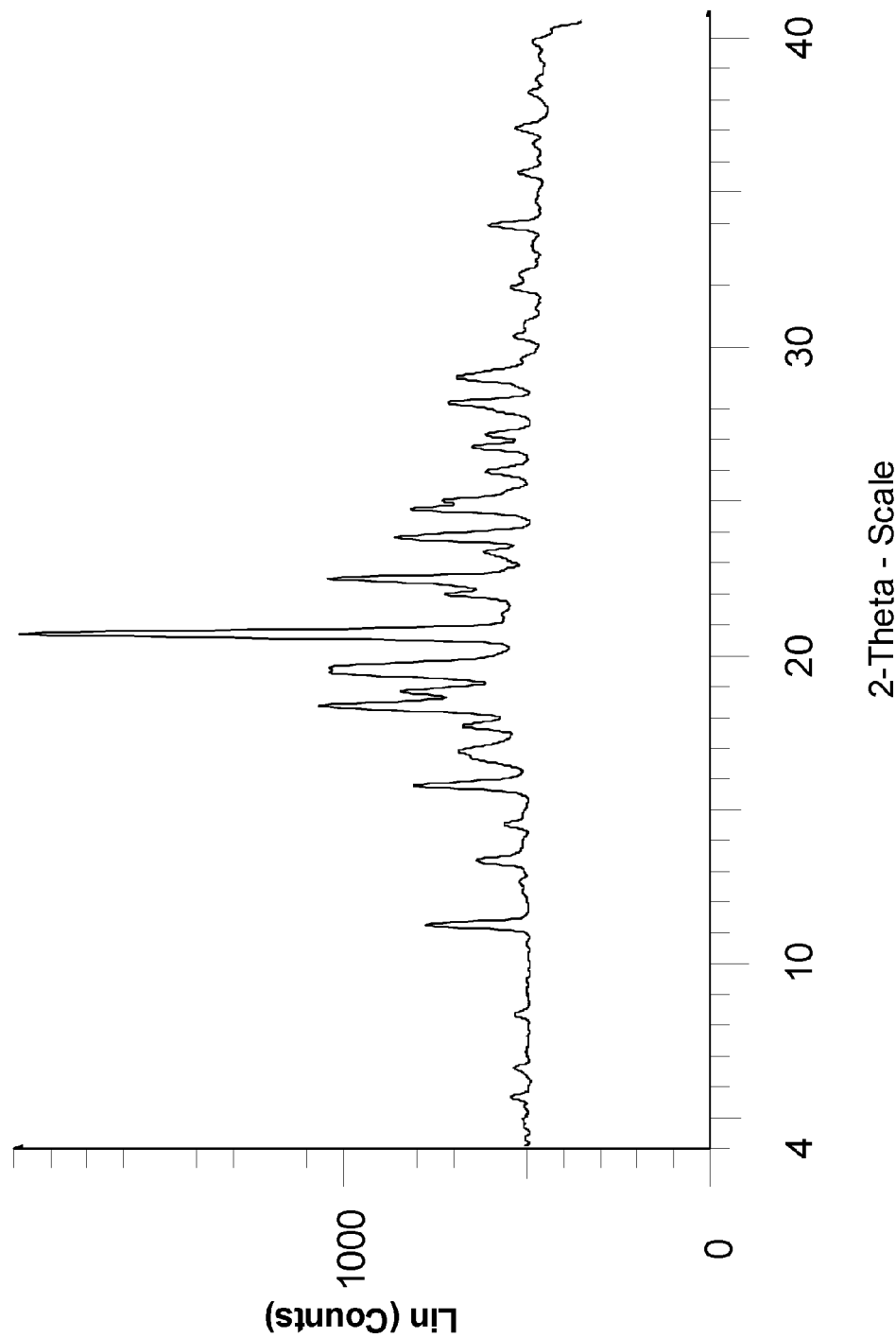
FIG. 5 is an X-ray diffraction pattern of a crystalline form of an anhydrous form of a phosphate salt of N-(1-{2-[5-(4-fluorobenzyl)-3-pyridin-4-yl-1H-pyrazol-1-yl]acetyl}piperidin-4-yl)methanesulfonamide from Example 144.

The compounds of the present invention may be administered to a mammal, such as a human, in combination with an additional compound so that there is an increase of the exposure of the mammal to the additional compound. The term "exposure," as used herein, refers to the concentration of an additional or second compound in the plasma of a mammal as measured over a period of time. An increase of the exposure of a mammal to an additional or second compound can be measured by first administering the additional or second compound to a mammal in an appropriate form and in the absence of the administration of a compound of the invention, withdrawing plasma samples at predetermined times, and measuring the amount of the compound in the plasma using an appropriate analytical technique, such as liquid chromatography or liquid chromatography/mass spectroscopy. The same study is then repeated, except that a compound of the present invention is co-administered with the additional or second compound. The amount of the additional or second compound present in the plasma at a certain time is determined and the concentration and time data from all the samples are plotted to afford a curve. The area under this curve is calculated and affords the exposure of the mammal to the compound. The difference in the areas under the curve in the presence and absence of a compound of the present invention affords a measure of the increase of the exposure to the additional or second compound in the plasma of the mammal. The terms "exposure," "area under the curve," and "area under the concentration/time curve" are intended to have the same meaning and may be used interchangeably throughout.

Such co-administration to a mammal of a compound of the present invention and a second or additional compound, as described above, may occur such that a compound or compounds of the present invention are present in the same formulation as the additional agents described above. Alternatively, such a combination may be administered such that the compound or compounds of the present invention are present in a formulation that is separate from the formulation in which the additional agent is found. If the compound or compounds of the present invention are administered separately from the additional agent, such administration may take place at the same or sequentially with an appropriate period of time in between. The choice of whether to include the compound or compounds of the present invention in the same formulation as the additional agent or agents is within the knowledge of one of ordinary skill in the art.

In accordance with a convention used in the art, the symbol

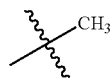

is used in structural formulas herein to depict the bond that is the point of attachment of the moiety or substituent to the core or backbone structure. In accordance with another convention, in some structural formulae herein the carbon atoms and their bound hydrogen atoms are not explicitly depicted, e.g.,

represents a methyl group,

represents an ethyl group,

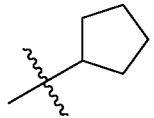

represents a cyclopentyl group, etc.

The term "stereoisomers" refers to compounds that have identical chemical constitution, but differ with regard to the arrangement of their atoms or groups in space. In particular, the term "enantiomers" refers to two stereoisomers of a compound that are non-superimposable mirror images of one another. The terms "racemic" or "racemic mixture," as used herein, refer to a 1:1 mixture of enantiomers of a particular compound. The term "diastereomers", on the other hand, refers to the relationship between a pair of stereoisomers that comprise two or more asymmetric centers and are not mirror images of one another.

The compounds of the present invention may have asymmetric carbon atoms. The bonds between atoms in the compounds of the present invention may be depicted herein using a solid line (------), a solid wedge ( ▬ ),or a dotted wedge ( ......... ).The use of a solid line to depict bonds from asymmetric carbon atoms is meant to indicate that all possible stereoisomers at that carbon atom are included. The use of either a solid or dotted wedge to depict bonds from asymmetric carbon atoms is meant to indicate that only the stereoisomer shown is meant to be included. It is possible that compounds of the invention may contain more than one asymmetric carbon atom. In those compounds, the use of a solid line to depict bonds from asymmetric carbon atoms is meant to indicate that all possible stereoisomers are meant to be included. The use of a solid line to depict bonds from one or more asymmetric carbon atoms in a compound of the invention and the use of a solid or dotted wedge to depict bonds from other asymmetric carbon atoms in the same compound is meant to indicate that a mixture of diastereomers is present.

If a derivative used in the method of the invention is a base, a desired salt may be prepared by any suitable method known to the art, including treatment of the free base with an inorganic acid, such as hydrochloric acid; hydrobromic acid; sulfuric acid; nitric acid; phosphoric acid; and the like, or with an organic acid, such as acetic acid; maleic acid; succinic acid; mandelic acid; fumaric acid; malonic acid; pyruvic acid; oxalic acid; glycolic acid; salicylic acid; pyranosidyl acid, such as glucuronic acid or galacturonic acid; alpha-hydroxy acid, such as citric acid or tartaric acid; amino acid, such as aspartic acid or glutamic acid; aromatic acid, such as benzoic acid or cinnamic acid; sulfonic acid, such as p-toluenesulfonic acid or ethanesulfonic acid; and the like.

If a derivative used in the method of the invention is an acid, a desired salt may be prepared by any suitable method known to the art, including treatment of the free acid with an inorganic or organic base, such as an amine (primary, secondary, or tertiary); an alkali metal or alkaline earth metal hydroxide; or the like. Examples of suitable salts include organic salts derived from amino acids such as glycine and arginine; ammonia; primary, secondary, and tertiary amines; and cyclic amines, such as piperidine, morpholine, and piperazine; as well as inorganic salts derived from sodium, calcium, potassium, magnesium, manganese, iron, copper, zinc, aluminum, and lithium.

A "solvate" is intended to mean a pharmaceutically acceptable solvate form of a specified compound that retains the biological effectiveness of such compound. Examples of solvates include, but are not limited to, compounds of the invention in combination with water, isopropanol, ethanol, methanol, dimethylsulfoxide (DMSO), ethyl acetate, acetic acid, ethanolamine, or mixtures thereof.

A "pharmaceutically acceptable salt" is intended to mean a salt that retains the biological effectiveness of the free acids and bases of the specified derivative, containing pharmacologically acceptable anions, and is not biologically or otherwise undesirable. Examples of pharmaceutically acceptable salts include, but are not limited to, acetate, acrylate, benzenesulfonate, benzoate (such as chlorobenzoate, methylbenzoate, dinitrobenzoate, hydroxybenzoate, and methoxybenzoate), bicarbonate, bisulfate, bisulfite, bitartrate, borate, bromide, butyne-1,4-dioate, calcium edetate, camsylate, carbonate, chloride, caproate, caprylate, clavulanate, citrate, decanoate, dihydrochloride, dihydrogenphosphate, edetate, edislyate, estolate, esylate, ethylsuccinate, formate, fumarate, gluceptate, gluconate, glutamate, glycollate, glycollylarsanilate, heptanoate, hexyne-1,6-dioate, hexylresorcinate, hydrabamine, hydrobromide, hydrochloride, γ-hydroxybutyrate, iodide, isobutyrate, isothionate, lactate, lactobionate, laurate, malate, maleate, malonate, mandelate, mesylate, metaphosphate, methane-sulfonate, methylsulfate, monohydrogenphosphate, mucate, napsylate, naphthalene-1-sulfonate, naphthalene-2-sulfonate, nitrate, oleate, oxalate, pamoate (embonate), palmitate, pantothenate, phenylacetates, phenylbutyrate, phenylpropionate, phthalate, phospate/diphosphate, polygalacturonate, propanesulfonate, propionate, propiolate, pyrophosphate, pyrosulfate, salicylate, stearate, subacetate, suberate, succinate, sulfate, sulfonate, sulfite, tannate, tartrate, teoclate, tosylate, triethiodode, and valerate salts.

The compounds of the present invention that are basic in nature are capable of forming a wide variety of different salts with various inorganic and organic acids. Although such salts must be pharmaceutically acceptable for administration to animals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention can be prepared by treating the base compound with a substantially equivalent amount of the selected mineral or organic acid in an aqueous solvent medium or in a suitable organic solvent, such as methanol or ethanol. Upon evaporation of the solvent, the desired solid salt is obtained. The desired acid salt can also be precipitated from a solution of the free base in an organic solvent by adding an appropriate mineral or organic acid to the solution.

Those compounds of the present invention that are acidic in nature are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of the present invention. Such non-toxic base salts include those derived from such pharmacologically acceptable cations as sodium, potassium calcium and magnesium, etc. These salts can be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

In the case of agents that are solids, it is understood by those skilled in the art that the inventive compounds, agents and salts may exist in different crystal or polymorphic forms, all of which are intended to be within the scope of the present invention and specified formulas.

The compounds of the present invention may be formulated into pharmaceutical compositions as described below in any pharmaceutical form recognizable to the skilled artisan as being suitable. Pharmaceutical compositions of the invention comprise a therapeutically effective amount of at least one compound of the present invention and an inert, pharmaceutically acceptable carrier or diluent.

The pharmaceutical carriers employed may be either solid or liquid. Exemplary solid carriers are lactose, sucrose, talc, gelatin, agar, pectin, acacia, magnesium stearate, stearic acid and the like. Exemplary liquid carriers are syrup, peanut oil, olive oil, water and the like. Similarly, the inventive compositions may include time-delay or time-release material known in the art, such as glyceryl monostearate or glyceryl distearate alone or with a wax, ethylcellulose, hydroxypropylmethylcellulose, methylmethacrylate or the like. Further additives or excipients may be added to achieve the desired formulation properties. For example, a bioavailability enhancer, such as Labrasol®, Gelucire® or the like, or formulator, such as CMC (carboxy-methylcellulose), PG (propyleneglycol), or PEG (polyethyleneglycol), may be added. Gelucire®, a semi-solid vehicle that protects active ingredients from light, moisture and oxidation, may be added, e.g., when preparing a capsule formulation.

If a solid carrier is used, the preparation can be tableted, placed in a hard gelatin capsule in powder or pellet form, or formed into a troche or lozenge. The amount of solid carrier may vary, but generally will be from about 25 mg to about 1 g. If a liquid carrier is used, the preparation may be in the form of syrup, emulsion, soft gelatin capsule, sterile injectable solution or suspension in an ampoule or vial or non-aqueous liquid suspension. If a semi-solid carrier is used, the preparation may be in the form of hard and soft gelatin capsule formulations. The inventive compositions are prepared in unit-dosage form appropriate for the mode of administration, e.g., parenteral or oral administration.

To obtain a stable water-soluble dose form, a pharmaceutically acceptable salt of a compound of the present invention may be dissolved in an aqueous solution of an organic or inorganic acid, such as 0.3 M solution of succinic acid or citric acid. If a soluble salt form is not available, the agent may be dissolved in a suitable cosolvent or combinations of cosolvents. Examples of suitable cosolvents include alcohol, propylene glycol, polyethylene glycol 300, polysorbate 80, glycerin and the like in concentrations ranging from 0-60% of the total volume. In an exemplary embodiment, a compound of Formula I is dissolved in DMSO and diluted with water. The composition may also be in the form of a solution of a salt form of the active ingredient in an appropriate aqueous vehicle such as water or isotonic saline or dextrose solution.

Proper formulation is dependent upon the route of administration selected. For injection, the agents of the compounds of the present invention may be formulated into aqueous solutions, preferably in physiologically compatible buffers such as Hanks solution, Ringer's solution, or physiological saline buffer. For transmucosal administration, penetrants appropriate to the barrier to be permeated are used in the formulation. Such penetrants are generally known in the art.

For oral administration, the compounds can be formulated by combining the active compounds with pharmaceutically acceptable carriers known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained using a solid excipient in admixture with the active ingredient (agent), optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethylcellulose, sodium carboxymethylcellulose, or polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active agents.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

For administration intranasally or by inhalation, the compounds for use according to the present invention may be conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator and the like may be formulated containing a powder mix of the compound and a suitable powder base such as lactose or starch.

The compounds may be formulated for parenteral administration by injection, e.g., by bolus injection or continuous infusion. Formulations for injection may be presented in unit-dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active agents may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Alternatively, the active ingredient may be in powder form for constitution with a suitable vehicle, e.g., sterile pyrogen-free water, before use.

In addition to the formulations described above, the compounds of the present invention may also be formulated as a depot preparation. Such long-acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion-exchange resins, or as sparingly soluble derivatives, for example, as a sparingly soluble salt.

A pharmaceutical carrier for hydrophobic compounds is a cosolvent system comprising benzyl alcohol, a nonpolar surfactant, a water-miscible organic polymer, and an aqueous phase. The cosolvent system may be a VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD: 5W) contains VPD diluted 1:1 with a 5% dextrose in water solution. This co-solvent system dissolves hydrophobic compounds well, and itself produces low toxicity upon systemic administration. The proportions of a co-solvent system may be suitably varied without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may be substituted for dextrose.

Alternatively, other delivery systems for hydrophobic pharmaceutical compounds may be employed. Liposomes and emulsions are known examples of delivery vehicles or carriers for hydrophobic drugs. Certain organic solvents such as dimethylsulfoxide also may be employed, although usually at the cost of greater toxicity due to the toxic nature of DMSO. Additionally, the compounds may be delivered using a sustained-release system, such as semipermeable matrices of solid hydrophobic polymers containing the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid- or gel-phase carriers or excipients. These carriers and excipients may provide marked improvement in the bioavailability of poorly soluble drugs. Examples of such carriers or excipients include calcium carbonate, calcium phosphate, sugars, starches, cellulose derivatives, gelatin, and polymers such as polyethylene glycols. Furthermore, additives or excipients such as Gelucire®, Capryol®, Labrafil®, Labrasol®, Lauroglycol®, Plurol®, Peceol® Transcutol® and the like may be used. Further, the pharmaceutical composition may be incorporated into a skin patch for delivery of the drug directly onto the skin.

It will be appreciated that the actual dosages of the agents of this invention will vary according to the particular agent being used, the particular composition formulated, the mode of administration, and the particular site, host, and disease being treated. Those skilled in the art using conventional dosage-determination tests in view of the experimental data for a given compound may ascertain optimal dosages for a given set of conditions. For oral administration, an exemplary daily dose generally employed will be from about 0.001 to about 1000 mg/kg of body weight, with courses of treatment repeated at appropriate intervals.

Furthermore, the pharmaceutically acceptable formulations of the present invention may contain a compound of the present invention, or a pharmaceutically acceptable salt or solvate thereof, in an amount of about 10 mg to about 2000 mg, or from about 10 mg to about 1500 mg, or from about 10 mg to about 1000 mg, or from about 10 mg to about 750 mg, or from about 10 mg to about 500 mg, or from about 25 mg to about 500 mg, or from about 50 to about 500 mg, or from about 100 mg to about 500 mg.

Additionally, the pharmaceutically acceptable formulations of the present invention may contain a compound of the present invention, or a pharmaceutically acceptable salt or solvate thereof, in an amount from about 0.5 w/w % to about 95 w/w %, or from about 1 w/w % to about 95 w/w %, or from about 1 w/w % to about 75 w/w %, or from about 5 w/w % to about 75 w/w %, or from about 10 w/w % to about 75 w/w %, or from about 10 w/w % to about 50 w/w %.

To treat or prevent diseases or conditions mediated by HIV, a pharmaceutical composition of the invention in a suitable formulation is administered in combination with at least one anti-HIV agent. A combined formulation of a compound of the present invention and an at least anti-HIV agent may be prepared by combining a therapeutically effective amount (i.e., an HIV replication-inhibiting amount effective to achieve therapeutic efficacy) of at least one compound of the present invention (as an active ingredient) with one or more anti-HIV agents and at least one pharmaceutically suitable carrier, which may be selected, for example, from diluents, excipients and auxiliaries that facilitate processing of the active compounds into the final pharmaceutical preparations.

Alternatively, to treat or prevent diseases or conditions mediated by HIV, a pharmaceutical composition of the invention in a suitable formulation is administered at the same time as at least one anti-HIV agent that is in a separate, pharmaceutically acceptable formulation. Such a dosing regimen may be designed such that a compound of the present invention is administered to an HIV-infected mammal prior to, at the same time as, or after the administration of the pharmaceutical formulation containing at least one anti-HIV agent. The pharmaceutically acceptable formulation of the compound of the present invention may be prepared by combining the compound and at least one pharmaceutically suitable carrier, which may be selected, for example, from diluents, excipients and auxiliaries that facilitate processing of the active compounds into the final pharmaceutical preparations.

The compounds of the present invention, or a pharmaceutically acceptable salt or solvate thereof, may be administered to a mammal suffering from infection with HIV, such as a human, either alone or as part of a pharmaceutically acceptable formulation, once a day, twice a day, or three times a day in combination with an anti-HIV agent.

Those of ordinary skill in the art will understand that with respect to the compounds of the present invention, the particular pharmaceutical formulation, the dosage, and the number of doses given per day to a mammal requiring such treatment, and the choice of a particular anti-HIV agent or agents are all choices within the knowledge of one of ordinary skill in the art and can be determined without undue experimentation. For example, see "Guidelines for the Use of Antiretroviral Agents in HIV-1 Infected Adults and Adolescents," United States Department of Health and Human Services, available at http://www.aidsinfo.nih.gov/quidelines/ as of May 31, 2006.

The compounds of the present invention may be administered in combination with an additional agent or agents for the treatment of a mammal, such as a human, that is suffering from an infection with the HIV virus, AIDS, AIDS-related complex (ARC), or any other disease or condition which is related to infection with the HIV virus. The agents that may be used in combination with the compounds of the present invention include, but are not limited to, those useful as HIV protease inhibitors, HIV reverse transcriptase inhibitors, non-nucleoside HIV reverse transcriptase inhibitors, inhibitors of HIV integrase, CCR5 inhibitors, HIV fusion inhibitors, compounds useful as immunomodulators, compounds that inhibit the HIV virus by an unknown mechanism, compounds useful for the treatment of herpes viruses, compounds useful as anti-infectives, and others as described below.

Compounds useful as HIV protease inhibitors that may be used in combination with the compounds of the present invention include, but are not limited to, 141 W94 (amprenavir), CGP-73547, CGP-61755, DMP-450, nelfinavir, ritonavir, saquinavir (invirase), lopinavir, TMC-126, atazanavir, palinavir, GS-3333, KN I-413, KNI-272, LG-71350, CGP-61755, PD 173606, PD 177298, PD 178390, PD 178392, U-140690, ABT-378, DMP-450, AG-1776, MK-944, VX-478, indinavir, tipranavir, TMC-114, DPC-681, DPC-684, fosamprenavir calcium (Lexiva), benzenesulfonamide derivatives disclosed in WO 03053435, R-944, Ro-03-34649, VX-385, GS-224338, OPT-TL3, PL-100, SM-309515, AG-148, DG-35-VIII, DMP-850, GW-5950X, KNI-1039, L-756423, LB-71262, LP-130, RS-344, SE-063, UIC-94-003, Vb-19038, A-77003, BMS-182193, BMS-186318, SM-309515, JE-2147, GS-9005, and (4R)-N-allyl-3-{(2S,3S)-2-hydroxy-3-[(3-hydroxy-2-methylbenzoyl) amino]-4-phenylbutanoyl}-5,5-dimethyl-1,3-thiazolidine-4-carboxamide.

Compounds useful as inhibitors of the HIV reverse transcriptase enzyme that may be used in combination with the compounds of the present invention include, but are not limited to, abacavir, FTC, GS-840, lamivudine, adefovir dipivoxil, beta-fluoro-ddA, zalcitabine, didanosine, stavudine, zidovudine, tenofovir, amdoxovir, SPD-754, SPD-756, racivir, reverset (DPC-817), MIV-210 (FLG), beta-L-Fd4C (ACH-126443), MIV-310 (alovudine, FLT), dOTC, DAPD, entecavir, GS-7340, emtricitabine, and alovudine.

Compounds useful as non-nucleoside inhibitors of the HIV reverse transcriptase enzyme that may be used in combination with the compounds of the present invention include, but are not limited to, efavirenz, HBY-097, nevirapine, TMC-120 (dapivirine), TMC-125, etravirine, delavirdine, DPC-083, DPC-961, TMC-120, capravirine, GW-678248, GW-695634, calanolide, and tricyclic pyrimidinone derivatives as disclosed in WO 03062238.

Compounds useful as CCR5 inhibitors that may be used in combination with the compounds of the present invention include, but are not limited to, TAK-779, SC-351125, SCH-D, (N-{(1S)-3-[3-isopropyl-5-methyl-4H-1,2,4-triazole-4- yl]-exo-8-azabicyclo[3.2.1]oct-8-yl}-1-phenylpropyl)-4,4-difluorocyclohexanecarboxamide), ethyl 1-endo-{8-[(3S)-3-(acetylamino)-3-(3-fluorophenyl)propyl]-8-azabicyclo [3.2.1]oct-3-yl}-2-methyl-4,5,6,7-tetrahydro-1H-imidazo[4,5-c]pyridine-5-carboxylate, or N-{(1 S)-3-[3-endo-(5-Isobutyryl-2-methyl-4,5,6,7-tetrahydro-1H-imidazo[4,5-c]pyridin-1-yl)-8-azabicyclo[3.2.1 ]oct-8-yl]-1-(3-fluorophenyl)propyl}acetamide)7, PRO-140, and GW-873140 (Ono-4128, AK-602).

Compounds useful as inhibitors of HIV integrase enzyme that may be used in combination with the compounds of the present invention include, but are not limited to, GW-810781, 1,5-naphthyridine-3-carboxamide derivatives disclosed in WO 03062204, compounds disclosed in WO 03047564, compounds disclosed in WO 03049690, and 5-hydroxypyrimidine-4-carboxamide derivatives disclosed in WO 03035076.

Fusion inhibitors for the treatment of HIV that may be used in combination with the compounds of the present invention include, but are not limited to enfuvirtide (T-20), T-1249, AMD-3100, and fused tricyclic compounds disclosed in JP 2003171381.

Other compounds that are useful inhibitors of HIV that may be used in combination with the compounds of the present invention include, but are not limited to, Soluble CD4, TNX-355, PRO-542, BMS-806, tenofovir disoproxil fumarate, and compounds disclosed in JP 2003119137.

Compounds useful in the treatment or management of infection from viruses other than HIV that may be used in combination with the compounds of the present invention include, but are not limited to, acyclovir, fomivirsen, penciclovir, HPMPC, oxetanocin G, AL-721, cidofovir, cytomegalovirus immune globin, cytovene, fomivganciclovir, famciclovir, foscarnet sodium, Isis 2922, KNI-272, valacyclovir, virazole ribavirin, valganciclovir, ME-609, PCL-016

Compounds that act as immunomodulators and may be used in combination with the compounds of the present invention include, but are not limited to, AD-439, AD-519, Alpha Interferon, AS-101, bropirimine, acemannan, CL246, 738, EL10, FP-21399, gamma interferon, granulocyte macrophage colony stimulating factor, IL-2, immune globulin intravenous, IMREG-1, IMREG-2, imuthiol diethyl dithio carbamate, alpha-2 interferon, methionine-enkephalin, MTP-PE, granulocyte colony stimulating sactor, remune, rCD4, recombinant soluble human CD4, interferon alfa-2, SK&F106528, soluble T4 yhymopentin, tumor necrosis factor (TNF), tucaresol, recombinant human interferon beta, and interferon alfa n-3.

Anti-infectives that may be used in combination with the compounds of the present invention include, but are not limited to, atovaquone, azithromycin, clarithromycin, trimethoprim, trovafloxacin, pyrimethamine, daunorubicin, clindamycin with primaquine, fluconazole, pastill, ornidyl, eflornithine pentamidine, rifabutin, spiramycin, intraconazole-R51211, trimetrexate, daunorubicin, recombinant human erythropoietin, recombinant human growth hormone, megestrol acetate, testerone, and total enteral nutrition.

Antifungals that may be used in combination with the compounds of the present invention include, but are not limited to, anidulafungin, C31G, caspofungin, DB-289, fluconzaole, itraconazole, ketoconazole, micafungin, posaconazole, and voriconazole.

Other compounds that may be used in combination with the compounds of the present invention include, but are not limited to, acmannan, ansamycin, LM 427, AR177, BMS-232623, BMS-234475, CI-1012, curdlan sulfate, dextran sulfate, STOCRINE EL10, hypericin, lobucavir, novapren, peptide T octabpeptide sequence, trisodium phosphonoformate, probucol, and RBC-CD4.

In addition, the compounds of the present invention may be used in combination with anti-proliferative agents for the treatment of conditions such as Kaposi's sarcoma. Such agents include, but are not limited to, inhibitors of metallomatrix proteases, A-007, bevacizumab, BMS-275291, halofuginone, interleukin-12, rituximab, paclitaxel, porfimer sodium, rebimastat, and COL-3.

The particular choice of an additional agent or agents will depend on a number of factors that include, but are not limited to, the condition of the mammal being treated, the particular condition or conditions being treated, the identity of the compound or compounds of the present invention and the additional agent or agents, and the identity of any additional compounds that are being used to treat the mammal. The particular choice of the compound or compounds of the invention and the additional agent or agents is within the knowledge of one of ordinary skill in the art and can be made without undue experimentation.

The compounds of the present invention may be administered in combination with any of the above additional agents for the treatment of a mammal, such as a human, that is suffering from an infection with the HIV virus, AIDS, AIDS-related complex (ARC), or any other disease or condition which is related to infection with the HIV virus. Such a combination may be administered to a mammal such that a compound or compounds of the present invention are present in the same formulation as the additional agents described above. Alternatively, such a combination may be administered to a mammal suffering from infection with the HIV virus such that the compound or compounds of the present invention are present in a formulation that is separate from the formulation in which the additional agent is found. If the compound or compounds of the present invention are administered separately from the additional agent, such administration may take place concomitantly or sequentially with an appropriate period of time in between. The choice of whether to include the compound or compounds of the present invention in the same formulation as the additional agent or agents is within the knowledge of one of ordinary skill in the art.

The inventive agents may be prepared using the reaction routes and synthesis schemes as described below, employing the techniques available in the art using starting materials that are readily available. The preparation of certain embodiments of the present invention are described in detail in the following examples, but those of ordinary skill in the art will recognize that the preparations described may be readily adapted to prepare other embodiments of the present invention. For example, the synthesis of non-exemplified compounds according to the invention may be performed by modifications apparent to those skilled in the art, e.g., by appropriately protecting interfering groups, by changing to other suitable reagents known in the art, or by making routine modifications of reaction conditions. Alternatively, other reactions disclosed herein or known in the art will be recognized as having adaptability for preparing other compounds of the invention.

As depicted in Scheme A, a substituted phenyl acetone (such as 4-fluorophenylacetone, A-1) can be treated with a suitable base (such as sodium methoxide) and a heterocyclic alkyl carboxylate, A-2 (such as pyridine-4-methyl ester) or alternatively a heterocyclic Weinreb amide derivative A-2 (such as pyridazine-4-weinreb amide), in a suitable solvent (such as THF) to provide the corresponding beta-di-carbonyl compound. The beta-di-carbonyl compound can then be allowed to react with hydrazine to afford the pyrazole, A-3.

The pyrazole can allowed to react with a suitable electrophile (such as methyl bromo acetate) in the presence of a suitable base (such as sodium hydride) to provide a N-substituted pyrazole A-4. In the case where the N-substituted pyrazole A-4 compounds are obtained as a mix of regioisomers, such regioisomers can be separated using methods known to those of skill in the art, such as super-critical fluid chromatography (SFC) using commercially available columns, without undue experimentation. Compounds A-4 can be converted to the corresponding acid A-5 using conditions known to those of ordinary skill in the art (such as aqueous NaOH in methanol at ambient temperature). The corresponding acid can then be allowed to react with a primary or secondary amine, under conditions known to those of ordinary skill in the art (for example EDCI and HOBt in the presence of a suitable base such as N-methylmorpholine or triethylamine) to provide the corresponding the amide compounds, A-6.

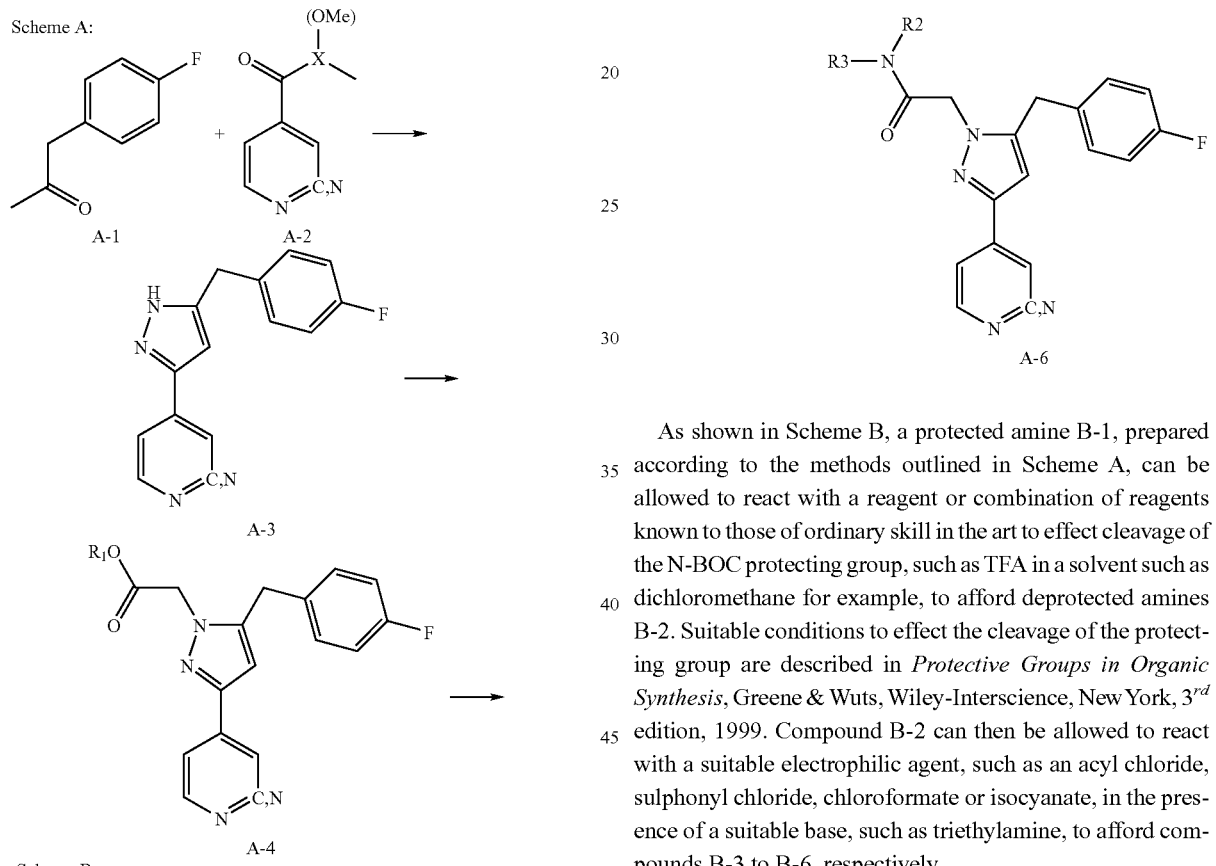

As shown in Scheme B, a protected amine B-1, prepared according to the methods outlined in Scheme A, can be allowed to react with a reagent or combination of reagents known to those of ordinary skill in the art to effect cleavage of the N-BOC protecting group, such as TFA in a solvent such as dichloromethane for example, to afford deprotected amines B-2. Suitable conditions to effect the cleavage of the protecting group are described in *Protective Groups in Organic Synthesis*, Greene & Wuts, Wiley-Interscience, New York, 3$^{rd}$ edition, 1999. Compound B-2 can then be allowed to react with a suitable electrophilic agent, such as an acyl chloride, sulphonyl chloride, chloroformate or isocyanate, in the presence of a suitable base, such as triethylamine, to afford compounds B-3 to B-6, respectively.

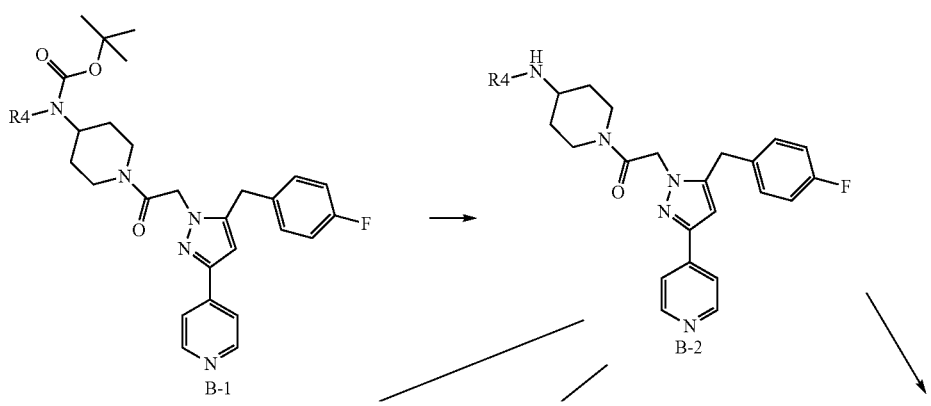

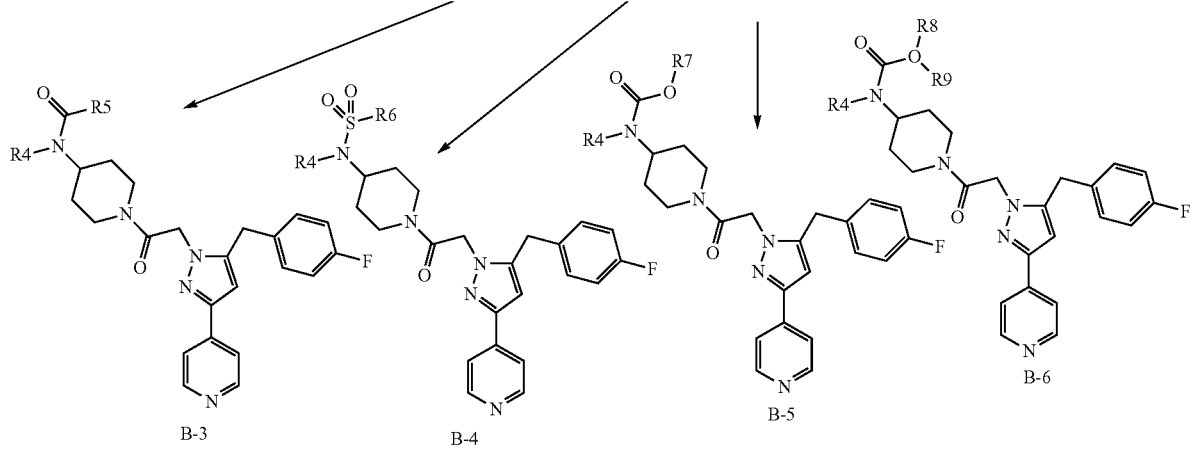

As depicted in Scheme C, a pyrazole compound, such as compound A-3, can be allowed to react with a reagent or combination of reagents that can function as an alkyl electrophile. For example, compound A-3 can be allowed to react with a suitable with a suitable benzhydryl-protected azetadine derivative in the presence of a suitable base, such as such as sodium hydride, to afford compound C-1. Compound C-1 can then be allowed to react with a reagent or combination of reagents to effect cleavage of the protecting group. For example, a benzhydryl group on a compound of formula C-1 can be removed using conditions known to those of ordinary skill in the art, such as the use of ammonium formate in the presence of palladium on charcoal (5 or 10% w/w) in a suitable solvent, such as methanol, and at room temperature to yield the deprotected product, C-2. Suitable conditons to affect the cleavage of the protecting group are described in *Protective Groups in Organic Synthesis*, Greene & Wuts, Wiley-Interscience, New York, 3$^{rd}$ edition, 1999. Compound C-2 can then be allowed to react with a carboxylic acid and a reagent or combination of reagents known to those of ordinary skill in the art to provide amide compound C-3. For example, compound C-2 can be allowed to react with an acid EDCI and HOBt in the presence of a suitable base, such as N-methylmorpholine or triethylamine, to afford C-3. Alternatively compounds of type C-3 can be prepared by treatment of C-2 with a suitable acyl halide, such as acetyl chloride, in the presence of a suitable base, such as triethylamine, and in an aprotic solvent, such as acetonitrile or chloroform, for example. Further, compound C-2 can be allowed to react with sulphonyl chlorides, which are either commercially available or can be prepared by methods known to those of ordinary skill in the art, to yield sulphonamide compounds C-4.

Scheme C:

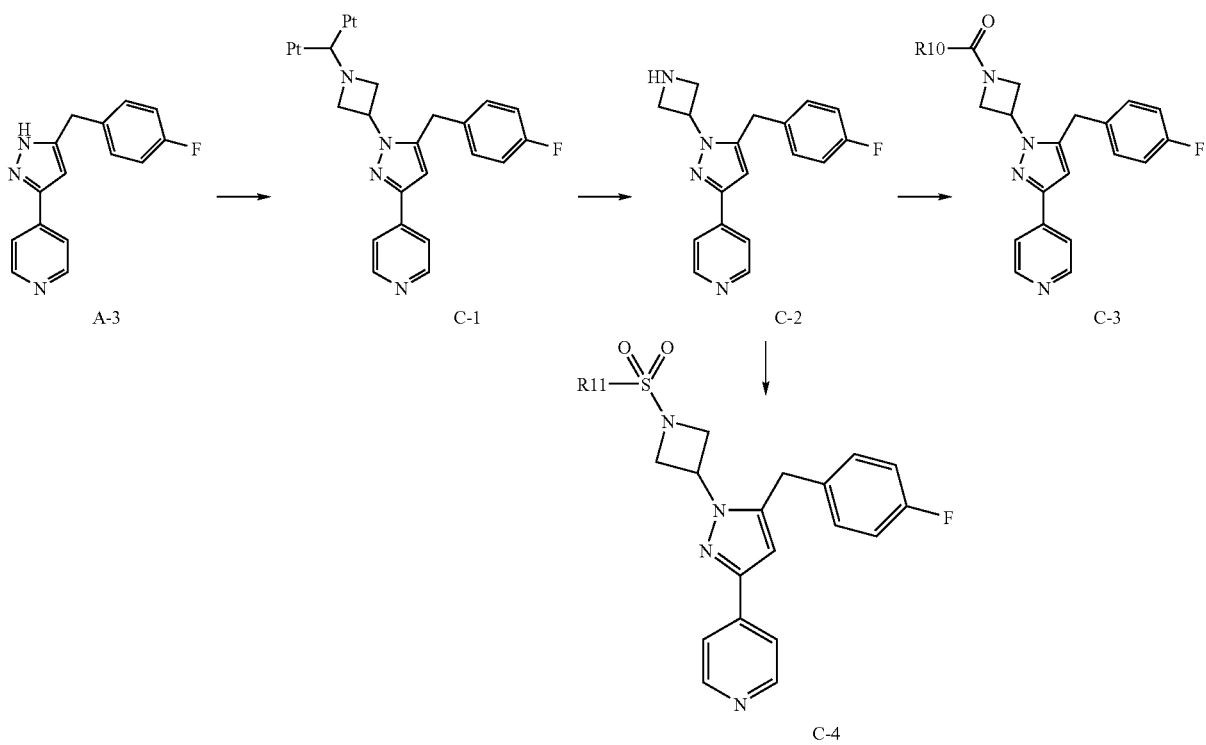

As shown in Scheme D, carboxylic acid compounds like A-5 can be allowed to react with a reagent or combination of reagents to afford oxadiazole compounds, such as compounds D-1 and D-3. For example, carboxylic acid compound A-5 can be allowed to react with CDI or EDCI and HOBt, followed by treatment with an amidoxime to yield an ester intermediate that can be cyclised to the corresponding oxadiazoles by treatment with tetrabutylammonium fluoride (see, for example, *Tetrahedron Letters*, 2001, 42, 1441). Amide oxadiazole compounds, such as D-2, can be prepared by treating the ester compounds such as D-1 with a suitable primary or secondary amine in a suitable solvent, such as methanol. Regioisomeric 1,3,4-oxadizlole compounds, such as D-4, can be prepared by treating carboxylic acid compounds, such as A-5, with a suitable activating agent, such as CDI, followed by coupling with an acetic hydrazide, to form a di-hydrazide intermediate that can be subsequently dehydrated with a reagent or combination of reagents, such as Burgess reagent (see *Tett Lett.* 1999, 40 (16), 3275), to provide the oxadiazole compounds D-4.

zole compound E-5. Compound E-5 may be obtained in predominantly one regioisomeric form or as a mix of regioisomers, which regioisomers may be separated using methods known to those of ordinary skill in the art, such as super-critical fluid chromatography (SFC) using commercially available columns, without undue experimentation. Compound E-5 may then be converted to the corresponding carboxylic acid compound under conditions known to those of ordinary skill in the art that will affect deprotection of the imidazole nitrogen atom and convert the ester to a carboxylic acid, such as the use of trifluoroacetic acid, in a solvent such as acetonitrile, to afford compound E-6. Suitable conditons to effect the cleavage of the protecting groups are described in *Protective Groups in Organic Synthesis*, Greene & Wuts, Wiley-Interscience, New York, $3^{rd}$ edition, 1999. Compound E-6 can then be allowed to react with a primary or secondary amine in the presence of a reagent or combination of reagents known to those of skill in the art, for example EDCI and HOBt in the presence of a suitable base such as N-methylmorpholine and triethylamine, to provide amide compound E-7.

Scheme D:

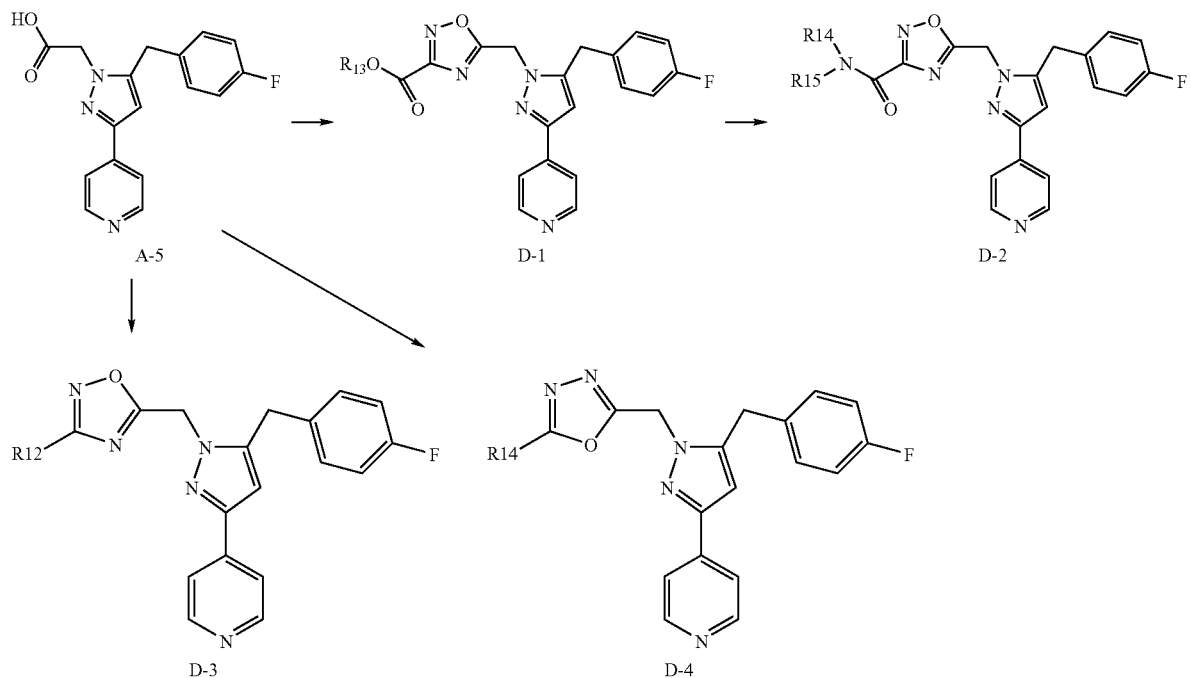

As depicted in Scheme E, a heterocyclic acetate compound E-2, such as 1-(1-trityl-1H-imidazol-4-yl)ethanone) for example, can be allowed to react with a suitable base, such as sodium methoxide, and a phenyl acetate compound E-1, such as methyl (4-fluorophenyl)acetate for example, in a in a suitable solvent, such as THF, to provide the beta-di-carbonyl compound E-3. A beta-di-carbonyl compound such as E-3 can be allowed to react with hydrazine to afford a pyrazole compound E-4. A pyrazole compound E-4 can the be allowed to react with a suitable electrophilic agent, such as tert-butyl bromo acetate for example, and a suitable base, such as sodium hydride for example, to provide a N-substituted pyra- Scheme E:

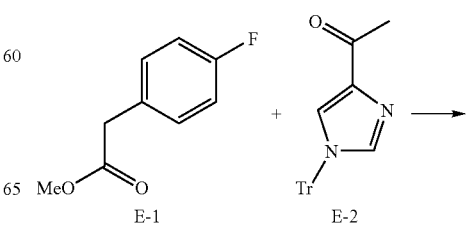

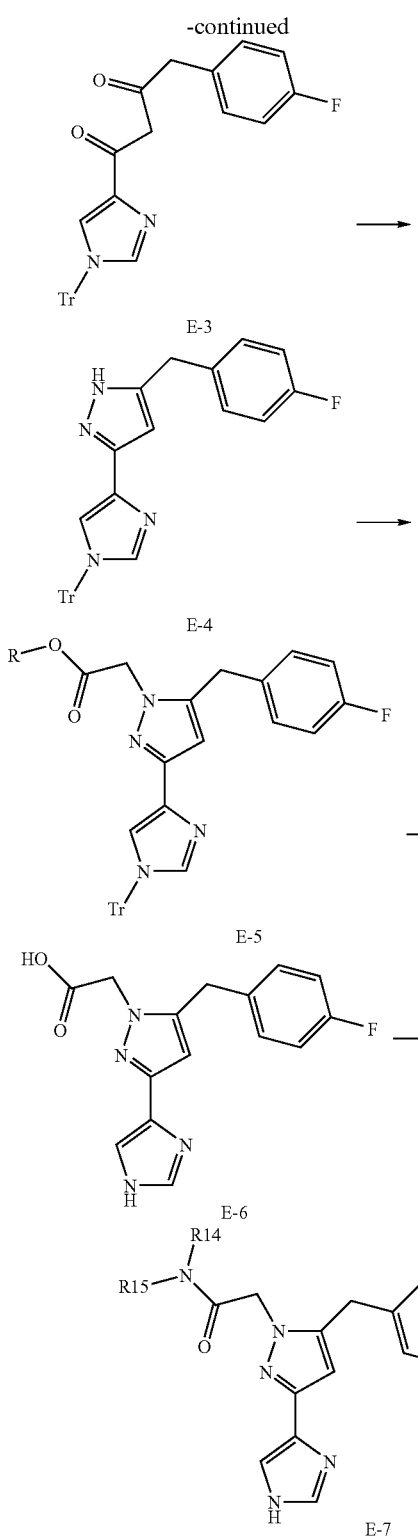

compound F-4. Pyrazole compound F-4 can then be allowed to react with a suitable electrophilic agent, such as tert-butyl bromo acetate for example, and a base, such as sodium hydride for example, to yield a N-substituted pyrazole compound F-5. Compound F-5 may be obtained in predominantly one regioisomeric form or as a mix of regioisomers, which regioisomers may be separated using methods known to those of ordinary skill in the art, such as super-critical fluid chromatography (SFC) using commercially available columns, without undue experimentation. Compound F-5 may then be allowed to react with a reagent or combination of reagents, for example aqueous sodium hydroxide in a miscible organic solvent that will effect conversion to the corresponding carboxylic acid compound F-6. Compound F-6 can then be allowed to react with a primary or secondary amine in the presence of a reagent or combination of reagents known to those of skill in the art, for example EDCI and HOBt in the presence of a suitable base such as N-methylmorpholine and triethylamine, to provide amide compound F-7. The protecting group in compound F-7 may then be cleaved using a reagent or combination or reagents known to those of ordinary skill in the art, such as treatment with trifluoroacetic acid when the protecting group is para-methoxybenzyl, to afford compound F-8. Suitable conditons to effect the cleavage of the protecting groups are described in *Protective Groups in Organic Synthesis*, Greene & Wuts, Wiley-Interscience, New York, 3$^{rd}$ edition, 1999.

Scheme F:

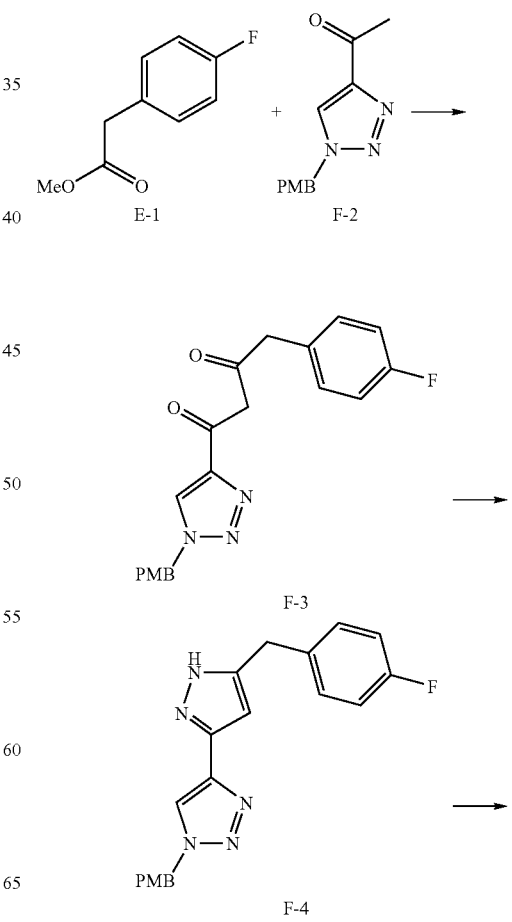

As depicted in Scheme F, a heterocyclic acetate compound F-2, such as 1-[1-(4-methoxybenzyl)-1H-1,2,3-triazol-4-yl] ethanone for example, can be allowed to react with a suitable base, such as sodium methoxide for example, and a substituted phenyl acetate compound, such as methyl (4-fluorophenyl)acetate E-1 for example, in a in a suitable solvent, such as THF, to afford a beta-di-carbonyl compound F-3. Compound F-3 can then be allowed to react hydrazine to afford a pyrazole

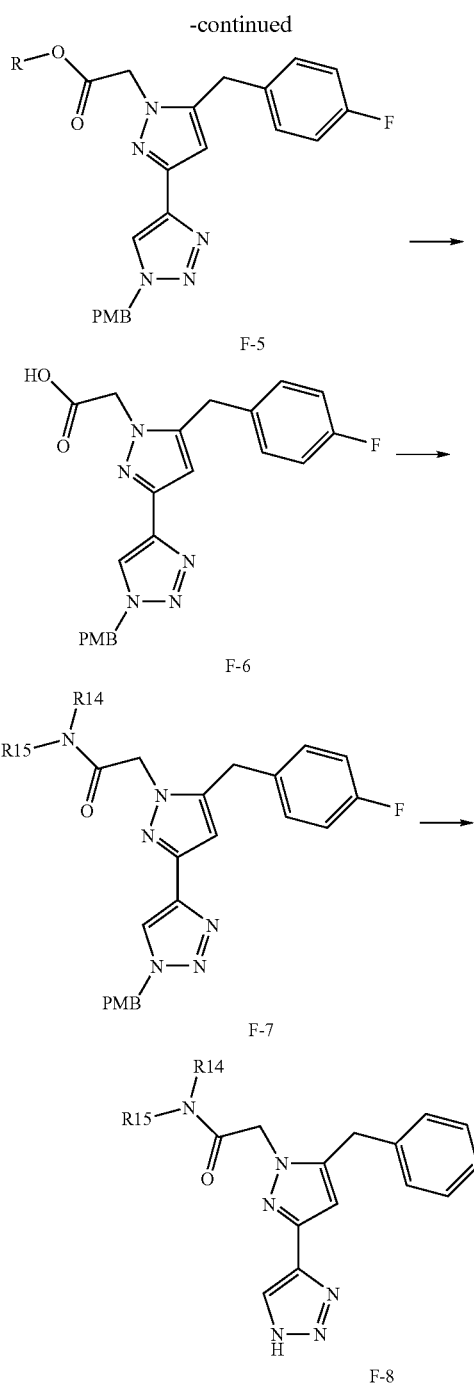

F-5

F-6

F-7

F-8

The inhibition of the cytochrome P450 enzyme system by a compound of the present invention can be determined according to methods known to those of skill in the art. For example, see Morrison, J. F., *Biochim Biophys Acta.*, 1969, 185: 269-86; and Szedlascek, S. E., Ostafe, V., Serban, M., and Vlad, M. O., *Biochem. J.*, 1988, 254:311-312.

EXAMPLES

The examples below are intended only to illustrate particular embodiments of the present invention and are not meant to limit the scope of the invention in any manner.

In the examples described below, unless otherwise indicated, all temperatures in the following description are in degrees Celsius (° C.) and all parts and percentages are by weight, unless indicated otherwise.

Various starting materials and other reagents were purchased from commercial suppliers, such as Aldrich Chemical Company or Lancaster Synthesis Ltd., and used without further purification, unless otherwise indicated.

The reactions set forth below were performed under a positive pressure of nitrogen, argon or with a drying tube, at ambient temperature (unless otherwise stated), in anhydrous solvents. Analytical thin-layer chromatography was performed on glass-backed silica gel 60° F. 254 plates (Analtech (0.25 mm)) and eluted with the appropriate solvent ratios (v/v). The reactions were assayed by high-pressure liquid chromotagraphy (HPLC) or thin-layer chromatography (TLC) and terminated as judged by the consumption of starting material. The TLC plates were visualized by UV, phosphomolybdic acid stain, or iodine stain.

Unless otherwise indicated, $^1$H-NMR spectra were recorded on a Bruker instrument operating at 300 MHz and $^{13}$C-NMR spectra were recorded at 75 MHz. NMR spectra were obtained as DMSO-d6 or CDCl$_3$ solutions (reported in ppm), using chloroform as the reference standard (7.25 ppm and 77.00 ppm) or DMSO-d6 ((2.50 ppm and 39.52 ppm)). Other NMR solvents were used as needed. When peak multiplicities are reported, the following abbreviations are used: s=singlet, d=doublet, t=triplet, m=multiplet, br=broadened, dd=doublet of doublets, dt=doublet of triplets. Coupling constants, when given, are reported in Hertz.

Infrared spectra were recorded on a Perkin-Elmer FT-IR Spectrometer as neat oils, as KBr pellets, or as CDCl$_3$ solutions, and when reported are in wave numbers (cm$^{-1}$). The mass spectra were obtained using LC/MS or APCI. All melting points are uncorrected.

All final products had greater than 95% purity (by HPLC at wavelengths of 220 nm and 254 nm).

All elemental analyses for compounds herein, unless otherwise specified, provided values for C, H, and N analysis that were within 0.4% of the theoretical value, and are reported as "C, H, N."

In the following examples and preparations, "LDA" means lithium diisopropyl amide, "Et" means ethyl, "Ac" means acetyl, "Me" means methyl, "Ph" means phenyl, (PhO)$_2$POCl means chlorodiphenylphosphate, "HCl" means hydrochloric acid, "EtOAc" means ethyl acetate, "Na$_2$CO$_3$" means sodium carbonate, "NaOH" means sodium hydroxide, "NaCl" means sodium chloride, "NEt$_3$" means triethylamine, "THF" means tetrahydrofuran, "DIC" means diisopropylcarbodiimide, "HOBt" means hydroxy benzotriazole, "H$_2$O" means water, "NaHCO$_3$" means sodium hydrogen carbonate, "K$_2$CO$_3$" means potassium carbonate, "MeOH" means methanol, "i-PrOAc" means isopropyl acetate, "MgSO$_4$" means magnesium sulfate, "DMSO" means dimethylsulfoxide, "AcCl" means acetyl chloride, "CH$_2$Cl$_2$" means methylene chloride, "MTBE" means methyl t-butyl ether, "DMF" means dimethyl formamide, "SOCl$_2$" means thionyl chloride, "H$_3$PO$_4$" means phosphoric acid, "CH$_3$SO$_3$H" means methanesulfonic acid, "Ac₂O" means acetic anhydride, "CH₃CN" means aceto-CN, and "KOH" means potassium hydroxide.

Example 1

4-[5-(4-fluorobenzyl)-1H-pyrazol-3-yl]pyridine

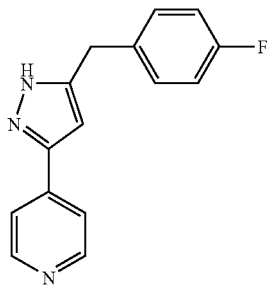

A 22 liter, three-neck, round bottom flask equipped with a mechanical stirrer, thermocouple, and reflux condenser with $N_2$ inlet adapter was charged with THF (6.0 L), methyl isonicotinate (259.1 g, 1.89 mol), and 4-fluorophenylacetone (287.5 g, 1.89 mol). Sodium methoxide (204.3 g, 3.78 mol) was added in several portions. The addition of sodium methoxide is slightly exothermic. The reaction mixture turned orange and was heated to reflux for 2 hours. After 2 hours, the absence of methyl isonicotinate and the formation of the β-diketone were verified by LC-MS. After the addition of ethanol (6 L) and acetic acid (380 mL), the temperature of the reaction mixture decreased to 45° C. The reflux condenser was then replaced with an addition funnel and hydrazine (387 g, 6.0 mol) was added drop-wise. During the addition the temperature of the reaction rose to 60° C. The reaction mixture was then stirred overnight slowly cooling to room temperature. The majority of the solvents were removed by rotary evaporation. The reaction mixture was partitioned between water (4.5 L) and ethyl acetate (4.5 L). The layers were separated and the aqueous layer extracted with ethyl acetate (4.5 L). The combined organic layers were then washed with dilute $NaHCO_3$, brine, dried ($Na_2SO_4$), filtered and concentrated. The resulting solid was triturated with ether (2 L) and the solid isolated by filtration. The solid was washed with ether (1.5 L) until the filtrate was colorless. This process gave 190 g (40%) of the title compound. Additional material (5 g) was then isolated by column chromatography using 5% methanol:95% methylene chloride. ¹H NMR (400 MHz, DMSO-D6) δ ppm 13.10 (s, 1 H), 8.44-8.60 (m, 2 H), 7.68 (d, 2 H), 7.30 (t, 2 H), 7.13 (t, 2 H), 6.62 (s, 1 H), 4.00 (s, 2 H); m/z (APCI+) for $C_{15}H_{12}N_3F$ 254.2 (M+H)⁺.

Example 2 methyl [5-(4-fluorobenzyl)-3-pyridin-4-yl-1H-pyrazol-1-yl]acetate

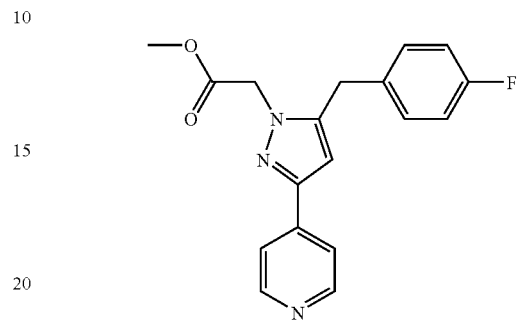

A 22 liter, three-neck, round bottom flask equipped with a mechanical stirrer, Claisen adapter with a thermocouple and $N_2$ inlet adapter, and a 250 ml addition funnel was charged with THF (10 L), and 4-[5-(4-fluorobenzyl)-1H-pyrazol-3-yl]pyridine (385.5 g, 1.52 mol). The resulting solution was cooled to 5° C. using a water/ice/salt bath. Sodium hydride (60% dispersion in mineral oil, 66.9 g, 1.67 mol) was then added in several portions at such that the internal temperature did not exceed 15° C. The resulting red mixture was stirred at 5° C. for 1.5 hours. Methyl bromoacetate (254 g, 1.67 mol) was then added drop-wise at such a rate that the temperature did not exceed 15° C. The mixture was then allowed to slowly reach room temperature overnight. The mixture was then filtered through celite, and the celite was washed with ethyl acetate. The majority of the THF was removed by rotary evaporation. Ethyl acetate (4 L) and water (4 L) were then added. The layers were separated and the aqueous layer was extracted with ethyl acetate (2×3 L). The combined organic layers were washed with brine, dried ($Na_2SO_4$), filtered and concentrated. The mixture of isomers (80:20 by GC-MS) was then eluted through silica gel using 100% ethyl acetate. The fractions that contained the isomers were concentrated and the solid suspended in ether (3 L). After heating to boiling, ethyl acetate (2 L) was added until the solid dissolved, followed by hexanes (4 L). After cooling overnight, the solid was filtered and dried under reduced vacuum to give the title compound as a red solid (235 g, 47%). ¹H NMR (400 MHz, CD₂Cl₂) δ ppm 8.56 (d, 2 H) 7.61 (d, 2 H) 7.20 (t, 2 H) 7.03

(t, 2 H) 6.42 (s, 1 H) 4.86 (s, 2 H) 3.96 (s, 2 H) 3.71 (s, 3 H); m/z (APCI+) for $C_{18}H_{16}N_3O_2F$ 326.1 $(M+H)^+$.

Example 3

[5-(4-fluorobenzyl)-3-pyridin-4-yl-1H-pyrazol-1-yl]acetic acid

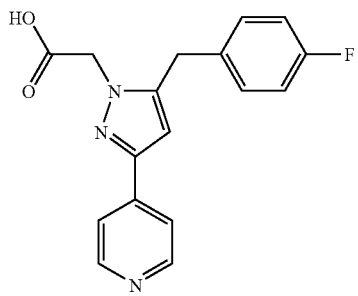

A 12 liter, three-neck, round bottom flask equipped with mechanical stirrer was charged with Methyl [5-(4-fluorobenzyl)-3-pyridin-4-yl-1H-pyrazol-1-yl]acetate (235 g, 0.72 mol), THF (3.5 L), methanol (1.2 L), and 2 M LiOH (1.2 L). The resulting solution was stirred at room temperature for 1.5 hours. After LC-MS showed the absence of starting material, the majority of the THF was removed by rotary evaporation. The solution was then acidified with 2 M HCl (pH=3) and the white precipitate was filtered and washed with water. After being dried under reduced pressure, 210 g (93%) of the title compound was obtained. $^1$H NMR (400 MHz, DMSO-D6) δ ppm 8.53 (d, 2 H), 7.68 (d, 2 H), 7.31 (t, 2 H), 7.14 (t, 2 H), 6.57 (s, 1 H), 5.00 (s, 2 H), 4.01 (s, 2 H); m/z (APCI+) for $C_{17}H_{14}N_3O_2F$ 312.2 $(M+H)^+$.

Example 4

1-{[5-(4-fluorobenzyl)-3-pyridin-4-yl-1H-pyrazol-1-yl]acetyl}-4-morpholin-4-ylazepane, maleic acid salt

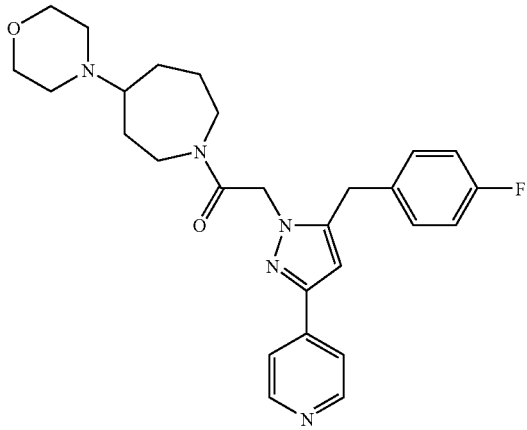

To a solution of [5-(4-fluorobenzyl)-3-pyridin-4-yl-1H-pyrazol-1-yl]acetic acid (150 mg, 0.48 mmol) in DMA (3 mL) at room temperature was added HOBt (72 mg, 0.53 mmol), EDCI (102 mg, 0.53 mmol), NMM (0.24 mL, 2.16 mmol) and 4-morpholin-4-ylazepane di-hydrochloride(185 mg, 0.72 mmol) and the mixture sonicated to a fine suspension and stirred for 16 hours at room temperature. The volatiles were removed under high vacuum and the residue partitioned between EtOAc (70 mL) and water (25 mL). The aqueous layer was removed and the organics washed with brine (30 mL), dried over MgSO$_4$, filtered and stripped to yield crude product that was purified by Biotage flash chromatography (25M column, eluting with a DCM/MeOH/NH$_4$OH gradient) to yield the parent compound as a colorless gum. The parent compound was taken up in EtOAc (7 mL) and a solution of maleic acid (112 mg, 0.96 mmol) in EtOAc (3 mL with sonication) was added with stirring. The solid that precipitated out was collected and washed with EtOAc (50 mL) and dried in-vacuo to yield the title compound as an off-white solid, 184 mg, 59% (1.5 eq. of maleic acid present). $^1$H NMR (400 MHz, DMSO-D6) δ ppm 8.54 (2 H, d, J=5.81 Hz) 7.68 (2 H, d, J=5.31 Hz) 7.29 (2 H, dd, J=8.46, 5.68 Hz) 7.03-7.20 (2 H, m) 6.54 (1 H, s) 6.09 (3 H, s) 5.02-5.37 (2 H, m) 3.95 (2 H, s) 3.02-3.91 (13 H, m) 1.42-2.38 (6 H, m); m/z (APCI+) for $C_{27}H_{32}N_5O_2F$ 478.1 $(M+H)^+$.

Example 5

1(1-{[5-(4-fluorobenzyl)-3-pyridin-4-yl-1H-pyrazol-1-yl]acetyl}piperidin-4-yl)pyrrolidin-2-one

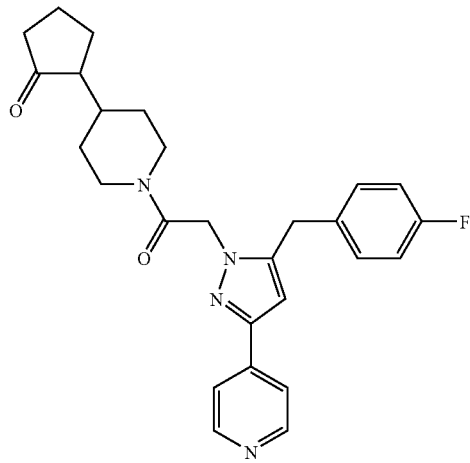

To a solution of [5-(4-fluorobenzyl)-3-pyridin-4-yl-1H-pyrazol-1-yl]acetic acid (164 mg, 0.53 mmol) in DMA (3 mL) at room temperature was added HOBt (78 mg, 0.58 mmol), EDCI (111 mg, 0.58 mmol), NMM (0.20 mL, 1.84 mmol) and 1-piperidin-4-ylpyrrolidin-2-one hydrochloride (150 mg, 0.73 mmol) and the mixture sonicated to a fine suspension and stirred for 64 hours at room temperature. The volatiles were removed under high vacuum and the residue partitioned between EtOAc (70 mL) and water (25 mL). The aqueous layer was removed and the organics washed with NaHCO$_3$ (30 mL), brine (30 mL), dried over MgSO$_4$, filtered and stripped to yield the title compound as an off-white solid, 123 mg, 51%. $^1$H NMR (400 MHz, DMSO-D6) δ ppm 8.51-8.54 (2 H, m), 7.64-7.69 (2 H, m), 7.25-7.35 (2 H, m), 7.11-7.21 (2 H, m), 6.53 (1 H, s), 5.11-5.28 (2 H, m), 4.37 (1 H, d, J=13.14 Hz), 3.90-4.05 (4 H, m), 3.23-3.31 (2 H, m), 3.08-

3.20 (1 H, m), 2.57-2.70 (1 H, m), 2.22 (2 H, t, J=8.08 Hz), 1.84-1.95 (2 H, m), 1.40-1.73 (4 H, m); m/z (APCI+) for $C_{26}H_{28}N_5O_2F$ 462.2 (M+H)$^+$.

Example 6

4-(5-(4-fluorobenzyl)-1-{2-[4-(methylsulfonyl)piperidin-1-yl]-2-oxoethyl}-1H-pyrazol-3-yl)pyridine

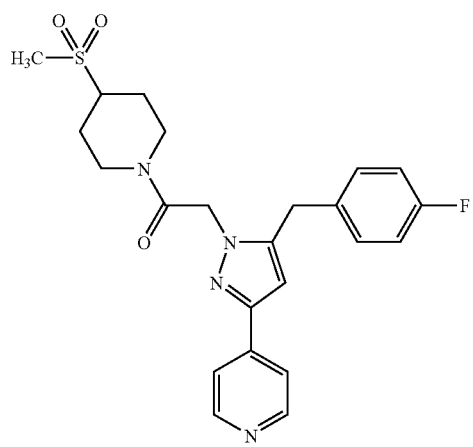

To a solution of [5-(4-fluorobenzyl)-3-pyridin-4-yl-1H-pyrazol-1-yl]acetic acid (150 mg, 0.48 mmol) in DMA (3 mL) at room temperature was added HOBt (72 mg, 0.53 mmol), EDCI (102 mg, 0.53 mmol), NMM (0.13 mL, 1.20 mmol) and 4-(methylsulfonyl)piperidine (117 mg, 0.72 mmol) and the mixture sonicated to a fine suspension and stirred for 18 hours at room temperature. The volatiles were removed under high vacuum and the residue partitioned between EtOAc (70 mL) and water (25 mL). The aqueous layer was removed and the organics washed with NaHCO$_3$ (30 mL), brine (30 mL), dried over MgSO$_4$, filtered and stripped to yield the title compound as an off-white solid, 144 mg, 66%. $^1$H NMR (400 MHz, DMSO-D6) δ ppm 8.46-8.56 (2 H, m), 7.60-7.71 (2 H, m), 7.25-7.37 (2 H, m), 7.07-7.19 (2 H, m), 6.53 (1 H, s), 5.10-5.41 (2 H, m), 4.40 (1 H, d, J=13.14 Hz), 3.97-4.15 (1 H, m), 3.95 (2 H, s), 3.34-3.49 (1 H, m), 3.12 (1 H, t, J=12.00 Hz), 2.96 (3 H, s), 2.64 (1 H, t, J=11.62 Hz), 2.06 (2 H, d, J=12.88 Hz), 1.59-1.79 (1 H, m), 1.36-1.54 (1 H, m); m/z (APCI+) for $C_{23}H_{25}N_4O_3F$ 457.1 (M+H)$^+$.

Example 7

1-{[5-(4-fluorobenzyl)-3-pyridin-4-yl-1H-pyrazol-1-yl]acetyl}-N-methylpiperidin-4-amine

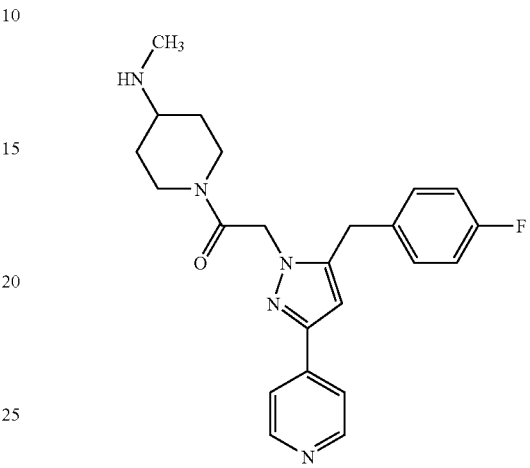

To a suspension of [5-(4-fluorobenzyl)-3-pyridin-4-yl-1H-pyrazol-1-yl]acetic acid (3.75 g, 12.06 mmol) in DMA (40 mL) at room temperature was added HOBt (1.79 g, 13.26 mmol), EDCI (2.54 g, 13.26 mmol), NMM (3.31 mL, 30.15 mmol) and tert-butyl methyl(piperidin-4-yl)carbamate (2.84 g, 13.26 mmol) and the mixture sonicated to a solution and stirred for 18 hours at room temperature. The volatiles were removed under high vacuum and the residue partitioned between EtOAc (300 mL) and water (100 mL). The aqueous layer was removed and the organics washed with NaHCO$_3$ (100 mL), water (100 mL), brine (100 mL), dried over MgSO$_4$, filtered and stripped to yield tert-butyl (1-{[5-(4-fluorobenzyl)-3-pyridin-4-yl-1H-pyrazol-1-yl]acetyl}piperidin-4-yl)methylcarbamate as a white solid. This was then taken into DCM (40 mL) and TFA (40 mL) added with stirring and the resulting solution stirred at ambient temperature for 18 hours. The volatiles were removed under vacuum and the residue suspended in DCM (200 mL) and 2 M NaOH added (200 mL) with stirring. The bi phasic solution was then stirred for 15 minutes and the phases separated. The organic layer was dried over MgSO4, filtered and stripped to yield the crude product which was then purified by Biotage flash chromatography (45 M cartridge), eluting with a DCM/MeOH/NH$_4$OH gradient to afford the title compound as a white solid, 4.6 g, 94%. $^1$H NMR (400 MHz, DMSO-D6) δ ppm 8.52 (d, 2 H), 7.66 (d, 2 H), 7.29 (t, 2 H), 7.15 (t, 2 H), 6.51 (s, 1 H), 5.16 (q, 2 H), 4.04 (d, 1 H), 3.95 (s, 2 H), 3.79 (d, 1 H), 3.07-3.17 (m, 1 H), 2.76-2.89 (m, 1 H), 2.27 (s, 3 H), 1.71-1.86 (m, 2 H), 1.59-1.65 (m, 1 H), 1.18-1.31 (m, 1 H), 1.03-1.14 (m, 1 H); m/z (APCI+) for $C_{23}H_{26}N_5OF$ 408.2 $(M+H)^+$.

Example 8

1-{[5-(4-fluorobenzyl)-3-pyridin-4-yl-1H-pyrazol-1-yl]acetyl}piperidin-4-amine

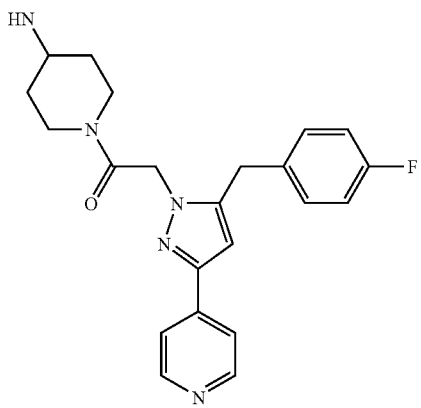

The title compound was prepared as in Example 7, except [5-(4-fluorobenzyl)-3-pyridin-4-yl-1H-pyrazol-1-yl]acetic acid (3.40 g, 10.93 mmol) and tert-butyl piperidin-4-ylcarbamate (2.36 g, 12.02 mmol) were used. The title compound was isolated as an off-white solid, 3.8 g, 90%. $^1$H NMR (400 MHz, DMSO-D6) δ ppm 8.53 (d, 2 H), 7.66 (d, 2 H), 7.30 (t, 2 H), 7.14 (t, 2 H), 6.51 (s, 1 H), 5.16 (q, 2 H), 4.09 (d, 1 H), 3.94 (s, 2 H), 3.78 (d, 1 H), 3.07 (t, 1 H), 2.68-2.83 (m, 2 H), 1.63-1.79 (m, 2 H), 1.13-1.28 (m, 1 H), 0.99-1.12 (m, 1 H); m/z (APCI+) for $C_{22}H_{24}N_5OF$ 394.2 $(M+H)^+$.

Example 9

1-{[5-(4-fluorobenzyl)-3-pyridin-4-yl-1H-pyrazol-1-yl]acetyl}-N-isopropylpiperidin-4-amine

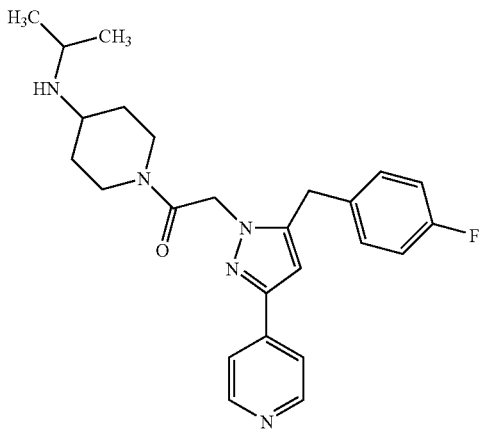

To a solution of 1-{[5-(4-fluorobenzyl)-3-pyridin-4-yl-1H-pyrazol-1-yl]acetyl}piperidin-4-amine (0.3 g, 0.76 mmol) in $CH_2Cl_2$ (5 mL) was added acetone (56 µL, 0.76 mmol) and the solution was stirred for 15 minutes at room temperature. This was followed by the addition of $NaBH(OAc)_3$ (0.242 g, 1.14 mmol) and the reaction mixture was stirred overnight at room temperature. The mixture was diluted with $CH_2Cl_2$ (20 mL) and 2 M NaOH and the biphasic solution was stirred for 20 minutes. The mixture was extracted with $CH_2Cl_2$ (2×25 mL) and the combined organic layers were dried over MgSO4, filtered and concentrated. The residue was purified by flash chromatography (90:10:1 $CH_2Cl_2$/MeOH/$NH_4OH$) to give the title compound as a white solid (0.19 g, 44%). $^1$H NMR (400 MHz, DMSO-D6) δ ppm 8.51 (d, 2 H), 7.66 (d, 2 H), 7.30 (t, 2 H), 7.14 (t, 2 H), 6.51 (s, 1 H), 5.13-5.20 (m, 2 H), 4.07-4.16 (m, 1 H), 3.93 (s, 2 H), 3.77-3.87 (m, 1 H), 3.04-3.14 (m, 1 H), 2.83-2.93 (m, 1 H), 2.69-2.79 (m, 2 H), 1.72-1.86 (m, 5H); m/z (APCI+) for $C_{25}H_{30}N_5OF$ 436.1 $(M+H)^+$.

Example 10

N-(1-{[5-(4-fluorobenzyl)-3-pyridin-4-yl-1H-pyrazol-1-yl]acetyl}piperidin-4-yl)-N-methylpropanamide

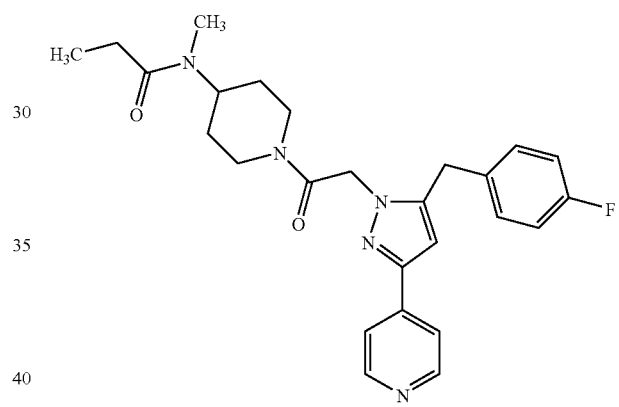

To a solution of 1-{[5-(4-fluorobenzyl)-3-pyridin-4-yl-1H-pyrazol-1-yl]acetyl}-N-methylpiperidin-4-amine (150 mg, 0.37 mmol) in DCM (3 mL) at room temperature was added triethylamine (56 µL, 0.40 mmol) followed by propanoyl chloride (32 µL, 0.37 mmol) and the solution stirred for 10 minutes. The solution was then loaded directly onto a pre-wetted Biotage 25M column for flash chromatography and eluted with 2-8% MeOH/DCM to yield the title compound as a white solid, 108 mg, 63%. $^1$H NMR (mix of rotamers, 400 MHz, DMSO-D6) δ ppm 8.52 (2 H, d, J=6.06 Hz) 7.57-7.76 (2 H, m), 7.30 (2 H, dd, J=8.46, 5.68 Hz, 7.15 (2 H, t, J=8.84 Hz), 6.52 (1 H, s), 5.05-5.43 (2 H, m), 4.46-4.62 (0.5 H, m), 4.38 (1 H, d, J=12.63 Hz), 3.85-4.00 (3.5 H, m), 3.05-3.23 (1 H, m), 2.77 (2 H, s), 2.65 (1 H, s), 2.55-2.63

(1 H, m), 2.39 (1 H, q, J=7.33 Hz), 2.29 (1 H, q, J=7.33 Hz), 1.41-1.80 (4 H, m), 0.98 (3 H, q, J=7.49 Hz); m/z (APCI+) for $C_{26}H_{30}N_5O_2F$ 464.2 (M+H)$^+$.

Example 11

N-(1-{[5-(4-fluorobenzyl)-3-pyridin-4-yl-1H-pyrazol-1-yl]acetyl}piperidin-4-yl)-N,2-dimethylpropanamide

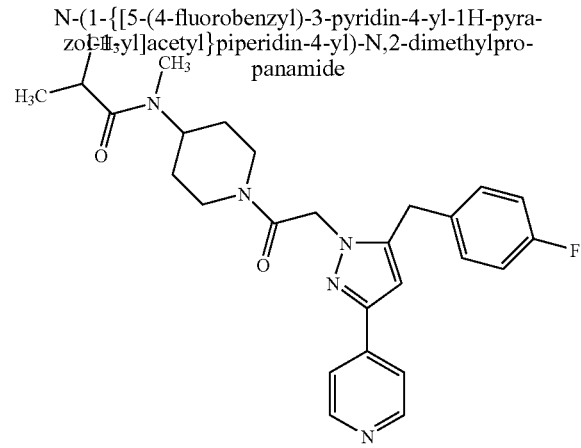

To a solution of 1-{[5-(4-fluorobenzyl)-3-pyridin-4-yl-1H-pyrazol-1-yl]acetyl}-N-methylpiperidin-4-amine (150 mg, 0.37 mmol) in DCM (3 mL) at room temperature was added triethylamine (56 μL, 0.40 mmol) followed by 2-methylpropanoyl chloride (32 μL, 0.37 mmol) and the solution stirred for 10 minutes. The solution was then loaded directly onto a pre-wetted Biotage 25M column for flash chromatography and eluted with 2-8% MeOH/DCM to yield the title compound as a white solid, 147 mg, 83%. $^1$H NMR (mix of rotomers, 400 MHz, DMSO-D6) δ ppm 8.47-8.60 (2 H, m) 7.62-7.72 (2 H, m) 7.31 (2 H, dd, J=8.46, 5.68 Hz) 7.15 (2 H, t, J=8.97 Hz) 6.53 (1 H, s) 5.07-5.35 (2 H, m) 4.43-4.61 (0.5 H, m) 4.38 (1 H, d, J=12.88 Hz) 3.95 (3.5 H, s) 3.05-3.29 (1 H, m) 2.88-3.04 (0.5 H, m) 2.53-2.89 (4.5 H, m) 1.39-1.86 (4 H, m) 0.91-1.08 (6 H, m); m/z (APCI+) for $C_{27}H_{32}N_5O_2F$ 478.2 (M+H)$^+$.

Example 12

N-(1-{[5-(4-fluorobenzyl)-3-pyridin-4-yl-1H-pyrazol-1-yl]acetyl}piperidin-4-yl)-N-methylcyclobutanecarboxamide

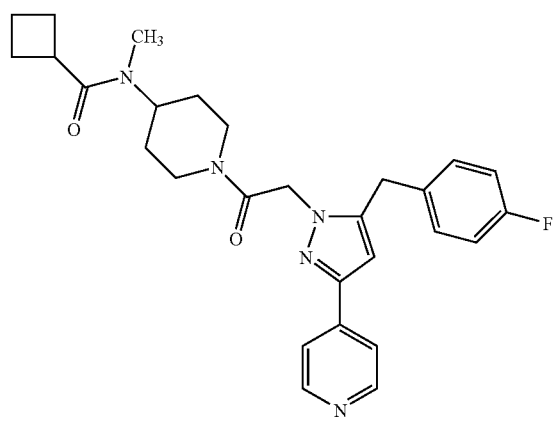

To a solution of 1-{[5-(4-fluorobenzyl)-3-pyridin-4-yl-1H-pyrazol-1-yl]acetyl}-N-methylpiperidin-4-amine (150 mg, 0.37 mmol) in DCM (3 mL) at room temperature was added triethylamine (56 μL, 0.40 mmol) followed by cyclobutanecarbonyl chloride (42 μL, 0.37 mmol) and the solution stirred for 10 minutes. The solution was then loaded directly onto a pre-wetted Biotage 25M column for flash chromatography and eluted with 2-8% MeOH/DCM to yield the title compound as a white solid, 154 mg, 85%; $^1$H NMR (mix of rotomers, 400 MHz, DMSO-D6) δ ppm 8.52 (2 H, d, J=6.06 Hz), 7.66 (2 H, d, J=6.06 Hz), 7.30 (2 H, dd, J=8.46, 5.68 Hz), 7.15 (2 H, t, J=8.97 Hz), 6.52 (1 H, s), 5.08-5.33 (2 H, m), 4.42-4.57 (0.5 H, m), 4.38 (1 H, d, J=13.39 Hz), 3.95 (3 H, s), 3.64-3.79 (0.5 H, m), 3.36-3.48 (0.5 H, m), 3.24-3.34 (0.5 H, m), 3.03-3.20 (1 H, m), 2.55-2.76 (4 H, m), 2.01-2.28 (4 H, m), 1.39-1.99 (6 H, m); m/z (APCI+) for $C_{28}H_{32}N_5O_2F$ 490.2 (M+H)$^+$.

Example 13

N-(1-{[5-(4-fluorobenzyl)-3-pyridin-4-yl-1H-pyrazol-1-yl]acetyl}piperidin-4-yl)-N-methylcyclopropanecarboxamide To a solution of 1-{[5-(4-fluorobenzyl)-3-pyridin-4-yl-1H-pyrazol-1-yl]acetyl}-N-methylpiperidin-4-amine (150 mg, 0.37 mmol) in DCM (3 mL) at room temperature was added triethylamine (56 μL, 0.40 mmol) followed by cyclopropanecarbonyl chloride (34 μL, 0.37 mmol) and the solution stirred for 10 minutes. The solution was then loaded directly onto a pre-wetted Biotage 25M column for flash chromatography and eluted with 2-8% MeOH/DCM to yield the title compound as a white solid, 162 mg, 92%. $^1$H NMR (rotomers seen, 400 MHz, DMSO-D6) δ ppm 8.43-8.59 (2 H, m), 7.59-7.72 (2 H, m), 7.31 (2 H, dd, J=8.46, 5.68 Hz), 7.15 (2 H, t, J=8.84 Hz), 6.52 (1 H, s), 5.10-5.36 (2 H, m), 4.22-4.60 (2 H, m), 3.95 (3 H, s), 3.03-3.26 (1 H, m), 2.53-3.01 (4

H, m), 1.42-2.10 (5 H, m), 0.62-0.79 (4 H, m); m/z (APCI+) for $C_{27}H_{30}N_5O_2F$ 476.2 (M+H)$^+$.

Example 14

N-(1-{[5-(4-fluorobenzyl)-3-pyridin-4-yl-1H-pyrazol-1-yl]acetyl}piperidin-4-yl)-N-methylmethanesulfonamide

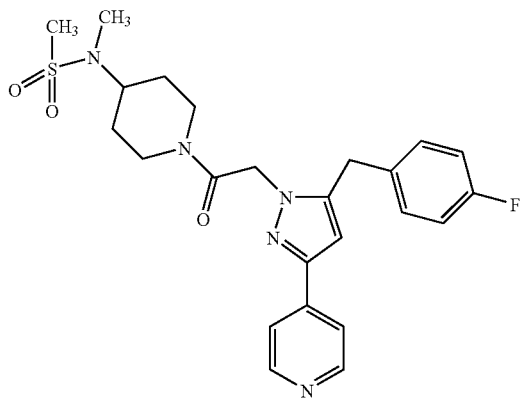

To a solution of 1-{[5-(4-fluorobenzyl)-3-pyridin-4-yl-1H-pyrazol-1-yl]acetyl}-N-methylpiperidin-4-amine (150 mg, 0.37 mmol) in DCM (3 mL) at room temperature was added triethylamine (56 µL, 0.40 mmol) followed by methanesulfonyl chloride (29 µL, 0.37 mmol) and the solution stirred for 10 minutes. The solution was then loaded directly onto a pre-wetted Biotage 25M column for flash chromatography and eluted with 2-8% MeOH/DCM to yield the title compound as a white solid, 137 mg, 76%. $^1$H NMR (400 MHz, DMSO-D6) δ ppm 8.47-8.56 (2 H, m), 7.61-7.68 (2 H, m), 7.23-7.35 (2 H, m), 7.03-7.19 (2 H, m), 6.52 (1 H, s), 5.10-5.29 (2 H, m), 4.37 (1 H, d, J=13.39 Hz), 3.90-3.99 (3 H, m), 3.74-3.89 (1 H, m), 3.06-3.19 (1 H, m), 2.93 (3 H, s), 2.68 (3 H, s), 2.58-2.65 (1 H, m), 1.62-1.77 (3 H, m), 1.42-1.59 (1 H, m); m/z (APCI+) for $C_{24}H_{28}N_5O_3FS$ 486.2 (M+H)$^+$.

Example 15

Methyl (1-{[5-(4-fluorobenzyl)-3-pyridin-4-yl-1H-pyrazol-1-yl]acetyl}piperidin-4-yl)methylcarbamate

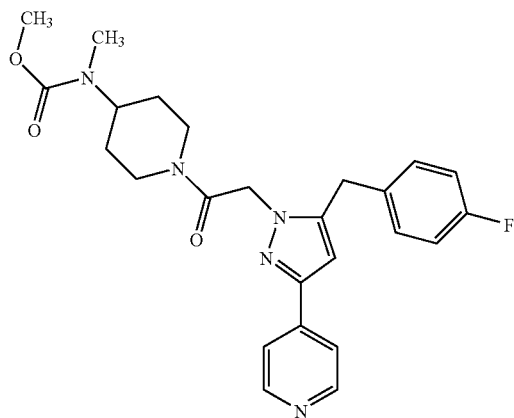

To a solution of 1-{[5-(4-fluorobenzyl)-3-pyridin-4-yl-1H-pyrazol-1-yl]acetyl}-N-methylpiperidin-4-amine (150 mg, 0.37 mmol) in DCM (3 mL) at room temperature was added triethylamine (56 µL, 0.40 mmol) followed by methyl chloroformate (29 µL, 0.37 mmol) and the solution stirred for 10 minutes. The solution was then loaded directly onto a pre-wetted Biotage 25M column for flash chromatography and eluted with 2-8% MeOH/DCM to yield the title compound as a white solid, 122 mg, 71%. $^1$H NMR (400 MHz, DMSO-D6) δ ppm 8.52 (2 H, d, J=4.80 Hz), 7.66 (2 H, d, J=5.05 Hz), 7.30 (2 H, dd, J=8.34, 5.81 Hz), 7.15 (2 H, t, J=8.72 Hz), 6.52 (1 H, s), 5.10-5.27 (2 H, m), 4.38 (1 H, d, J=12.63 Hz), 3.99-4.16 (1 H, m), 3.85-4.00 (3 H, m), 3.59 (3 H, s), 3.04-3.16 (1 H, m), 2.70 (3 H, s), 2.56-2.67 (1 H, m), 1.41-1.75 (4 H, m); m/z (APCI+) for $C_{25}H_{28}N_5O_3F$ 466.2 (M+H)$^+$.

Example 16

N-(1-{[5-(4-fluorobenzyl)-3-pyridin-4-yl-1H-pyrazol-1-yl]acetyl}piperidin-4-yl)-N'-isopropyl-N-methylurea

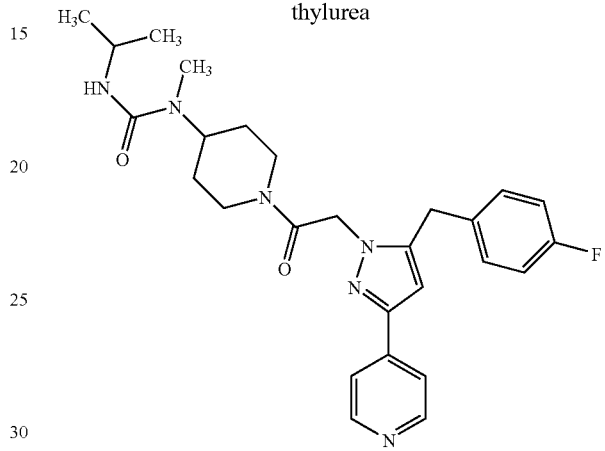

To a solution of 1-{[5-(4-fluorobenzyl)-3-pyridin-4-yl-1H-pyrazol-1-yl]acetyl}-N-methylpiperidin-4-amine (150 mg, 0.37 mmol) in DCM (3 mL) at room temperature was added isopropyl isocyanate (36 µL, 0.37 mmol) and the solution stirred for 10 minutes. The volatiles were removed under vacuum and the residue azeotroped with EtOAc to yield a solid that was triturated with EtOAc to afford title compound as a white solid, 102 mg, 56%. $^1$H NMR (400 MHz, DMSO-D6) δ ppm 8.52 (2 H, d, J=6.06 Hz), 7.66 (2 H, d, J=6.06 Hz), 7.30 (2 H, dd, J=8.46, 5.68 Hz), 7.15 (2 H, t, J=8.84 Hz), 6.52 (1 H, s), 5.87 (1 H, d, J=7.58 Hz), 5.05-5.30 (2 H, m), 4.37 (1 H, d, J=12.88 Hz), 4.11-4.24 (1 H, m), 3.95 (2 H, s), 3.92 (1 H, s), 3.69-3.83 (1 H, m), 3.08 (1 H, t, J=12.13 Hz), 2.54-2.65 (4 H, m), 1.32-1.71 (4 H, m), 1.05 (6 H, d, J=6.57 Hz); m/z (APCI+) for $C_{27}H_{33}N_6O_2F$ 493.2 (M+H)$^+$.

Example 17

N-(1-{[5-(4-fluorobenzyl)-3-pyridin-4-yl-1H-pyrazol-1-yl]acetyl}piperidin-4-yl)-N'-isopropylurea

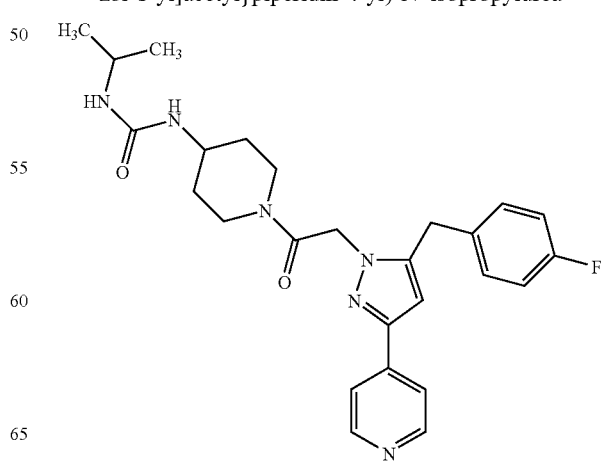

To a solution of 1-{[5-(4-fluorobenzyl)-3-pyridin-4-yl-1H-pyrazol-1-yl]acetyl}piperidin-4-amine (635 mg, 1.61 mmol) in THF (10 mL) at room temperature was added isopropyl isocyanate (164 mg, 1.93 mmol) and the solution stirred 50° C. for 16 h. The volatiles were removed under vacuum and the residue was triturated with water to afford a white solid, 627 mg, 82%. $^1$H NMR (400 MHz, DMSO-$d_6$) δ ppm 1.02 (d, J=6.55 Hz, 6 H), 1.08-1.21 (m, J=7.18, 7.18 Hz, 1 H), 1.23-1.39 (m, 1 H), 1.65-1.90 (m, 2 H), 2.81 (t, J=10.95 Hz, 1 H), 3.05-3.25 (m, J=11.33, 11.33 Hz, 1 H), 3.50-3.72 (m, 2 H), 3.80 (d, J=13.60 Hz, 1 H), 3.95 (s, 2 H), 4.07 (d, J=13.35 Hz, 1 H), 5.03-5.33 (m, 2 H), 5.58 (d, J=7.81 Hz, 1 H), 5.75 (d, J=7.81 Hz, 1 H), 6.56 (s, 1 H), 7.02-7.26 (m, 2 H), 7.22-7.40 (m, 2 H), 7.64-7.79 (m, 2 H), 8.56 (d, J=6.04 Hz, 2 H); m/z (APCI+) for $C_{26}H_{31}FN_6O_2$ 479.6 (M+H)$^+$.

Example 18

N-(1-{2-[5-(4-fluorobenzyl)-3-pyridin-4-yl-1H-pyrazol-1-yl]acetyl}piperidin-4-yl)cyclobutanecarboxamide

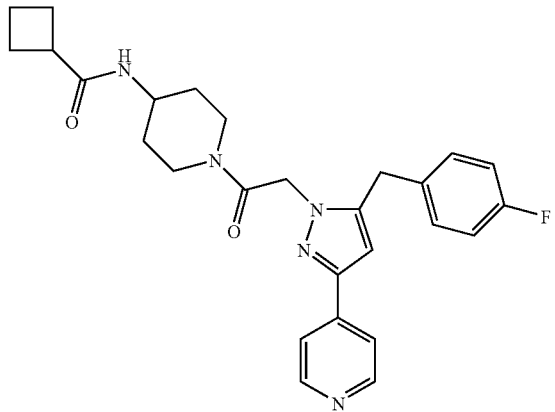

To a solution of 1-{[5-(4-fluorobenzyl)-3-pyridin-4-yl-1H-pyrazol-1-yl]acetyl}piperidin-4-amine (150 mg, 0.38 mmol) in DCM (4 mL) at room temperature was added triethylamine (56 µL, 0.40 mmol) followed by cyclobutanecarbonyl chloride (43 µL, 0.38 mmol) and the solution stirred for 10 minutes. The solution was then loaded directly onto a pre-wetted Biotage 25M column for flash chromatography and eluted with 2-8% MeOH/DCM to yield the title compound as a white solid, 138 mg, 76%. $^1$H NMR (400 MHz, DMSO-D6) δ ppm 8.43-8.56 (2 H, m), 7.60-7.70 (3 H, m), 7.24-7.35 (2 H, m), 7.09-7.21 (2 H, m), 6.51 (1 H, s), 5.09-5.31 (2 H, m), 4.13 (1 H, d, J=13.39 Hz), 3.93 (2 H, s), 3.70-3.88 (2 H, m), 3.15 (1 H, t, J=11.37 Hz), 2.89-3.04 (1 H, m), 2.69-2.82 (1 H, m), 2.03-2.17 (2 H, m), 1.93-2.03 (2 H, m), 1.81-1.92 (1 H, m), 1.66-1.80 (3 H, m,), 1.29-1.48 (1 H, m), 1.13-1.27 (1 H, m); m/z (APCI+) for $C_{27}H_{30}N_5O_2F$ 476.2 (M+H)$^+$.

Example 19

N-(1-{2-[5-(4-fluorobenzyl)-3-pyridin-4-yl-1H-pyrazol-1-yl]acetyl}piperidin-4-yl)methanesulfonamide

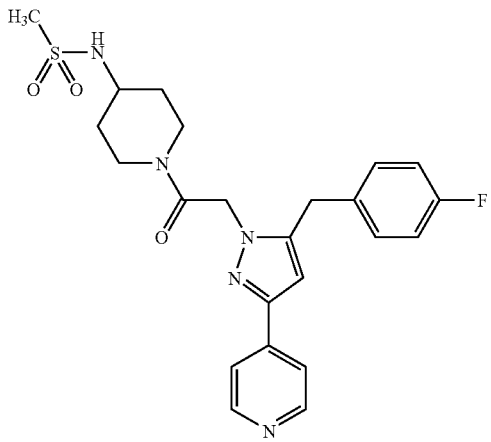

To a solution of 1-{[5-(4-fluorobenzyl)-3-pyridin-4-yl-1H-pyrazol-1-yl]acetyl}piperidin-4-amine (1.13 g, 2.87 mmol) in $CH_2Cl_2$ (10 mL) was added triethylamine (442.0 µL, 3.20 mmol) followed by sulfonyl chloride (223.0 µL, 2.87 mmol) and the reaction stirred at 25° C. for 1 hour. The solvent was removed in vacuo, and the residue was taken up in EtOAc (200 mL) and washed with water (2×50 mL), brine (100 mL), dried over MgSO$_4$, filtered and stripped. The resulting gum was azeotroped with EtOAc (2×200 mL) to yield a white solid. The white solid was taken up in MeOH (25 mL) with heating, and left to crystallize overnight to afford small colorless needles. The MeOH was decanted and the crystals washed with MeOH (3×15 mL), EtOAc (3×30 mL) and finally hexane (2×25 mL, then 100 mL) and dried at room temperature to yield the title compound as white needles, 968 mg, 72 %. $^1$H NMR (400 MHz, DMSO-D6) δ ppm 8.53 (d, 2 H), 7.65 (d, 2 H), 7.30 (t, 2 H), 7.20 (s, 1 H), 7.15 (t, 2 H), 6.52 (s, 1 H), 5.18 (q, 2 H), 4.10 (d, 1 H), 3.93 (s, 2 H), 3.83 (d, 1 H), 3.36-3.46 (m, 1 H), 3.17 (t, 1 H), 2.94 (s, 3 H), 2.80 (t, 1 H), 1.79-1.92 (m, 2 H), 1.41-1.52 (m, 1 H), 1.23-1.34 (m, 1 H); m/z (APCI+) for $C_{23}H_{26}N_5O_3FS$ 472.1 (M+H)$^+$.

The free base of the title compound (2.0 g, 4.24 mmol) was suspended in 1,4-dioxane (150 mL) and isopropyl alcohol (150 mL) at room temperature. The mixture became homogenous after ~15 min of stirring. To the solution was added the 1N methanesulfonic acid solution (4.67 mL, 4.67 mmol) and the resulting clear solution was stirred at room temperature for about 2 h and was then cooled in an ice bath. Stirring was continued for an additional 2 hours, after which time the mixture was allowed to stand in a refrigerator for about 16 hours, resulting in the formation of a white precipitate. The precipitate was isolated by filtration and dried in a 40° C. vacuum oven for about 8 hours. The solid (2.05 g) was then suspended in dry toluene (125 mL) and heated to about 90° C. with stirring for about 5 hours. The resulting solid was isolated by filtration and dried in a 40° C. vacuum oven to afford 1.96 g of the mesylate salt of the title compound. $^1$H NMR (400 MHz, DMSO-D6) δ ppm 8.85 (d, 2H) 8.29 (d, 2H)

7.39-7.15 (m, 5H) 6.85 (s, 1H) 5.36 (q, 2H) 4.14 (d, 1H) 4.00 (s, 2H) 3.85 (d, 1H) 3.43 (m, 1H) 3.21 (t, 1H) 2.99 (s, 3H) 2.82 (t, 1H) 2.32 (s, 3H) 1.99-1.81 (m, 2H) 1.61-1.25 (m, 2H).

| PXRD Peak Data: | |
|---|---|
| Angle (2-Theta °) | d value (Angstrom) |
| 5.81 | 15.21 |
| 6.98 | 12.65 |
| 7.59 | 11.63 |
| 10.26 | 8.62 |
| 13.80 | 6.41 |
| 15.03 | 5.89 |
| 15.85 | 5.59 |
| 17.22 | 5.15 |
| 18.44 | 4.81 |
| 19.32 | 4.59 |
| 19.74 | 4.49 |
| 20.47 | 4.34 |
| 22.31 | 3.98 |
| 23.31 | 3.81 |
| 24.95 | 3.57 |
| 26.22 | 3.40 |
| 27.79 | 3.21 |
| 29.67 | 3.01 |
| 30.23 | 2.95 |

Example 20

4-[1-[1-(diphenylmethyl)azetidin-3-yl]-5-(4-fluorobenzyl)-1H-pyrazol-3-yl]pyridine

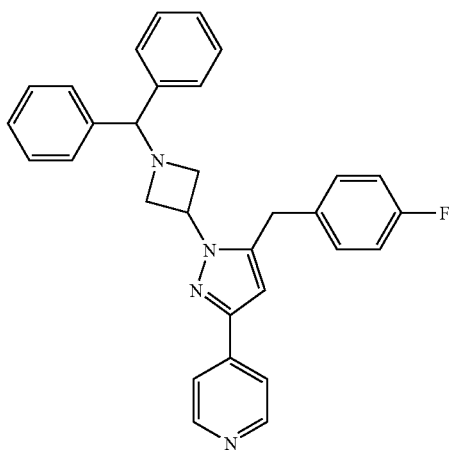

To a solution of 4-[5-(4-fluorobenzyl)-1H-pyrazol-3-yl]pyridine (3.7 g, 14.6 mmol) in DMF (40 mL) was added NaH (0.584 g, 14.6 mmol) and the solution was stirred for 10 minutes under nitrogen. 3-Iodo-N-benzhydryl-azetidine (5.61 g, 16.1 mmol) was then added and the reaction mixture was heated to 110° C. for 2 hours under nitrogen. The solvent was removed in-vacuo and the residue was diluted with H$_2$O and extracted with EtOAc. The organic layer was washed with H$_2$O, brine, dried over MgSO$_4$, filtered and stripped to yield a crude mix of regioisomers. The residue was purified by flash chromatography (5:95 MeOH/CH$_2$Cl$_2$) to yield a clean mix of regioisomers that were separated by SF chromatography to yield the title compound as a lyophilized solid (2.35 g, 34%. $^1$H NMR (400 MHz, CHLOROFORM-D) δ ppm 8.62 (d, 2 H), 7.69 (d, 2 H), 7.42 (d, 4 H), 7.24-7.31 (m, 4 H), 7.14-7.24 (m, 2 H), 7.02-7.09 (m, 2 H), 6.97 (s, 2 H), 6.36-6.39 (m, 1 H), 4.74-4.87 (m, 1 H), 4.57 (s, 1 H), 3.94 (s, 2 H), 3.51-3.62 (m, 4 H); m/z (APCI+) for C$_{32}$H$_{27}$N$_4$F 475.3 (M+H)$^+$.

Example 21

4-(5-(4-fluorobenzyl)-1-(azetidin-3-yl)-1H-pyrazol-3-yl)pyridine

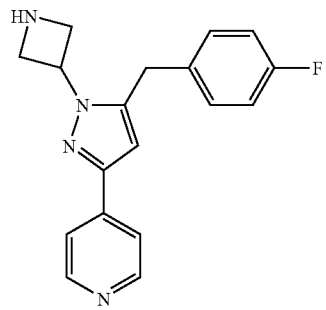

To a flask charged with NH$_4$CO$_2$H (6.2 g, 98.4 mmol) was added MeOH (50 mL) and stirred to a solution, followed by addition of a solution of 4-[1-[1-(diphenylmethyl)azetidin-3-yl]-5-(4-fluorobenzyl)-1H-pyrazol-3-yl]pyridine (2.3 g, 4.85 mmol) in EtOAc (50 mL), and the mixture stirred to a homogenous solution. This was added to a second flask containing 10% Pd/C (0.84 g) in MeOH (100 mL) under N$_2$, and the reaction mixture was heated to 57° C. under N$_2$ for 5 hours. The mixture was cooled to room temperature and the solids removed by filtration through a GF/F filter set. The filtrate was concentrated and diluted with water (50 mL) and then saturated with NaOH. The emulsion was then extracted with CH$_2$Cl$_2$ (3×100 mL) followed by Et$_2$O (4×100 mL). The combined organic layers were dried over MgSO$_4$, filtered and concentrated. The crude residue was purified by flash chromatography (90:10:1 CH$_2$Cl$_2$/MeOH/NH$_4$OH) to yield the title compound as a white solid, 0.892 g, 60%. $^1$H NMR (400 MHz, CHLOROFORM-D) δ ppm 8.61 (d, 2 H), 7.69 (d, 2 H), 7.06-7.14 (m, 2 H), 6.95-7.05 (m, 2 H), 6.42 (s, 1 H), 4.91-5.08 (m, 1 H), 4.29 (t, 2 H), 3.98 (s, 2 H), 3.61 (t, 2 H); m/z (APCI+) for C$_{18}$H$_{17}$N$_4$F 309.2 (M+H)$^+$.

Example 22

1-(3-(5-(4-fluorobenzyl)-3-(pyridin-4-yl)-1H-pyrazol-1-yl)azetidin-1-yl)propan-1-one

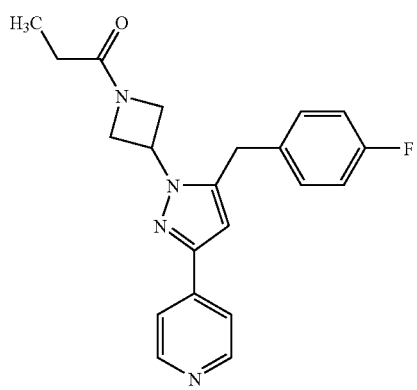

To a solution of 4-(5-(4-fluorobenzyl)-1-(azetidin-3-yl)-1H-pyrazol-3-yl)pyridine (75 mg, 0.24 mmol) in CH$_2$Cl$_2$ (2 mL) was added propionyl chloride (22 µL, 0.24 mmol) and triethylamine (37 µL, 0.26 mmol) and the reaction mixture was stirred at room temperature for 2 hours. The solution was then loaded directly onto a pre-wetted Biotage 25M column and purified by flash chromatography (0-5% MeOH/CH$_2$Cl$_2$) to give the title compound as a white solid, 68 mg, 78%. $^1$H NMR (400 MHz, DMSO-D6) δ ppm 8.57 (d, 2 H), 7.74 (d, 2 H), 7.26 (t, 2 H), 7.16 (t, 2 H), 6.72 (s, 1 H), 5.25-5.34 (m, 1 H), 4.32-4.45 (m, 2 H), 4.07-4.13 (m, 4 H), 2.09 (q, 2 H), 0.97 (t, 3 H); m/z (APCI+) for C$_{21}$H$_{21}$N$_4$FO 365.1 (M+H)$^+$.

Example 23

4-{5-(4-fluorobenzyl)-1-[1-(methylsulfonyl)azetidin-3-yl]-1H-pyrazol-3-yl}pyridine

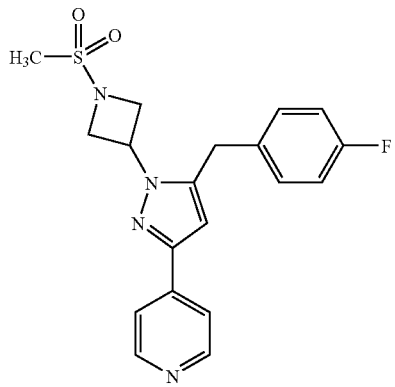

To a solution of 4-(5-(4-fluorobenzyl)-1-(azetidin-3-yl)-1H-pyrazol-3-yl)pyridine (75 mg, 0.24 mmol) in CH$_2$Cl$_2$ (2 mL) was added methanesulfonyl chloride (19 µL, 0.24 mmol) and triethylamine (37 µL, 0.26 mmol) and the reaction mixture was stirred at room temperature for 2 hours. The solution was then loaded directly onto a pre-wetted Biotage 25M column and purified by flash chromatography (0-5% MeOH/CH$_2$Cl$_2$) to give the title compound as a white solid, 77 mg, 83%. $^1$H NMR (400 MHz, CHLOROFORM-D) δ ppm 8.58-8.67 (2 H, m), 7.59-7.69 (2 H, m), 6.97-7.13 (4 H, m), 6.49 (1 H, s), 4.84-4.98 (1 H, m), 4.45 (2 H, dd, J=8.97, 6.44 Hz), 4.05 (2 H, t, J=8.34 Hz), 4.01 (2 H, s,) 3.05 (3 H, s); m/z (APCI+) for C$_{19}$H$_{19}$N$_4$O$_2$SF 387.1 (M+H)$^+$.

Example 24

4-{5-(4-fluorobenzyl)-1-[1-(1H-imidazol-2-ylcarbonyl)azetidin-3-yl]-1H-pyrazol-3-yl}pyridine

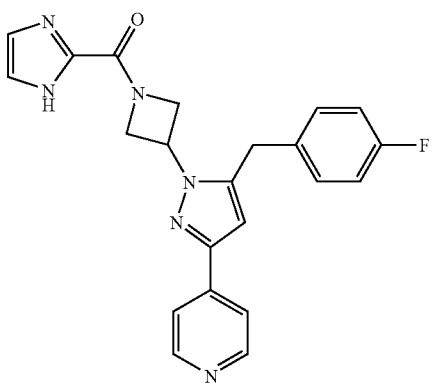

To a suspension of 4-(5-(4-fluorobenzyl)-1-(azetidin-3-yl)-1H-pyrazol-3-yl)pyridine (85 mg, 0.28 mmol) in DMF (3 mL) was added HOBt (45 mg, 0.33 mmol), EDCI (64 mg, 0.33 mmol), NMM (76 µL, 0.69 mmol) followed by imidazole-2-carboxylic acid (34 mg, 0.30 mmol) and the mixture stirred for 16 hours at room temperature. The volatiles were removed in vacuo and the residue purified directly by Biotage flash chromatography, eluting with 2-6% MeOH/DCM to yield a clear gum. Ether was added (5 mL) and the mix sonicated to give a white precipitate that was filtered off, washed with ether and dried in-vacuo to yield the title compound as a white solid, 78 mg, 70%. $^1$H NMR (400 MHz, DMSO-D6) δ ppm 13.04-13.12 (m, 1 H), 8.54 (d, 2 H), 7.74 (d, 2 H), 7.25-7.32 (m, 2 H), 7.18 (t, 2 H), 7.03-7.12 (m, 1 H), 6.66 (s, 1 H), 5.33-5.46 (m, 1 H), 4.77-4.92 (m, 2 H), 4.26-4.36 (m, 2 H), 4.12 (s, 2 H); m/z (APCI+) for C$_{22}$H$_{19}$N$_6$FO 403.1 (M+H)$^+$.

Example 25

2-(5-{[5-(4-fluorobenzyl)-3-pyridin-4-yl-1H-pyrazol-1-yl]methyl}-1,2,4-oxadiazol-3-yl)pyrimidine

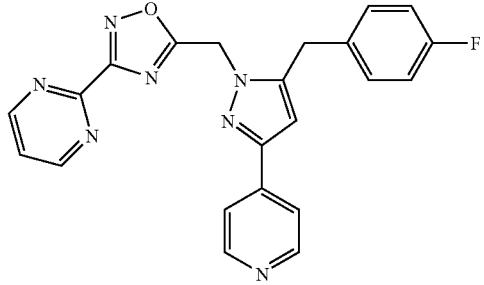

To a suspension of [5-(4-fluorobenzyl)-3-pyridin-4-yl-1H-pyrazol-1-yl]acetic acid (200 mg, 0.64 mmol) in THF (2 mL) and DMF (2 mL) was added CDI (240 mg, 1.41 mmol) and stirred for 2 hours forming a clear solution. To this was added N'-hydroxypyrimidine-2-carboximidamide (115 mg, 0.84 mmol) and the resulting suspension stirred for 18 hours at room temperature. The solid was filtered off to yield crude N'-({2-[5-(4-fluorobenzyl)-3-pyridin-4-yl-1H-pyrazol-1-yl]acetyl}oxy)pyrimidine-2-carboximidamide, and suspended in THF (2 mL) and a solution of TBAF (1 M in THF, 0.64 mL, 0.64 mmol) was added and the mixture stirred for 15 minutes at room temperature. The volatiles were then removed in vacuo and the residue purified by Biotage flash chromatography, eluting with 2-6% MeOH/DCM to afford the title compound as a waxy white solid, 100 mg, 37%. $^1$H NMR (400 MHz, DMSO-D6) δ ppm 9.00 (d, 2 H), 8.56 (d, 2 H), 7.68-7.73 (m, 3 H), 7.27-7.33 (m, 2 H), 7.05 (t, 2 H), 6.77 (s, 1 H), 6.00 (s, 2 H), 4.18 (s, 2 H); m/z (APCI+) for C$_{22}$H$_{16}$N$_7$FO 414.1 (M+H)$^+$.

Example 26 ethyl 5-{[5-(4-fluorobenzyl)-3-pyridin-4-yl-1H-pyrazol-i-yl]methyl}-1,4-oxadiazole-3-carboxylate

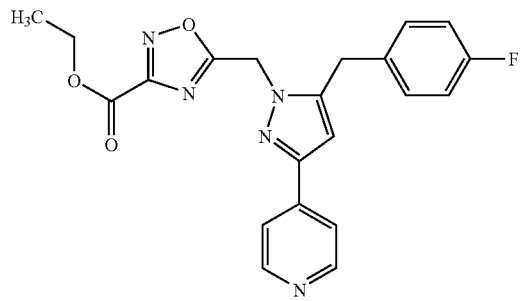

The title compound was prepared in a similar fashion to example 24 from [5-(4-fluorobenzyl)-3-pyridin-4-yl-1H-pyrazol-1-yl]acetic acid (1000 mg, 3.21 mmol) and ethyl (2Z)-amino(hydroxyimino)acetate (637 mg, 4.82 mmol) to afford the title compound as a white solid, 313 mg, 52%. $^1$H NMR (400 MHz, CHLOROFORM-D) δ ppm 8.55-8.70 (2 H, m), 7.62 (2 H, dd, J=4.55, 1.52 Hz), 7.13 (2 H, dd, J=8.34, 5.31 Hz), 6.99 (2 H, t, J=8.72 Hz), 6.48 (1 H, s), 5.52 (2 H, s), 4.49 (2 H, q, J=7.07 Hz), 4.08 (2 H, s), 1.43 (3 H, t, J=7.07 Hz); m/z (APCI+) for $C_{21}H_{18}N_5O_3F$ 408.1 (M+H)$^+$.

Example 27

5-{[5-(4-fluorobenzyl)-3-pyridin-4-yl-1H-pyrazol-1-yl]methyl}-N,N-dimethyl-1,2,4-oxadiazole-3-carboxamide (maleic acid salt)

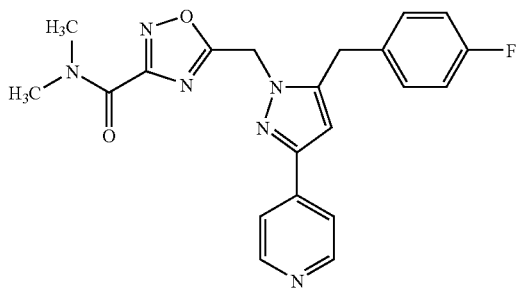

To a suspension of ethyl 5-{[5-(4-fluorobenzyl)-3-pyridin-4-yl-1H-pyrazol-1-yl]methyl}-1,2,4-oxadiazole-3-carboxylate (73 mg, 0.18 mmol) in EtOH (3 ml) was added dimethylamine (2 M in MeOH, 4 mL) and the mixture was stirred overnight at room temperature. The solvent was removed and the residue was purified by flash chromatography (2:98 MeOH/CH$_2$Cl$_2$) to give a clear oil. This was taken up in EtOAc (5 ml) and a solution of maleic acid (15 mg, 0.13 mmol) in EtOAc (2 mL) was added to the solution. The resulting salt suspension was stirred for 30 min, filtered and dried overnight to give the title compound (57 mg, 89%) as an off white solid. $^1$H NMR (400 MHz, DMSO-D6) δ ppm 8.62 (d, 2 H), 7.82 (d, 2 H), 7.26-7.35 (m, 2 H), 7.12 (t, 2 H,) 6.82 (s, 1 H), 6.00 (s, 2 H), 4.18 (s, 2 H), 3.03 (s, 3 H), 2.95 (s, 3 H); m/z (APCI+) for $C_{21}H_{19}N_6O_2F$ 407.1 (M+H)$^+$.

Example 28

4-{5-(4-fluorobenzyl)-1-[(5-methyl-1,3,4-oxadiazol-2-yl)methyl]-1H-pyrazol-3-yl}pyridine

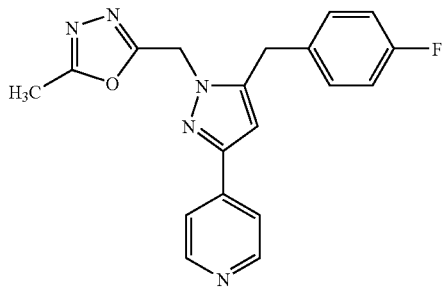

To a suspension of [5-(4-fluorobenzyl)-3-pyridin-4-yl-1H-pyrazol-1-yl]acetic acid (300 mg, 0.96 mmol) in THF (5 mL) and DMF (2 mL) was added CDI (345 mg, 2.12 mmol) and the suspension sonicated for 5 minutes to give a solution that was stirred for 2 hours at room temperature. To this was added acetic hydrazide (210 mg, 2.89 mmol) and the resulting suspension stirred for 18 hours at room temperature. The resulting suspension was diluted with water (50 mL) and the solid filtered off and washed with water (30 mL) and EtOAc (50 mL) to yield pure N'-acetyl-2-[5-(4-fluorobenzyl)-3-pyridin-4-yl-1H-pyrazol-1-yl]acetohydrazide. This was suspended in THF (5 mL) then Burgess' reagent (279 mg, 1.17 mmol) was added and the mixture heated to reflux for 2 hours. The reaction was cooled to ambient temperature, the volatiles removed in vacuo, and the residue was taken into EtOAc (50 mL) and washed with water (2×50 mL), brine (50 mL), dried over MgSO4, filtered and stripped. The residue was purified by Biotage flash chromatography, eluting with 1-4% MeOH/DCM to afford the title compound as a white solid, 200 mg, 73%. $^1$H NMR (400 MHz, CHLOROFORM-D) δ ppm 8.50-8.68 (2 H, m), 7.52-7.70 (2 H, m), 7.16 (2 H, dd, J=8.59, 5.31 Hz), 6.93-7.08 (2 H, m), 6.44 (1 H, s), 5.40 (2 H, s), 4.08 (2 H, s), 2.47 (3 H, s); m/z (APCI+) for $C_{19}H_{16}N_5FO$ 350.1 (M+H)$^+$.

Example 29

2-[5-(4-fluorobenzyl)-3-pyridin-4-yl-1H-pyrazol-1-yl]ethanol

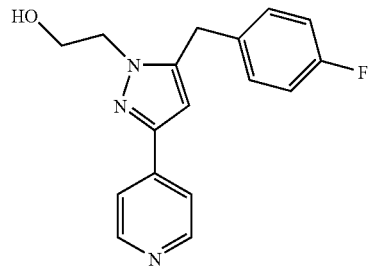

To a solution of methyl isonicotinate (2 g, 14.58 mmol) in THF (50 mL) was added 4-fluorophenylacetone (2.54 mL, 18.9 mmol) and sodium methoxide powder (1.6 g, 29.17 mmol) was added in one portion with stirring. The resulting suspension was heated to 75° C. for 2 hours under nitrogen, then cooled to ambient and AcOH added (3 mL) followed by EtOH (60 mL) forming a dark orange solution. 2-hydrazinoethanol (3.5 mL, excess) was then added and the mix stirred for 16 hours at room temperature. The volatiles were removed in vacuo and the residue diluted with EtOAc (250 mL) and washed with water (3×50 mL), brine (50 mL), dried over MgSO$_4$, filtered and stripped to a red oil. TLC revealed a mixture of regioisomers that were purified by Biotage flash chromatography, eluting with 2-6% MeOH/DCM, then separated by chiral SF chromatography to afford pure isomers that were characterized by NOE NMR. The title compound was isolated as a white solid, 1.0 g, 23%. $^1$H NMR (400 MHz, CHLOROFORM-D) δ ppm 8.48-8.62 (2 H, m), 7.52-7.65 (2 H, m), 7.14 (2 H, dd, J=8.59, 5.31 Hz), 6.94-7.08 (2 H, m), 6.38 (1 H, s), 4.05-4.14 (2 H, m), 3.94-4.05 (4 H, m), 3.42-3.60 (1 H, m); m/z (APCI+) for $C_{17}H_{16}N_3FO$ 297.9 (M+H)+.

Example 30

2-[3-(4-fluorobenzyl)-5-pyridin-4-yl-1H-pyrazol-1-yl]ethanol

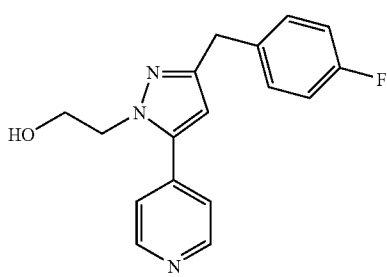

The title compound was isolated by chiral SF chromatography from the prep indicated for example 29 as a white solid, 817 mg, 19%. $^1$H NMR (400 MHz, CHLOROFORM-D) δ ppm 8.53-8.75 (2 H, m), 7.29-7.37 (2 H, m), 7.17-7.29 (2 H, m), 6.99 (2 H, t, J=8.72 Hz), 6.14 (1 H, s), 4.17-4.30 (2 H, m), 3.99-4.09 (2 H, m), 3.97 (2 H, s), 3.69-3.80 (1 H, m); m/z (APCI+) for $C_{17}H_{16}N_3FO$ 297.9 (M+H)+.

Example 31

4-(5-(4-fluorobenzyl)-1-(2-methoxyethyl)-1H-pyrazol-3-yl)pyridine

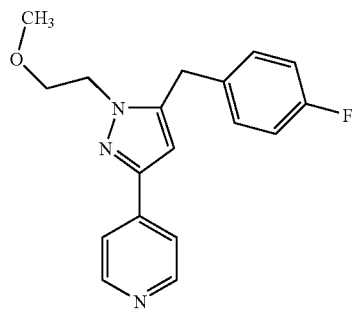

To a solution of 4-[5-(4-fluorobenzyl)-1H-pyrazol-3-yl]pyridine (0.122 g, 0.48 mmol) in DMF (3 ml) was added NaH (19 mg, 0.48 mmol) and the suspension was stirred for 20 minutes under nitrogen. Methoxyethylbromide (45 μL, 0.48 mmol) was then added and the reaction mixture was heated to 100° C. under nitrogen for 18 hours. The solvent was removed in vacuo and the residue was purified by radial chromatography (2 mm plate, eluting with EtOAc) to give the title compound as a clear oil (90 mg, 60%). $^1$H NMR (400 MHz, DICHLOROMETHANE-D2) δ ppm 8.54 (d, 2 H), 7.61 (d, 2 H), 7.18-7.24 (m, 2 H), 7.03 (t, 2 H), 6.32 (s, 1 H), 4.19 (t, 2 H), 4.05 (s, 2 H), 3.72 (t, 2 H), 3.28 (s, 3 H); m/z (APCI+) for $C_{18}H_{18}N_3FO$ 312.0 (M+H)+.

Example 32

3-(5-(4-fluorobenzyl)-3-(pyridin-4-yl)-1H-pyrazol-1-yl)propan-1-ol

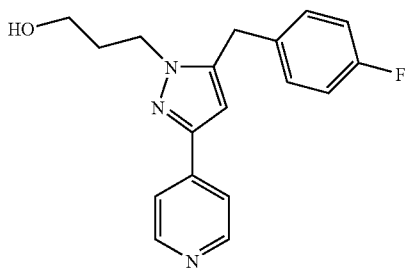

To a solution of 4-[5-(4-fluorobenzyl)-1H-pyrazol-3-yl]pyridine (0.5 g, 1.97 mmol) in DMF (10 mL) was added NaH (80 mg, 1.97 mmol) and the suspension was stirred for 20 minutes under nitrogen. This was followed by the addition of (3-bromopropoxy)(tert-butyl)dimethylsilane (457 μL, 1.97 mmol) and the reaction mixture was heated to 100° C. under nitrogen overnight. The solvent was removed to yield crude 4-(5-(4-fluorobenzyl)-1-(3-(tert-butyldimethylsilyloxy)propyl)-1H-pyrazol-3-yl)pyridine that was taken into THF (10 mL) at 0° C. and TBAF (1 M in THF, 1.97 mL, 1.97 mmol) was added. The mixture was stirred at 0° C. for 1 hour followed by stirring at room temperature for 1 hour. The solvent was removed and the residue was diluted with EtOAc and washed with $H_2O$, brine, dried over $MgSO_4$, filtered and concentrated. The residue was purified by flash chromatography (2-5% MeOH/$CH_2Cl_2$) then again using 3% MeOH/EtOAc followed by trituration with $Et_2O$ to yield the title compound as a white solid (0.33 g, 54%). $^1$H NMR (400 MHz, DICHLOROMETHANE-D2) δ ppm 8.55 (d, 2 H), 7.60 (d, 2 H), 7.16-7.24 (m, 2 H), 7.04 (t, 2 H), 6.40 (s, 1 H), 4.18 (t, 2 H), 4.03 (s, 2 H), 3.57 (t, 2 H), 1.87-1.96 (m, 2 H); m/z (APCI+) for $C_{18}H_{18}N_3FO$ 312.2 (M+H)+.

Example 33

1-trityl-1H-imidazole-4-carbaldehyde

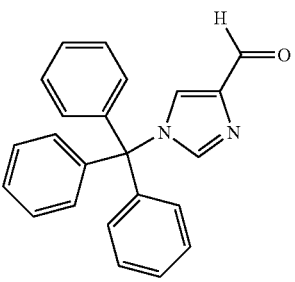

To a solution of 1H-imidazole-4-carbaldehyde (30.0 g, 0.30 mol) in DMF (200 mL) was added $Et_3N$ (70 mL, 0.375 mol) under ice bath, and then Trt-Cl (105 g, 0.375 mol) was added in portions and the mixture stirred at RT overnight. The mixture was evaporated in vacuo and the residue was washed with anhydrous Et₂O (4×50 mL), and the resulting precipitate was dried to yield the title compound (100 g, 100%) as a yellow solid.

Example 34

Preparation of Intermediate 8:
1-(1-trityl-1H-imidazol-4-yl)ethanol

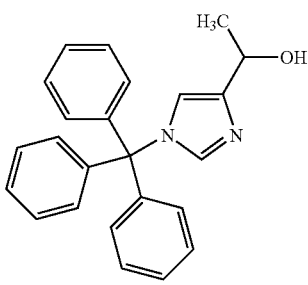

To a solution of 1-trityl-1H-imidazole-4-carbaldehyde (10.0 g, 0.03 mol) in anhydrous THF (100 mL) was added dropwise methyl magnesium bromide (1.4 M in hexane, 52.8 mL, 0.075 mol) at 0° C. After the addition, the mixture was stirred at RT overnight. The reaction was quenched with sat. aq. NH₄Cl (50 mL) and the mixture extracted with CH₂Cl₂ (3×50 mL). The organic layers were combined, washed with 1 N aq. NaOH (3×20 mL), water (3×20 mL) and brine (100 mL), dried over MgSO₄ and evaporated. The residue was purified via column chromatography (silica gel, EtOAc/Petroleum ether 1:5) to yield the title compound (8.0 g, 75.0%) as a white solid.

Example 35

Preparation of Intermediate 9:
1-(1-trityl-1H-imidazol-4-yl)ethanone

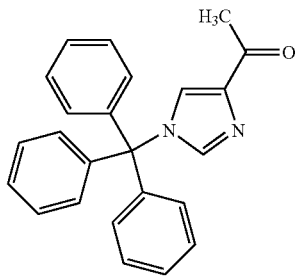

To a solution of 1-(1-trityl-1H-imidazol-4-yl)ethanol (4.0 g, 11.3 mmol) in anhydrous 1,4-dioxane (150 mL) was added activated MnO₂ (2.5 g, 28.2 mmol) at 0° C. The mixture was refluxed for 2 hours. TLC (EtOAc/Petroleum ether 1:2) showed the starting material was consumed completely, and the mixture was filtered. The filter cake was washed with dry CH₂Cl₂ (5×50 mL) and the filtrate was evaporated to afford the title compound (4.0 g, 100%) as a white solid.

Example 36

4-(4-fluorophenyl)-1-(1-trityl-1H-imidazol-4-yl)butane-1,3-dione

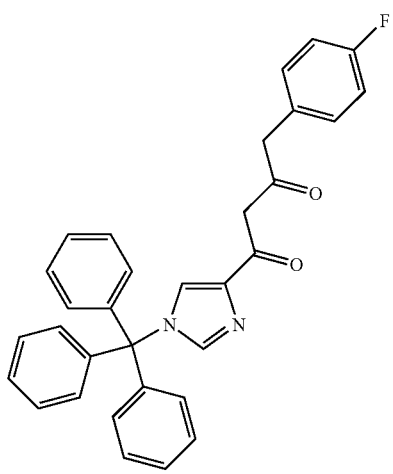

To a solution of 1-(1-trityl-1H-imidazol-4-yl)ethanone (1.5 g, 4.26 mmol) in anhydrous THF (25 mL) was added NaH (0.23 g, 8.52 mmol) at 0° C. The mixture was stirred at RT for 2 hours, and methyl (4-fluorophenyl)acetate (1.43 g, 12.78 mmol) was added at 0° C. The mixture was refluxed overnight. The mixture was evaporated and the residue was purified via column chromatography (silica gel, EtOAc/Petroleum ether 1:5) to yield the title compound (1.018 g, 48.0%) as colorless oil.

Example 37

5-(4-fluorobenzyl)-3-(1-trityl-1H-imidazol-4-yl)-1H-pyrazole

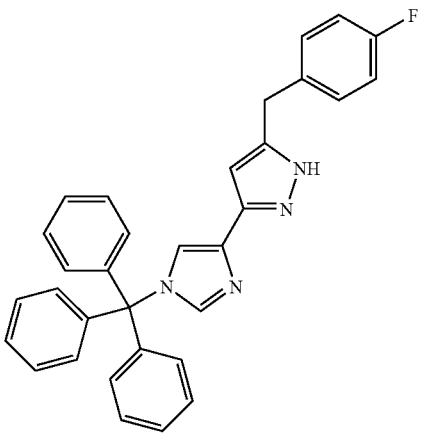

To a mixture of 4-(4-fluorophenyl)-1-(1-trityl-1H-imidazol-4-yl)butane-1,3-dione (80 g, 0.165 mol) and anhydrous EtOH/AcOH (400 mL/100 mL) was added NH₂NH₂·H₂O (80 mL, 0.96 mol) dropwise at 0° C. After the addition, the mixture was stirred at RT overnight. The solvent mixture was evaporated, the residue washed with anhydrous Et₂O (4×250 mL) and the resulting precipitate was dried in oven to yield the title compound (58.8 g, 73.0%) as a yellow solid.

Example 38 tert-butyl [5-(4-fluorobenzyl)-3-(1-trityl-1H-imidazol-4-yl)-1H-pyrazol-1-yl]acetate

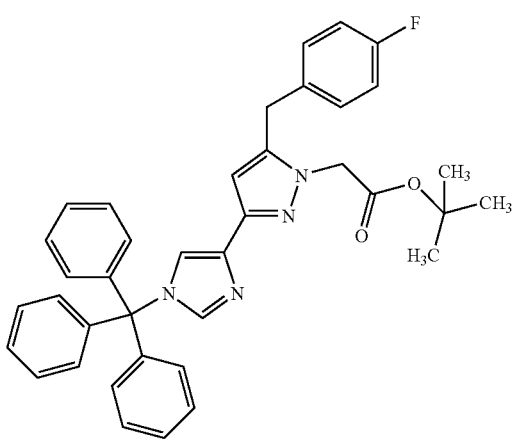

To a solution of 5-(4-fluorobenzyl)-3-(1-trityl-1H-imidazol-4-yl)-1H-pyrazole (0.5 g, 1.03 mmol) in anhydrous THF (15 mL) was added NaH (0.045 g, 1.10 mmol) at 0° C. The mixture was stirred at RT for 2 hours and tert-butyl bromo acetate (0.24 g, 1.20 mmol) was added at 0° C. After the addition, the mixture was stirred at RT overnight. The mixture was evaporated and the residue was purified via column chromatography (silica gel, EtOAc/Petroleum ether 1:1) to yield the title compound (0.4 g, 65.0%) as a white solid.

Example 39

[5-(4-fluorobenzyl)-3-(1H-imidazol-4-yl)-1H-pyrazol-1-yl]acetic acid

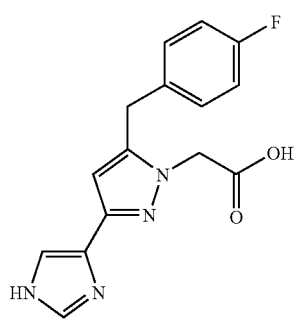

To a solution of tert-butyl [5-(4-fluorobenzyl)-3-(1-trityl-1H-imidazol-4-yl)-1H-pyrazol-1-yl]acetate (0.5 g, 0.80 mmol) in CH₂Cl₂ (10 mL) was added dropwise TFA (10 mL) at 0° C. After the addition, the mixture was stirred at 0° C. for 2 hours. The solvent was removed in vacuo and the residue was washed with Et₂O (3×10 mL) and dried in oven to yield the title compound (0.2 g, 80.0%) as a white solid.

Example 40

(3R)-1-{[5-(4-fluorobenzyl)-3-(1H-imidazol-4-yl)-1H-pyrazol-1-yl]acetyl}piperidin-3-ol

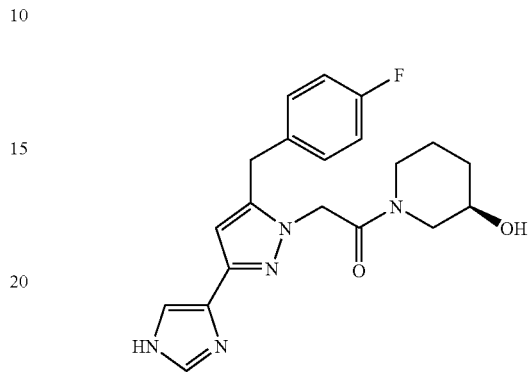

A mixture of [5-(4-fluorobenzyl)-3-(1H-imidazol-4-yl)-1H-pyrazol-1-yl]acetic acid (0.5 g, 1.67 mmol), (R)-piperidin-3-ol (0.30 g, 2.50 mmol), EDCI (0.58 g, 3.0 mmol), HOBt (0.40 g, 3.0 mmol) and NMM (1.0 mL, 10.0 mmol) in DMF (15 mL) was stirred at room temperature overnight. The mixture was concentrated in vacuo and the residue was diluted with water (5 mL). The mixture was extracted with CH₂Cl₂ (3×5 mL) and the organics combined, washed with 1 N aq. NaOH (3×10 mL), water (3×5 mL) and brine (25 mL), dried over MgSO₄ and evaporated. The residue was purified via column chromatography (silica gel, EtOAc/Petroleum ether 1:4) to yield crude material (201.0 mg), which was further purified via prep. HPLC to yield the title compound (100 mg, 15%) as a white solid. ¹H NMR (400 MHz, MeOD): δ ppm 8.837 (s, 1H), 7.699 (s, 1 H), 7.303 (m, 2 H), 7.078 (m, 2 H), 6.337 (s, 1 H), 3.992-3.039 (m, 7 H), 1.994-1.400 (m, 4 H).

Example 41

Preparation of Intermediate 14: ethyl 1-(4-methoxybenzyl)-1H-1,2,3-triazole-4-carboxylate

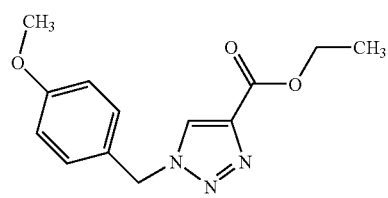

To a solution of para-methoxy benzyl azide (125.0 g, 0.77 mol) in anhydrous DMF (300 mL) was added dropwise propionic acid ethyl ester-(166 g, 1.77 mol) at 0° C. After the addition, the mixture was stirred at RT overnight. The mixture was evaporated in vacuo to yield crude title compound (190.0 g, 95.0%) as yellow oil that was used without further purification.

Example 42

1-(4-methoxybenzyl)-1H-1,2,3-triazole-4-carboxylic acid

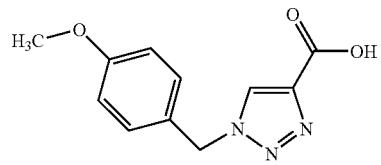

To a mixture of ethyl 1-(4-methoxybenzyl)-1H-1,2,3-triazole-4-carboxylate (190.0 g, 0.73 mol) and MeOH/H$_2$O (350 mL/100 mL) was added LiOH.H$_2$O (42.0 g, 0.97 mol) in portions at 0° C. and the reaction mixture was stirred at room temperature overnight. The mixture was evaporated, the residue was diluted with water (250 mL), then extracted with Et$_2$O (3×75 mL) to remove neutral impurities. The aqueous layer was adjusted to pH=3-4 with conc. HCl and the precipitate was filtered to afford the title compound (160 g, 94.0%) as a white solid.

Example 43

N-methoxy-1-(4-methoxybenzyl)-N-methyl-1H-1,2, 3-triazole-4-carboxamide

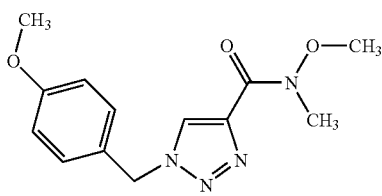

To a solution of 1-(4-methoxybenzyl)-1H-1,2,3-triazole-4-carboxylic acid (33.0 g, 0.14 mol) in anhydrous CH$_2$Cl$_2$ (80 mL) was added CDI (27.5 g, 0.16 mol) in an ice bath. The mixture was stirred at RT for 1 hour, and then O, N-dimethylhydroxylamine (14.5 g, 0.15 mol) was added and the mixture was stirred at RT overnight. The mixture was diluted with water (120 mL) and was then extracted with CH$_2$Cl$_2$ (3×100 mL). The combined organic phases were washed with water (3×50 mL), brine (100 mL), dried over Na$_2$SO$_4$ and evaporated to afford the title compound (35.0 g, 84.4 %) as a white solid.

Example 44

1-[-(4-methoxybenzyl)-1H-1,2,3-triazol-4-yl]ethanone

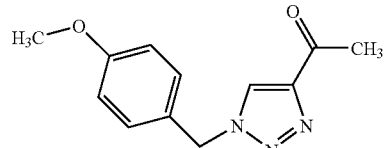

To a solution of N-methoxy-1-(4-methoxybenzyl)-N-methyl-1H-1,2,3-triazole-4-carboxamide (8.0 g, 0.03 mol) in anhydrous THF (75 mL) was added dropwise methyl magnesium bromide (3.0 M in hexane, 20 mL, 0.058 mol) at 0° C. After the addition, the mixture was stirred at RT overnight. The mixture was quenched with sat. aq. NH$_4$Cl (30 mL) then extracted with CH$_2$Cl$_2$ (3×50 mL). The organics were combined, washed with 1 N aq. NaOH (3×20 mL), water (3×20 mL), brine (50 mL), dried over MgSO$_4$ and evaporated to yield the title compound (8.0 g, 75.0%) as a white solid.

Example 45

4-(4-fluorophenyl)-1-[1-(4-methoxybenzyl)-1H-1,2, 3-triazol-4-yl]butane-1,3-dione

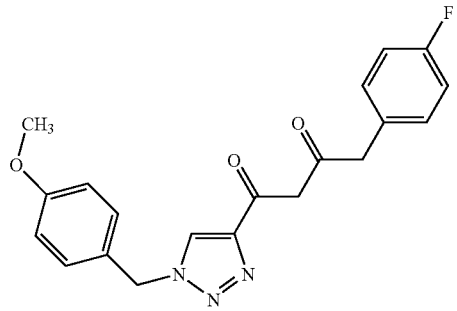

To a solution of 1-[1-(4-methoxybenzyl)-1H-1,2,3-triazol-4-yl]ethanone (1.0 g, 4.30 mmol) in anhydrous THF (25 mL) was added NaH (0.38 g, 9.5 mmol) at 0° C. The mixture was stirred at RT for 1 hour, and (4-fluoro-phenyl)-acetic acid methyl ester (1.67 g, 10.0 mmol) was added at 0° C. and the mixture was refluxed overnight. The reaction mixture was evaporated and the residue was purified via column chromatography (silica gel, EtOAc/Petroleum ether 1:5) to yield the title compound (0.6 g, 38.0%) as a colorless oil.

Example 46

4-[5-(4-fluorobenzyl)-1H-pyrazol-3-yl]-1-(4-methoxybenzyl)-1H-1,2,3-triazole

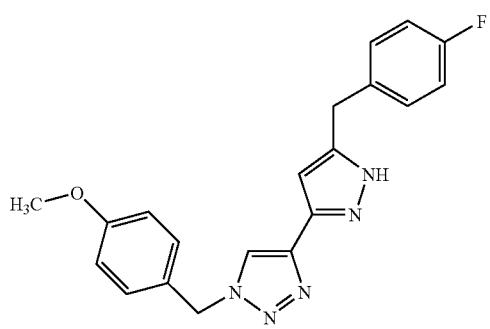

To a mixture of 4-(4-fluorophenyl)-1-[1-(4-methoxybenzyl)-1H-1,2,3-triazol-4-yl]butane-1,3-dione (0.6 g, 1.6 mmol) and anhydrous EtOH/AcOH (20 mL/5 mL) was added dropwise $NH_2NH_2.H_2O$ (1.0 mL, 9.6 mmol) at 0° C. and the mixture was stirred at RT overnight. The mixture was evaporated, the residue washed with anhydrous $Et_2O$ (4×5 mL) and the resulting precipitate was dried in oven to yield the title compound (0.5 g, 84.0%) as a yellow solid.

Example 47 tert-butyl {5-(4-fluorobenzyl)-3-[1-(4-methoxybenzyl)-1H-1,2,3-triazol-4-yl]-1H-pyrazol-1-yl}acetate

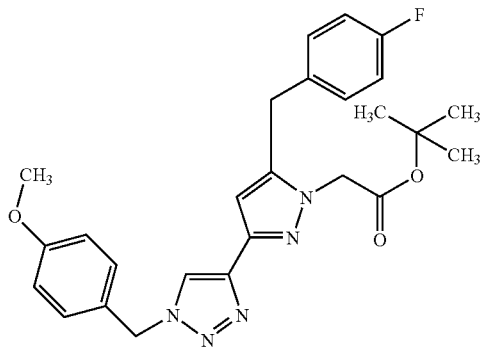

To a solution of 4-[5-(4-fluorobenzyl)-1H-pyrazol-3-yl]-1-(4-methoxybenzyl)-1H-1,2,3-triazole (19.0 g, 0.052 mol) in anhydrous THF (100 mL) was added NaH (2.6 g, 0.06 mol) at 0° C. and the mixture was stirred at RT for 2 hours. tert-butyl bromoacetate (12.5 g, 0.057 mol) was then added at 0° C. and the mixture was stirred at RT for 2 hours. The mixture was evaporated and the residue was purified via column chromatography (silica gel, EtOAc/Petroleum ether 1:1) to yield the title compound (20.0 g, 76.0%) as a yellow solid.

Example 48

{5-(4-fluorobenzyl)-3-[1-(4-methoxybenzyl)-1H-1,2,3-triazol-4-yl]-1H-pyrazol-1-yl}acetic acid

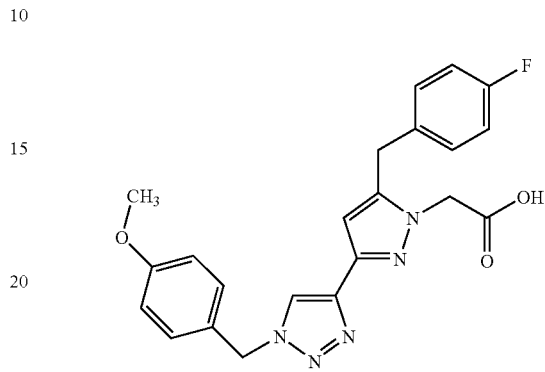

To a solution of tert-butyl {5-(4-fluorobenzyl)-3-[1-(4-methoxybenzyl)-1H-1,2,3-triazol-4-yl]-1H-pyrazol-1-yl}acetate (14.0 g, 29.3 mmol) in mixed solvent of MeOH/THF (60 mL/20 mL) was added a solution of NaOH (3.5 g, 88 mmol) in $H_2O$ (20 mL) and the reaction mixture was stirred at room temperature for an hour. The mixture was evaporated and the residue was diluted with water (100 mL) and washed with EtOAc (2×100 mL). The aqueous layer was adjusted to pH=3-4 with conc. HCl. The precipitate was filtered and dried in vacuo to afford the title compound (11.0 g, 90.0%) as a yellow solid.

Example 49

N-(1,1-dimethyl-2-morpholin-4-ylethyl)-2-{5-(4-fluorobenzyl)-3-[1-(4-methoxybenzyl)-1H-1,2,3-triazol-4-yl]-1H-pyrazol-1-yl}acetamide

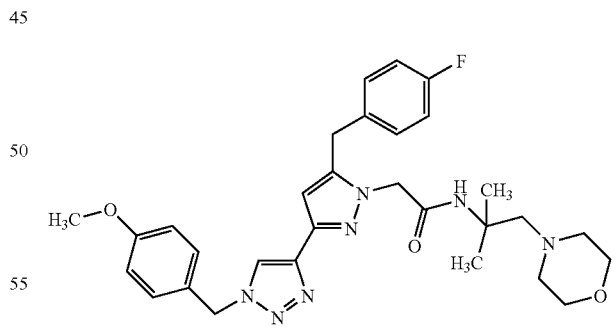

A mixture of {5-(4-fluorobenzyl)-3-[1-(4-methoxybenzyl)-1H-1,2,3-triazol-4-yl]-1H-pyrazol-1-yl}acetic acid (1.0 g, 2.37 mmol), 1,1-dimethyl-2-morpholin-4-yl-ethylamine (0.375 g, 2.37 mmol), HATU (0.71 g, 2.85 mmol) and $Et_3N$ (0.71 g, 7.1 mol) in DMF (20 mL) was stirred at room temperature overnight. The mixture was concentrated in vacuo and the residue was treated with water (50 mL) and $CH_2Cl_2$ (50 mL). The aqueous layer was extracted with $CH_2Cl_2$ (2×20 mL). The combined organics were dried over $Na_2SO_4$ and evaporated to afford crude title compound (1.3 g, 92%) as yellow oil that was used without further purification in next step.

Example 50

N-(1,1-dimethyl-2-morpholin-4-ylethyl)-2-[5-(4-fluorobenzyl)-3-(1H-1,2,3-triazol-4-yl)-1H-pyrazol-1-yl]acetamide

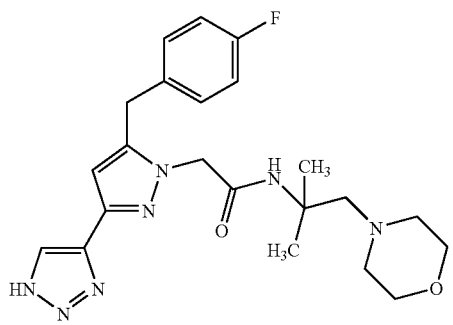

A solution of N-(1,1-dimethyl-2-morpholin-4-ylethyl)-2-{5-(4-fluorobenzyl)-3-[1-(4-methoxybenzyl)-1H-1,2,3-triazol-4-yl]-1H-pyrazol-1-yl}acetamide (1.3 g, 2.31 mmol) in TFA (30 mL) was refluxed overnight. The mixture was concentrated in vacuo and the residue was treated with water (30 mL) and $CH_2Cl_2$ (40 mL). The mixture was adjusted to pH 8-9 with $Et_3N$. The organic layer was separated, dried over $Na_2SO_4$ and concentrated. The residue was purified via prep. HPLC to yield the title compound (380 mg, 38%) as yellow syrup. $^1$H NMR (400 MHz, MeOD) δ ppm 8.003 (s, 1H), 7.322 (m, 2 H), 7.100 (m 2 H), 6.399 (s, 1 H), 4.916 (m, 3 H), 4.089 (s, 2 H), 3.899-3.189 (m, 9 H), 1.472 (s, 6 H).

Examples 51 to 133

Examples 51 to 133, found in the table below, can be prepared by those of ordinary skill in the art without undue experimentation by appropriately modifying the methods, reagents, and starting materials described above for the preparation of Examples 1 to 50. Appropriate starting materials for the preparation of Examples 51 to 133 are either commercially available or can be prepared by those of ordinary skill in the art without undue experimentation.

| Example No. | Structure | Name | $^1$H NMR |
|---|---|---|---|
| 51 | 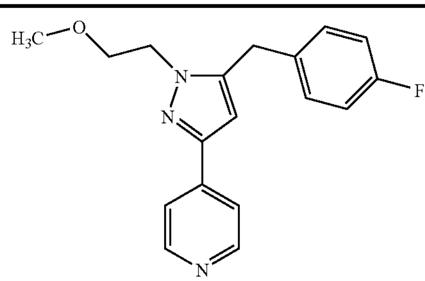 | 4-[5-(4-fluorobenzyl)-1-(2-methoxyethyl)-1H-pyrazol-3-yl]pyridine | (400 MHz, DICHLOROMETHANE-D2) δ ppm 8.54 (d, 2 H) 7.61 (d, 2 H) 7.18-7.24 (m, 2 H) 7.03 (t, 2 H) 6.32 (s, 1 H) 4.19 (t, 2 H) 4.05 (s, 2 H) 3.72 (t, 2 H) 3.28 (s, 3 H) |
| 52 | 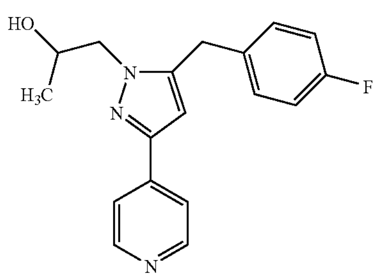 | 1-[5-(4-fluorobenzyl)-3-pyridin-4-yl-1H-pyrazol-1-yl]propan-2-ol | (400 MHz, DICHLOROMETHANE-D2) δ ppm 8.56 (d, 2 H) 7.62 (d, 2 H) 7.14-7.23 (m, 2 H) 7.03 (t, 2 H) 6.41 (s, 1 H) 4.11-4.19 (m, 1 H) 4.01-4.06 (m, 2 H) 3.81-3.91 (m, 1 H) 3.71-3.75 (m, 1 H) 1.16 (d, 3 H) |
| 53 | 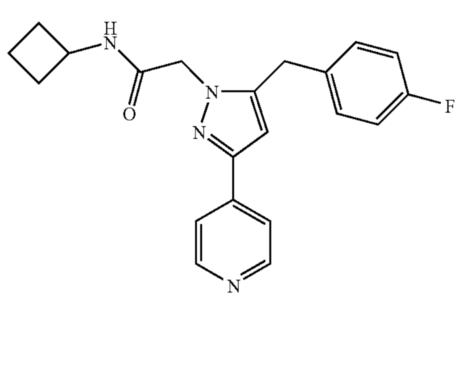 | N-cyclobutyl-2-[5-(4-fluorobenzyl)-3-pyridin-4-yl-1H-pyrazol-1-yl]acetamide | (400 MHz, DICHLOROMETHANE-D2) δ ppm 8.59 (d, 2 H) 7.66 (d, 2 H) 7.14-7.25 (m, 2 H) 7.02 (t, 2 H) 6.50 (s, 1 H) 5.88-6.03 (m, 1 H) 4.68 (s, 2 H) 4.17-4.33 (m, 1 H) 4.03 (s, 2 H) 2.14-2.33 (m, 2 H) 1.59-1.83 (m, 4 H) |

-continued

| Example No. | Structure | Name | ¹H NMR |
|---|---|---|---|
| 54 | 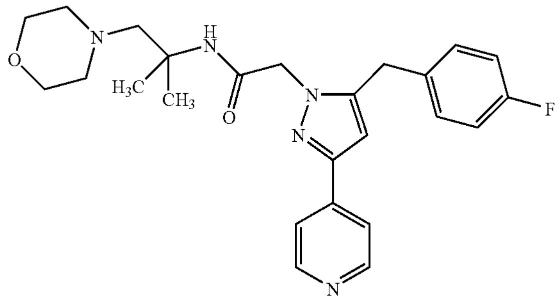 | N-(1,1-dimethyl-2-morpholin-4-ylethyl)-2-[5-(4-fluorobenzyl)-3-pyridin-4-yl-1H-pyrazol-1-yl]acetamide | (400 MHz, DICHLOROMETHANE-D2) δ ppm 8.59 (d, 2 H) 7.65 (d, 2 H) 7.17-7.24 (m, 2 H) 7.02 (t, 2 H) 6.51 (s, 1 H) 6.30-6.36 (m, 1 H) 4.66 (s, 2 H) 3.99 (s, 2 H) 3.26-3.32 (m, 4 H) 2.25-2.33 (m, 4 H) 2.23 (s, 2 H) 1.26 (s, 6 H) |
| 55 | 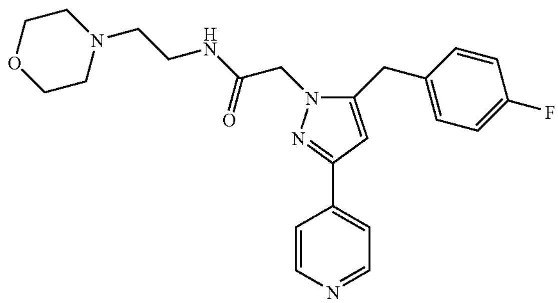 | 2-[5-(4-fluorobenzyl)-3-pyridin-4-yl-1H-pyrazol-1-yl]-N-(2-morpholin-4-ylethyl)acetamide | (400 MHz, DICHLOROMETHANE-D2) δ ppm 8.59 (d, 2 H) 7.66 (d, 2 H) 7.17-7.24 (m, 2 H) 7.03 (t, 2 H) 6.52 (s, 1 H) 6.32-6.40 (m, 1 H) 4.73 (s, 2 H) 4.00 (s, 2 H) 3.30-3.38 (m, 4 H) 3.16-3.24 (m, 2 H) 2.32 (t, 2 H) 2.19-2.28 (m, 4 H) |
| 56 | 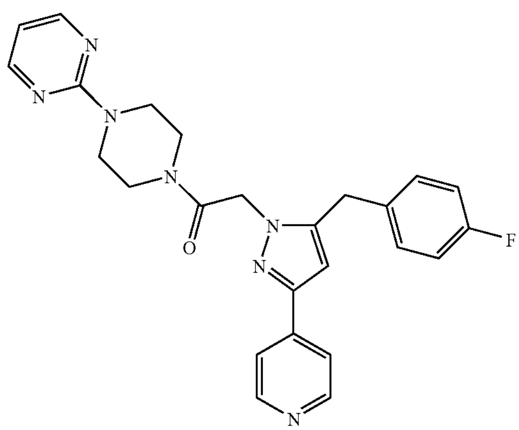 | 2-(4-{[5-(4-fluorobenzyl)-3-pyridin-4-yl-1H-pyrazol-1-yl]acetyl}piperazin-1-yl)pyrimidine | (400 MHz, DICHLOROMETHANE-D2) δ ppm 8.55 (d, 2 H) 8.33 (d, 2 H) 7.61 (d, 2 H) 7.20-7.26 (m, 2 H) 7.03 (t, 2 H) 6.55 (t, 1 H) 6.41 (s, 1 H) 4.95 (s, 2 H) 4.01 (s, 2 H) 3.80-3.89 (m, 4 H) 3.64-3.69 (m, 2 H) 3.54-3.60 (m, 2 H) |
| 57 | 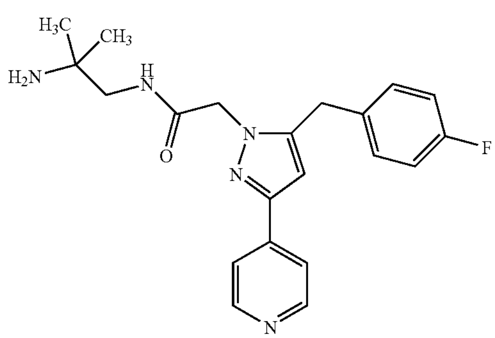 | N-(2-amino-2-methylpropyl)-2-[5-(4-fluorobenzyl)-3-pyridin-4-yl-1H-pyrazol-1-yl]acetamide | (400 MHz, DMSO-D6) δ ppm 8.55 (d, 2 H) 8.48 (t, 1 H) 7.73-7.80 (m, 2 H) 7.69 (d, 2 H) 7.30 (t, 2 H) 7.15 (t, 2 H) 6.56 (s, 1 H) 4.91-4.94 (m, 2 H) 4.03 (s, 2 H) 3.26 (d, 2 H) 1.20 (s, 6 H) |

-continued

| Example No. | Structure | Name | ¹H NMR |
|---|---|---|---|
| 58 | 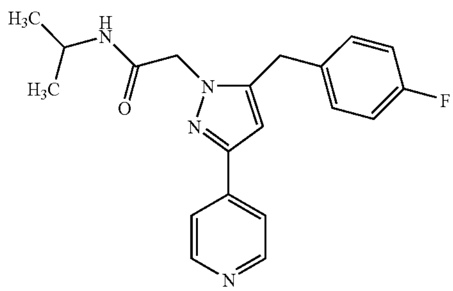 | 2-[5-(4-fluorobenzyl)-3-pyridin-4-yl-1H-pyrazol-1-yl]-N-isopropylacetamide | (400 MHz, DICHLOROMETHANE-D2) δ ppm 8.59 (d, 2 H) 7.65 (d, 2 H) 7.16-7.23 (m, 2 H) 7.03 (t, 2 H) 6.47 (s, 1 H) 5.67-5.76 (m, 1 H) 4.67 (s, 2 H) 4.01 (s, 2 H) 3.90-3.98 (m, 1 H) 1.04 (d, 6 H) |
| 59 | 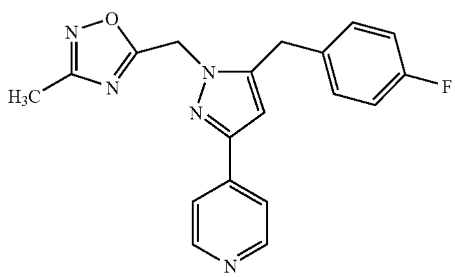 | 4-{5-(4-fluorobenzyl)-1-[(3-methyl-1,2,4-oxadiazol-5-yl)methyl]-1H-pyrazol-3-yl}pyridine | (400 MHz, CHLOROFORM-D) δ ppm 8.60 (d, 2 H) 7.63 (d, 2 H) 7.12-7.17 (m, 2 H) 7.00 (t, 2 H) 6.46 (s, 1 H) 5.42 (s, 2 H) 4.07 (s, 2 H) 2.36 (s, 3 H) |
| 60 | 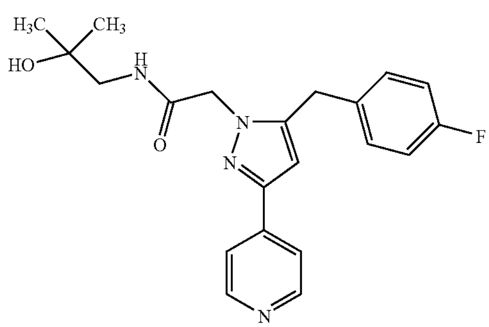 | 2-[5-(4-fluorobenzyl)-3-pyridin-4-yl-1H-pyrazol-1-yl]-N-(2-hydroxy-2-methylpropyl)acetamide | (400 MHz, CHLOROFORM-D) δ ppm 8.59 (d, 2 H) 7.62 (d, 2 H) 7.15 (t, 2 H) 7.02 (t, 2 H) 6.49-6.58 (m, 1 H) 6.42 (s, 1 H) 4.76 (s, 2 H) 4.00 (s, 2 H) 3.19 (d, 2 H) 1.15 (s, 6 H) |
| 61 | 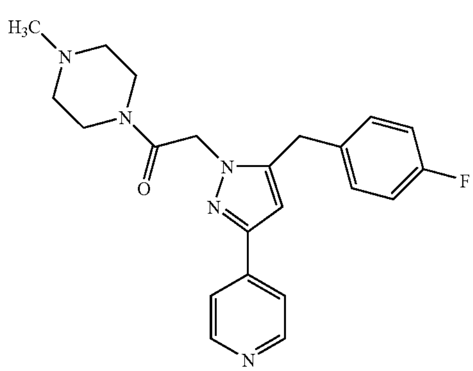 | 1-{[5-(4-fluorobenzyl)-3-pyridin-4-yl-1H-pyrazol-1-yl]acetyl}-4-methylpiperazine | (400 MHz, CHLOROFORM-D) δ ppm 8.58 (d, 2 H) 7.60 (d, 2 H) 7.19 (t, 2 H) 7.02 (t, 2 H) 6.38 (s, 1 H) 4.88 (s, 2 H) 4.00 (s, 2 H) 3.60-3.66 (m, 2 H) 3.48-3.56 (m, 2 H) 2.36-2.41 (m, 4 H) 2.30 (s, 3 H) |

| Example No. | Name | ¹H NMR |
|---|---|---|
| 62 | 1-{[5-(4-fluorobenzyl)-3-pyridin-4-yl-1H-pyrazol-1-yl]acetyl}piperazine | (400 MHz, CHLOROFORM-D) δ ppm 8.58 (2 H, d, J = 5.31 Hz) 7.61 (2 H, d, J = 5.31 Hz) 7.20 (2 H, dd, J = 8.21, 5.43 Hz) 7.03 (2 H, t, J = 8.46 Hz) 6.39 (1 H, s) 4.88 (2 H, s) 4.03 (2 H, s) 3.56-3.67 (2 H, m) 3.45-3.54 (2 H, m) 2.76-2.94 (4 H, m) |
| 63 | 2-[5-(4-fluorobenzyl)-3-pyridin-4-yl-1H-pyrazol-1-yl]-N-[(2R)-2-hydroxypropyl]acetamide | (400 MHz, CHLOROFORM-D) δ ppm 8.51 (d, 2 H) 7.60 (d, 2 H) 7.11-7.20 (m, 2 H) 7.00 (t, 2 H) 6.85 (s, 1 H) 6.38 (s, 1 H) 4.71 (s, 2 H) 3.99 (s, 2 H) 3.73-3.83 (m, 1 H) 3.27-3.40 (m, 1 H) 2.90-3.01 (m, 1 H) 1.10 (d, 3 H) |
| 64 | 2-[5-(4-fluorobenzyl)-3-pyridin-4-yl-1H-pyrazol-1-yl]-N-[(2S)-2-hydroxypropyl]acetamide | (400 MHz, CHLOROFORM-D) δ ppm 8.46 (d, 2 H) 7.58 (d, 2 H) 7.07-7.17 (m, 2 H) 6.96 (t, 2 H) 6.35 (s, 1 H) 4.67 (s, 2 H) 3.97 (s, 2 H) 3.69-3.80 (m, 1 H) 3.26-3.33 (m, 1 H) 2.88-2.99 (m, 1 H) 1.06 (d, 3 H) |
| 65 | (3R)-1-{[5-(4-fluorobenzyl)-3-pyridin-4-yl-1H-pyrazol-1-yl]acetyl}pyrrolidin-3-amine | (1:1 rotamers, 400 MHz, CHLOROFORM-D) δ ppm 8.57 (2 H, d, J = 6.06 Hz) 7.53-7.69 (2 H, m) 7.20 (2 H, dd, J = 8.46, 5.43 Hz) 6.87-7.11 (2 H, m) 6.37 (2 H, d, J = 1.77 Hz) 4.69-4.93 (2 H, m) 4.04 (2 H, s) 3.59-3.80 (3 H, m) 3.47-3.59 (1 H, m) 3. |

-continued

| Example No. | Structure | Name | ¹H NMR |
|---|---|---|---|
| 66 | 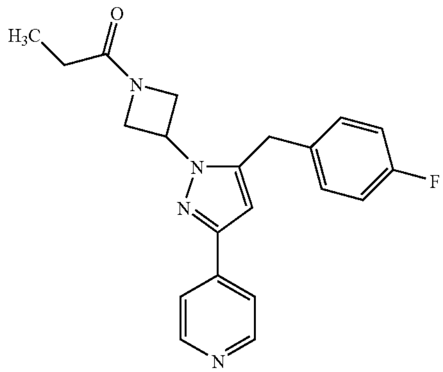 | 4-[5-(4-fluorobenzyl)-1-(1-propionylazetidin-3-yl)-1H-pyrazol-3-yl]pyridine | (400 MHz, DMSO-D6) δ ppm 8.57 (d, 2 H) 7.74 (d, 2 H) 7.26 (t, 2 H) 7.16 (t, 2 H) 6.72 (s, 1 H) 5.25-5.34 (m, 1 H) 4.32-4.45 (m, 2 H) 4.07-4.13 (m, 4 H) 2.09 (q, 2 H) 0.97 (t, 3 H) |
| 67 | 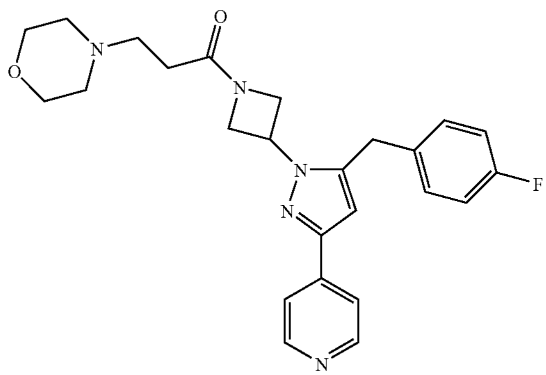 | 4-(3-{3-[5-(4-fluorobenzyl)-3-pyridin-4-yl-1H-pyrazol-1-yl]azetidin-1-yl}-3-oxopropyl)morpholine | (400 MHz, DMSO-D6) δ ppm 8.60 (d, 2 H) 7.78 (d, 2 H) 7.23-7.30 (m, 2 H) 7.16 (t, 2 H) 6.76 (s, 1 H) 5.26-5.37 (m, 1 H) 4.35-4.51 (m, 2 H) 4.18-4.21 (m, 2 H) 4.12 (s, 2 H) 3.67-3.92 (m, 4 H) 3.27-3.35 (m, 4 H) 2.55-2.67 (m, 2 H) 1.08 (t, 2 |
| 68 | 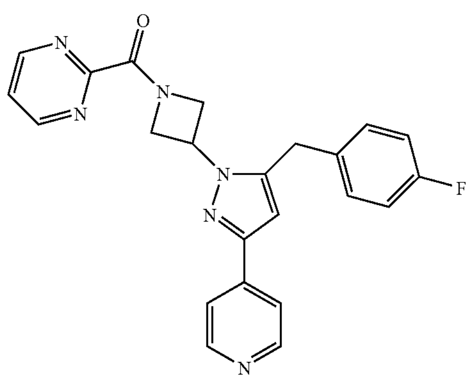 | 2-({3-[5-(4-fluorobenzyl)-3-pyridin-4-yl-1H-pyrazol-1-yl]azetidin-1-yl}carbonyl)pyrimidine | (400 MHz, CHLOROFORM-D) δ ppm 8.87 (d, 2 H) 8.60 (d, 2 H) 7.68 (d, 2 H) 7.38 (t, 1 H) 7.07-7.14 (m, 2 H) 7.03 (t, 2 H) 6.52 (s, 1 H) 5.05-5.13 (m, 1 H) 4.94-5.04 (m, 1 H) 4.79-4.88 (m, 1 H) 4.65-4.73 (m, 1 H) 4.40-4.49 (m, 1 H) 4.03 (s |
| 69 | 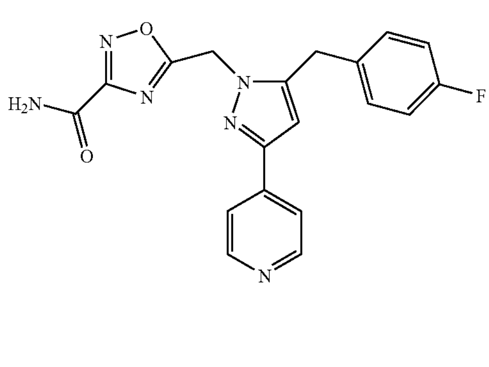 | 5-{[5-(4-fluorobenzyl)-3-pyridin-4-yl-1H-pyrazol-1-yl]methyl}-1,2,4-oxadiazole-3-carboxamide | (400 MHz, DMSO-D6) δ ppm 8.55 (d, 2 H) 8.23-8.28 (m, 1 H) 8.08-8.13 (m, 1 H) 7.69 (d, 2 H) 7.24-7.32 (m, 2 H) 7.10 (t, 2 H) 6.73 (s, 1 H) 5.93 (s, 2 H) 4.16 (s, 2 H) |

-continued

| Example No. | Structure | Name | ¹H NMR |
|---|---|---|---|
| 70 | 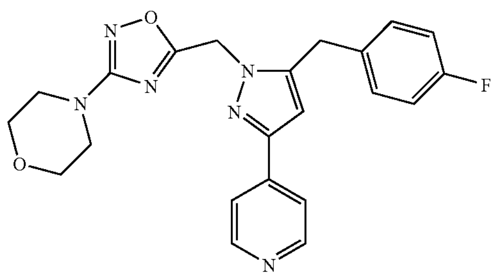 | 4-(5-{[5-(4-fluorobenzyl)-3-pyridin-4-yl-1H-pyrazol-1-yl]methyl}-1,2,4-oxadiazol-3-yl)morpholine | (400 MHz, DMSO-D6) δ ppm 8.61 (d, 2 H) 7.81 (d, 2 H) 7.21-7.30 (m, 2 H) 7.11 (t, 2 H) 6.81 (S, 1 H) 5.75 (S, 2 H) 4.13 (S, 2 H) 3.59-3.65 (m, 4 H) 3.17-3.25 (m, 4 H) |
| 71 | 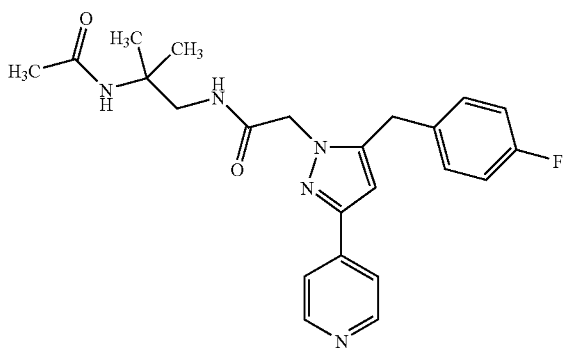 | N-[2-(acetylamino)-2-methylpropyl]-2-[5-(4-fluorobenzyl)-3-pyridin-4-yl-1H-pyrazol-1-yl]acetamide | (400 MHz, DMSO-D6) δ ppm 8.59 (d, 2 H) 8.11 (t, 1 H) 7.82 (d, 2 H) 7.39 (s, 1 H) 7.27-7.34 (m, 2 H) 7.15 (t, 2 H) 6.60 (s, 1 H) 4.91 (s, 2 H) 4.01 (s, 2 H) 3.36 (d, 2 H) 1.75 (s, 3 H) 1.16 (s, 6 H) |
| 72 | 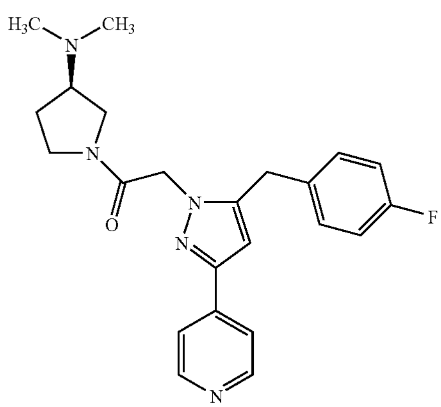 | (3R)-1-{[5-(4-fluorobenzyl)-3-pyridin-4-yl-1H-pyrazol-1-yl]acetyl}-N,N-dimethylpyrrolidin-3-amine | (400 MHz, DMSO-D6) δ ppm 8.53 (d, 2 H) 7.69 (d, 2 H) 7.27-7.33 (m, 2 H) 7.14 (t, 2 H) 6.55 (d, 1 H) 5.07-5.20 (m, 2 H) 3.92-3.97 (m, 3 H) 3.72-3.86 (m, 2 H) 3.49-3.61 (m, 2 H) 3.35-3.46 (m, 2 H) 2.82 (d, 6 H) |
| 73 | 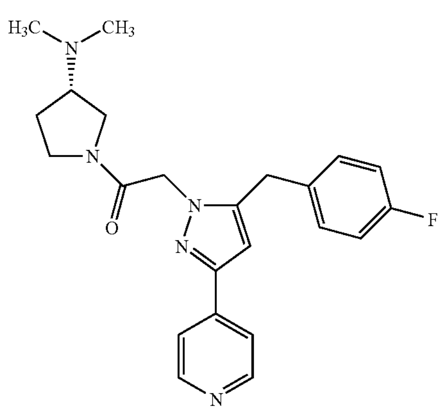 | (3S)-1-{[5-(4-fluorobenzyl)-3-pyridin-4-yl-1H-pyrazol-1-yl]acetyl}-N,N-dimethylpyrrolidin-3-amine | (400 MHz, DMSO-D6) δ ppm 8.54 (d, 2 H) 7.71 (d, 2 H) 7.26-7.34 (m, 2 H) 7.15 (t, 2 H) 6.56 (d, 1 H) 5.13 (q, 2 H) 3.95 (s, 2 H) 3.73-3.87 (m, 2 H) 3.63-3.73 (m, 1 H) 3.49-3.63 (m, 1 H) 3.25-3.47 (m, 3 H) 2.83 (d, 6 H) |

| Example No. | Structure | Name | ¹H NMR |
|---|---|---|---|
| 74 | 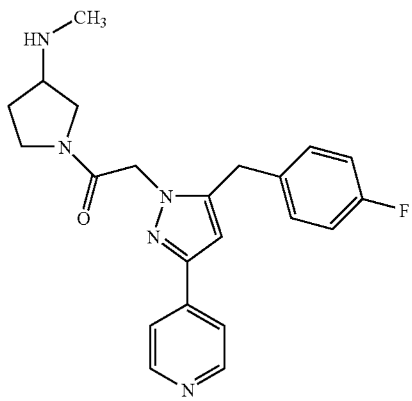 | 1-{[5-(4-fluorobenzyl)-3-pyridin-4-yl-1H-pyrazol-1-yl]acetyl}-N-methylpyrrolidin-3-amine | (400 MHz, CHLOROFORM-D) δ ppm 8.57 (2 H, d, J = 5.56 Hz) 7.61 (2 H, d, J = 5.05 Hz) 7.20 (2 H, dd, J = 8.34, 5.56 Hz) 7.02 (2 H, t, J = 8.46 Hz) 6.36 (1 H, d, J = 3.79 Hz) 4.73-4.94 (2 H, m) 4.04 (2 H, s) 3.46-3.71 (3 H, m) 3.32-3.45 (1 H, m) 3.18-3 |
| 75 | 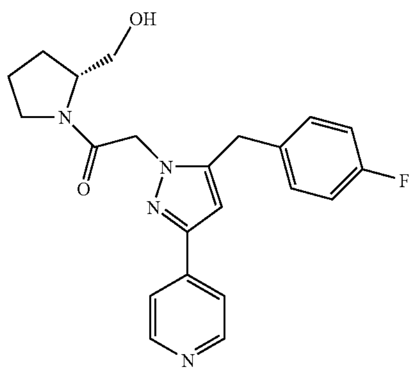 | [(2R)-1-{[5-(4-fluorobenzyl)-3-pyridin-4-yl-1H-pyrazol-1-yl]acetyl}pyrrolidin-2-yl]methanol | (400 MHz, CHLOROFORM-D) δ ppm 8.56 (d, 2 H) 7.61 (d, 2 H) 7.15-7.22 (m, 2 H) 6.97-7.08 (m, 2 H) 6.40 (s, 1 H) 4.81 (q, 2 H) 4.27-4.35 (m, 1 H) 4.15-4.25 (m, 1 H) 4.07-4.16 (m, 1 H) 3.40 (s, 2 H) 3.65-3.78 (m, 1 H) 3.51-3.64 (m, 2 H) |
| 76 | 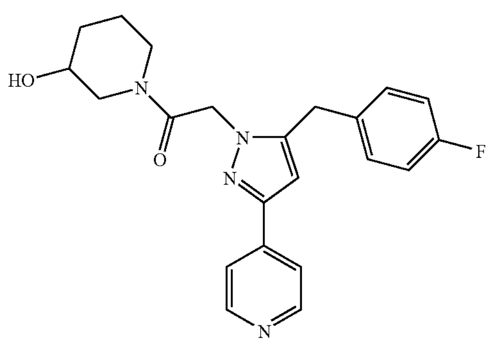 | 1-{[5-(4-fluorobenzyl)-3-pyridin-4-yl-1H-pyrazol-1-yl]acetyl}piperidin-3-ol | (400 MHz, CHLOROFORM-D) δ ppm 8.56 (d, 2 H) 7.60 (d, 2 H) 7.16-7.22 (m, 2 H) 7.01 (t, 2 H) 6.36 (d, 1 H) 4.81-4.99 (m, 2 H) 4.01 (d, 2 H) 3.73-3.92 (m, 2 H) 3.54-3.64 (m, 1 H) 3.39-3.51 (m, 1 H) 3.18-3.37 (m, 1 H) 1.78-1.92 (m, 2 H) |
| 77 | 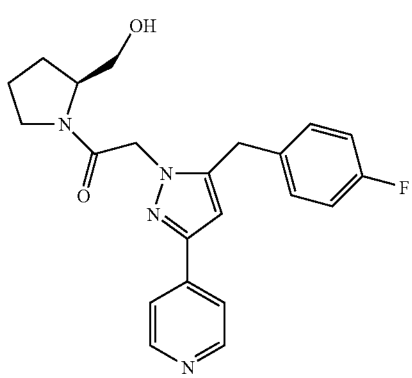 | [(2S)-1-{[5-(4-fluorobenzyl)-3-pyridin-4-yl-1H-pyrazol-1-yl]acetyl}pyrrolidin-2-yl]methanol | (400 MHz, CHLOROFORM-D) δ ppm 8.58 (d, 2 H) 7.61 (d, 2 H) 7.14-7.22 (m, 2 H) 6.98-7.07 (m, 2 H) 6.40 (s, 1 H) 4.81 (q, 2 H) 4.25-4.31 (m, 1 H) 4.17-4.24 (m, 1 H) 4.03 (s, 2 H) 3.69-3.78 (m, 1 H) 3.51-3.62 (m, 2 H) 3.42-3.51 (m, 1 H) |

| Example No. | Structure | Name | ¹H NMR |
|---|---|---|---|
| 78 | 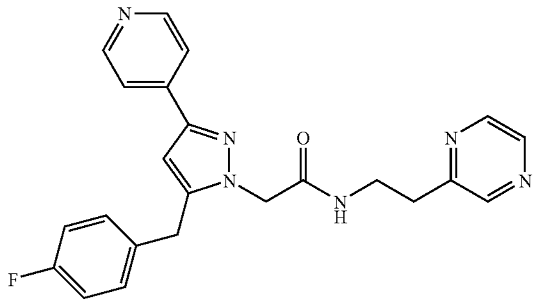 | 2-[5-(4-fluorobenzyl)-3-pyridin-4-yl-1H-pyrazol-1-yl]-N-(2-pyrazin-2-ylethyl)acetamide | (400 MHz, MeOD) δ ppm 8.39-8.46 (m, 3 H) 8.34-8.38 (m, 1 H) 8.27-8.31 (m, 1 H) 7.67 (d, 2 H) 7.12-7.18 (m, 2 H) 6.94 (t, 2 H) 6.47 (s, 1 H) 4.69 (s, 2 H) 3.91 (s, 2 H) 3.49 (t, 2 H) 2.89 (t, 2 H) |
| 79 | 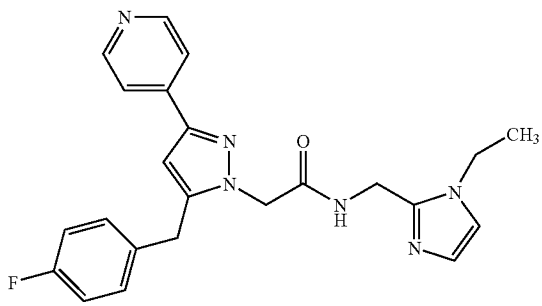 | N-[(1-ethyl-1H-imidazol-2-yl)methyl]-2-[5-(4-fluorobenzyl)-3-pyridin-4-yl-1H-pyrazol-1-yl]acetamide | (500 MHz, DEUTERIUM OXIDE) δ ppm 8.99 (1 H, s) 8.67 (2 H, s) 7.97 (2 H, s) 7.70 (1 H, d, J = 1.37 Hz) 7.61 (1 H, s) 7.20-7.35 (2 H, m) 7.12 (2 H, t, J = 8.79 Hz) 6.70 (1 H, s) 4.98 (2 H, s) 4.60 (2 H, d, J = 5.49 Hz) 4.11 (2 H, q, J = 7.42 Hz) 3.98 (2 H |
| 80 | 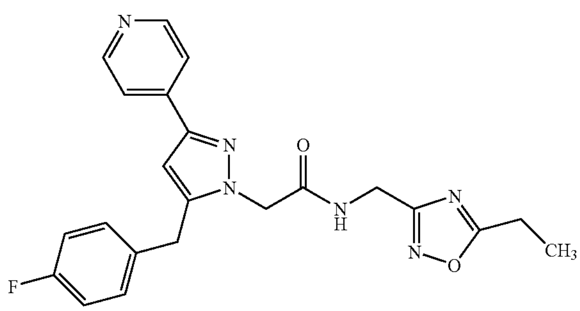 | N-[(5-ethyl-1,2,4-oxadiazol-3-yl)methyl]-2-[5-(4-fluorobenzyl)-3-pyridin-4-yl-1H-pyrazol-1-yl]acetamide | (500 MHz, DEUTERIUM OXIDE) δ ppm 8.88 (1 H, s) 8.67 (2 H, s) 8.03 (2 H, s) 7.27 (2 H, dd, J = 8.10, 5.91 Hz) 7.12 (2 H, t, J = 8.65 Hz) 6.69 (1 H, s) 4.94 (2 H, s) 4.38 (2 H, d, J = 5.77 Hz) 3.99 (2 H, s) 2.87 (2 H, q, J = 7.51 Hz) 1.21 (3 H, t, J = 7.69 Hz |
| 81 | 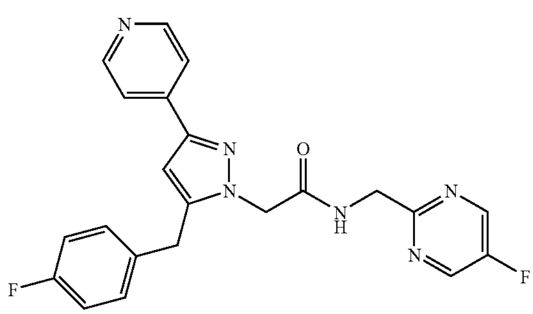 | 2-[5-(4-fluorobenzyl)-3-pyridin-4-yl-1H-pyrazol-1-yl]-N-[(5-fluoropyrimidin-2-yl)methyl]acetamide | (500 MHz, DEUTERIUM OXIDE) δ ppm 8.81 (2 H, s) 8.70 (2 H, d, J = 5.49 Hz) 8.08 (2 H, s) 7.27 (2 H, dd, J = 8.38, 5.63 Hz) 7.11 (2 H, t, J = 8.65 Hz) 6.72 (1 H, s) 4.99 (2 H, s) 4.49 (2 H, d, J = 5.77 Hz) 4.02 (2 H, s) |
| 82 | 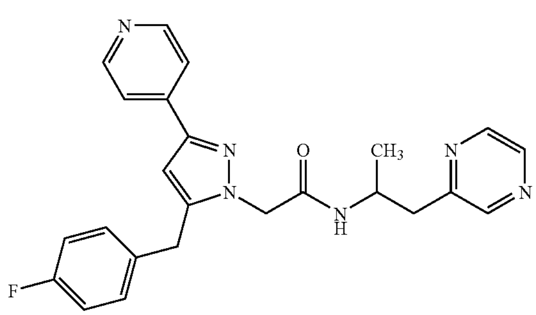 | 2-[5-(4-fluorobenzyl)-3-pyridin-4-yl-1H-pyrazol-1-yl]-N-(1-methyl-2-pyrazin-2-ylethyl)acetamide | (500 MHz, DEUTERIUM OXIDE) δ ppm 8.70 (2 H, d, J = 6.04 Hz) 8.49 (2 H, d, J = 10.16 Hz) 8.40 (1 H, d, J = 2.20 Hz) 8.23 (1 H, d, J = 8.24 Hz) 8.07 (2 H, s) 7.18-7.26 (2 H, m) 7.12 (2 H, t, J = 8.79 Hz) 6.69 (1 H, s) 4.69-4.85 (2 H, m) 4.12-4.22 (1 H, |

| Example No. | Structure | Name | ¹H NMR |
|---|---|---|---|
| 83 | 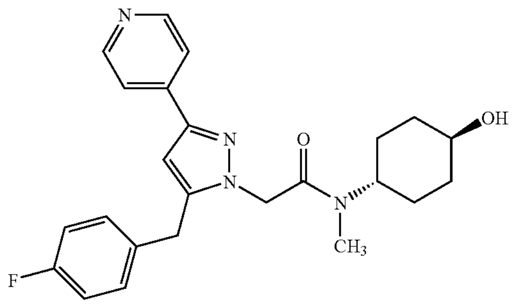 | 2-[5-(4-fluorobenzyl)-3-pyridin-4-yl-1H-pyrazol-1-yl]-N-(trans-4-hydroxycyclohexyl)-N-methylacetamide | (400 MHz, DMSO-D6) δ ppm 8.52 (d, 2 H) 7.66 (d, 2 H) 7.24-7.34 (m, 2 H) 7.15 (t, 2 H) 6.51 (s, 1 H) 5.21 (s, 1 H) 5.10 (s, 1 H) 4.56 (dd, 1 H) 4.05-4.15 (m, 0.5 H) 3.93 (d, 2 H) 3.60-3.72 (m, 0.5 H) 3.33-3.42 (m, 1 H) 2.83 (s, 2 H) 2.67 (s |
| 84 | 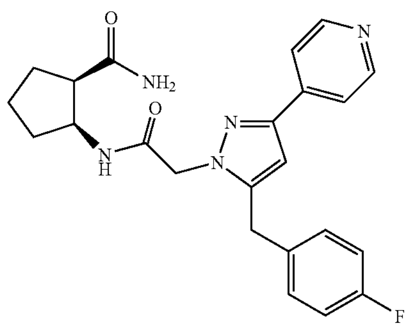 | (1R,2S)-2-({[5-(4-fluorobenzyl)-3-pyridin-4-yl-1H-pyrazol-1-yl]acetyl}amino)cyclopentanecarboxamide | (500 MHz, DEUTERIUM OXIDE) δ ppm 8.67 (2 H, s) 8.05 (2 H, s) 7.85-8.00 (1 H, m) 7.27 (2 H, dd, J = 8.52, 5.49 Hz) 7.16-7.23 (1 H, m) 7.12 (2 H, t, J = 8.65 Hz) 6.71 (2 H, s) 4.64-4.96 (2 H, m) 4.21 (1 H, d, J = 7.69 Hz) 3.83-4.05 (2 H, m) 2.62- |
| 85 | 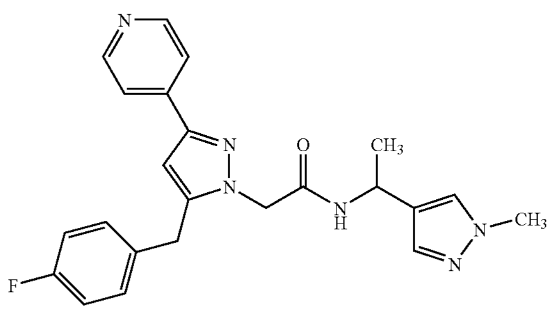 | 2-[5-(4-fluorobenzyl)-3-pyridin-4-yl-1H-pyrazol-1-yl]-N-[1-(1-methyl-1H-pyrazol-4-yl)ethyl]acetamide | (500 MHz, DEUTERIUM OXIDE) δ ppm 8.69 (2 H, s) 8.41-8.56 (1 H, m) 8.07 (2 H, s) 7.54 (1 H, s) 7.21-7.38 (3 H, m) 7.12 (2 H, t, J = 8.79 Hz) 6.71 (1 H, s) 4.71-4.94 (3 H, m) 4.00 (2 H, s) 3.73 (3 H, s) 1.32 (3 H, d, J = 7.14 Hz) |
| 86 | 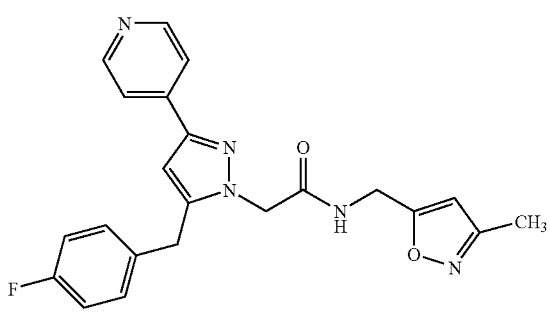 | 2-[5-(4-fluorobenzyl)-3-pyridin-4-yl-1H-pyrazol-1-yl]-N-[(3-methylisoxazol-5-yl)methyl]acetamide | (500 MHz, DEUTERIUM OXIDE) δ ppm 8.83 (1 H, s) 8.65 (2 H, s) 7.98 (2 H, s) 7.20-7.40 (2 H, m) 7.12 (2 H, t, J = 8.93 Hz) 6.67 (1 H, s) 6.16 (1 H, s) 4.86-5.09 (2 H, m) 4.37 (2 H, d, J = 5.77 Hz) 3.99 (3 H, s) 2.14 (2 H, s) |
| 87 | 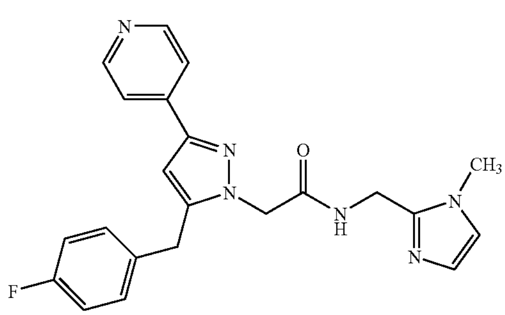 | 2-[5-(4-fluorobenzyl)-3-pyridin-4-yl-1H-pyrazol-1-yl]-N-[(1-methyl-1H-imidazol-2-yl)methyl]acetamide | (500 MHz, DEUTERIUM OXIDE) δ ppm 8.91-9.09 (1 H, m) 8.67 (2 H, s) 7.98 (2 H, s) 7.60 (1 H, s) 7.56 (1 H, s) 7.25 (2 H, dd, J = 7.83, 5.91 Hz) 7.12 (2 H, t, J = 8.79 Hz) 6.70 (1 H, s) 4.99 (2 H, s) 4.58 (2 H, d, J = 5.49 Hz) 3.98 (2 H, s) 3.75 (3 H, s) |

| Example No. | Structure | Name | ¹H NMR |
|---|---|---|---|
| 88 | 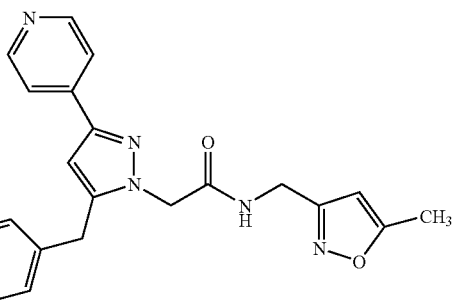 | 2-[5-(4-fluorobenzyl)-3-pyridin-4-yl-1H-pyrazol-1-yl]-N-[(5-methylisoxazol-3-yl)methyl]acetamide | (500 MHz, DEUTERIUM OXIDE) δ ppm 8.71-8.84 (1 H, m) 8.66 (2 H, s) 8.01 (2 H, s) 7.27 (2 H, dd, J = 8.24, 5.77 Hz) 7.12 (2 H, t, J = 8.65 Hz) 6.69 (1 H, s) 6.08 (1 H, s) 4.92 (2 H, s) 4.26 (2 H, d, J = 6.04 Hz) 4.00 (2 H, s) 2.32 (3 H, s) |
| 89 | 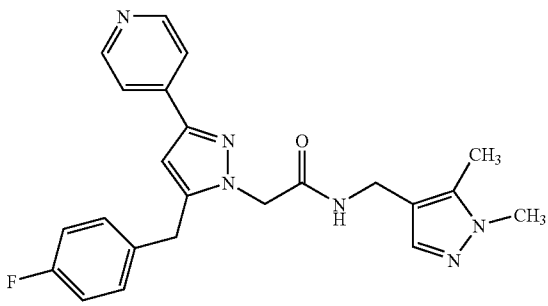 | N-[(1,5-dimethyl-1H-pyrazol-4-yl)methyl]-2-[5-(4-fluorobenzyl)-3-pyridin-4-yl-1H-pyrazol-1-yl]acetamide | (400 MHz, DMSO-D6) δ ppm 8.50 (d, 2 H) 8.37 (t, 1 H) 7.65 (d, 2 H) 7.26-7.33 (m, 2 H) 7.24 (s, 1 H) 7.13 (t, 2 H) 6.51 (s, 1 H) 4.79 (s, 2 H) 4.06 (d, 2 H) 3.99 (s, 2 H) 3.67 (s, 3 H) 2.18 (s, 3 H) |
| 90 | 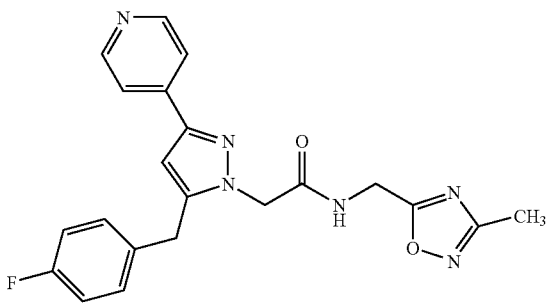 | 2-[5-(4-fluorobenzyl)-3-pyridin-4-yl-1H-pyrazol-1-yl]-N-[(3-methyl-1,2,4-oxadiazol-5-yl)methyl]acetamide | (400 MHz, DMSO-D6) δ ppm 8.99 (t, 1 H) 8.53 (d, 2 H) 7.67 (d, 2 H) 7.26-7.35 (m, 2 H) 7.15 (t, 2 H) 6.52 (s, 1 H) 4.96 (s, 2 H) 4.57 (d, 2 H) 4.02 (s, 2 H) 2.31 (s, 3 H) |
| 91 | 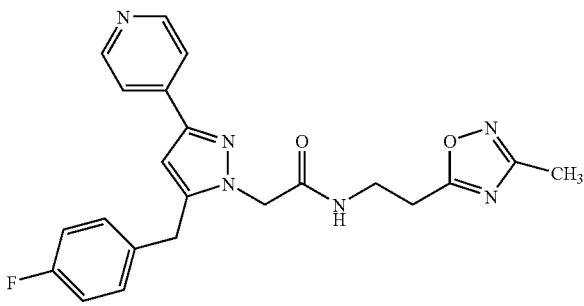 | 2-[5-(4-fluorobenzyl)-3-pyridin-4-yl-1H-pyrazol-1-yl]-N-[2-(3-methyl-1,2,4-oxadiazol-5-yl)ethyl]acetamide | (400 MHz, DMSO-D6) δ ppm 8.50 (d, 2 H) 8.33 (t, 1 H) 7.63 (d, 2 H) 7.24-7.33 (m, 2 H) 7.14 (t, 2 H) 6.53 (s, 1 H) 4.78 (s, 2 H) 3.97 (s, 2 H) 3.48 (q, 2 H) 3.03 (t, 2 H) 2.26 (s, 3 H) |

| Example No. | Structure | Name | ¹H NMR |
|---|---|---|---|
| 92 | 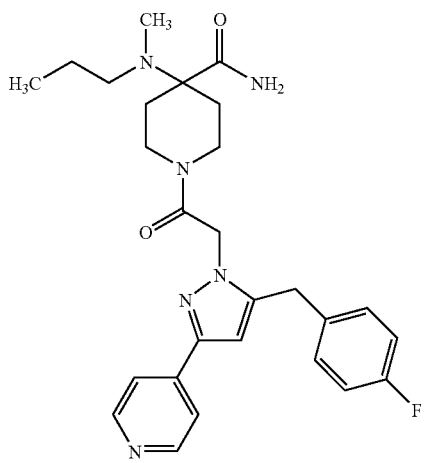 | 1-{[5-(4-fluorobenzyl)-3-pyridin-4-yl-1H-pyrazol-1-yl]acetyl}-4-[methyl(propyl)amino]piperidine-4-carboxamide | (400 MHz, DMSO-D6) δ ppm 8.54 (d, 2 H) 7.66 (d, 2 H) 7.25-7.34 (m, 2 H) 7.09-7.18 (m, 3 H) 7.06 (s, 1 H) 6.52 (s, 1 H) 5.18 (q, 2 H) 3.95 (s, 2 H) 3.72-3.85 (m, 1 H) 3.63-3.73 (m, 1 H) 3.03-3.08 (m, 1 H) 3.19-3.30 (m, 1 H) 2.23-2.32 (m, |
| 93 | 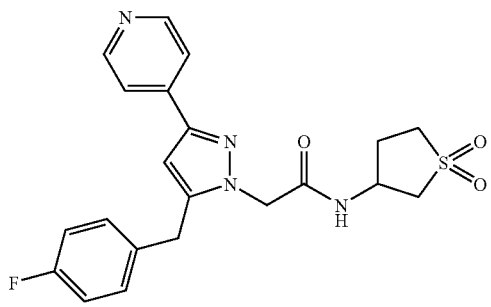 | N-(1,1-dioxidotetrahydro-3-thienyl)-2-[5-(4-fluorobenzyl)-3-pyridin-4-yl-1H-pyrazol-1-yl]acetamide | (400 MHz, DMSO-D6) δ ppm 8.67 (d, 1 H) 8.52 (d, 2 H) 7.66 (d, 2 H) 7.26-7.34 (m, 2 H) 7.14 (t, 2 H) 6.54 (s, 1 H) 4.85 (q, 2 H) 4.40-4.50 (m, 1 H) 4.01 (s, 2 H) 3.36-3.46 (m, 1 H) 3.23-3.28 (m, 1 H) 3.10-3.21 (m, 1 H) 2.88-2.95 (m, 1 H |
| 94 | 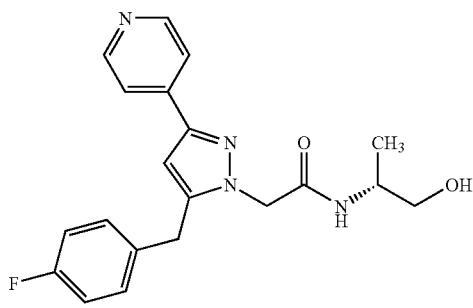 | 2-[5-(4-fluorobenzyl)-3-pyridin-4-yl-1H-pyrazol-1-yl]-N-[(1R)-2-hydroxy-1-methylethyl]acetamide | (400 MHz, DMSO-D6) δ ppm 8.52 (d, 2 H) 8.02 (d, 1 H) 7.66 (d, 2 H) 7.28-7.34 (m, 2 H) 7.15 (t, 2 H) 6.51 (s, 1 H) 4.82 (s, 2 H) 4.74 (t, 1 H) 4.01 (s, 2 H) 3.73-3.81 (m, 1 H) 3.32-3.40 (m, 1 H) 3.23-3.30 (m, 1 H) 1.05 (d, 3 H) |
| 95 | 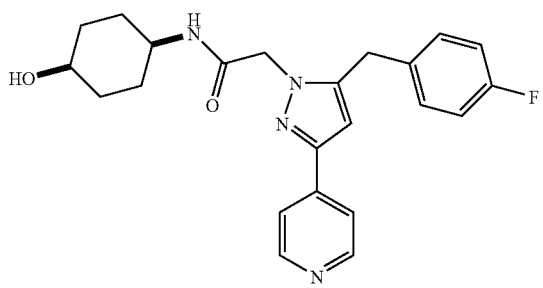 | 2-[5-(4-fluorobenzyl)-3-pyridin-4-yl-1H-pyrazol-1-yl]-N-(cis-4-hydroxycyclohexyl)-acetamide | (400 MHz, DMSO-D6) δ ppm 8.51 (d, 2 H) 8.10 (d, 1 H) 7.66 (d, 2 H) 7.26-7.34 (m, 2 H) 7.14 (t, 2 H) 6.51 (s, 1 H) 4.83 (s, 2 H) 4.42 (d, 1 H) 4.00 (s, 2 H) 3.62-3.68 (m, 1 H) 3.54-3.62 (m, 1 H) 1.52-1.64 (m, 4 H) 1.42-1.51 (m, 4 H) |

-continued

| Example No. | Structure | Name | ¹H NMR |
|---|---|---|---|
| 96 | 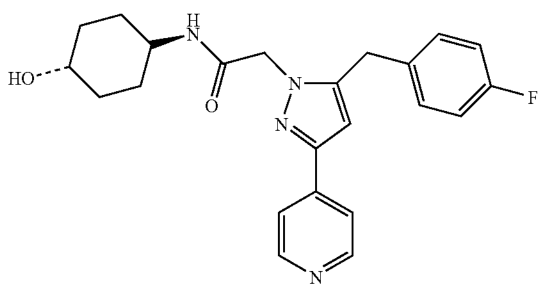 | 2-[5-(4-fluorobenzyl)-3-pyridin-4-yl-1H-pyrazol-1-yl]-N-(trans-4-hydroxycyclohexyl)-acetamide | (400 MHz, DMSO-D6) δ ppm 8.51 (d, 2 H) 8.07 (d, 1 H) 7.65 (d, 2 H) 7.27-7.34 (m, 2 H) 7.15 (t, 2 H) 6.50 (s, 1 H) 4.78 (s, 2 H) 4.53 (d, 1 H) 4.00 (s, 2 H) 3.42-3.51 (m, 1 H) 1.73-1.83 (m, 4 H) 1.16-1.23 (m, 4 H) |
| 97 | 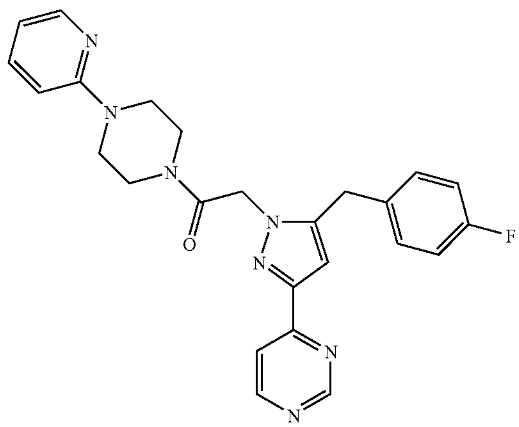 | 4-{5-(4-fluorobenzyl)-1-[2-oxo-2-(4-pyridin-2-ylpiperazin-1-yl)ethyl]-1H-pyrazol-3-yl}pyrimidine | (400 MHz, DMSO-D6) δ ppm 9.09 (d, 1 H) 8.73 (d, 1 H) 8.12 (dd, 1 H) 7.82 (dd, 1 H) 7.52-7.58 (m, 1 H) 7.28-7.33 (m, 2 H) 7.14 (t, 2 H) 6.86 (d, 1 H) 6.62-6.65 (m, 1 H) 6.52 (s, 1 H) 5.30 (s, 2 H) 3.97 (s, 2 H) 3.58-3.64 (m, 4 H) 3.47-3.55 |
| 98 | 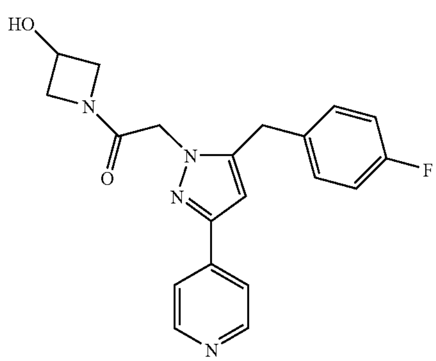 | 1-{[5-(4-fluorobenzyl)-3-pyridin-4-yl-1H-pyrazol-1-yl]acetyl}azetidin-3-ol | (400 MHz, DMSO-D6) δ ppm 8.53 (d, 2 H) 7.67 (d, 2 H) 7.31 (t, 2 H) 7.17 (t, 2 H) 6.53 (s, 1 H) 5.77 (d, 1 H) 4.90-4.93 (m, 2 H) 4.43-4.51 (m, 1 H) 4.24-4.32 (m, 1 H) 4.02-4.09 (m, 1 H) 3.97 (s, 2 H) 3.84-3.91 (m, 1 H) 3.56-3.65 (m, 1 H |
| 99 | 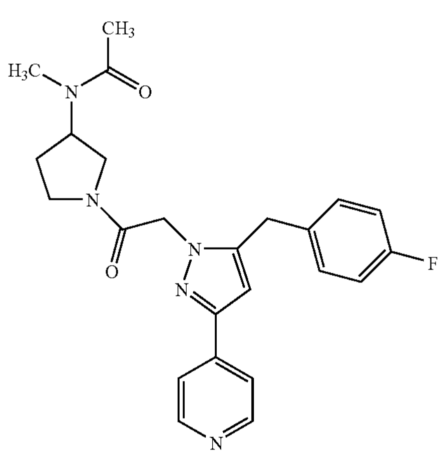 | N-(1-{[5-(4-fluorobenzyl)-3-pyridin-4-yl-1H-pyrazol-1-yl]acetyl}pyrrolidin-3-yl)-N-methylacetamide | 400 MHz, DMSO-D6) δ ppm 8.61 (d, 2 H) 7.82 (d, 2 H) 7.27-7.35 (m, 2 H) 7.15 (t, 2 H) 6.57-6.64 (m, 1 H) 5.05-5.19 (m, 2 H) 4.00 (s, 2 H) 3.64-3.83 (m, 1 H) 3.32-3.59 (m, 3 H) 3.10-3.29 (m, 2 H) 2.67-2.92 (m, 3 H) 1.99-2.06 (d, 1 H) |

| Example No. | Structure | Name | ¹H NMR |
|---|---|---|---|
| 100 | 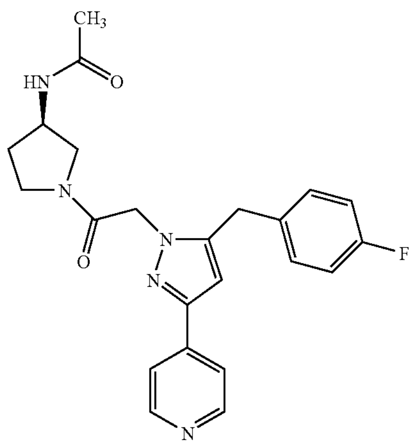 | N-[(3R)-1-{2-[5-(4-fluorobenzyl)-3-pyridin-4-yl-1H-pyrazol-1-yl]acetyl}pyrrolidin-3-yl]acetamide | (1:1 rotomers, 400 MHz, DMSO-D6) δ ppm 8.52 (2 H, d, J = 6.06 Hz) 8.15 (0.5 H, d, J = 6.82 Hz) 8.11 (0.5 H, d, J = 6.57 Hz) 7.66 (2 H, d, J = 6.06 Hz) 7.26-7.35 (2 H, m) 7.10-7.20 (2 H, m) 6.48-6.53 (1 H, m) 4.96-5.15 (2 H, m) 4.25-4.36 (0.5 H) |
| 101 | 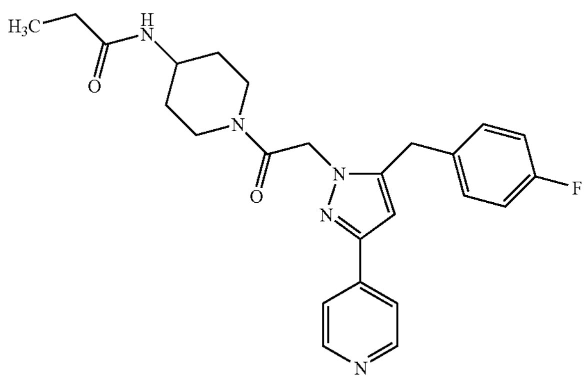 | N-(1-(2-[5-(4-fluorobenzyl)-3-pyridin-4-yl-1H-pyrazol-1-yl]acetyl}piperidin-4-yl)propanamide | (400 MHz, DMSO-D6) δ ppm 8.52 (2 H, d, J = 6.06 Hz) 7.76 (1 H, d, J = 7.58 Hz) 7.60-7.69 (2 H, m) 7.30 (2 H, dd, J = 8.59, 5.56 Hz) 7.15 (2 H, t, J = 8.84 Hz) 6.52 (1 H, s) 5.06-5.33 (2 H, m) 4.12 (1 H, d, J = 13.14 Hz) 3.93 (2 H, s) 3.71-3.88 (2 H, m |
| 102 | 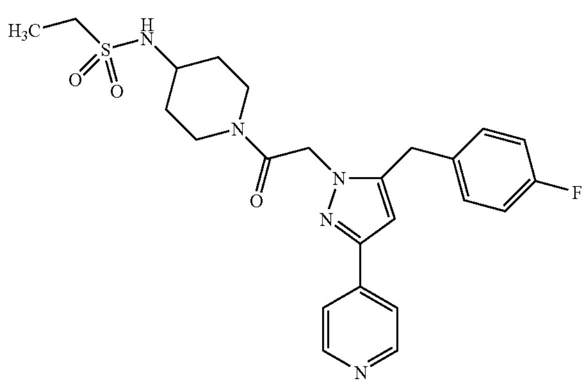 | N-(1-(2-[5-(4-fluorobenzyl)-3-pyridin-4-yl-1H-pyrazol-1-yl]acetyl}piperidin-4-yl)ethanesulfonamide | (400 MHz, DMSO-D6) δ ppm 8.44-8.59 (2 H, m) 7.61-7.69 (2 H, m) 7.26-7.32 (2 H, m) 7.23 (1 H, d, J = 6.82 Hz) 7.09-7.19 (2 H, m) 6.52 (1 H, s) 5.10-5.29 (2 H, m) 4.11 (1 H, d, J = 13.64 Hz) 3.93 (2 H, s) 3.83 (1 H, d, J = 14.15 Hz) 3.32-3.44 |

-continued

| Example No. | Structure | Name | ¹H NMR |
|---|---|---|---|
| 103 | 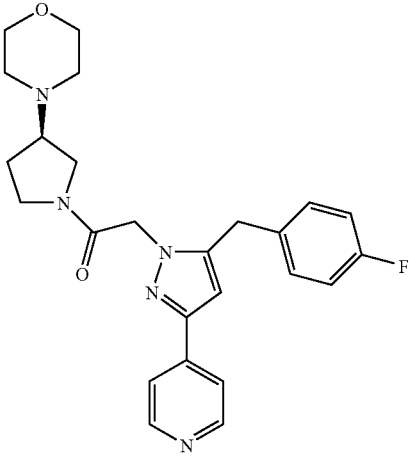 | 4-[(3R)-1-{[5-(4-fluorobenzyl)-3-pyridin-4-yl-1H-pyrazol-1-yl]acetyl}piperidin-4-yl]morpholine | (400 MHz, DMSO-D6) δ ppm 8.57 (2 H, d, J = 5.05 Hz) 7.75 (2 H, d, J = 4.55 Hz) 7.31 (2 H, dd, J = 8.46, 5.68 Hz) 7.15 (2 H, t, J = 8.84 Hz) 6.58 (1 H, d, J = 3.28 Hz) 5.03-5.24 (2 H, m) 3.87-4.01 (3 H, m) 2.77-3.85 (12 H, m) 1.84-2.41 (2 H, m) |
| 104 | 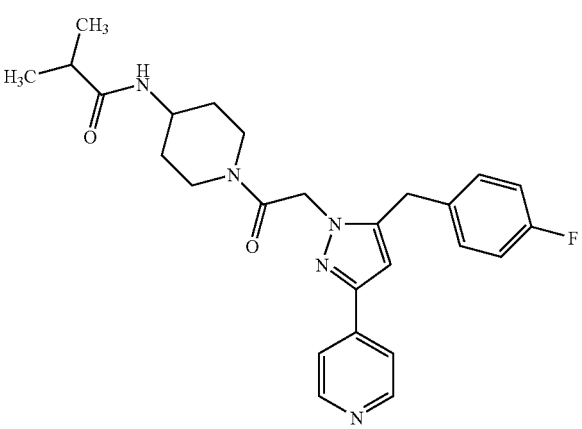 | N-(1-{[5-(4-fluorobenzyl)-3-pyridin-4-yl-1H-pyrazol-1-yl]acetyl}piperidin-4-yl)-2-methylpropanamide | (400 MHz, DMSO-D6) δ ppm 8.45-8.64 (2 H, m) 7.71 (1 H, d, J = 7.58 Hz) 7.58-7.68 (2 H, m) 7.30 (2 H, dd, J = 8.59, 5.56 Hz) 7.06-7.20 (2 H, m) 6.52 (1 H, s) 5.07-5.38 (2 H, m) 4.13 (1 H, d, J = 13.64 Hz) 3.93 (2 H, s) 3.69-3.88 (2 H, m) 3.16 ( |
| 105 | 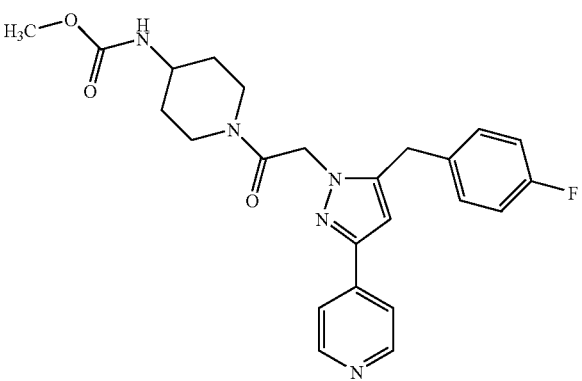 | methyl (1-{[5-(4-fluorobenzyl)-3-pyridin-4-yl-1H-pyrazol-1-yl]acetyl}piperidin-4-yl)carbamate | (400 MHz, DMSO-D6) δ ppm 8.50-8.57 (2 H, m) 7.61-7.70 (2 H, m) 7.21-7.37 (3 H, m) 7.05-7.20 (2 H, m) 6.51 (1 H, s) 5.01-5.27 (2 H, m) 4.11 (1 H, d, J = 13.14 Hz) 3.93 (2 H, s) 3.83 (1 H, d, J = 13.39 Hz) 3.45-3.61 (4 H, m) 3.15 (1 H, t, J = |

| Example No. | Structure | Name | ¹H NMR |
|---|---|---|---|
| 106 | 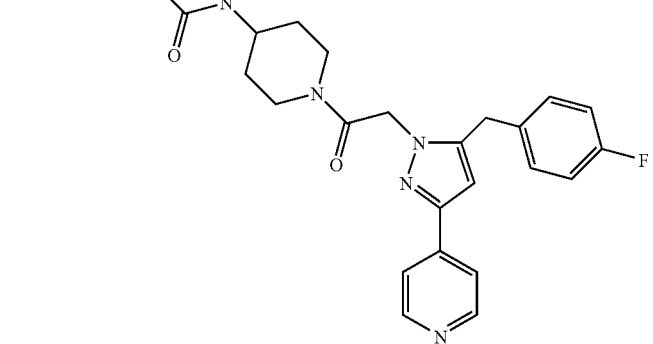 | 1-ethyl-3-(1-{[5-(4-fluorobenzyl)-3-pyridin-4-yl-1H-pyrazol-1-yl]acetyl}piperidin-4-yl)urea | (400 MHz, DMSO-D6) δ ppm 8.39-8.62 (2 H, m) 7.60-7.69 (2 H, m) 7.22-7.38 (2 H, m) 7.04-7.19 (2 H, m) 6.52 (1 H, s) 5.85 (1 H, d, J = 7.83 Hz) 5.70 (1 H, t, J = 5.56 Hz) 5.05-5.31 (2 H, m) 4.02-4.15 (1 H, m) 3.94 (2 H, s) 3.79 (1 H, d, J = 13 |
| 107 | 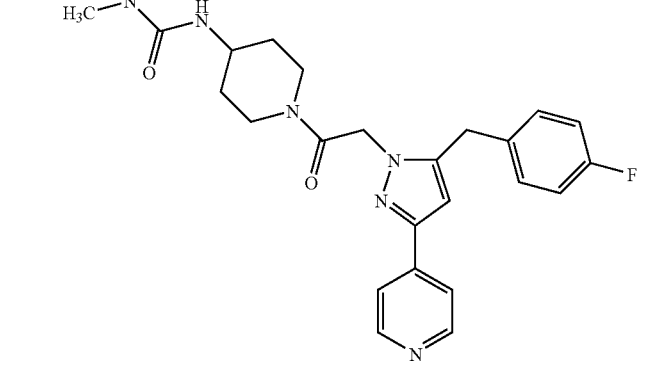 | 1-(1-{[5-(4-fluorobenzyl)-3-pyridin-4-yl-1H-pyrazol-1-yl]acetyl}piperidin-4-yl)-3-methylurea | (400 MHz, DMSO-D6) δ ppm 8.44-8.56 (2 H, m) 7.59-7.72 (2 H, m) 7.22-7.35 (2 H, m) 7.09-7.19 (2 H, m) 6.52 (1 H, s) 5.92 (1 H, d, J = 7.83 Hz) 5.63 (1 H, q, J = 4.46 Hz) 5.18 (2 H, q, J = 16.93 Hz) 4.08 (1 H, d, J = 13.14 Hz) 3.94 (2 H, s) 3.80 (1 |
| 108 | 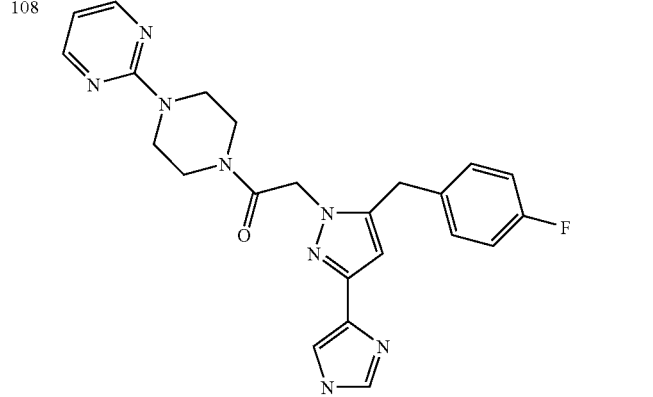 | 2-(4-{[5-(4-fluorobenzyl)-3-(1H-imidazol-4-yl)-1H-pyrazol-1-yl]acetyl}piperazin-1-yl)pyrimidine | (400 MHz, MeOD) δ ppm 8.844 (d, 1 H), 8.397 (d, 2 H), 7.704 (s, 1 H), 7.295 (m, 2 H), 7.057 (m, 2 H), 6.706 (m, 1 H), 6.372 (s, 1 H), 5.303 (s, 2 H), 4.072 (s, 2 H), 3.905 (dd, 4 H), 3.671 (m, 4 H). |

| Example No. | Structure | Name | $^1$H NMR |
|---|---|---|---|
| 109 | 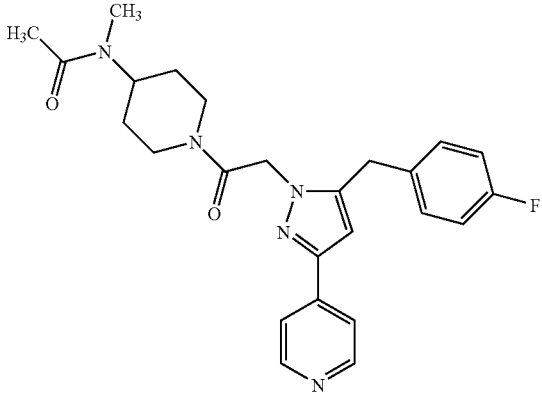 | N-(1-{[5-(4-fluorobenzyl)-3-pyridin-4-yl-1H-pyrazol-1-yl]acetyl}piperidin-4-yl)-N-methylacetamide | (400 MHz, DMSO-D6) δ ppm 8.52 (2 H, d, J = 6.06 Hz) 7.63-7.69 (2 H, m) 7.30 (2 H, dd, J = 8.46, 5.68 Hz) 7.15 (2 H, t, J = 8.84 Hz) 6.52 (1 H, s) 5.08-5.37 (2 H, m) 4.33-4.61 (1.5 H, m) 3.79-3.98 (3.5 H, m) 3.02-3.23 (1 H, m) 2.53-2.84 (4 H, |
| 110 | 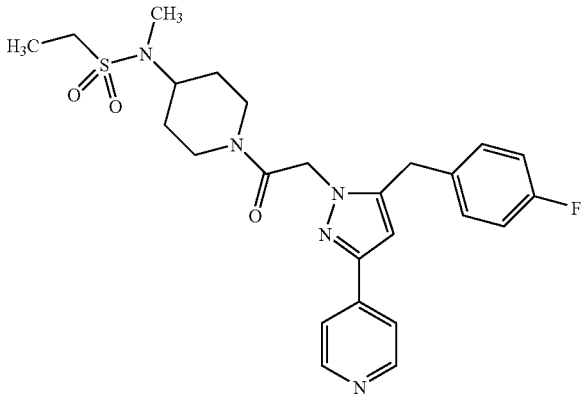 | N-(1-{[5-(4-fluorobenzyl)-3-pyridin-4-yl-1H-pyrazol-1-yl]acetyl}piperidin-4-yl)-N-methylethane-sulfonamide | (400 MHz, DMSO-D6) δ ppm 8.46-8.61 (2 H, m) 7.60-7.74 (2 H, m) 7.25-7.36 (2 H, m) 7.06-7.19 (2 H, m) 6.52 (1 H, s) 5.08-5.28 (2 H, m) 4.38 (1 H, d, J = 12.88 Hz) 3.90-3.99 (3 H, m) 3.67-3.87 (1 H, m) 3.01-3.20 (3 H, m) 2.56-2.73 (4 |
| 111 | 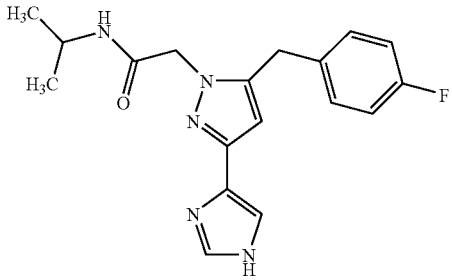 | 2-[5-(4-fluorobenzyl)-3-(1H-imidazol-4-yl)-1H-pyrazol-1-yl]-N-isopropylacetamide | (400 MHz, MeOD) δ ppm 8.840 (d, 1 H), 7.739 (d, 1 H), 7.296 (m, 2 H), 7.087 (m, 2 H), 6.358 (s, 1 H), 4.808 (s, 2 H), 4.043 (s, 2 H), 3.981 (m, 1 H), 1.154 (d, 6 H). |
| 112 | 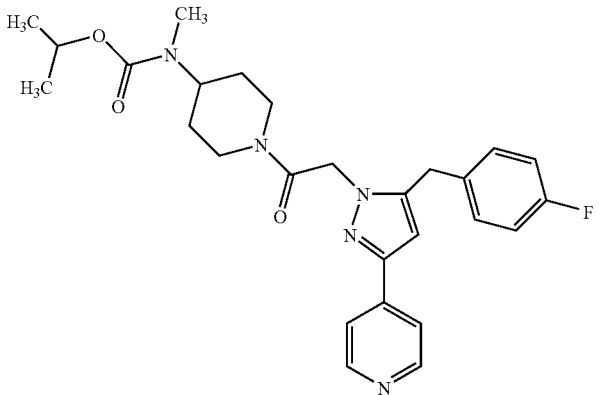 | isopropyl (1-{[5-(4-fluorobenzyl)-3-pyridin-4-yl-1H-pyrazol-1-yl]acetyl}piperidin-4-yl)methylcarbamate | (400 MHz, DMSO-D6) δ ppm 8.48-8.63 (2 H, m) 7.56-7.70 (2 H, m) 7.23-7.36 (2 H, m) 7.02-7.19 (2 H, m) 6.52 (1 H, s) 5.03-5.32 (2 H, m) 4.67-4.86 (1 H, m) 4.38 (1 H, d, J = 13.39 Hz) 3.86-4.15 (4 H, m) 3.03-3.16 (1 H, m) 2.68 (3 H, s) |

| Example No. | Structure | Name | $^1$H NMR |
|---|---|---|---|
| 113 | 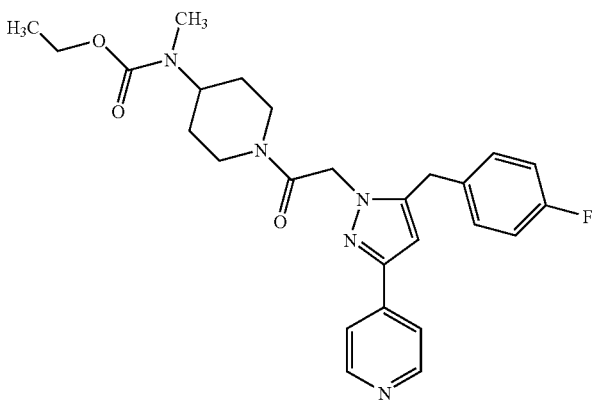 | ethyl (1-{[5-(4-fluorobenzyl)-3-pyridin-4-yl-1H-pyrazol-1-yl]acetyl}piperidin-4-yl)methylcarbamate | (400 MHz, DMSO-D6) δ ppm 8.45-8.63 (2 H, m) 7.59-7.73 (2 H, m) 7.30 (2 H, dd, J = 8.46, 5.68 Hz) 7.04-7.20 (2 H, m) 6.52 (1 H, s) 5.12-5.28 (2 H, m) 4.36 (1 H, s) 3.88-4.14 (6 H, m) 3.03-3.22 (1 H, m) 2.70 (3 H, s) 2.61 (1 H, t, J = 11.49 |
| 114 | 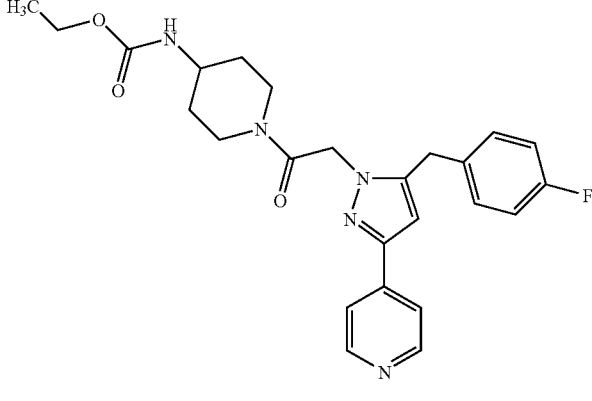 | isopropyl (1-{[5-(4-fluorobenzyl)-3-pyridin-4-yl-1H-pyrazol-1-yl]acetyl}piperidin-4-yl)carbamate | (400 MHz, DMSO-D6) δ ppm 8.52 (2 H, d, J = 6.06 Hz) 7.54-7.74 (2 H, m) 7.29 (2 H, dd, J = 8.46, 5.68 Hz) 7.23 (1 H, d, J = 7.58 Hz) 7.08-7.19 (2 H, m) 6.52 (1 H, s) 5.06-5.33 (2 H, m) 4.05-4.18 (1 H, m) 3.90-4.04 (4 H, m) 3.83 (1 H, d, J = 13.64 |
| 115 | 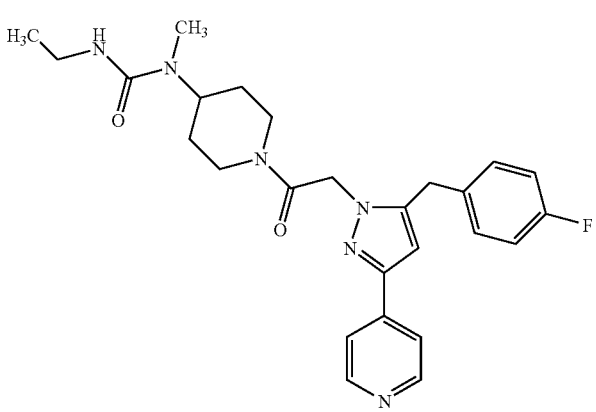 | 3-ethyl-1-(1-{[5-(4-fluorobenzyl)-3-pyridin-4-yl-1H-pyrazol-1-yl]acetyl}piperidin-4-yl)-1-methylurea | (400 MHz, DMSO-D6) δ ppm 8.52 (2 H, d, J = 6.06 Hz) 7.66 (2 H, d, J = 6.06 Hz) 7.30 (2 H, dd, J = 8.46, 5.68 Hz) 7.15 (2 H, t, J = 8.84 Hz) 6.52 (1 H, s) 6.24 (1 H, t, J = 5.31 Hz) 4.93-5.31 (2 H, m) 4.37 (1 H, d, J = 12.63 Hz) 4.08-4.27 (1 H, m) 3.80-3 |

-continued

| Example No. | Structure | Name | ¹H NMR |
|---|---|---|---|
| 116 | 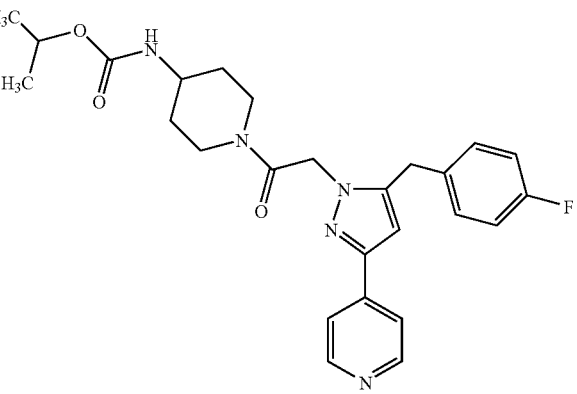 | isopropyl (1-{[5-(4-fluorobenzyl)-3-pyridin-4-yl-1H-pyrazol-1-yl]acetyl}piperidin-4-yl)carbamate | (400 MHz, DMSO-D6) δ ppm 8.52 (2 H, d, J = 4.55 Hz) 7.57-7.71 (2 H, m) 7.23-7.36 (2 H, m) 7.05-7.21 (3 H, m) 6.52 (1 H, s) 5.05-5.30 (2 H, m) 4.59-4.88 (1 H, m) 4.02-4.23 (1 H, m) 3.93 (2 H, s) 3.83 (1 H, d, J = 13.39 Hz) 3.43-3.63 (1 H, |
| 117 | 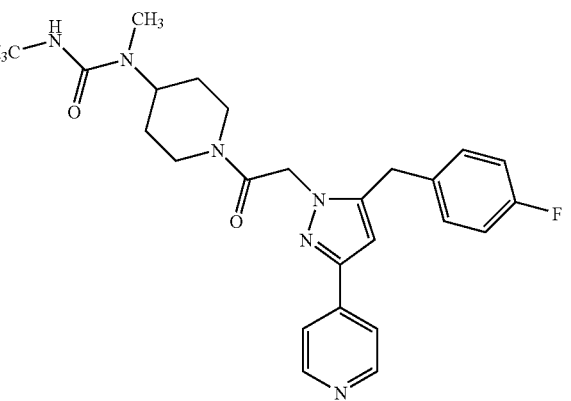 | 1-(1-{[5-(4-fluorobenzyl)-3-pyridin-4-yl-1H-pyrazol-1-yl]acetyl}piperidin-4-yl)-1,3-dimethylurea | |
| 118 | 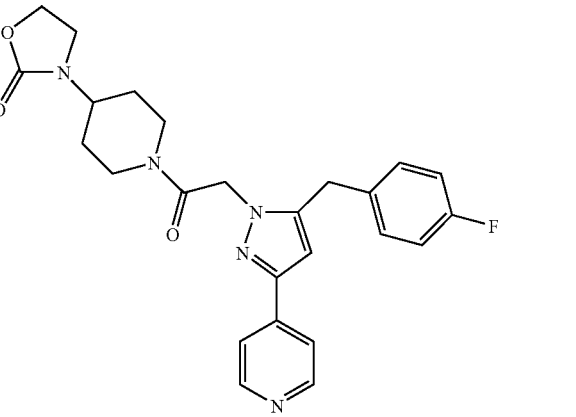 | 3-(1-{[5-(4-fluorobenzyl)-3-pyridin-4-yl-1H-pyrazol-1-yl]acetyl}piperidin-4-yl)-1,3-oxazolidin-2-one | (400 MHz, DMSO-D6) δ ppm 8.52 (2 H, d, J = 6.06 Hz) 7.58-7.74 (2 H, m) 7.30 (2 H, dd, J = 8.46, 5.68 Hz) 7.15 (2 H, t, J = 8.84 Hz) 6.53 (1 H, s) 5.10-5.34 (2 H, m) 4.37 (1 H, d, J = 13.39 Hz) 4.25 (2 H, t, J = 8.21 Hz) 3.90-4.00 (3 H, m) 3.66-3.83 |

| Example No. | Structure | Name | ¹H NMR |
|---|---|---|---|
| 119 | 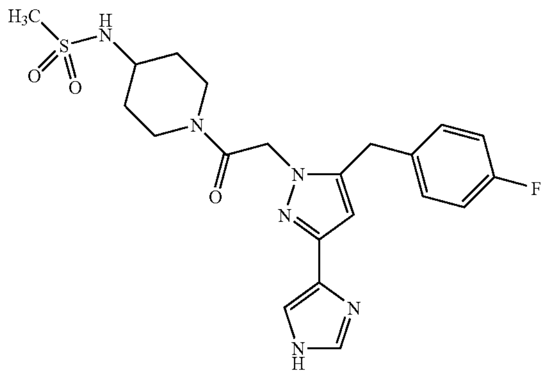 | N-(1-{2-[5-(4-fluorobenzyl)-3-(1H-imidazol-4-yl)-1H-pyrazol-1-yl]acetyl}piperidin-4-yl)methanesulfonamide | (400 MHz, MeOD) δ ppm 8.852 (d, 1 H), 7.716 (d, 1 H), 7.301 (m, 2 H), 7.089 (m, 2 H), 6.354 (s, 1 H), 5.150 (d, 2 H), 4.228 (d, 1 H), 3.992 (s, 2 H), 3.950 (d, 1 H), 3.519 (m, 1 H), 3.297 (m, 1 H), 2.984 (m, 4 H), 2.024 (m, 2 H), 1.600 (m, 2 H). |
| 120 | 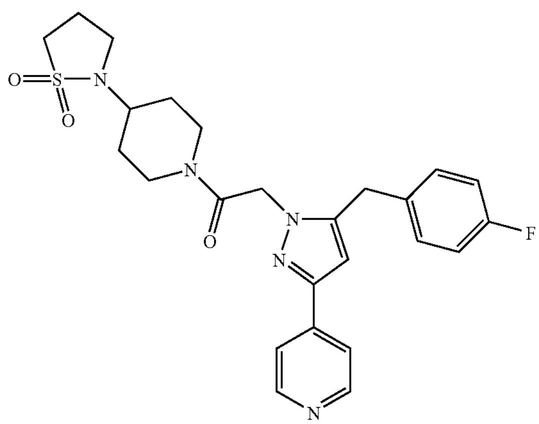 | 4-[1-{2-[4-(1,1-dioxidoisothiazolidin-2-yl)piperidin-1-yl]-2-oxoethyl}-5-(4-fluorobenzyl)-1H-pyrazol-3-yl]pyridine | (400 MHz, DMSO-D6) δ ppm 8.49-8.58 (2 H, m) 7.63-7.69 (2 H, m) 7.24-7.35 (2 H, m) 7.08-7.18 (2 H, m) 6.52 (1 H, s) 5.09-5.27 (2 H, m) 4.26 (1 H, d, J = 14.40 Hz) 3.86-3.97 (3 H, m) 3.45-3.60 (1 H, m) 3.09-3.25 (5 H, m) 2.67-2.79 (1 |
| 121 | 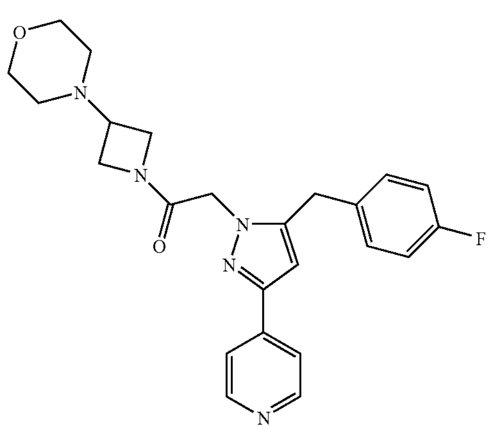 | 4-(1-{[5-(4-fluorobenzyl)-3-pyridin-4-yl-1H-pyrazol-1-yl]acetyl}azetidin-3-yl)morpholine | (400 MHz, DMSO-D6) δ ppm 8.49-8.59 (2 H, m) 7.66 (2 H, dd, J = 4.55, 1.52 Hz) 7.31 (2 H, dd, J = 8.59, 5.81 Hz) 7.15 (2 H, t, J = 8.84 Hz) 6.55 (1 H, s) 4.93 (2 H, s) 4.14 (1 H, t, J = 8.08 Hz) 3.96-4.04 (3 H, m) 3.81-3.91 (1 H, m) 3.72 (1 H, dd, J = |

-continued

| Example No. | Structure | Name | ¹H NMR |
|---|---|---|---|
| 122 | 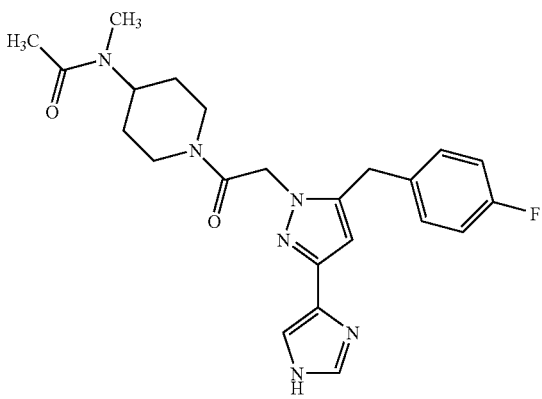 | N-(1-{[5-(4-fluorobenzyl)-3-(1H-imidazol-4-yl)-1H-pyrazol-1-yl]acetyl}piperidin-4-yl)-N-methylacetamide | (400 MHz, MeOD) δ ppm 8.862 (s, 1 H), 7.725 (s, 1 H), 7.318 (m, 2 H), 7.094 (m, 2 H), 6.368 (s, 1 H), 5.263 (m, 2 H), 4.580 (m, 2 H), 4.021 (s, 3 H), 3.299 (m, 12 H), 2.942 (s, 2 H), 2.775 (m, 2 H), 2.188 (s, 3 H), 1.792-1.569 (m, 4 H). |
| 123 | 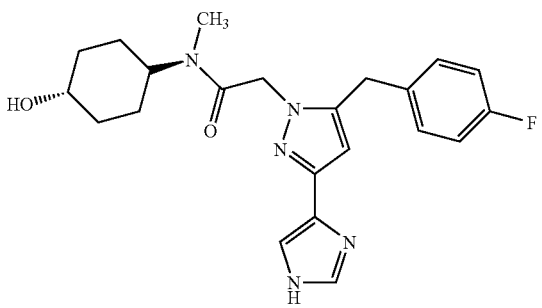 | 2-[5-(4-fluorobenzyl)-3-(1H-imidazol-4-yl)-1H-pyrazol-1-yl]-N-(trans-4-hydroxycyclohexyl)-N-methylacetamide | (400 MHz, MeOD) δ ppm 8.867 (s, 1 H), 7.734 (m, 1 H), 7.301 (m 2 H), 7.082 (m, 2 H), 6.346 (s, 1 H), 5.185 (s, 1 H), 5.096 (s, 1 H), 4.249 (m, 0.5 H), 4.002 (m, 2 H), 3.712 (m, 1.5 H), 2.961 (s, 2 H), 2.863 (s, 1 H), 2.026 (m, 2 H), 1.786-1.357 (m, |
| 124 | 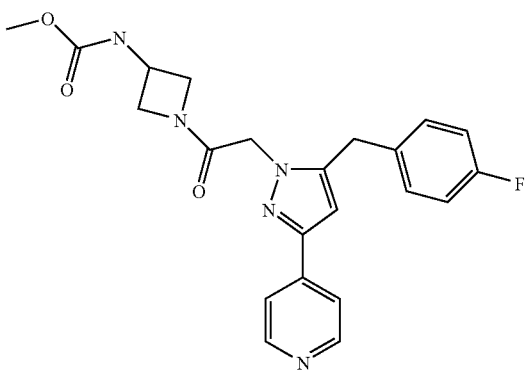 | methyl (1-{[5-(4-fluorobenzyl)-3-pyridin-4-yl-1H-pyrazol-1-yl]acetyl}azetidin-3-yl)carbamate | (400 MHz, DMSO-D6) δ ppm 8.47-8.63 (2 H, m) 7.88 (1 H, d, J = 5.56 Hz) 7.66 (2 H, dd, J = 4.67, 1.39 Hz) 7.24-7.38 (2 H, m) 7.16 (2 H, t, J = 8.84 Hz) 6.53 (1 H, s) 4.91 (2 H, s) 4.23-4.44 (2 H, m) 4.05-4.15 (1 H, m) 3.97 (3 H, s) 3.68-3.82 (1 |
| 125 | 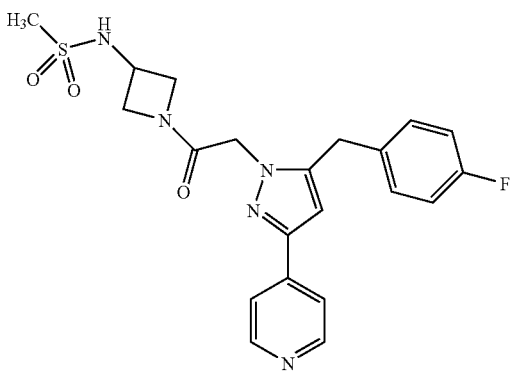 | N-(1-{2-[5-(4-fluorobenzyl)-3-pyridin-4-yl-1H-pyrazol-1-yl]acetyl}azetidin-3-yl)methanesulfonamide | (400 MHz, DMSO-D6) δ ppm 8.53 (2 H, d, J = 6.06 Hz) 7.91 (1 H, s) 7.52-7.72 (2 H, m) 7.31 (2 H, dd, J = 8.46, 5.68 Hz) 7.16 (2 H, t, J = 8.84 Hz) 6.53 (1 H, s) 4.93 (2 H, s) 4.42 (1 H, t, J = 7.83 Hz) 4.11-4.30 (2H, m) 4.05 (1 H, dd, J = 8.84, 4.55 Hz) |

| Example No. | Structure | Name | ¹H NMR |
|---|---|---|---|
| 126 | 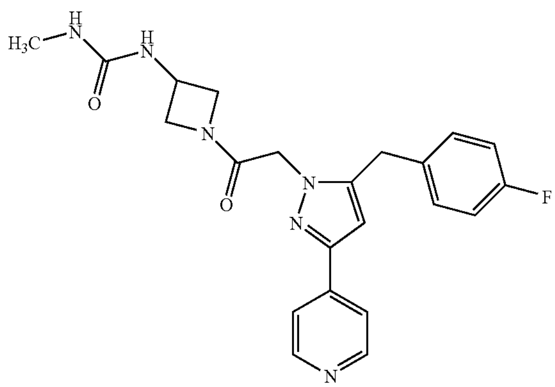 | 1-(1-{[5-(4-fluorobenzyl)-3-pyridin-4-yl-1H-pyrazol-1-yl]acetyl}azetidin-3-yl)-3-methylurea | (400 MHz, DMSO-D6) δ ppm 8.52 (2 H, d, J = 6.06 Hz) 7.60-7.75 (2 H, m) 7.31 (2 H, dd, J = 8.46, 5.68 Hz) 7.16 (2 H, t, J = 8.84 Hz) 6.60 (1 H, d, J = 7.07 Hz) 6.53 (1 H, s) 5.90 (1 H, q, J = 4.46 Hz) 4.91 (2 H, s) 4.25-4.51 (2 H, m) 4.07 (1 H, t, J = 8.72 |
| 127 | 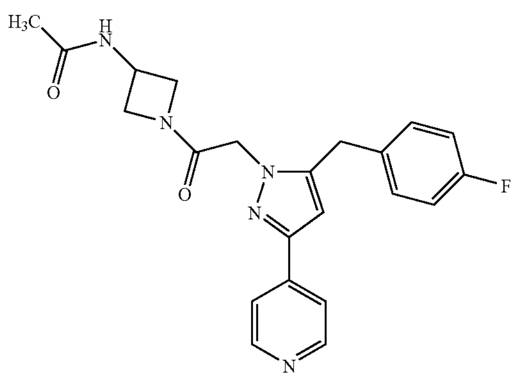 | N-(1-{2-[5-(4-fluorobenzyl)-3-pyridin-4-yl-1H-pyrazol-1-yl]acetyl}azetidin-3-yl)acetamide | (400 MHz, DMSO-D6) δ ppm 8.40-8.61 (3 H, m) 7.59-7.74 (2 H, m) 7.26-7.38 (2 H, m) 7.06-7.21 (2 H, m) 6.54 (1 H, s) 4.92 (2 H, s) 4.37-4.51 (1 H, m) 4.34 (1 H, t, J = 8.34 Hz) 4.04-4.20 (1 H, m) 3.98 (2 H, s) 3.92 (1 H, dd, J = 8.72, 5.18 H |
| 128 | 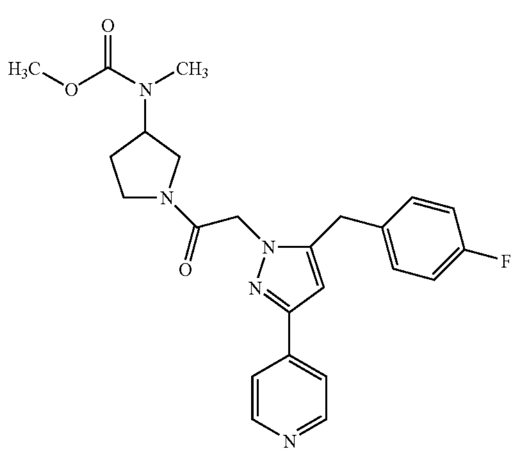 | methyl (1-{[5-(4-fluorobenzyl)-3-pyridin-4-yl-1H-pyrazol-1-yl]acetyl}pyrrolidin-3-yl)methylcarbamate | (1:1 rotomers, 400 MHz, DMSO-D6) δ ppm 8.54 (2 H, d, J = 5.81 Hz) 7.63-7.76 (2 H, m) 7.33 (2 H, dd, J = 8.46, 5.68 Hz) 7.09-7.22 (2 H, m) 6.54 (1 H, d, J = 379 Hz) 5.00-5.27 (2 H, m) 4.68-4.82 (0.5 H, m) 4.50-4.67 (0.5 H, m) 3.98 (2 H, s) 3.6 |

| Example No. | Structure | Name | $^1$H NMR |
|---|---|---|---|
| 129 | 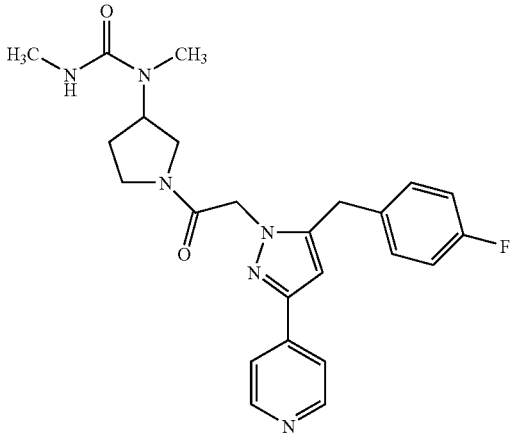 | 1-(1-{[5-(4-fluorobenzyl)-3-pyridin-4-yl-1H-pyrazol-1-yl]acetyl}pyrrolidin-3-yl)-1,3-dimethylurea | (1:1 rotomers, 400 MHz, DMSO-D6) δ ppm 8.52 (2 H, d, J = 5.81 Hz) 7.58-7.72 (2 H, m) 7.26-7.39 (2 H, m) 7.15 (2 H, t, J = 8.84 Hz) 6.49-6.58 (1 H, m) 6.25-6.40 (1 H, m) 4.99-5.23 (2 H, m) 4.82-4.96 (0.5 H, m) 4.69-4.82 (0.5 H, m) 3.96 (2 |
| 130 | 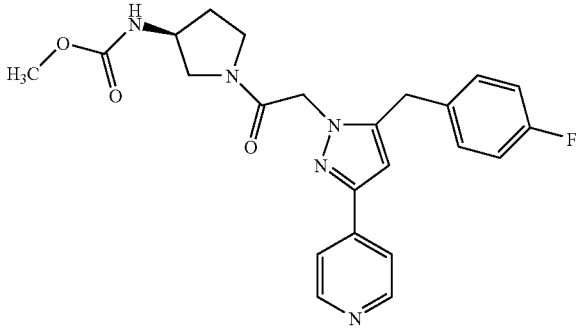 | methyl [(3S)-1-{[5-(4-fluorobenzyl)-3-pyridin-4-yl-1H-pyrazol-1-yl]acetyl}pyrrolidin-3-yl]carbamate | (400 MHz, DMSO-d6) δ ppm 1.58-2.27 (m, 2 H) 3.22 (dd, J = 11.58, 3.27 Hz, 0.8 H) 3.27-3.45 (m, 2 H) 3.44-3.56 (m, 1 H) 3.51-3.68 (m, 3.6 H) 3.67-3.81 (m, J = 9.82, 6.04 Hz, 0.6 H) 3.97 (s, 2 H) 4.08 (dd, 1 H) 4.94-5.20 (m, 2 H) 6.52 (s, 1 |
| 131 | 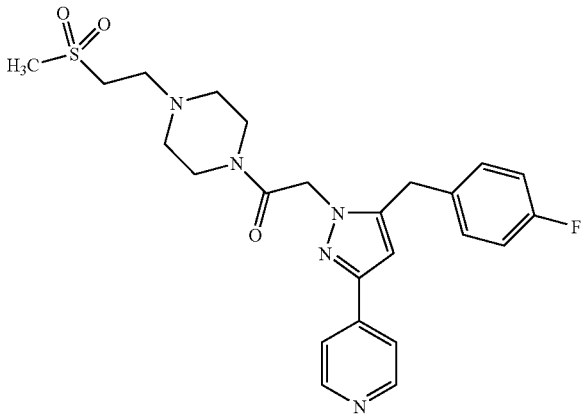 | 1-{[5-(4-fluorobenzyl)-3-pyridin-4-yl-1H-pyrazol-1-yl]acetyl}-4-[2-(methylsulfonyl)ethyl]piperazine | (400 MHz, DMSO-D6) δ ppm 8.40-8.68 (2 H, m) 7.58-7.69 (2 H, m) 7.24-7.35 (2 H, m) 7.06-7.19 (2 H, m) 6.53 (1 H, s) 5.19 (2 H, s) 3.94 (2 H, s) 3.45-3.52 (2 H, m) 3.37-3.45 (2 H, m) 3.26-3.35 (4 H, m) 3.04 (3 H, s) 2.69-2.80 (2 H, m |

| Example No. | Structure | Name | ¹H NMR |
|---|---|---|---|
| 132 | 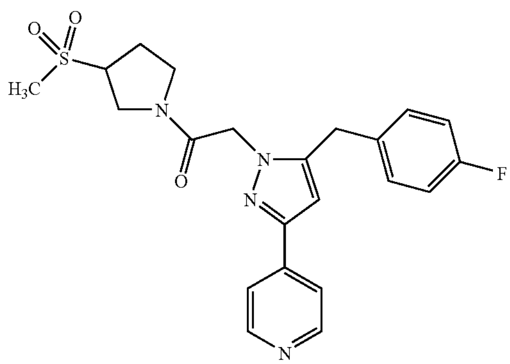 | 4-[5-(4-fluorobenzyl)-1-{2-[3-(methylsulfonyl)-pyrrolidin-1-yl]-2-oxoethyl}-1H-pyrazol-3-yl]pyridine | (1:1 rotomers, 400 MHz, DMSO-D6) δ ppm 8.43-8.57 (2 H, m) 7.64-7.71 (2 H, m) 7.31 (2 H, dd, J = 7.71, 5.94 Hz) 7.14 (2 H, t, J = 8.84 Hz) 6.53 (1 H, s) 5.08-5.26 (2 H, m) 3.91-4.16 (4 H, m) 3.57-3.78 2 H, m) 3.36-3.54 (1 H, m) 3.09 (1.5 H, |
| 133 | 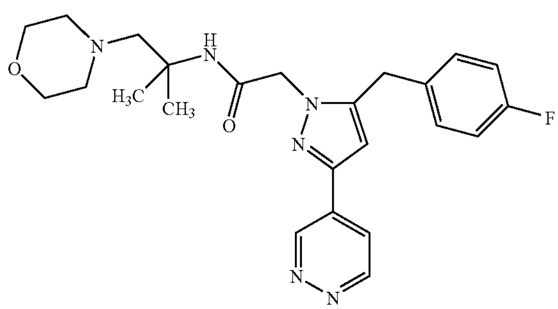 | N-(1,1-dimethyl-2-morpholin-4-ylethyl)-2-[5-(4-fluorobenzyl)-3-pyridazin-4-yl-1H-pyrazol-1-yl]acetamide | (400 MHz, MeOD) δ ppm 9.693 (s, 1 H), 9.288 (d, 1 H), 8.323 (d, 1 H), 7.336 (m, 21 H), 7.099 (m, 2 H), 6.801 (s, 1 H), 5.003 (s, 2 H), 4.110 (s, 2 H), 3.894 (m, 4 H), 3.522 (m, 4 H), 3.298 (m, 2 H), 1.526 (s, 6 H). |
| 134 | 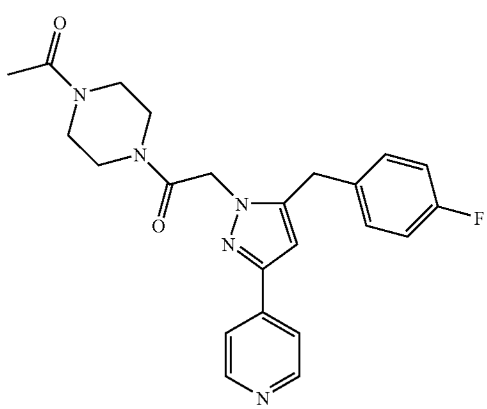 | 1-acetyl-4-{[5-(4-fluorobenzyl)-3-pyridin-4-yl-1H-pyrazol-1-yl]acetyl}piperazine | (400 MHz, CHLOROFORM-d) δ ppm 8.59 (d, J = 6.04 Hz, 2 H), 7.60 (d, J = 6.29 Hz, 2 H), 7.13-7.24 (m, 2 H), 7.03 (t, J = 8.56 Hz, 2 H), 6.40 (s, 2 H), 4.90 (s, 2 H), 4.03 (s, 2 H), 3.73 (s, 3 H), 3.53-3.65 (m, 4 H), 3.48 (br. s., 4 H) |
| 135 | 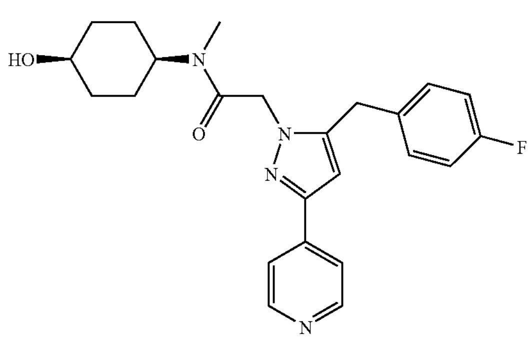 | 2-[5-(4-fluorobenzyl)-3-pyridin-4-yl-1H-pyrazol-1-yl]-N-(cis-4-hydroxycyclohexyl)-N-methylacetamide | (400 MHz, DMSO-D6) δ ppm 8.61 (2 H, d, J = 6.32 Hz) 7.81-7.90 (2 H, m) 7.31 (2 H, dd, J = 8.34, 5.56 Hz) 7.16 (2 H, t, J = 8.84 Hz) 6.61 (1 H, s) 6.20 (2 H, s) 5.24 (1 H, s) 5.17 (1 H, s) 4.11-4.21 (1 H, m) 3.96 (2 H, d, J = 6.82 Hz) 3.76-3.86 (2 H, m) 3.61-3.74 (1 H, m) 2.89 (1.5 H, s) 2.72 (1.5 H, s) 1.67-2.00 (4 H, m) 1.35-1.61 (3 H, m) 1.23 (2 H, d, J = 10.36 Hz) |

| Example No. | Structure | Name | ¹H NMR |
|---|---|---|---|
| 136 | 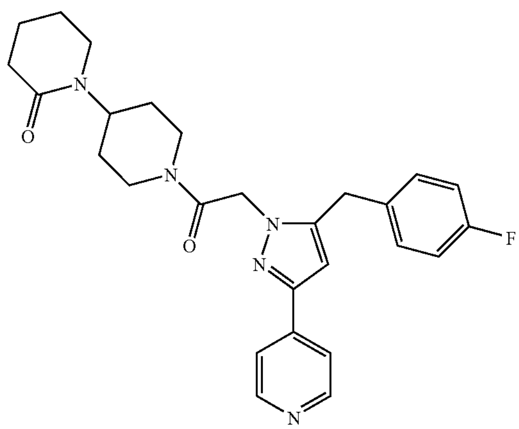 | 1'-{[5-(4-fluorobenzyl)-3-pyridin-4-yl-1H-pyrazol-1-yl]acetyl}-1,4'-bipiperidin-2-one | (400 MHz, DMSO-D6) δ ppm 8.45-8.59 (2 H, m) 7.58-7.73 (2 H, m) 7.24-7.38 (2 H, m) 7.04-7.22 (2 H, m) 6.53 (1 H, s) 5.18 (2 H, q, J = 16.93 Hz) 4.45-4.59 (1 H, m) 4.38 (1 H, d, J = 12.63 Hz) 3.88-3.98 (3 H, m) 3.03-3.18 (3 H, m) 2.54-2.68 (1 H, m) 2.23 (2 H, t, J = 6.32 Hz) 1.59-1.77 (5 H, m) 1.45-1.57 (3 H, m) |
| 137 | 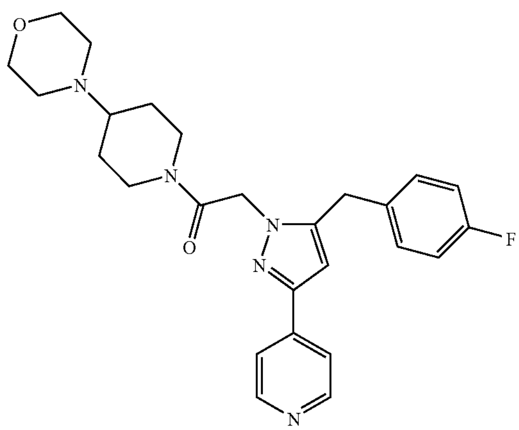 | 4-(1-{[5-(4-fluorobenzyl)-3-pyridin-4-yl-1H-pyrazol-1-yl]acetyl}piperidin-4-yl)morpholine | (400 MHz, DMSO-D6) δ ppm 8.44-8.65 (2 H, m) 7.60-7.71 (2 H, m) 7.29 (2 H, dd, J = 8.59, 5.56 Hz) 7.05-7.20 (2 H, m) 6.52 (1 H, s) 5.04-5.26 (2 H, m) 4.24 (1 H, d, J = 13.39 Hz) 3.94 (2 H, s) 3.89 (1 H, d, J = 13.14 Hz) 3.51-3.64 (4 H, m) 3.04 (1 H, t, J = 11.87 Hz) 2.62 (1 H, t, J = 11.49 Hz) 2.33-2.47 (5 H, m) 1.78 (2 H, t, J = 12.25 Hz) 1.32-1.48 (1H, m) 1.09-1.30 (1 H, m) |

Example 138

In vitro Activity Data for Examples 1 to 137

1. Determination of Compound $K_{iapp}$

A determination of the $K_{iapp}$ of the compounds of the invention against recombinant CYP3A4 enzyme was performed as follows. The assay was performed in a 100 mM sodium phosphate buffer pH 7.0, 5 mM TCEP and containing 2% dimethylformamide (final concentration) upon addition of substrate and inhibitor. A typical reaction for the determination of $K_{iapp}$ values was carried at room temperature in a solid black Costar u-bottom 96-well polypropylene plate. In each well, recombinant CYP3A4 enzyme (5.5 nM or 8 nM, final concentration depending on the commercial source of the enzyme) was pre-incubated in the presence of the inhibitor for at least 30 minutes in the assay buffer. When pre-incubation was completed (~30 min), the reaction was initiated by adding NADPH (200 uM, final concentration), and 7-benzyloxy-4-(trifluoromethyl)-coumarin (BFC) (5 uM, final concentration). The oxidation of the coumarin substrate was recorded by a 96-well plate reader POLARstar (BMG LABTECH, Offenburg, Germany).

The initial reaction velocities were measured during the first 5 min of the reaction when the release of the fluorescent product is linear with time, in the absence and in the presence of various concentrations of inhibitors. For non-partial & partial inhibitors, the $K_{iapp}$ values were determined by using the equation for tight-binding inhibitor developed by Morrison, J F (Morrison J F. Biochim Biophys Acta. 1969, 185: 269-86) and by Szedlaseck S E et al. (Szedlascek, S. E., Ostafe, V., Serban, M., and Vlad, M. O. Biochem. J. 1988, 254:311-312), respectively.

The fluorescent substrate BFC was purchased from Sigma (St Louis, Mo.). Two commercial sources of recombinant enzymes were used in this study: recombinant CYP3A4-b5 enzyme (Baculosomes®) was purchased from Invitrogen (Carlsbad, Calif.) and the recombinant CYP3A4+b5 enzyme (Supersomes®) was purchased from BD Biosciences (Woburn, Mass.).

2. Determination of $IC_{50}$ Against CYP3A4 by Measurement of Inhibition of Testosterone Metabolism This assay was performed using a standard 96 well plate design. IC50 values are calculated from the percent inhibition determined for each test compound at 6 concentrations (for example: 750, 250, 83.3, 27.8, 9.3 and 3.1 nM). The incubation substrate mix contains 25 μM testosterone, 0.1 mg/mL human liver microsomes, 1 mM NADPH, and potassium phosphate buffer (100 mM, pH 7.4). Quantitation of metabolite peak area ratio against an internal standard is determined by LC-MS/MS analysis. The production of 6-β-OH-testosterone from testosterone metabolism is determined after incubation for eight minutes by comparison to a standard curve generated for the metabolite Samples were analyzed in the MRM mode using a Sciex API 3000 mass spectrometer (Applied Biosystems, Foster City, Calif.) with a Paradigm MS4 binary pump (Michrom BioResources Inc., Auburn, Calif.) and a LEAP CTC PAL autosampler (LEAP Technologies, Carrboro, N.C.). A Phenomenex Synergi, 4μ, Polar-RP, 10×2.0 mm column (Phenomenex, Torrance, Calif.) was used for separation with a mobile phase composition of: 0.1% formic acid in water (A) and: 0.1% formic acid in methanol (B). The following gradient was used:

| Time (minutes) | % B | Flow rate (mL/min) |
|---|---|---|
| 0.0 | 0 | 0.8 |
| 0.1 | 95 | 0.8 |
| 0.55 | 95 | 0.8 |
| 0.6 | 0 | 0.8 |

The sample injection volume was 10 μL and flow was split post-column with 0.4 mL/min going to the mass spectrometer. Analysis was performed using the following API 3000 mass spectrometer settings:

| Instrument settings | |
|---|---|
| Ionization Method | ESI, positive |
| Interface | Turbo-ionspray |
| Desolvation Temperature (TEM) | 450° C. |
| Ionspray Voltage (IS) | 5000 |
| Curtain Gas (CUR) | 15 |
| Nebulizer (NEB) | 10 |
| Collision Gas (CAD) | 6 |
| Entrance Potential (EP) | 10 |

| Compound | | Transition (m/z) | DP | FP | CE | CXP | Ret. Time (min) |
|---|---|---|---|---|---|---|---|
| 6-OH-Testosterone | Analyte | 305.4 > 269.2 | 56 | 170 | 21 | 18 | 0.44 |

3. Determination of $IC_{50}$ Against CYP3A4 by Measurement of Inhibition of Midazolam Metabolism This assay was performed using a standard 96 well plate design. IC50s are calculated from the percent inhibition determined for each test compound at 6 concentrations (for example: 750, 250, 83.3, 27.8, 9.3 and 3.1 nM). The incubation substrate mix contains 2 μM midazolam, 0.1 mg/mL human liver microsomes, 1 mM NADPH, and potassium phosphate buffer (100 mM, pH 7.4). Quantitation of metabolite peak area ratio against internal standard is determined by LC-MS/MS analysis. The production of 1-hydroxymidazolam from midazolam metabolism is determined after incubation for eight minutes by comparison to a standard curve generated for the metabolite.

Samples were analyzed in the MRM mode using a Sciex API 3000 mass spectrometer (Applied Biosystems, Foster City, Calif.) with a Paradigm MS4 binary pump (Michrom BioResources Inc., Auburn, Calif.) and a LEAP CTC PAL autosampler (LEAP Technologies, Carrboro, N.C.). A Phenomenex Synergi, 4μ, Polar-RP, 10×2.0 mm column (Phenomenex, Torrance, Calif.) was used for separation with a mobile phase composition of: 0.1% formic acid in water (A) and: 0.1% formic acid in methanol (B). The following gradient was used:

| Time (minutes) | % B | Flow rate (mL/min) |
|---|---|---|
| 0.0 | 0 | 0.8 |
| 0.1 | 95 | 0.8 |
| 0.55 | 95 | 0.8 |
| 0.6 | 0 | 0.8 |

The sample injection volume was 10 μL and flow was split post-column with 0.4 mL/min going to the mass spectrometer. Analysis was performed using the following API 3000 mass spectrometer settings:

| Instrument settings | |
|---|---|
| Ionization Method | ESI, positive |
| Interface | Turbo-ionspray |
| Desolvation Temperature (TEM) | 450° C. |
| Ionspray Voltage (IS) | 5000 |
| Curtain Gas (CUR) | 15 |
| Nebulizer (NEB) | 10 |
| Collision Gas (CAD) | 6 |
| Entrance Potential (EP) | 10 |

| Compound | | Transition (m/z) | DP | FP | CE | CXP | Ret. time |
|---|---|---|---|---|---|---|---|
| 1-hydroxymidazolam | Analyte | 342.2 > 203.1 | 46 | 130 | 29 | 18 | 0.44 |

| Example No. | IC50, µM (HLM, testosterone) | IC50, µM (HLM, midazolam) | Kiapp, µM (Baculosomes ®, BFC) | Kiapp, µM (Supersomes ®, BFC) |
|---|---|---|---|---|
| 1 | <0.0220 | 0.077 | 0.0557 | 0.0064 |
| 2 | 0.956 | | 0.13 | |
| 3 | 0.077 | 0.094 | 0.533 | |
| 4 | 0.057 | 0.023 | 0.0211 | 0.0061 |
| 5 | 0.033 | 0.01 | 0.085 | |
| 6 | 0.024 | 0.0218 | 0.0237 | 0.0118 |
| 7 | 0.105 | 0.073 | 0.196 | 0.033 |
| 8 | 0.273 | 0.114 | 0.547 | |
| 9 | 0.056 | | 0.202 | |
| 10 | 0.033 | 0.013 | 0.0297 | |
| 11 | 0.012 | <0.00300 | 0.00841 | |
| 12 | 0.009 | <0.00300 | 0.00701 | |
| 13 | 0.009 | <0.00346 | 0.0111 | |
| 14 | 0.015 | 0.013 | 0.0236 | |
| 15 | 0.013 | 0.009 | 0.0222 | |
| 16 | 0.016 | 0.00707 | 0.0369 | 0.0139 |
| 17 | 0.035 | 0.0115 | 0.0667 | 0.0231 |
| 18 | 0.018 | | 0.0706 | |
| 19 | 0.033 | 0.0138 | 0.128 | 0.0057 |
| 20 | 0.251 | 0.228 | 0.0365 | |
| 22 | 0.072 | 0.084 | 0.166 | |
| 23 | 0.218 | 0.375 | 0.159 | |
| 24 | 0.047 | 0.027 | 0.0772 | |
| 25 | <0.0120 | 0.045 | 0.0568 | |
| 26 | | | | |
| 27 | 0.021 | 0.086 | 0.12 | |
| 28 | 0.0305 | 0.0792 | 0.608 | |
| 29 | 0.054 | | 0.159 | |
| 30 | 0.446 | 0.773 | 0.646 | |
| 31 | 0.0225 | 0.0466 | 0.105 | |
| 32 | 0.015 | 0.061 | 0.12 | |
| 40 | >0.750 | 0.446 | >1.00 | |
| 50 | 0.168 | 0.132 | 0.729 | 0.389 |
| 51 | 0.0225 | 0.0466 | 0.105 | |
| 52 | 0.056 | 0.071 | 0.175 | |
| 53 | 0.095 | 0.028 | 0.034 | |
| 54 | <0.0120 | <0.0120 | 0.0085 | |
| 55 | <0.0120 | 0.044 | 0.101 | |
| 56 | <0.0120 | <0.0120 | 0.0303 | |
| 57 | 0.062 | 0.064 | 0.124 | |
| 58 | 0.027 | 0.043 | 0.103 | |
| 59 | 0.0665 | 0.0944 | 0.142 | |
| 60 | 0.032 | 0.02 | 0.0765 | |
| 61 | 0.038 | 0.016 | 0.134 | |
| 62 | 0.111 | 0.047 | 0.604 | |
| 63 | 0.048 | 0.04 | 0.178 | |
| 64 | 0.032 | 0.028 | 0.185 | |
| 65 | 0.134 | 0.059 | 0.673 | |
| 66 | 0.072 | 0.084 | 0.166 | |
| 67 | 0.052 | 0.042 | 0.074 | |
| 68 | 0.081 | 0.091 | 0.137 | |
| 69 | 0.0203 | 0.0555 | 0.18 | |
| 70 | <0.0120 | 0.019 | 0.0238 | |
| 71 | 0.035 | 0.034 | 0.0599 | 0.0237 |
| 72 | 0.026 | 0.026 | 0.226 | |
| 73 | 0.0435 | 0.018 | 0.211 | 0.0339 |
| 74 | 0.114 | 0.046 | 0.19 | |
| 75 | 0.0215 | 0.0175 | 0.118 | |
| 76 | 0.0333 | <0.0184 | 0.117 | |
| 77 | 0.0545 | 0.0511 | 0.166 | |
| 78 | 0.04 | | 0.0834 | |
| 79 | 0.019 | 0.016 | 0.052 | |
| 80 | 0.065 | 0.064 | 0.0516 | |
| 81 | 0.068 | 0.063 | 0.124 | |
| 82 | 0.025 | 0.023 | 0.109 | |
| 83 | 0.0235 | 0.015 | 0.0458 | |

-continued

| Example No. | IC50, μM (HLM, testosterone) | IC50, μM (HLM, midazolam) | Kiapp, μM (Baculosomes ®, BFC) | Kiapp, μM (Supersomes ®, BFC) |
|---|---|---|---|---|
| 84 | 0.041 | 0.021 | 0.156 | |
| 85 | 0.028 | 0.031 | 0.0843 | |
| 86 | 0.013 | 0.018 | 0.0571 | |
| 87 | 0.019 | 0.019 | 0.108 | |
| 88 | 0.016 | 0.024 | 0.0753 | |
| 89 | 0.015 | 0.016 | 0.0728 | |
| 90 | 0.012 | 0.019 | 0.0773 | |
| 91 | 0.018 | 0.019 | 0.112 | |
| 92 | 0.015 | 0.007 | 0.0241 | |
| 93 | 0.007 | 0.014 | 0.0134 | 0.0039 |
| 94 | 0.022 | | 0.112 | |
| 95 | <0.0210 | <0.0120 | 0.0871 | 0.0059 |
| 96 | <0.0225 | <0.0130 | 0.0227 | |
| 97 | <0.0120 | 0.045 | 0.232 | |
| 98 | 0.082 | 0.108 | 0.378 | |
| 99 | 0.064 | 0.032 | 0.248 | 0.0178 |
| 100 | 0.0845 | 0.044 | 0.298 | 0.0225 |
| 101 | 0.035 | 0.0105 | 0.158 | |
| 102 | 0.023 | 0.012 | 0.107 | |
| 103 | 0.068 | 0.025 | 0.106 | |
| 104 | 0.046 | | 0.106 | |
| 105 | 0.036 | | 0.055 | |
| 106 | 0.023 | | 0.0782 | |
| 107 | 0.029 | | 0.165 | |
| 108 | 0.241 | | 0.0881 | |
| 109 | 0.036 | | 0.0643 | |
| 110 | 0.016 | | 0.0158 | |
| 111 | 0.714 | 0.223 | 0.838 | |
| 112 | 0.009 | 0.006 | 0.002 | |
| 113 | 0.011 | 0.009 | 0.00676 | |
| 114 | 0.019 | 0.01 | 0.0227 | |
| 115 | 0.015 | 0.004 | 0.0338 | |
| 116 | 0.008 | <0.00300 | 0.0141 | |
| 117 | 0.018 | 0.011 | 0.0702 | |
| 118 | 0.013 | 0.00837 | 0.0442 | 0.0065 |
| 119 | >0.750 | 0.167 | 0.314 | 0.166 |
| 120 | 0.027 | 0.017 | 0.003 | 0.0068 |
| 121 | 0.088 | 0.045 | 0.0978 | 0.0136 |
| 122 | >0.750 | 0.62 | 0.482 | 0.178 |
| 123 | 0.554 | 0.397 | 0.459 | 0.167 |
| 124 | 0.032 | 0.025 | 0.123 | 0.0147 |
| 125 | 0.027 | 0.022 | 0.0666 | 0.00884 |
| 126 | 0.059 | 0.034 | 0.196 | 0.031 |
| 127 | 0.08 | 0.041 | 0.141 | 0.0191 |
| 128 | 0.026 | 0.022 | 0.0488 | 0.00507 |
| 129 | 0.066 | 0.022 | 0.312 | 0.017 |
| 130 | 0.032 | 0.015 | 0.0276 | 0.00618 |
| 131 | 0.037 | 0.0139 | 0.0111 | 0.00283 |
| 132 | 0.04 | 0.023 | 0.0996 | 0.0716 |
| 133 | 0.044 | 0.083 | 0.21 | 0.174 |
| 134 | 0.051 | 0.0169 | 0.131 | 0.0168 |
| 135 | 0.021 | 0.00867 | 0.108 | 0.0358 |
| 136 | 0.023 | <0.00833 | 0.0291 | 0.0119 |
| 137 | 0.031 | 0.0101 | 0.0129 | 0.0036 |

Example 139

Acquisition of Powder X-Ray Diffraction (PXRD) Data

Powder X-ray diffraction data was obtained on a Bruker D8 Discover Powder X-ray Diffractometer with a GADDS detector. The X-ray source was Cu, the voltage was 40 KV and the current was 40 mA. Typically, about 3 to 4 mg of a sample compound was packed evenly into a circle with a diameter of about 0.2 inch on a nickel plate. The acquisition time was 2 minutes with XY-oscillation.

Example 140

Acquisition of Differential Scanning Calorimetry (DSC) Data

Differential scanning calorimetry data was obtained on a DSC-1000 from TA Instruments using a hermetic pan with a pinhole and at a scanning rate of 10° C. per minute. Typically, about 1 to 2 mg of a sample compound was used.

Example 141

N-(1-{2-[5-(4-fluorobenzyl)-3-pyridin-4-yl-1H-pyrazol-1-yl]acetyl}-piperidin-4-yl)methanesulfonamide N-(1-{2-[5-(4-fluorobenzyl)-3-pyridin-4-yl-1H-pyrazol-1-yl]acetyl}piperidin-4-yl)methanesulfonamide (200 mg)

was added to EtOAc and the mixture was heated until the solid was mostly dissolved. Norit was added and the resulting mixture was gently heated and then filtered. The resulting solution was concentrated, a small amount of hexanes were added, and the solution was allowed to cool to room temperature. The resulting white solid was collected, washed with 30% EtOAc/hexanes, and dried under vacuum at 60° C. and about 12 Torr.

PXRD Peak data:

| Angle (2-Theta °) | d value (Angstrom) |
|---|---|
| 7.25 | 12.19 |
| 14.36 | 6.16 |
| 15.33 | 5.77 |
| 16.09 | 5.50 |
| 17.99 | 4.93 |
| 18.71 | 4.74 |
| 19.59 | 4.53 |
| 20.67 | 4.29 |
| 21.17 | 4.19 |
| 22.27 | 3.99 |
| 23.66 | 3.76 |
| 24.52 | 3.63 |
| 25.14 | 3.54 |
| 26.36 | 3.38 |
| 28.47 | 3.13 |
| 29.83 | 2.99 |
| 31.05 | 2.88 |

Example 142

Hydrate Form of a Mesylate Salt of N-(1-{2-[5-(4-fluorobenzyl)-3-pyridin-4-yl-1H-pyrazol-1-yl]acetyl}piperidin-4-yl)methanesulfonamide N-(1-{2-[5-(4-fluorobenzyl)-3-pyridin-4-yl-1H-pyrazol-1-yl]acetyl}piperidin-4-yl)methanesulfonamide (51 mg, 0.11 mmol) of was dissolved in a mixture of isopropyl alcohol (4 mL) and 1,4-Dioxane (4 mL). To the resulting solution was added 1N methanesulfonic acid (121 µL, 0.12mmol). The resulting clear mixture was stirred at room temperature for 2 hours and then was cooled and stirred for an additional 2 hours. The resulting solid was filtered, providing about 57 mg of a hydrate form of a mesylate salt of N-(1-{2-[5-(4-fluorobenzyl)-3-pyridin-4-yl-1H-pyrazol-1-yl]acetyl}piperidin-4-yl)methanesulfonamide that was dried in a vacuum oven overnight at 40° C.

PXRD Peak data:

| Angle (2-Theta °) | d value (Angstrom) |
|---|---|
| 9.47 | 9.33 |
| 11.45 | 7.72 |
| 15.03 | 5.89 |
| 16.85 | 5.26 |
| 17.80 | 4.98 |
| 19.46 | 4.56 |
| 21.70 | 4.09 |
| 25.13 | 3.54 |
| 26.24 | 3.39 |
| 28.86 | 3.09 |

Example 143

Anhydrous Form of a Mesylate Salt of N-(1-{2-[5-(4-fluorobenzyl)-3-pyridin-4-yl-1H-pyrazol-1-yl]acetyl}piperidin-4-yl)methanesulfonamide The hydrate form of a mesylate salt of N-(1-{2-[5-(4-fluorobenzyl)-3-pyridin-4-yl-1H-pyrazol-1-yl]acetyl}piperidin-4-yl)methanesulfonamide (from Example 141) was slurried in toluene at 90° C. for 2 hours. The resulting solid was collected by filtration and dried under vacuum at 40° C. to provide a solid.

PXRD Peak data:

| Angle (2-Theta °) | d value (Angstrom) |
|---|---|
| 6.51 | 13.56 |
| 10.50 | 8.42 |
| 12.88 | 6.87 |
| 13.75 | 6.44 |
| 16.51 | 5.36 |
| 17.05 | 5.20 |
| 18.78 | 4.72 |
| 20.15 | 4.40 |
| 21.33 | 4.16 |
| 22.35 | 3.97 |
| 23.65 | 3.76 |
| 25.32 | 3.51 |
| 26.27 | 3.39 |
| 27.71 | 3.22 |
| 30.50 | 2.93 |
| 33.57 | 2.67 |
| 34.56 | 2.59 |
| 35.44 | 2.53 |

Example 144

A Phosphate Salt of N-(1-{2-[5-(4-fluorobenzyl)-3-pyridin-4-yl-1H-pyrazol-1-yl]acetyl}piperidin-4-yl)methanesulfonamide A crystalline form of a phosphate salt of N-(1-{2-[5-(4-fluorobenzyl)-3-pyridin-4-yl-1H-pyrazol-1-yl]acetyl}piperidin-4-yl)methanesulfonamide was prepared by dissolving N-(1-{2-[5-(4-fluorobenzyl)-3-pyridin-4-yl-1H-pyrazol-1-yl]acetyl}piperidin-4-yl)methanesulfonamide (197 mg) in acetonitrile (10 mL) that was warmed to 65° C. The resulting solution was allowed to cool to room temperature and 2M phosphoric acid (210 µL) was added, which caused a precipitate to form. The resulting mixture was stirred at 65° C. for 30 min, cooled to room temperature, and the resulting white solid was collected by vacuum filtration (235 mg (wet)). The solid was dried in vacuum oven at 60° C., slurried in toluene at 90° C. overnight, filtered, and dried in a vacuum oven at 60° C. to provide an anhydrous phosphate salt of N-(1-{2-[5-(4-fluorobenzyl)-3-pyridin-4-yl-1H-pyrazol-1-yl]acetyl}piperidin-4-yl)methanesulfonamide.

PXRD Peak data:

| Angle (2-Theta °) | d value (Angstrom) |
|---|---|
| 11.21 | 7.89 |
| 13.31 | 6.64 |

-continued

| PXRD Peak data: | |
|---|---|
| Angle (2-Theta °) | d value (Angstrom) |
| 15.76 | 5.62 |
| 16.88 | 5.25 |
| 17.69 | 5.01 |
| 18.33 | 4.84 |
| 18.81 | 4.71 |
| 19.43 | 4.57 |
| 20.68 | 4.29 |
| 21.97 | 4.04 |
| 22.47 | 3.95 |
| 23.34 | 3.81 |
| 23.81 | 3.73 |
| 24.75 | 3.59 |
| 25.97 | 3.43 |
| 26.76 | 3.33 |
| 27.17 | 3.28 |
| 28.19 | 3.16 |
| 29.01 | 3.08 |
| 31.94 | 2.80 |
| 33.97 | 2.64 |
| 35.67 | 2.51 |
| 37.14 | 2.42 |

We claim:
1. A compound of formula (IIb),

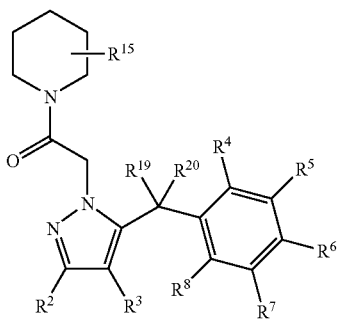

(IIb)

wherein:
$R^2$ is 5-9 membered heteroaryl, optionally substituted with one or more $R^{11}$ groups;
$R^3$, $R^4$, $R^5$, $R^6$, $R^7$, and $R^8$ are each independently selected from hydrogen, halo, $C_1$-$C_8$ alkyl, $C_2$-$C_8$ alkenyl, $C_2$-$C_8$ alkynyl, —$(CR^9R^{10})_t(C_3$-$C_8$ cycloalkyl), —$(CR^9R^{10})_t$ $OR^{11}$, —$(CR^9R^{10})_tN(R^{11}R^{12})$, —CN, —$NO_2$, —$CF_3$, —$C(O)R^9$, and —$C(O)_2R^9$;
each $R^9$ and $R^{10}$ is independently selected from hydrogen, $C_1$-$C_8$ alkyl, $C_3$-$C_8$ cycloalkyl, $C_6$-$C_{10}$ aryl, 3-10 membered heterocyclyl, and 5-9 membered heteroaryl;
each $R^{11}$ and $R^{12}$ is independently selected from hydrogen, $C_1$-$C_8$ alkyl, $C_3$-$C_8$ cycloalkyl, $C_6$-$C_{10}$ aryl, 3-10 membered heterocyclyl, 5-9 membered heteroaryl, —CN, halo, —$(CR^{16}R^{17})_tOR^{18}$, and —$(CR^{16}R^{17})_tC(O)R^{18}$, wherein each of said $C_1$-$C_8$ alkyl, $C_3$-$C_8$ cycloalkyl, $C_6$-$C_{10}$ aryl, 3-10 membered heterocyclyl, and 5-9 membered heteroaryl groups is optionally substituted with one more $R^{15}$ groups;
each $R^{15}$ is independently selected from —$(CR^9R^{10})_tR^{16}$, —$(CR^9R^{10})_t$(3-10 membered heterocyclyl), —$(CR^9R^{10})_t(C_3$-$C_8$ cycloalkyl), —$(CR^9R^{10})_t$(5-9 membered heteroaryl), —$(CR^9R^{10})_t(C_6$-$C_{10}$ aryl), —$(CR^9R^{10})_tN(R^{16}R^{17})$, —$(CR^9R_{10})NR^{16}C(O)R^{17}$, —$(CR^9R^{10})_tOR^{16}$, —$(CR^9R^{10})_tC(O)R^{16}$, —$(CR^9R^{10})_t$ $C(O)_2R^{16}$, —$(CR^9R^{10})_tC(O)N(R^{16}R^{17})$, —$(CR^9R^{10})_t$ $NR^{16}C(O)OR^{17}$, —$(CR^9R^{10})_tNR^{16}S(O)N(R^{17}R^{18})$, —$(CR^9R^{10})_tNR^{16}S(O)_2N(R^{17}R^{18})$, —$(CR^9R^{10})_tNR^{16}S$ $(O)R^{17}$, —$(CR^9R^{10})_tNR^{16}S(O)_2R^{17}$, —$(CR^9R^{10})_t$ $NR^{16}C(O)N(R^{17}R^{18})$, —$(CR^9R^{10})_t$(halo), —$(CR^9R^{10})_t$ —$OR^{16}$, and —$(CR^9R^{10})_tS(O)_2R^{16}$, wherein each said 3-10 membered heterocyclyl, $C_3$-$C_8$ cycloalkyl, 5-9 membered heteroaryl, and $C_6$-$C_{10}$ aryl is optionally substituted with one or more $R^{16}$ groups;
each $R^{16}$, $R^{17}$, and $R^{18}$ is independently selected from hydrogen, $C_1$-$C_8$ alkyl, —$(CH_2)_t(C_3$-$C_8$ cycloalkyl), —$(CH_2)_t(C_6$-$C_{10}$ aryl), —$(CH_2)_t$(5-9 membered heteroaryl), —$(CH_2)_t$(3-10 membered heterocyclyl), halo, —$OCH_3$, and —OH;
$R^{19}$ and $R^{20}$ are independently selected from hydrogen and $C_1$-$C_8$ alkyl; and
each t is independently selected from 0, 1, 2, 3, and 4; or a pharmaceutically acceptable salt thereof.

2. A compound of formula (IIc),

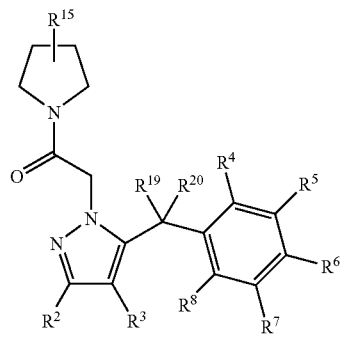

(IIc)

wherein:
$R^2$ is 5-9 membered heteroaryl, optionally substituted with one or more $R^{11}$ groups;
$R^3$, $R^4$, $R^5$, $R^6$, $R^7$, and $R^8$ are each independently selected from hydrogen, halo, $C_1$-$C_8$ alkyl, $C_2$-$C_8$ alkenyl, $C_2$-$C_8$ alkynyl, —$(CR^9R^{10})_t(C_3$-$C_8$ cycloalkyl), —$(CR^9R^{10})_t$ $OR^{11}$, —$(CR^9R^{10})_tN(R^{11}R^{12})$, —CN, —$NO_2$, —$CF_3$, —$C(O)R^9$, and —$C(O)_2R^9$;
each $R^9$ and $R^{10}$ is independently selected from hydrogen, $C_1$-$C_8$ alkyl, $C_3$-$C_8$ cycloalkyl, $C_6$-$C_{10}$ aryl, 3-10 membered heterocyclyl, and 5-9 membered heteroaryl;
each $R^{11}$ and $R^{12}$ is independently selected from hydrogen, $C_1$-$C_8$ alkyl, $C_3$-$C_8$ cycloalkyl, $C_6$-$C_{10}$ aryl, 3-10 membered heterocyclyl, 5-9 membered heteroaryl, —CN, halo, —$(CR^{16}R^{17})_tOR^{18}$, and —$(CR^{16}R^{17})_tC(O)R^{18}$, wherein each of said $C_1$-$C_8$ alkyl, $C_3$-$C_8$ cycloalkyl, $C_6$-$C_{10}$ aryl, 3-10 membered heterocyclyl, and 5-9 membered heteroaryl groups is optionally substituted with one more $R^{15}$ groups;
each $R^{15}$ is independently selected from —$(CR^9R^{10})_tR^{16}$, —$(CR^9R^{10})_t$(3-10 membered heterocyclyl), —$(CR^9R^{10})_t(C_3$-$C_8$ cycloalkyl), —$(CR^9R^{10})_t$(5-9 membered heteroaryl), —$(CR^9R^{10})_t(C_6$-$C_{10}$ aryl), —$(CR^9R^{10})_tN(R^{16}R^{17})$, —$(CR^9R^{10})_tNR^{16}C(O)R^{17}$, —$(CR^9R^{10})_tOR^{16}$, —$(CR^9R^{10})_tC(O)R^{16}$, —$(CR^9R^{10})_t$ $C(O)_2R^{16}$, —$(CR^9R^{10})_tC(O)N(R^{16}R^{17})$, —$(CR^9R^{10})_t$ $NR^{16}C(O)OR^{17}$, —$(CR^9R^{10})_tNR^{16}S(O)N(R^{17}R^{18})$, —$(CR^9R^{10})_tNR^{16}S(O)_2N(R^{17}R^{18})$, —$(CR^9R^{10})_tNR^{16}S$ $(O)R^{17}$, —$(CR^9R^{10})_tNR^{16}S(O)_2R^{17}$, —$(CR^9R^{10})_t$ $NR^{16}C(O)N(R^{17}R^{18})$, —$(CR^9R^{10})_t$(halo), —$(CR^9R^{10})_t$ —$OR^{16}$, and —$(CR^9R^{10})_tS(O)_2R^{16}$, wherein each said 3-10 membered heterocyclyl, $C_3$-$C_8$ cycloalkyl, 5-9 membered heteroaryl, and $C_6$-$C_{10}$ aryl is optionally substituted with one or more $R^{16}$ groups;

each $R^{16}$, $R^{17}$, and $R^{18}$ is independently selected from hydrogen, $C_1$-$C_8$ alkyl, —$(CH_2)_t(C_3$-$C_8$ cycloalkyl), —$(CH_2)_t(C_6$-$C_{10}$ aryl), —$(CH_2)_t$(5-9 membered heteroaryl), —$(CH_2)_t$(3-10 membered heterocyclyl), halo, —$OCH_3$, and —OH;

$R^{19}$ and $R^{20}$ are independently selected from hydrogen and $C_1$-$C_8$ alkyl; and each t is independently selected from 0, 1, 2, 3, and 4; or a pharmaceutically acceptable salt thereof.

3. A compound of formula (IId),

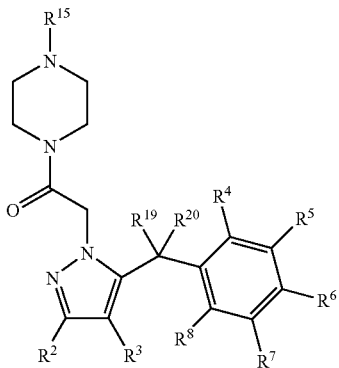

(IId)

wherein:
$R^2$ is 5-9 membered heteroaryl, optionally substituted with one or more $R^{11}$ groups;

$R^3$, $R^4$, $R^5$, $R^6$, $R^7$, and $R^8$ are each independently selected from hydrogen, halo, $C_1$-$C_8$ alkyl, $C_2$-$C_8$ alkenyl, $C_2$-$C_8$ alkynyl, —$(CR^9R^{10})_t(C_3$-$C_8$ cycloalkyl), —$(CR^9R^{10})_t OR^{11}$, —$(CR^9R^{10})_t N(R^{11}R^{12})$, —CN, —$NO_2$, —$CF_3$, —$C(O)R^9$, and —$C(O)_2R^9$;

each $R^9$ and $R^{10}$ is independently selected from hydrogen, $C_1$-$C_8$ alkyl, $C_3$-$C_8$ cycloalkyl, $C_6$-$C_{10}$ aryl, 3-10 membered heterocyclyl, and 5-9 membered heteroaryl;

each $R^{11}$ and $R^{12}$ is independently selected from hydrogen, $C_1$-$C_8$ alkyl, $C_3$-$C_8$ cycloalkyl, $C_6$-$C_{10}$ aryl, 3-10 membered heterocyclyl, 5-9 membered heteroaryl, —CN, halo, —$(CR^{16}R^{17})_t OR^{18}$, and —$(CR^{16}R^{17})_t C(O)R^{18}$, wherein each of said $C_1$-$C_8$ alkyl, $C_3$-$C_8$ cycloalkyl, $C_6$-$C_{10}$ aryl, 3-10 membered heterocyclyl, and 5-9 membered heteroaryl groups is optionally substituted with one more $R^{15}$ groups;

each $R^{15}$ is independently selected from —$(CR^9R^{10})_t R^{16}$, —$(CR^9R^{10})_t$(3-10 membered heterocyclyl), —$(CR^9R^{10})_t(C_3$-$C_8$ cycloalkyl), —$(CR^9R^{10})_t$(5-9 membered heteroaryl), —$(CR^9R^{10})_t(C_6$-$C_{10}$ aryl), —$(CR^9R^{10})_t N(R^{16}R^{17})$, —$(CR^9R^{10})_t NR^{16}C(O)R^{17}$, —$(CR^9R^{10})_t OR^{16}$, —$(CR^9R^{10})_t C(O)R^{16}$, —$(CR^9R^{10})_t C(O)_2R^{16}$, —$(CR^9R^{10})_t C(O)N(R^{16}R^{17})$, —$(CR^9R^{10})_t NR^{16}C(O)OR^{17}$, —$(CR^9R^{10})_t NR^{16}S(O)N(R^{17}R^{18})$, —$(CR^9R^{10})_t NR^{16}S(O)_2N(R^{17}R^{18})$, —$(CR^9R^{10})_t NR^{16}S(O)R^{17}$, —$(CR^9R^{10})_t NR^{16}S(O)_2R^{17}$, —$(CR^9R^{10})_t NR^{16}C(O)N(R^{17}R^{18})$, —$(CR^9R^{10})_t$(halo), —$(CR^9R^{10})_t$—$OR^{16}$, and —$(CR^9R^{10})_t S(O)_2R^{16}$, wherein each said 3-10 membered heterocyclyl, $C_3$-$C_8$ cycloalkyl, 5-9 membered heteroaryl, and $C_6$-$C_{10}$ aryl is optionally substituted with one or more $R^{16}$ groups;

each $R^{16}$, $R^{17}$, and $R^{18}$ is independently selected from hydrogen, $C_1$-$C_8$ alkyl, —$(CH_2)_t(C_3$-$C_8$ cycloalkyl), —$(CH_2)_t(C_6$-$C_{10}$ aryl), —$(CH_2)_t$(5-9 membered heteroaryl), —$(CH_2)_t$(3-10 membered heterocyclyl), halo, —$OCH_3$, and —OH;

$R^{19}$ and $R^{20}$ are independently selected from hydrogen and $C_1$-$C_8$ alkyl; and each t is independently selected from 0, 1, 2, 3, and 4; or a pharmaceutically acceptable salt thereof.

4. A compound of formula

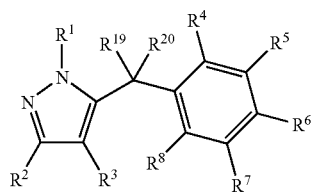

wherein:
$R^1$ is —$(CR^9R^{10})_t C(O) N(R^{13}R^{14})$;

$R^2$ is 5-9 membered heteroaryl, optionally substituted with one or more $R^{11}$ groups;

$R^3$, $R^4$, $R^5$, $R^6$, $R^7$, and $R^8$ are each independently selected from hydrogen, halo, $C_1$-$C_8$ alkyl, $C_2$-$C_8$ alkenyl, $C_2$-$C_8$ alkynyl, —$(CR^9R^{10})_t(C_3$-$C_8$ cycloalkyl), —$(CR^9R^{10})_t OR^{11}$, —$(CR^9R^{10})_t N(R^{11}R^{12})$, —CN, —$NO_2$, —$CF_3$, —$C(O)R^9$, and —$C(O)_2R^9$, each $R^9$ and $R^{10}$ is independently hydrogen, $C_1$-$C_8$ alkyl, $C_3$-$C_8$ cycloalkyl, $C_6$-$C_{10}$ aryl, 3-10 membered heterocyclyl, and 5-9 membered heteroaryl;

each $R^{11}$ and $R^{12}$ is independently selected from hydrogen, $C_1$-$C_8$ alkyl, $C_3$-$C_8$ cycloalkyl, $C_6$-$C_{10}$ aryl, 3-10 membered heterocyclyl, 5-9 membered heteroaryl, —CN, halo, —$(CR^{16}R^{17})_t OR^{18}$, and —$(CR^{16}R^{17})_t C(O)R^{18}$, wherein each of said $C_1$-$C_8$ alkyl, $C_3$-$C_8$ cycloalkyl, $C_6$-$C_{10}$ aryl, 3-10 membered heterocyclyl, and 5-9 membered heteroaryl groups is optionally substituted with one more $R^{15}$ groups;

$R^{13}$ and $R^{14}$, together with the nitrogen atom to which they are attached, form a 3-10 membered heterocyclyl group, optionally substituted with one or more $R^{15}$ groups;

each $R^{15}$ is independently selected from —$(CR^9R^{10})_t R^{16}$, —$(CR^9R^{10})_t$(3-10 membered heterocyclyl), —$(CR^9R^{10})_t(C_3$-$C_8$ cycloalkyl), —$(CR^9R^{10})_t$(5-9 membered heteroaryl), —$(CR^9R^{10})_t(C_6$-$C_{10}$ aryl), —$(CR^9R^{10})_t N(R^{16}R^{17})$, —$(CR^9R^{10})_t NR^{16}C(O)R^{17}$, —$(CR^9R^{10})_t OR^{16}$, —$(CR^9R^{10})_t C(O)R^{16}$, —$(CR^9R^{10})_t C(O)_2R^{16}$, —$(CR^9R^{10})_t C(O)N(R^{16}R^{17})$, —$(CR^9R^{10})_t NR^{16}C(O)OR^{17}$, —$(CR^9R^{10})_t NR^{16}S(O)N(R^{17}R^{18})$, —$(CR^9R^{10})_t NR^{16}S(O)_2N(R^{17}R^{18})$, —$(CR^9R^{10})_t NR^{16}S(O)R^{17}$, —$(CR^9R^{10})_t NR^{16}S(O)_2R^{17}$, —$(CR^9R^{10})_t NR^{16}C(O)N(R^{17}R^{18})$, —$(CR^9R^{10})_t$(halo), —$(CR^9R^{10})_t$—$OR^{16}$, and —$(CR^9R^{10})_t S(O)_2R^{16}$, wherein each said 3-10 membered heterocyclyl, $C_3$-$C_8$ cycloalkyl, 5-9 membered heteroaryl and $C_6$-$C_{10}$ aryl is optionally substituted with one or more $R^{16}$ groups;

each $R^{16}$, $R^{17}$, and $R^{18}$ is independently from hydrogen, $C_1$-$C_8$ alkyl, —$(CH_2)_t(C_3$-$C_8$ cycloalkyl), —$(C_2)_t(C_6$-$C_{10}$ aryl), —$(CH_2)_t$(5-9 membered heteroaryl, —$(CH_2)_t$(3-10 membered heterocyclyl), halo, —$OCH_3$, and —OH;

$R^{19}$ and $R^{20}$ are independently selected from hydrogen and $C_1$-$C_8$ alkyl; and each t is independently selected from 0, 1, 2, 3, and 4; or a pharmaceutically acceptable salt thereof.

5. A compound according to claim 4, wherein $R^2$ is selected from pyridyl, pyrazolyl, pyrimidinyl, and imidazolyl, or a pharmaceutically acceptable salt thereof.

6. A compound according to claim 5, wherein $R^2$ is selected from 2-pyridinyl, 3-pyridinyl, 4-pyridinyl, 4-pyrazolyl, 3-pyrimidinyl, and 4-imidazolyl, or a pharmaceutically acceptable salt thereof.

7. A compound according to claim 6, wherein $R^2$ is 4-pyridinyl, or a pharmaceutically acceptable salt thereof.

8. A compound according to claim 4, wherein $R^3$ is hydrogen, or a pharmaceutically acceptable salt thereof.

9. A compound according to claim 4, wherein $R^{19}$ and $R^{20}$ are hydrogen, or a pharmaceutically acceptable salt thereof.

10. A compound according to claim 4, selected from the group consisting of:
- 1-(1-{[5-(4-fluorobenzyl)-3-pyridin-4-yl-1H-pyrazol-1-yl]acetyl}piperidin-4-yl)pyrrolidin-2-one;
- 4-(5-(4-fluorobenzyl)-1-{2-[4-methylsulfonyl)piperidin-1-yl]-2-oxoethyl}-1H-pyrazol-3-yl)pyridine;
- 1-{[5-(4-fluorobenzyl)-3-pyridin-4-yl-1H-pyrazol-1-yl]acetyl}-N-methylpiperidin-4-amine;
- 1-{[5-(4-fluorobenzyl)-3-pyridin-4-yl-1H-pyrazol-1-yl]acetyl}piperidin-4-amine;
- 1-{[5-(4-fluorobenzyl)-3-pyridin-4-yl-1H-pyrazol-1-yl]acetyly}N-isopropylpiperidin-4-amine;
- N-(1-{[5-(4-fluorobenzyl)-3-pyridin-4-yl-1H-pyrazol-1-yl]acetyl}piperidin-4-yl)-N-methylpropanamide;
- N-(1-{[5-(4-fluorobenzyl)-3-pyridin-4-yl-1H-pyrazol-1-yl]acetyl}piperidin-4-yl)-N,2-dimethylpropanamide;
- N-(1-{[5-(4-fluorobenzyl)-3-pyridin-4-yl-1H-pyrazol-1-yl]acetyl}piperidin-4-yl)-N-methylcyclobutanecarboxamide;
- N-(1-{[5-(4-fluorobenzyl)-3-pyridin-4-yl-1H-pyrazol-1-yl]acetyl}piperidin-4-yl)-N-methylcyclopropanecarboxamide;
- N-(1-{[5-(4-fluorobenzyl)-3-pyridin-4-yl-1H-pyrazol-1-yl]acetyl}piperidin-4-yl)-N-methylmethanesulfonamide;
- methyl (1-{[5-(4-fluorobenzyl)-3-pyridin-4-yl-1H-pyrazol-1-yl]acetyl}piperidin-4-yl)methylcarbamate;
- N-(1-{[5-(4-fluorobenzyl)-3-pyridin-4-yl-1H-pyrazol-1-yl]acetyl}piperidin-4-yl)-N'-isopropyl-N-methylurea;
- N-(1{[5-(4-fluorobenzyl)-3-pyridin-4-yl-1H-pyrazol-1-yl]acetyl}piperidin-4-yl)-N'-isopropylurea;
- N-(1-{2-[5-(4-fluorobenzyl)-3-pyridin-4-yl-1H-pyrazol-1-yl]acetyl}piperidin-4-yl)cyclobutanecarboxamide;
- N-(1-{2-[5-(4-fluorobenzyl)-3-pyridin-4-yl-1H-pyrazol-1-yl]acetyl}piperidin-4-yl)methanesulfonamide;
- 1-{[5-(4-fluorobenzyl)-3-pyridin-4-yl-1H-pyrazol-1-yl]acetyl}piperidin-3-ol;
- 1-{[5-(4-fluorobenzyl)-3-pyridin-4-yl-1H-pyrazol-1-yl]acetyl}-4-[methyl(propyl)amino]piperidine-4-carboxamide;
- N-(1-{2-[5-(4-fluorobenzyl)-3-pyridin-4-yl-1H-pyrazol-1-yl]acetyl}piperidin-4-yl)propanamide;
- N-(1-{2-[5-(4-fluorobenzyl)-3-pyridin-4-yl-1H-pyrazol-1-yl]acetyl}piperidin-4-yl)ethanesulfonamide;
- N-(1-{[5-(4-fluorobenzyl)-3-pyridin-4-yl-1H-pyrazol-1-yl]acetyl}piperidin-4-yl)-2-methylpropanamide;
- methyl (1-{[5-(4-fluorobenzyl)-3-pyridin-4-yl-1H-pyrazol-1-yl]acetyl}piperidin-4-yl)carbamate;
- 1-ethyl-3-(1-{[5-(4-fluorobenzyl)-3-pyridin-4-yl-1H-pyrazol-1-yl]acetyl}piperidin-4-yl)urea;
- 1-(1-{[5-(4-fluorobenzyl)-3-pyridin-4-yl-1H-pyrazol-1-yl]acetyl}piperidin-4-yl)-3-methylurea;
- N-(1-{[5-(4-fluorobenzyl)-3-pyridin-4-yl-1H-pyrazol-1-yl]acetyl}piperidin-4-yl)-N-methylacetamide;
- N-(1-{[5-(4-fluorobenzyl)-3-pyridin-4-yl-1H-pyrazol-1-yl]acetyl}piperidin-4-yl)-N-methylethanesulfonamide;
- isopropyl (1-{[5-(4-fluorobenzyl)-3-pyridin-4-yl-1H-pyrazol-1-yl]acetyl}piperidin-4-yl)methylcarbamate;
- ethyl (1-{[5-(4-fluorobenzyl)-3-pyridin-4-yl-1H-pyrazol-1-yl]acetyl}piperidin-4-yl)methylcarbamate;
- ethyl (1-{[5-(4-fluorobenzyl)-3-pyridin-4-yl-1H-pyrazol-1-yl]acetyl}piperidin-4-yl)carbamate;
- 3-ethyl-1-(1-{[5-(4-fluorobenzyl)-3-pyridin-4-yl-1H-pyrazol-1-yl]acetyl}piperidin-4-yl)-1-methylurea;
- isopropyl (1-{[5-(4-fluorobenzyl)-3-pyridin-4-yl-1H-pyrazol-1-yl]acetyl}piperidin-4-yl)carbamate;
- 1-(1-{[5-(4-fluorobenzyl)-3-pyridin-4-yl-1H-pyrazol-1-yl]acetyl}piperidin-4-yl)-1,3-dimethylurea;
- 3-(1-{[5-(4-fluorobenzyl)-3-pyridin-4-yl-1H-pyrazol-1-yl]acetyl}piperidin-4-yl)-1,3-oxazolidin-2-one;
- N-(1-{2-[5-(4-fluorobenzyl)-3-(1H-imidazol-4-yl)-1H-pyrazol-1-yl]acetyl}piperidin-4-yl)methanesulfonamide;
- 4-[1-{2-[4-(1,1-dioxidoisothiazolidin-2-yl)piperidin-1-yl]-2-oxoethyl}-5-(4-fluorobenzyl)-1H -pyrazol-3-yl]pyridine; and
- N-(1-{[5-(4-fluorobenzyl)-3-(1H-imidazol-4-yl)-1H-pyrazol-1-yl]acetyl}piperidin-4-yl)-N-methylacetamide;

or a pharmaceutically acceptable salt of each of the foregoing compounds.

11. A pharmaceutical composition, comprising an effective amount of at least one compound according claim 4, or a pharmaceutically acceptable salt thereof, and a pharmaceutically acceptable carrier.

12. A method of inhibiting the metabolism in a mammal of a first compound that is metabolized by cytochrome P450, comprising administering to said mammal said first compound and an effective amount of a second compound, wherein said second compound is a compound according to claim 4, or a pharmaceutically acceptable salt thereof.

13. A method of improving the pharmacokinetics in a mammal of a first compound, comprising administering to said mammal said first compound and an effective amount of a second compound, wherein said second compound is a compound according to claim 4, or a pharmaceutically acceptable salt thereof.

14. N-(1-(2-(5-(4-fluorobenzyl)-3-(pyridin-4-yl)-1H-pyrazol-1-yl)acetyl)piperidin-4-yl)methanesulfonamide, or a pharmaceutically acceptable salt thereof.

* * * * *